US008389269B2

(12) United States Patent
Sagt et al.

(10) Patent No.: US 8,389,269 B2
(45) Date of Patent: Mar. 5, 2013

(54) PRODUCTION OF SECRETED PROTEINS BY FILAMENTOUS FUNGI

(75) Inventors: Cornelis Maria Jacobus Sagt, Utrect (NL); Cornelis Theodorus Verrips, Houten (NL); Walraven Henry Muller, Dordrecht (NL); Noël Nicolaas Maria Elisabeth Van Peij, Delfgauw (NL)

(73) Assignee: DSM IP Assets B.V., Heerlen (NL)

( * ) Notice: Subject to any disclaimer, the term of this patent is extended or adjusted under 35 U.S.C. 154(b) by 603 days.

(21) Appl. No.: 12/444,760

(22) PCT Filed: Oct. 31, 2007

(86) PCT No.: PCT/EP2007/061765
§ 371 (c)(1),
(2), (4) Date: Apr. 30, 2009

(87) PCT Pub. No.: WO2008/053018
PCT Pub. Date: May 8, 2008

(65) Prior Publication Data
US 2010/0093030 A1 Apr. 15, 2010

(30) Foreign Application Priority Data
Nov. 2, 2006 (EP) .................................. 06123392

(51) Int. Cl.
*C12N 1/00* (2006.01)
(52) U.S. Cl. ............. 435/254.11; 435/254.3; 435/254.5; 435/254.6
(58) Field of Classification Search .................. None
See application file for complete search history.

(56) References Cited

U.S. PATENT DOCUMENTS

| | | | |
|---|---|---|---|
| 6,344,341 | B1 | 2/2002 | Keranen et al. |
| 7,968,312 | B2 | 6/2011 | Sagt et al. |
| 2001/0034045 | A1 | 10/2001 | Penttila et al. |
| 2002/0068325 | A1 | 6/2002 | Ng et al. |
| 2003/0025202 | A1 | 2/2003 | Mikagi et al. |
| 2003/0119013 | A1 | 6/2003 | Jiang et al. |
| 2005/0239164 | A1 | 10/2005 | Perrone et al. |
| 2009/0004693 | A1 | 1/2009 | Sagt et al. |
| 2011/0070612 | A1* | 3/2011 | Wang .......................... 435/69.2 |

FOREIGN PATENT DOCUMENTS

| | | |
|---|---|---|
| WO | 9902716 A1 | 1/1999 |
| WO | 01/72783 | 10/2001 |
| WO | 02086090 A3 | 12/2003 |
| WO | 2004/003217 | 1/2004 |
| WO | 20040025202 A1 | 3/2004 |
| WO | 2005/123763 | 12/2005 |
| WO | 2006/107990 | 10/2006 |

OTHER PUBLICATIONS

Sorenson et al. (Biochimica et Biophysica Acta 1619 (2003) 89-97).*
Guillemette et al. "Genomic analysis of the secretion stress response in the enzyme-producing cell factory *Aspergillus niger*" BMC Genomics, vol. 8, No. 1, pp. 1-17 (Jun. 2007).
Jacobs et al. "Effective lead selection for improved protein production in *Aspergillus niger* based on integrated genomics" Fungal Genetics and Biology, vol. 46, suppl. 1, pp. S141-S152 (online Sep. 2008).
Pel et al. "Genome sequencing and analysis of the versatile cell factory *Aspergillus niger* CBS 513.88" Nature Biotechnol., vol. 25, No. 2, pp. 221-231 (Feb. 2007).
International Search Report for PCT/EP2007/061765, mailed Jan. 13, 2009.
Cao et al., "The general protein secretory pathway; Phylogenetic analyses leading to evolutionary conclusions" Biochim. Bioplays. Acta 1609: 115-125 Jan. 2003.
Conesa et al., "The secretion pathway in filamentous fungi: A biotechnolgical view" Fungal Gen. Biol. 33:155-171 (2001).
Gouka et al., "Efficient production of secreted proteins by *Aspergillus*: Progress, limitations and prospects" Appl. Microbiol. Biotechnol. 47:1-11(1997).
Punt et al., "Filamentous fungi as cell factories for heterologous protein production" Trends in Biotechnol. 20:200-206, 2002.
UniProtKB, "Hypothetical protein" Database Accession No. Q5AVF9, May 2005.
UnitProtKB, "Protein transport protein SEC61 alpha subunit", Database Accession No. SC61A_NEUCR, Oct. 2004.
UniProtKB, Putative SEC61 (Fragment), Database Accession No. Q6UP01, Jul. 2004.
Valkonen et al., "Improvement of foreign-protein production in *Aspergillus niger* var. awamori by constitutive induction of the unfolded-protein response", Appl. Environ. Microbiol. 69:6979-6986, Dec. 2003.

* cited by examiner

*Primary Examiner* — Suzanne M Noakes
*Assistant Examiner* — Jae W Lee
(74) *Attorney, Agent, or Firm* — Baker Donelson Bearman Caldwell & Berkowitz, PC

(57) ABSTRACT

The present invention relates to a method to improve the secretion of a protein of interest by a filamentous fungal cell comprising inducing a phenotype in the cell selected from the group consisting of a lowered ERAD, an elevated UPR that does not induce an elevated ERAD, wherein ERAD preferably is lowered. The invention further relates to the filamentous fungal cell comprising the phenotype described above. The invention also relates to polynucleotides and polypeptides whose expression can be modulated in the filamentous fungal cell to obtain the above-described phenotype.

18 Claims, 6 Drawing Sheets

US 8,389,269 B2

PRODUCTION OF SECRETED PROTEINS BY FILAMENTOUS FUNGI

This application is the U.S. national phase of International Application No. PCT/EP2007/061765, filed 31 Oct. 2007, which designated the U.S. and claims priority to Application No. EP 06123392.0, filed 2 Nov. 2006; the entire contents of each of which are hereby incorporated by reference.

FIELD OF THE INVENTION

The invention relates to filamentous fungal cells, which display improved secretion of protein, to a method of obtaining these filamentous fungal cells and to the use of such filamentous fungal cells for production of protein.

BACKGROUND OF THE INVENTION

It is well known that filamentous fungi can be used to produce valuable compounds. Due to their glycosylation and secretion capacities, filamentous fungi are preferred hosts for secreting proteins. Secretion is a crucial step in the production of proteins and may become limiting when reaching higher production levels. High-level expression of proteins may compromise protein-folding reactions in the endoplasmic reticulum (ER), causing unfolded or aberrant proteins to accumulate. This stressful situation causes the cell to activate a variety of mechanisms. One adaptive response includes the transcriptional activation of genes encoding ER-resident chaperones and folding catalysts and protein degrading complexes that augment ER folding capacity, as well as translational attenuation to limit further accumulation of unfolded proteins in the ER (Kaufman, 1999; Mori, 2000). This signal transduction cascade is termed the unfolded protein response (UPR). Another means to deal with aberrant ER proteins is through their proteolysis via an ER-Associated Degradation (ERAD) pathway. Thus, UPR and ERAD serve one common goal, which is to decrease stress invoked by accumulation of (aberrant) proteins in the ER, either by decreasing accumulation through increasing solubility of ER localized proteins (UPR), or by increasing degradation of ER localized proteins (ERAD).

UPR and ERAD collaborate to decrease protein accumulation in the ER since it has been shown that increased UPR simultaneously results in increased ERAD (Brodsky, J. L., Werner, E. D., Dubas, M. E., Goeckeler, J. L., Kruse, K. B. and McCracken, A. A. (1999) J. Biol. Chem. 274; 3453-3460).

Recently, WO 01/72783 described a strategy to improve the protein secretion of recombinant eukaryotic cells by manipulating three genes involved in UPR (HAC1, PTC2, IRE1) in eukaryotic cells, to obtain an elevated UPR.

To improve protein secretion capacities of eukaryotic protein production strains it would be highly desirable to avail of strains that possess the capacity to translocate large amounts of a protein of interest through the secretory pathway without accumulating substantial amounts thereof in the ER.

It is an objective of the present invention to provide a method to improve protein secretion capacities of eukaryotic protein producing strains.

DETAILED DESCRIPTION OF THE INVENTION

Figure 1:
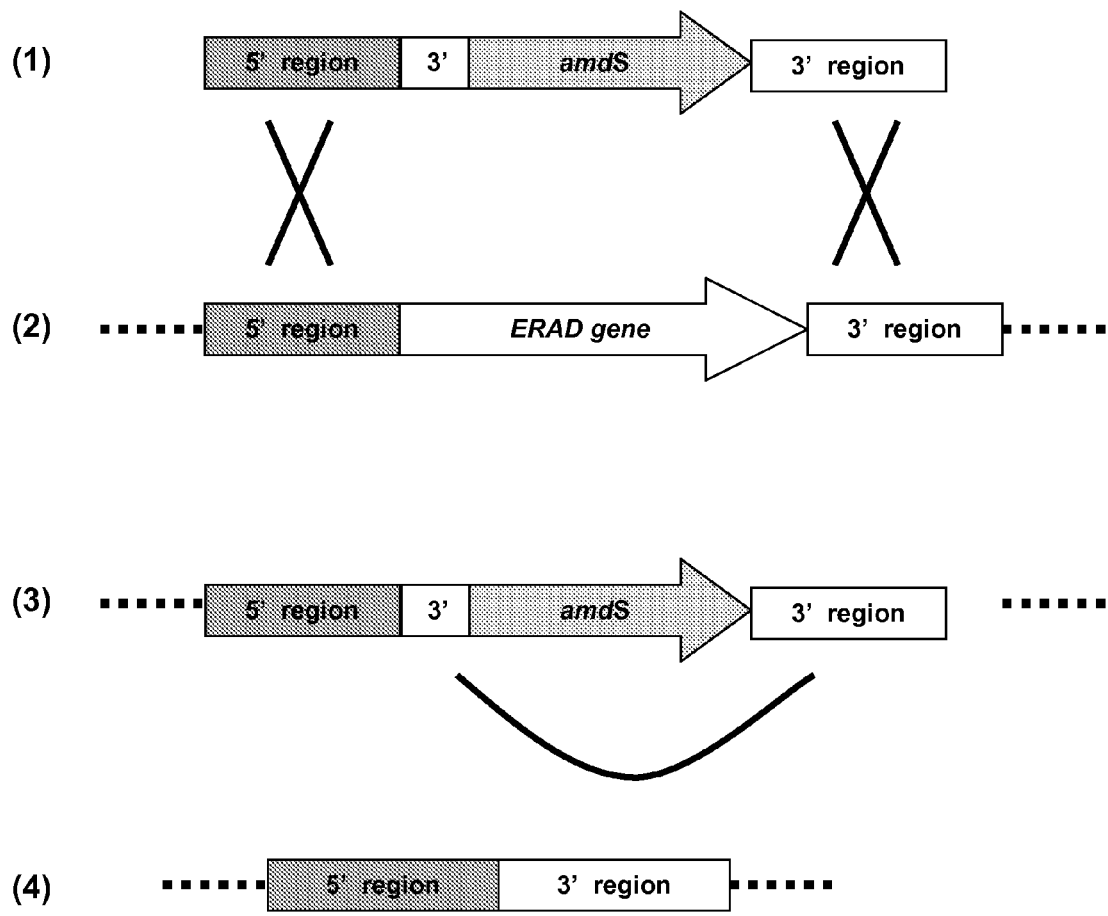
FIG. 1. Disruption strategy. The basics of the disruption are depicted. Integration and subsequent removal of the disruption cassette results in removal of one of the ERAD genes.

The present invention provides, in a first aspect, a method to improve the secretion of a protein of interest by a filamentous fungal cell comprising inducing a phenotype in the cell selected from the group consisting of
  (i) a lowered ERAD,
  (ii) an elevated UPR that does not induce an elevated ERAD,
  (iii) an elevated UPR that does not induce an elevated ERAD, wherein ERAD is lowered.

In the methods of the prior art as reflected by WO 01/72783, increased protein secretion capacities of eukaryotic protein producing strains rely on the manipulation of expression of only a single component of the secretion machinery of the cell; i.e. UPR.

Improved secretion of a protein of interest in the context of the invention means that the amount of secreted protein may be increased as compared to the parental cell the obtained cell originates from, and/or the kinetics of secretion may be elevated, and/or the quality of the protein of interest may be enhanced (e.g. higher specific activity of an enzyme by increased folding capacity of the filamentous fungal cell).

ERAD is lowered to reduce or to prevent retro-transport of the protein of interest from the ER to the cytosol, in order to reduce or to prevent its degradation. By elevating the UPR of the cell, the solubility of proteins in the ER is increased.

Changes in ERAD and/or UPR in a fungal cell may be monitored using techniques known in the art. Examples of such techniques (e.g. determining expression levels of UPR and/or ERAD related genes, pulse chase method for monitoring ERAD and biomarker assay for UPR) are described here below. A preferred assay for monitoring changes in UPR and/or ERAD is transcriptional profiling of UPR and ERAD related genes, preferably using micro arrays.

The amount of mRNA of UPR and ERAD related genes present in a cell may be monitored by transcriptional profiling (e.g. using micro arrays) and/or Northern blotting and/or real time PCR (see: Sambrook & Russell, *Molecular Cloning: A Laboratory Manual*, 3rd Ed., CSHL Press, Cold Spring Harbor, N.Y., 2001) and/or by quantifying the amount of corresponding protein present in a cell by Western blotting. The mRNA amount may also be monitored by DNA array analysis (Eisen, M. B. and Brown, P. O. DNA arrays for analysis of gene expression. Methods Enzymol. 1999:303:179-205).

A quantitative method may be applied to monitor ERAD. This method comprises determining the kinetics of protein secretion and degradation by the pulse chase technique as described by: Santerre Henriksen, A. L., Carlsen, M., de Bang, H. and Nielsen, J. (Kinetics of alpha-amylase secretion in *Aspergillus oryzae*. Biotechnol. Bioeng. 1999 Oct. 5; 65(1):76-82), and van Gemeren, I. A., Beijersbergen, A., van den Hondel C. A. and Verrips, C. T. (Expression and secretion of defined cutinase variants by *Aspergillus awamori*. Appl Environ. Microbiol. 1998, August; 64(8):2794-9). This pulse chase technique can be used to determine the ERAD dependent degradation kinetics of a protein of interest, when used in combination with the proteosomal inhibitor clasto-lactacystin-β-lactone (Affinity Research Products Ltd., CW8405-Z02185). Typically, the rapid degradation of proteins by ERAD is characterized by a protein half-life (t1/2) comprised between 5 and 60 minutes. t1/2 is a parameter, which can vary for each protein of interest. Preferably, t1/2 is determined for each protein. In the context of the invention, the ERAD activity is decreased when t1/2 is higher than 60 min, preferably higher than 62 min, more preferably higher than 63 min, most preferably higher than 65 min, even most preferably higher than 70 min (as described in Rabinovich, E., Kerem, A., frohlich, K. U., Diamant, N. and Bar-Nun, S. AAA-ATPase p97/Cdc48p, a cytosolic chaperone required for endoplasmic reticulum-associated protein degradation. Mol Cell Biol. 2002 January; 22(2): 626-34).

For monitoring UPR, several biomarkers are available. As a first example, it is known that the KAR2 gene, encoding the BiP protein, is induced when UPR is elevated (C. M. J. Sagt, W. H. Müller, J. Boonstra, A. J. Verkleij, and C. T. Verrips, Impaired Secretion of a Hydrophobic Cutinase by *Saccharomyces cerevisiae* Correlates with an Increased Association with Immunoglobulin Heavy-Chain Binding Protein (BiP) Appl. Envir. Microbiol. 1998 64: 316-324. The amount of mRNA level of KAR2 and/or of BiP protein could therefore be used as biomarker for UPR activity. Preferably, PDI or an homologue thereof is used as a biomarker (Ngiam C., Jeenes, D. J., Punt, P. J., van den Hondel, C. A. and Archer, D. B. Characterization of a foldase, protein disulfide isomerase A, in the protein secretory pathway of *Aspergillus niger*. Appl Environ Microbiol. 2000 February; 66(2):775-82.). Another preferred UPR biomarker gene is CYPB or homologue thereof (Derkx, P. M. and Madrid, S. M. The foldase CYPB is a component of the secretory pathway of *Aspergillus niger* and contains the endoplasmic reticulum retention signal HEEL. Mol Genet Genomics. 2001 December; 266(4): 537-45.). Another preferred biomarker gene for UPR is the spliced mRNA of had mRNA or a homologue thereof (Mon. K., Ogawa, N., Kawahara, T., Yanagi, H., Yura, T. mRNA splicing-mediated C-terminal replacement of transcription factor Hac1p is required for efficient activation of the unfolded protein response. Proc Natl Acad Sci USA. 2000 Apr. 25; 97(9):4660-5, and WO 01/72783).

The fungal cell of this invention preferably is a filamentous fungal cell. A filamentous fungus is herein defined as a eukaryotic micro-organism of the subdivision Eumycota and Oomycota in filamentous form, i.e. the vegetative growth of which occurs by hyphal elongation. The filamentous fungi are characterized by a mycelia wall composed of chitin, cellulose, glucan, chitosan, mannan, and other complex polysaccharides. Vegetative growth is by hyphal elongation and carbon catabolism is obligately aerobic. Filamentous fungal species include, but are not limited to, those of the genus *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, and *Trichoderma*. Preferably, the filamentous fungal cell is selected from the group consisting of the genera *Aspergillus, Trichoderma, Fusarium, Penicillium*, and *Acremonium*. Aspergilli are mitosporic fungi characterized by an aspergillum comprised of a conidiospore stipe with no known teleomorphic states terminating in a vesicle, which in turn bears one or two layers of synchronously formed specialized cells, variously referred to as sterigmata or phialides, and asexually formed spores referred to as conidia. Known teleomorphs of *Aspergillus* include *Eurotium, Neosartorya*, and *Emericella*. Strains of *Aspergillus* and teleomorphs thereof are readily accessible to the public in a number of culture collections.

More preferably, the filamentous fungal cell is selected from the group consisting of *A. nidulans, A. oryzae, A. sojae*, Aspergilli of the *A. niger* group, *Trichoderma reesei* and *Fusarium oxysporum*. The *A. niger* group is herein defined according to Raper and Fennell (1965, In: The Genus *Aspergillus*, The Williams & Wilkins Company, Baltimore, pp 293-344) and comprises all (black) Aspergilli included in the citation. Even more preferably, the filamentous fungal cell of the present invention is selected from the group consisting of *Aspergillus niger* CBS 513.88, *Aspergillus oryzae* ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006, and derivatives thereof. Most preferably, the filamentous fungal cell of the present invention is *Aspergillus niger* CBS 513.88. It is herein defined that *A. niger* CBS513.88 is a preferred parental cell to obtain the filamentous fungal cell of the present invention from and CBS513.88 is a preferred control cell in the analysis of "lowered", "elevated", "up-" or "down-regulation" of gene expression throughout the description of the present invention.

"Lowered" in the context of the present invention means at least lower as compared to the level measured in the parental cell the obtained cell originates from, the parental and obtained cell grown under the same culture conditions and analysed using the same assay conditions. Preferably, lowered means at least two times lower, more preferably at least three times lower, even more preferably at least four times lower, most preferably not detectable using Northern, or Western blotting or array analysis.

"Elevated" in the context of the present invention means at least higher as compared to the level measured in the parental cell the obtained cell originates from, the parental and obtained cell grown under the same culture conditions and analyzed using the same assay conditions. Preferably, elevated means at least two times higher, more preferably at least three times higher and most preferably at least four times higher.

The present invention also provides a method to improve the secretion of a protein of interest from a filamentous fungal cell comprising modulating the expression of at least one DNA sequence selected from the group consisting of SEQ ID NO's: 1, 4, 7, 10, 13, 16, 19, 22, 25, 28, 31, 34, 37, 40, 43, 46, 49, 52, 55, 58, or a homologue thereof.

Preferably, said modulating the expression of a DNA sequence as specified above advantageously induces a phenotype in the cell selected from the group consisting of (i) a lowered ERAD, (ii) an elevated UPR that does not induce an elevated ERAD, wherein ERAD preferably is lowered.

"Modulating the expression of a DNA sequence" is defined herein that the expression of the DNA sequence may be up regulated or down regulated as compared to the expression level in the parental cell the obtained cell originates from, the parental and obtained cell grown under the same culture conditions and analyzed using the same assay conditions.

The expression level of a DNA sequence is down-regulated when the expression level of this DNA sequence in the obtained cell is lower than the expression level of the same DNA sequence in the parental cell it originates from, preferably at least two times lower, more preferably at least three times lower, even more preferably at least four times lower, most preferably not detectable.

The expression level of a DNA sequence is up regulated when its expression level is higher in the obtained cell than its expression level in the parental cell it originates from, preferably at least two times higher, more preferably at least three times higher, most preferably at least four times higher.

The modulation of the expression level of any of the above DNA sequences is preferentially monitored by transcriptional profiling using microarrays as defined previously.

According to a preferred embodiment of the invention, the expression level of a DNA sequence selected from the group consisting of SEQ ID NO's: 1, 4, 7, 10, 13, 16, 19, 22, 25, 28, 31, 34, 37, 40, or a homologue thereof, is up regulated.

According to another preferred embodiment of the invention, at least one DNA sequence selected from the group consisting of SEQ ID NO's: 43, 46, 49, 52, 55, 58, or a homologue thereof, is down regulated.

According to a more preferred embodiment of the invention, the expression level of at least one of the DNA sequences having the following SEQ ID NO or homologues thereof given below or a combination of at least one taken from each subgroup a), b) c), d), or e) given below, or a combination thereof is up regulated:
  a) 4, 25, 34, 40,
  b) 25,
  c) 10, 13, 22, 25, 28, 31, 31,
  d) 25,
  e) 1, 4, 7, 10, 13, 16, 19, 22, 25, 28, 31, 34, 37, 40,
  and/or the expression level of at least one of the DNA sequences having the following SEQ ID NO or homologues thereof, or a combination thereof is down regulated: 43, 46, 49, 52, 55, 58.

Filamentous fungal strains having:
  (i) an up regulated expression level of a DNA sequence selected from the group consisting of (a) in the embodiment above, and
  (ii) a down regulated expression level of a DNA sequence selected from the group consisting of SEQ ID NO's: 43, 46, 49, 52, 55, 58, are particularly attractive for producing proteins rich in disulphide bridges. Proteins rich in disulphide bridges are proteins that have at least two disulphide bridges, preferably at least three and more preferably at least four. Examples of proteins rich in disulphide bridges are porcine PLA2 (seven disulphide bridges), *Aspergillus* phytase (five disulphide bridges) or thaumatine (eight disulphide bridges).

Filamentous fungal strains having:
  (i) an up regulated expression level of a DNA sequence selected from the group consisting of (b) in the embodiment above, and
  (ii) a down regulated expression level of a DNA sequence selected from the group consisting of SEQ ID NO's: 43, 46, 49, 52, 55, 58, are particularly attractive for producing proteins with exposed hydrophobic patches, having a tendency to aggregate, like mutated proteins (Sagt, C. M. J., Muller, W. H., Boonstra, J., Verkleij, A. J. Verrips, C. T. Impaired secretion of a hydrophobic cutinase by *Saccharomyces cerevisiae* correlates with an increased association with immunoglobulin heavy-chain binding protein (BiP). Appl Environ Microbiol. 1998 January; 64(1):316-24.), or proteins unable to dimerize, or glycoproteins which are not sufficiently glycosylated (Parodi, A. J., Protein glucosylation and its role in protein folding. Annu Rev Biochem. 2000; 69:69-93. Review.).

Filamentous fungal strains having:
  (i) an up regulated expression level of a DNA sequence selected from the group consisting of (c) in the embodiment above, and
  (ii) a down regulated expression level of a DNA sequence selected from the group consisting of SEQ ID NO's: 43, 46, 49, 52, 55, 58, are particularly attractive for producing glycoproteins, like glucoamylase or phytase.

Filamentous fungal strains having:
  (i) an up regulated expression level of a DNA sequence selected from the group consisting of (d) in the embodiment above, and
  (ii) a down regulated expression level of a DNA sequence selected from the group consisting of SEQ ID NO's: 43, 46, 49, 52, 55, 58, are particularly attractive for producing proteins rich in proline. Proteins rich in proline are proteins that have at least 1 proline/1 kDa, preferably at least 1.5, and more preferably at least 2, like verprolin (Donnely, S. F., Pocklington, M. J., Pallotta, D., Orr, E. A proline-rich protein, verprolin, involved in cytoskeletal organization and cellular growth in the yeast *Saccharomyces cerevisiae*. Mol. Microbiol. 1993 November; 10(3):585-96.).

Filamentous fungal strains having:
  (i) an up regulated expression level of a DNA sequence selected from the group consisting of (e) in the embodiments above, and
  (ii) a down regulated expression level of a DNA sequence selected from the group consisting of SEQ ID NO's: 43, 46, 49, 52, 55, 58, have good protein secretion capacities.

According to a more preferred embodiment, at least one distinct pair of genes or homologues thereof (pairs 1 to 84, table 1), or any combination of pairs is modulated (i.e. a gene is up regulated and a corresponding gene in the table is down regulated). An example of a combination of modulated pairs is: Gene pair numbers 2, 5 and 44 wherein SEQ ID NO's: 1 and 22 are up regulated and SEQ ID NO's: 46 and 55 are down regulated.

TABLE 1

Gene pairs to be modulated.

| Gene pair number | Up regulated SEQ ID NO: | Down regulated SEQ ID NO: |
|---|---|---|
| 1 | 1 | 43 |
| 2 | 1 | 46 |
| 3 | 1 | 49 |
| 4 | 1 | 52 |
| 5 | 1 | 55 |
| 6 | 1 | 58 |
| 7 | 4 | 43 |
| 8 | 4 | 46 |
| 9 | 4 | 49 |
| 10 | 4 | 52 |
| 11 | 4 | 55 |
| 12 | 4 | 58 |
| 13 | 7 | 43 |
| 14 | 7 | 46 |
| 15 | 7 | 49 |
| 16 | 7 | 52 |
| 17 | 7 | 55 |
| 18 | 7 | 58 |
| 19 | 10 | 43 |
| 20 | 10 | 46 |
| 21 | 10 | 49 |
| 22 | 10 | 52 |
| 23 | 10 | 55 |
| 24 | 10 | 58 |
| 25 | 13 | 43 |
| 26 | 13 | 46 |
| 27 | 13 | 49 |
| 28 | 13 | 52 |
| 29 | 13 | 55 |
| 30 | 13 | 58 |
| 31 | 16 | 43 |
| 32 | 16 | 46 |
| 33 | 16 | 49 |
| 34 | 16 | 52 |
| 35 | 16 | 55 |
| 36 | 16 | 58 |
| 37 | 19 | 43 |
| 38 | 19 | 46 |
| 39 | 19 | 49 |
| 40 | 19 | 52 |
| 41 | 19 | 55 |
| 42 | 19 | 58 |
| 43 | 22 | 43 |
| 44 | 22 | 46 |
| 45 | 22 | 49 |
| 46 | 22 | 52 |
| 47 | 22 | 55 |
| 48 | 22 | 58 |
| 49 | 25 | 43 |
| 50 | 25 | 46 |
| 51 | 25 | 49 |
| 52 | 25 | 52 |
| 53 | 25 | 55 |
| 54 | 25 | 58 |
| 55 | 28 | 43 |
| 56 | 28 | 46 |
| 57 | 28 | 49 |
| 58 | 28 | 52 |
| 59 | 28 | 55 |
| 60 | 28 | 58 |
| 61 | 31 | 43 |
| 62 | 31 | 46 |
| 63 | 31 | 49 |
| 64 | 31 | 52 |
| 65 | 31 | 55 |
| 66 | 31 | 58 |
| 67 | 34 | 43 |
| 68 | 34 | 46 |
| 69 | 34 | 49 |
| 70 | 34 | 52 |
| 71 | 34 | 55 |
| 72 | 34 | 58 |
| 73 | 37 | 43 |
| 74 | 37 | 46 |
| 75 | 37 | 49 |
| 76 | 37 | 52 |
| 77 | 37 | 55 |
| 78 | 40 | 58 |
| 79 | 40 | 43 |
| 80 | 40 | 46 |
| 81 | 40 | 49 |
| 82 | 40 | 52 |
| 83 | 40 | 55 |
| 84 | 40 | 58 |

According to another more preferred embodiment: the expression of at least one DNA sequence selected from the group consisting of SEQ ID NO's: 1, 4, 7, 10, 13, 16, 19, 22, 25, 28, 31, 34, 37, 40, or a homologue thereof, is up regulated, and the expression level of a DNA sequence selected from the group consisting of SEQ ID NO's: 43, 46, 49, 52, 55, 58, or a homologue thereof, is down regulated.

According to an even more preferred embodiment, expression of SEQ ID NO: 16 and/or SEQ ID NO: 34 is up regulated and/or expression of SEQ ID NO: 55 is down regulated. More preferably, expression of SEQ ID NO: 16 and SEQ ID NO: 34 is up regulated and/or expression of SEQ ID NO: 55 is down regulated. Even more preferably, expression of SEQ ID NO: 16 and SEQ ID NO: 34 is up regulated and expression of SEQ ID NO: 55 is down regulated.

According to another even more preferred embodiment, expression of SEQ ID NO: 16 and/or SEQ ID NO: 34 is up regulated and/or expression of SEQ ID NO: 49 is down regulated. More preferably, expression of SEQ ID NO: 16 and SEQ ID NO: 34 is up regulated and/or expression of SEQ ID NO: 49 is down regulated. Even more preferably, expression of SEQ ID NO: 16 and SEQ ID NO: 34 is up regulated and expression of SEQ ID NO: 49 is down regulated.

According to another even more preferred embodiment, expression of SEQ ID NO: 16 and/or SEQ ID NO: 34 is up regulated. More preferably, expression of SEQ ID NO: 16 and SEQ ID NO: 34 is up regulated.

According to another even more preferred embodiment, expression of SEQ ID NO: 49 is down regulated.

In addition to the above-mentioned methods, it is also possible to obtain a lowered ERAD by a specific one-way mutation of the sec61 translocation channel between ER and cytoplasm as described in WO2005/123763. Such mutation confers a phenotype wherein de novo synthesised polypeptides can enter the ER through sec61, however, retrograde transport through sec61 is impaired in the one-way mutant. In the method of this embodiment of the invention, expression of the native sec61 gene is preferably impaired, said method further comprising synthesis in the filamentous fungal cell of:

(i) a sec61 polypeptide according to SEQ ID NO: 63, and/or (ii) a sec61 polypeptide according to SEQ ID NO: 63, wherein the amino acid at position 376 is replaced by phenylalanine, tyrosine or histidine.

This specific way of lowering ERAD is preferably used in combination with above mentioned ways of lowering ERAD and/or elevated UPR.

According to a preferred embodiment of the invention, the expression level of a DNA sequence which is down regulated is lower in the obtained filamentous fungus than the expression level of the corresponding DNA sequence in the parental filamentous fungus the filamentous fungus originates from, preferably three times lower, more preferably four times lower, most preferably more than four times lower and even most preferably not detectable using northern, or western blotting or array technique.

According to another preferred embodiment of the invention, the expression level of a DNA sequence which is up regulated is higher in the obtained filamentous fungus than the expression level of the corresponding DNA sequence in the parental filamentous fungus the filamentous fungus originates from, preferably three times higher, more preferably four times higher and most preferably more than four times higher using northern, or western blotting or array technique.

The modulation of the expression level in a filamentous fungal cell of a DNA sequence as specified above may be obtained by subjecting the filamentous fungal cell to mutagenic treatment, such as recombinant genetic manipulation techniques and/or classical mutagenesis techniques, screening mutagenised cells by monitoring the expression level of said DNA sequence and, optionally, the protein secretion capacity of the filamentous fungus and identifying cells that display a modulated expression level.

Classical mutagenesis techniques comprise UV and/or chemical mutagenesis treatment commonly known in the art.

Preferably, the modulation of the expression of a DNA sequence as specified above, is achieved with recombinant genetic manipulation techniques.

The group of DNA sequences as specified above (consisting of SEQ ID NO's: 1, 4, 7, 10, 13, 16, 19, 22, 25, 28, 31, 34, 37, 40, 43, 46, 49, 52, 55, 58, 61) is comprised of genomic DNA sequences. The skilled person will know that the corresponding cDNA sequences (SEQ ID NO's: 2, 5, 8, 11, 14, 17, 20, 21, 23, 26, 29, 32, 35, 38, 41, 44, 47, 50, 53, 56, 59, 62), or homologues thereof, can be used alternatively or in combination with genomic DNA sequences in recombinant genetic techniques to achieve modulation of gene expression. Furthermore, a DNA sequence may be a synthetic nucleic acid sequence. The synthetic nucleic acid may be optimized in its codon use, preferably according to the methods described in WO2006/077258 and/or PCT/EP2007/055943.

To achieve down-regulation of a DNA sequence, said DNA sequence may be inactivated by deleting part or all of the DNA sequence or by replacing the DNA sequence by a non-functional variant thereof. The deletion and replacement may be done by gene replacement, preferably as described in EP 357 127. The specific deletion of a DNA sequence may be performed using the amdS gene as a selection marker, as described in EP 635 574.

Alternatively or in combination with other mentioned techniques, a technique based on in vivo recombination of cosmids in *E. coli* can be used, as described in: A rapid method for efficient gene replacement in the filamentous fungus *Aspergillus nidulans* (2000) Chaveroche, M-K., Ghico, J-M. and d'Enfert C; Nucleic acids Research, vol 28, no 22. This technique is applicable to other filamentous fungi like for example *A. niger*.

Down regulating the expression of a DNA sequence may also be achieved by using anti sense nucleic acids (see: Characterization of a foldase, protein disulfide isomerase A, in the protein secretory pathway of *Aspergillus niger*. Ngiam C, Jeenes D J, Punt P J, Van Den Hondel C A, Archer D B. Appl Environ Microbiol. 2000 February; 66(2):775-82, or Zrenner R, Willmitzer L, Sonnewald U. Analysis of the expression of potato uridinediphosphate-glucose pyrophosphorylase and its inhibition by antisense RNA. Planta. (1993);190(2):247-52.). Alternatively, down regulating expression of a DNA sequence may be achieved using RNAi techniques (see: FEMS Microb. Lett. 237 (2004): 317-324, or WO2005/05672A1, or WO2005/026356A1).

In addition to the above-mentioned techniques or as an alternative, it is also possible to obtain a lowered ERAD by inhibiting the activity of the proteins, which are involved in ERAD and encoded by a DNA sequence selected from the group consisting of SEQ ID NO's: 1, 4, 7, 10, 13, 16, 19, 22, 25, 28, 31, 34, 37, 40, or a homologue thereof. Additionally, or alternatively an ERAD-involved protein can be re-localized by means of an alternative signal sequence (Ramon de Lucas, J., Martinez O, Perez P., Isabel Lopez, M., Valenciano, S, and Laborda, F. The *Aspergillus nidulans* carnitine carrier encoded by the acuH gene is exclusively located in the mitochondria. FEMS Microbiol Lett. 2001 Jul. 24; 201(2):193-8.) or retention signal (Derkx, P. M. and Madrid, S. M. The foldase CYPB is a component of the secretory pathway of *Aspergillus niger* and contains the endoplasmic reticulum retention signal HEEL. Mol. Genet. Genomics. 2001 December; 266(4):537-45.).

Alternatively or in combination with above-mentioned techniques, inhibition of protein activity can also be obtained by UV or chemical mutagenesis (Mattern, I. E., van Noort J. M., van den Berg, P., Archer, D. B., Roberts, I. N. and van den Hondel, C. A., Isolation and characterization of mutants of *Aspergillus niger* deficient in extracellular proteases. Mol Gen Genet. 1992 August; 234(2):332-6.) or by the use of inhibitors like the proteasomal inhibitor of Affinity (clasto-lactacystin-β-lactone, Affinity Research Products Ltd., CW8405-Z02185).

To achieve up regulation of a DNA sequence, a filamentous fungal cell may be transformed with a DNA construct comprising a DNA sequence as specified above, preferably said DNA sequence being operably linked to a promoter of a highly expressed gene. The chosen promoter may be stronger than the endogenous promoter of the DNA sequence to be over-expressed. The promoter for expression of the DNA sequence is preferably derived from a highly expressed fungal gene.

A number of preferred highly expressed fungal genes are given by way of example: the amylase, glucoamylase, alcohol dehydrogenase, xylanase, glyceraldehyde-phosphate dehydrogenase or cellobiohydrolase genes from *Aspergilli* or *Trichoderma*. Most preferred highly expressed genes for these purposes are an *Aspergillus niger* glucoamylase gene, an *Aspergillus oryzae* TAKA-amylase gene, an *Aspergillus nidulans* gpdA gene or a *Trichoderma reesei* cellobiohydrolase gene. These highly expressed genes are suitable both as target loci for integration of cloning vectors and as source of highly expressed fungal genes. The glucoamylase promoter is a preferred promoter to be used. Other preferred promoters are the promoters described in WO2006/092396 and WO2005/100573.

Up regulation may also be achieved by increasing the copy number of a DNA sequence as specified above in the eukaryotic cell, preferably by integrating into its genome copies of the DNA sequence, more preferably by targeting the integration of the DNA sequence at a highly expressed locus, for instance at a fungal glucoamylase locus.

To achieve targeted integration, an integrative cloning vector is used comprising a DNA fragment, which is homologous to a DNA sequence present in a predetermined target locus in the genome of the filamentous fungal cell, for targeting the integration of the cloning vector to this predetermined locus. In order to promote targeted integration, the cloning vector is preferably linearized prior to transformation of the filamentous fungal cell. Linearization is preferably performed such that at least one but preferably either end of the cloning vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the efficiency of targeted integration into the genome of the filamentous fungal cell, i.e. integration in a predetermined target locus, is increased by augmented homologous recombination abilities of the filamentous fungal cell. Such phenotype of the cell preferably involves a deficient ku70 gene as described in WO2005/095624. WO2005/095624 discloses a preferred method to obtain a filamentous fungal cell comprising increased efficiency of targeted integration.

Preferably, the DNA sequence in the cloning vector, which is homologous to the target locus is derived from a highly expressed locus meaning that it is derived from a gene, which is capable of high expression level in the filamentous fungal cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (as described in EP 357 127).

To increase even more the number of copies of the DNA sequence to be over-expressed, the technique of gene conversion as described in WO98/46772 may be used.

The skilled person will appreciate the possibility that the homologous DNA sequence for targeting and the promoter sequence can coincide in one DNA fragment. The list of highly expressed genes given above is also suited as target locus.

For most filamentous fungi tested thus far it was found that they could be transformed using transformation protocols developed for *Aspergillus* (derived from inter alia Tilburn et al. 1983, Gene 26: 205-221). The skilled person will recognise that successful transformation of the filamentous fungal species is not limited to the use of vectors, selection marker systems, promoters and transformation protocols specifically exemplified herein. The skilled person would also understand that to obtain a filamentous fungus with both a lowered ERAD and an elevated UPR, one may use at least one of each technique described for respectively down- and up-regulating the expression of a DNA sequence in a filamentous fungus. Preferably, all the techniques performed on the filamentous fungus to obtain a recombinant filamentous fungus having both a lowered ERAD and an elevated UPR have been performed using a dominant and bi-directional selection marker, preferably an acetamidase gene, more preferably an acetamidase gene from *Aspergillus nidulans* or *Aspergillus niger*.

The transformed eukaryotic cells may subsequently be screened by monitoring the expression level of said DNA sequence as specified above by using for example Northern and/or Western blotting and/or array analysis. Optionally, the protein secretion capacity of the cell is monitored. The secretion capacity of a filamentous fungus may be monitored by measuring the amount of a protein secreted into the fermentation medium and/or the activity of a protein present in the fermentation medium after a certain fermentation period. This protein may be a marker protein or a protein of interest.

Depending on the identity of the protein of interest, the skilled person will choose a suitable detection assay. By way of example, these assay systems include but are not limited to assays based on clearing zones around colonies on solid media, as well as colorimetric, photometric, turbidimetric, viscosimetric, immunological, biological, chromatographic, and other available assays.

In a second aspect, the present invention provides a filamentous fungal cell comprising an individual feature and/or a combination of features as specified above under the first aspect. Thus, the present invention provides a filamentous fungal cell displaying a modulated expression of a DNA sequence as specified above under the first aspect.

The present invention also provides filamentous fungal cells displaying a phenotype selected from the group consisting of:
(i) a lowered ERAD,
(ii) an elevated UPR that does not induce an elevated ERAD,
(iii) an elevated UPR that does not induce an elevated ERAD, wherein ERAD is lowered.

In addition to modulated expression of a DNA sequence as specified under the first aspect and the phenotype described in the paragraph above, the filamentous fungal cell of the present invention may comprise by a specific one-way mutation of the sec61 translocation channel between ER and cytoplasm as described in WO2005/123763. Such mutation confers a phenotype wherein de novo synthesised polypeptides can enter the ER through sec61, however, retrograde transport through sec61 is impaired in this one-way mutant.

The filamentous fungal cell of the invention is preferably obtainable by the method as described above under the first aspect. The filamentous fungal cell of the invention may be obtained by classical genetic methods, may be a recombinant cell, or may be obtained by a combination of classical and recombinant genetic methods.

The filamentous fungal cell of the present invention preferably is a filamentous fungus as specified in the first aspect of the invention.

Optionally, the filamentous fungal cell is genetically modified to obtain a phenotype displaying lower protease expression and/or protease secretion compared to the wild-type cell in order to enhance production abilities of a polypeptide of interest. Such phenotype may be obtained by deletion and/or modification and/or inactivation of a transcriptional regulator of expression of proteases. Such a transcriptional regulator is e.g. prtT. Lowering expression of proteases by modulation of prtT may be performed by techniques described in US2004/0191864A1. Alternatively, or in combination with a phenotype displaying lower protease expression and/or protease secretion, the filamentous fungal cell displays an oxalate deficient phenotype in order to enhance the yield of production of a polypeptide of interest. An oxalate deficient phenotype may be obtained by techniques described in WO2004/070022A2. Alternatively, or in combination with a phenotype displaying lower protease expression and/or protease secretion and/or oxalate deficiency, the filamentous fungal cell displays a combination of phenotypic differences compared to the wild cell to enhance the yield of production of the polypeptide of interest. These differences may include, but are not limited to, lowered expression of glucoamylase and/or neutral alpha-amylase A and/or neutral alpha-amylase B, protease, and oxalic acid hydrolase. Said phenotypic differences displayed by the filamentous fungal cell may be obtained by genetic modification according to the techniques described in US2004/0191864A1.

In another aspect, the present invention provides a polypeptide having an amino acid sequence selected from the group consisting of SEQ ID NO's: 3, 6, 9, 12, 15, 18, 21, 24, 27, 30, 33, 36, 39, 42, 45, 48, 51, 54, 57, 60, 63, or a homologue thereof. or a degenerated DNA sequence obtainable there from.

In yet another aspect, the present invention provides a polynucleotide comprising a DNA sequence encoding the polypeptide of the previous aspect. Preferably, the DNA sequence is selected from the group consisting of SEQ ID NO's: 1, 4, 7, 10, 13, 16, 19, 22, 25, 28, 31, 34, 37, 40, 43, 46, 49, 52, 55, 58, 61, or a homologue thereof, or a degenerated DNA sequence obtainable there from.

The nucleotide sequence information as provided herein should not be so narrowly construed as to require inclusion of erroneously identified bases. The specific sequences disclosed herein can be readily used to isolate the complete gene from filamentous fungi, in particular *A. niger* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

In the context of the invention, a "homologue" or "homologous sequence" of a DNA sequence as specified above is defined as a DNA sequence encoding a polypeptide that displays at least one activity of the polypeptide encoded by the specified DNA sequence and has an amino acid sequence possessing a degree of identity to the amino acid sequence of the protein encoded by the specified DNA sequence of at least 50%, preferably at least 60%, more preferably at least 70%, even more preferably at least 80%, even more preferably at least 90%, even more preferably at least 95%, even more preferably at least 96%, even more preferably at least 97%, even more preferably at least 98% and most preferably at least 99%. A homologous sequence may encompass polymorphisms that may exist in cells from different populations or within a population due to natural allelic or intra-strain variation. A homologue may further be derived from a fungus other than the fungus where the specified DNA sequence originates from, or may be artificially designed and synthesized. DNA sequences related to the specified DNA sequences and obtained by degeneration of the genetic code are also part of the invention.

A "homologue" of a polypeptide is defined as a polypeptide having an amino acid sequence possessing a degree of identity to the specified amino acid sequence of at least 50%, preferably at least 60%, more preferably at least 70%, even more preferably at least 80%, even more preferably at least 90%, even more preferably at least 95%, even more preferably at least 96%, even more preferably at least 97%, even more preferably at least 98% and most preferably at least 99%, and displaying at least one activity of the polypeptide having the specified amino acid sequence.

Homologues may also encompass biologically active fragments of the full-length sequence.

For the purpose of the present invention, the degree of identity between two amino acid sequences refers to the percentage of amino acids that are identical between the two sequences. The degree of identity is determined using the BLAST algorithm, which is described in Altschul, et al., J. Mol. Biol. 215: 403-410 (1990). Software for performing BLAST analyses is publicly available through the National Center for Biotechnology Information. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89: 10915 (1989)) alignments (B) of 50, expectation (E) of 10, M=5, N=−4, and a comparison of both strands. The DNA sequences of the invention may be obtained by techniques commonly known in the art. For instance by screening cDNA or genomic libraries with a suitable probe derived from a DNA sequence of the invention. It is also possible to perform PCR with suitable (degenerate) oligonucleotide primers derived from a DNA sequence of the invention. The template for such a PCR reaction may be cDNA obtained by reverse transcription of mRNA prepared from strains known or suspected to express a DNA sequence according to the invention. The PCR product may be subcloned and sequenced to ensure that the amplified sequence represents the appropriate sequence. The PCR fragment may then be used to isolate a full-length cDNA clone by a variety of known methods.

Homologues may contain only conservative substitutions of one or more amino acids of the specified amino acid sequences or substitutions, insertions or deletions of non-essential amino acids. Accordingly, a non-essential amino acid is a residue that can be altered in one of these sequences without substantially altering the biological function. For example, amino acid residues that are conserved amongst the UPR and/or ERAD proteins of the present invention, are predicted to be particularly unamenable to alteration. Furthermore, amino acids conserved among the UPR and/or ERAD proteins according to the present invention are not likely to be amenable to alteration.

The term "conservative substitution" is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

According to a further aspect, the present invention provides a process for the production of a protein of interest using as production organism the filamentous fungus provided by a previous aspect of this invention, the filamentous fungal cell further comprising a DNA construct comprising a DNA sequence encoding said protein of interest.

The process for the production of a protein of interest comprises culturing said filamentous fungal cell under conditions conducive to the expression of the DNA sequence encoding the protein of interest, and recovering the protein of interest, as described for example in the following references:

Li, Z. J., Shukla, V., Fordyce, A. P., Pedersen, A. G., Wenger, K. S., Marten, M. R. Fungal morphology and fragmentation behavior in a fed-batch *Aspergillus oryzae* fermentation at the production scale. Biotechnol Bioeng. 2000 Nov. 5; 70(3):300-12

Withers, J. M., Swift, R. J., Wiebe, M. G., Robson, G. D., Punt, P. J., van den Hondel, C. A. Optimization and stability of glucoamylase production by recombinant strains of *Aspergillus niger* in chemostat culture. Biotechnol Bioeng. 1998 Aug. 20; 59(4):407-18.

Amanullah, A., Christensen, L. H., Hansen, K., Nienow, A. W., Thomas, R. C. Dependence of morphology on agitation intensity in fed-batch cultures of *Aspergillus oryzae* and its implications for recombinant protein production. Biotechnol Bioeng. 2002 Mar. 30; 77(7):815-26.

The filamentous fungal cell of the present invention is preferably cultivated in a nutrient medium suitable for production of the polypeptide of interest. For example, the cells may be cultivated by shake flask cultivation, small-scale or large-scale fermentation (including continuous, batch, fed batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., Bennett, J. W. and LaSure, L., eds., More Gene Manipulations in Fungi, Academic Press, CA, 1991). Suitable media are available from commercial suppliers or may be prepared using published compositions (e.g., in catalogues of the American Type Culture Collection). A suitable medium may comprise an essential cofactor for the protein of interest, e.g. flavin adenine dinucleotide (FAD). If the polypeptide is secreted into the nutrient medium, the polypeptide can be recovered directly from the medium. If the polypeptide is not secreted, it is recovered from cell lysates.

The resulting polypeptide may be isolated by methods known in the art. For example, the polypeptide may be isolated from the nutrient medium by conventional procedures including, but not limited to, centrifugation, filtration, extraction, spray drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing, differential solubility (e.g., ammonium sulfate precipitation), or extraction (see, e.g., Protein Purification, J.-C. Janson and Lars Ryden, editors, VCH Publishers, New York, 1989).

Preferably, the gene encoding the protein of interest is inserted into an expression vector, which is subsequently used to transform the filamentous fungal cell of the previous aspect. In the expression vector, the DNA sequence may be operably linked to appropriate expression signals, such as a promoter, a secretion signal sequence and a terminator, which are capable of directing the expression and secretion of the protein in the host organism.

More preferably, the gene encoding the protein of interest is operably linked to a promoter and to a secretion signal. The strategy, which can be used to express the gene encoding the protein of interest is the same as the one described for up regulating the expression of a DNA sequence: increasing copy number, targeting integration, use of a promoter of a highly expressed gene, choice of the selection marker gene, and combinations thereof. If the protein of interest is not naturally secreted, the nucleic acid encoding the protein may be modified to have a signal sequence in accordance with techniques known in the art. The secreted protein of interest may be one or more endogenous protein(s) which is (are) expressed naturally, but also may be a heterologous protein. Heterologous means that the protein is not produced under native conditions in the filamentous fungus.

The protein of interest is preferably an enzyme. Examples of enzymes which may be produced by the filamentous fungus of the invention are carbohydrases, e.g. cellulases such as endoglucanases, β-glucanases, cellobiohydrolases or β-glucosidases, hemicellulases, pectinolytic enzymes such as xylanases, xylosidases, mannanases, galactanases, galactosidases, rhamnogalacturonases, arabanases, galacturonases, lyases, or amylolytic enzymes; phosphatases such as phytases; esterases such as lipases; proteolytic enzymes; oxidoreductases such as oxidases, transferases, or isomerases.

Preferably, the filamentous fungus obtained has improved secretion capacity of the protein of interest as compared to the parental filamentous fungus it originates from.

In one embodiment, the secretion capacity of the filamentous fungal strain obtained is increased with respect to the secretion rate of the obtained strain. This rate is increased (g compound/g dry weight/hour), resulting in a decreased fermentation time, which results in a more cost effective process.

The present invention is further illustrated by the following examples.

EXAMPLES

WT1: The *Aspergillus niger* strain used as wild type and for internal control was already deposited under number CBS 513.88.

WT 2: This *A. niger* strain is a WT 1 strain comprising a deletion of the gene encoding glucoamylase (glaA). WT 2 is constructed by using the "MARKER-GENE FREE" approach as described in EP 0 635 574, wherein it is described how to delete glaA specific DNA sequences in the genome of CBS 513.88. The procedure results in a MARKER-GENE FREE ΔglaA recombinant *A. niger* CBS513.88 strain, possessing no foreign DNA sequences.

WT 3: This *A. niger* strain is a WT 2 strain comprising a deletion of the pepA gene encoding the major extracellular aspartic protease PepA. WT 3 is constructed by using the "MARKER-GENE FREE" approach as described in EP 0 635 574. The method described in this patent is used to delete pepA specific DNA sequences in the genome of CBS 513.88, as described by van den Hombergh et al. (van den Hombergh J P, Sollewijn Gelpke M D, van de Vondervoort P J, Buxton F P, Visser J. (1997)—Disruption of three acid proteases in *Aspergillus niger*—effects on protease spectrum, intracellular proteolysis, and degradation of target proteins—Eur J. Biochem. 247(2): 605-13). The procedure results in a MARKER-GENE FREE ΔpepA, ΔglaA recombinant *A. niger* CBS513.88 strain, possessing no foreign DNA sequences.

EPO1: This *A. niger* strain is a WT 2 strain comprising multiple copies of the *A. niger* epo gene coding for the proline specific endoprotease, which has been published elsewhere (WO 02/45524). EPO 1 is constructed by co-transformation of an amdS selectable marker-gene containing vector, which is designated pGBAAS-1 (constructed as described in EP 635 574) and the pGBTOPEPO-1 vector comprising the gene coding for the proline specific endoprotease as described in WO98/46772 and WO99/32617. The transformation and counterselection procedure results in a MARKER-GENE FREE EPO 1 *A. niger* strain containing multiple copies of the proline specific endoprotease encoding gene under control of the glucoamylase promoter.

PLA1: The heterologous porcine phospholipase A2 (PLA2) protein is selected as a model protein. It has been shown earlier that this protein is difficult to produce in *A. niger* in high quantities (Roberts I. N., Jeenes D. J., MacKenzie D. A., Wilkinson A. P., Sumner I. G. and Archer D. B. (1992)—Heterologous gene expression in *Aspergillus niger*: a glucoamylase-porcine pancreatic phospholipase $A_2$ fusion protein is secreted and processed to yield mature enzyme (Gene 122: 155-161). The fragment for overexpression of PLA2 is made as a fusion of propLA2 with a native glucoamylase A gene of *A. niger* and is prepared as described by Roberts et al. (1992). The fusion protein contains a kex1 splicing site in order to be processed in the Golgi. This glaA-pla2 fusion gene is cloned into an *A. niger* pGBTOP expression vector using the same techniques as described in WO 98/46772 and WO 99/32617, resulting in pGBTOPPLA-1. The PLA 1 *A. niger* strain is a WT 3 strain comprising multiple copies of the glucoamylase-porcine pancreatic phospholipase $A_2$ fusion protein encoding gene. PLA1 is constructed by co-transformation of the amdS selectable marker-gene containing vector pGBAAS-1 and the pGBTOPPLA-1 vector. The transformation and counterselection procedure results in a MARKER-GENE FREE PLA1 strain containing multiple copies of the glucoamylase-porcine pancreatic phospholipase $A_2$ fusion protein encoding gene under control of the glucoamylase promoter.

SEC1: The *Aspergillus niger* strain as strain PLA1 described above, expressing a modified sec61* translocation channel as described in WO2005/123763. This strain contains a specific one-way mutation of the sec61 translocation channel between ER and cytoplasm as described in WO2005/123763. Such mutation confers a phenotype wherein de novo synthesised polypeptides can enter the ER through sec61, however, retrograde transport through sec61 is impaired in this one-way mutant.

In these strains, using molecular biology techniques known to the skilled person (see: Sambrook & Russell, *Molecular Cloning: A Laboratory Manual,* 3rd Ed., CSHL Press, Cold Spring Harbor, N.Y., 2001), several genes were over expressed and others were down regulated as described below. Examples of the general design of expression vectors for gene over expression and disruption vectors for down-regulation, transformation, use of markers and selective media can be found in WO199846772, WO199932617, WO2001121779, WO2005095624, EP 635574B and WO2005100573.

*A. niger* Shake Flask Fermentations

*A. niger* strains are precultured in 20 ml preculture medium as described in the Examples: "*Aspergillus niger* shake flask fermentations" section of WO 99/32617. After overnight growth, 10 ml of this culture is transferred to Fermentation Medium (FM). Fermentation medium (FM) contains per liter: 82.5 g Glucose.$1H_2O$, 25 g Maldex 15 (Boom Meppel, Netherlands), 2 g Citric acid, 4.5 g $NaH_2PO_4.1H_2O$, 9 g $KH_2PO_4$, 15 g $(NH_4)_2SO_4$, 0.02 g $ZnCl_2$, 0.1 g $MnSO_4.1H_2O$, 0.015 g $CuSO_4.5H_2O$, 0.015 g $CoCl_2.6H_2O$, 1 g $MgSO_4.7H_2O$, 0.1 g $CaCl_2.2H_2O$, 0.3 g $FeSO_4.7H_2O$, 30 g MES (2-[N-Morpholino]ethanesulfonic acid), pH=6.

Fermentation in FM is performed in 500 ml flasks with baffle with 100 ml fermentation broth at 34° C. and 170 rpm for the number of days indicated.

Example 1

Identification of UPR and ERAD Genes and Construction of Disruption and Overexpression Vectors Genomic DNA of *Aspergillus niger* strain CBS513.88 was sequenced and analyzed (Pel et al, Genome sequencing and analysis of the versatile cell factory *Aspergillus niger* CBS513.88, Nature Biotechnology, Volume 25, 2, February 2007, p 221-231). Sequences of all UPR & ERAD genes were identified, comprising the open reading frame (ORF) (with introns) and approximately 1000 by 5' and 3' of the genes, are shown in sequence listings as indicated in Table 2. A number of ERAD-related genes with translated proteins annotated as described below and involved in the processes of protein secretion were named as for example derA, doaA and hrdC. In addition, UPR-related genes with translated proteins annotated as described below and involved in the processes of protein secretion were named as for example hacA, pdiA, tigA, cnxA, prpA, ostA, gptA, sstC, etc. (Table 2).

TABLE 2

UPR & ERAD-related genes from *A. niger*.

| Gene SEQ ID NO: | CDS SEQ ID NO: | Protein SEQ ID NO: | Function | Gene (UPR/ERAD) | Vector (overexpression pGBFIN# or disruption pGBDEL#) |
|---|---|---|---|---|---|
| 1 | 2 | 3 | similarity to regulator of unfolded protein response (UPR) Hac1 - *Saccharomyces cerevisiae* | hacA (UPR) | pGBFINhacA |
| 4 | 5 | 6 | PDI related protein A prpA - *Aspergillus niger* | prpA (UPR) | pGBFINprpA |
| 7 | 8 | 9 | strong similarity to protein kinase Ire1 - *Saccharomyces cerevisiae* | ireA (UPR) | pGBFINireA |
| 10 | 11 | 12 | strong similarity to calcium-binding protein precursor cnx1p - *Schizosaccharomyces pombe* | cnxK (UPR) | pGBFINcnxK |
| 13 | 14 | 15 | oligosaccharyltransferase alpha subunit ostA - *Aspergillus niger* | ostA (UPR) | pGBFINostA |
| 16 | 17 | 18 | protein disulfide isomerase A pdiA - *Aspergillus niger* | pdiA (UPR) | pGBFINpdiA |
| 19 | 20 | 21 | strong similarity to ER membrane translocation facilitator Sec61 - *Yarrowia lipolytica* | Sec61 (UPR) | pGBFINsec61 |

TABLE 2-continued

UPR & ERAD-related genes from *A. niger*.

| Gene SEQ ID NO: | CDS SEQ ID NO: | Protein SEQ ID NO: | Function | Gene (UPR/ERAD) | Vector (overexpression pGBFIN# or disruption pGBDEL#) |
|---|---|---|---|---|---|
| 22 | 23 | 24 | strong similarity to glycoprotein glucosyltransferase gpt1p - *Schizosaccharomyces pombe* | gptA (UPR) | pGBFINgptA |
| 25 | 26 | 27 | strong similarity to luminal ER-protein retention receptor ERD2 - *Kluyveromyces marxianus* | erdB (UPR) | pGBFINerdB |
| 28 | 29 | 30 | strong similarity to alpha-glucosidase ModA - *Dictyostelium discoideum* | modA (UPR) | pGBFINmodA |
| 31 | 32 | 33 | strong similarity to 80K protein H precursor G19P1 - *Homo sapiens* | phpA (UPR) | pGBFINphpA |
| 34 | 35 | 36 | strong similarity to endoplasmatic reticulum oxidising protein Ero1 - *Saccharomyces cerevisiae* | eroA (UPR) | pGBFINeroA |
| 37 | 38 | 39 | strong similarity to translation initiation factor 3 47 kDa subunit stt3p - *Schizosaccharomyces pombe* | sstC (UPR) | pGBFINsstC |
| 40 | 41 | 42 | disulfide isomerase tigA - *Aspergillus niger* | tigA (UPR) | pGBFINtigA |
| 43 | 44 | 45 | similarity to tumour suppressor protein TSA305 from patent WO9928457-A1 - *Homo sapiens* | hrdC (ERAD) | pGBDELhrdC |
| 46 | 47 | 48 | weak similarity to stress protein Herp - *Mus musculus* | hrpA (ERAD) | pGBDELhrpA |
| 49 | 50 | 51 | strong similarity to WD-repeat protein required for ubiquitin-mediated proteolysis Doa1 - *Saccharomyces cerevisiae* | doaA (ERAD) | pGBDELdoaA |
| 52 | 53 | 54 | strong similarity to protein phosphatase type 2C Ptc2 - *Saccharomyces cerevisiae* | ptcB (ERAD) | pGBDELptcB |
| 55 | 56 | 57 | strong similarity to hypothetical protein GABA-A receptor epsilon subunit - *Caenorhabditis elegans* | derA (ERAD) | pGBDELderA |
| 58 | 59 | 60 | strong similarity to alpha-mannosidase Mns1 - *Saccharomyces cerevisiae* | mnsA (ERAD) | pGBDELmnsA |

Gene replacement vectors for derA, doaA and hrdC (pGBDELderA, pGBDELdoaA, pGBDELhrdC respectively) were designed according to known principles and constructed according to routine cloning procedures (see FIG. 1). In essence, these vectors comprise approximately 1000-1500 by flanking regions of the ORFs (for SEQ ID NO. of all genes see Table 2) for homologous recombination at the predestined genomic loci. In addition, they contain the *A. nidulans* bi-directional amdS selection marker, in-between direct repeats. The general design of these deletion vectors were previously described in EP635574B and WO 98/46772. Additional flanking sequences for all ORF's mentioned can be found at the NCBI or EBI web servers.

Figure 2:
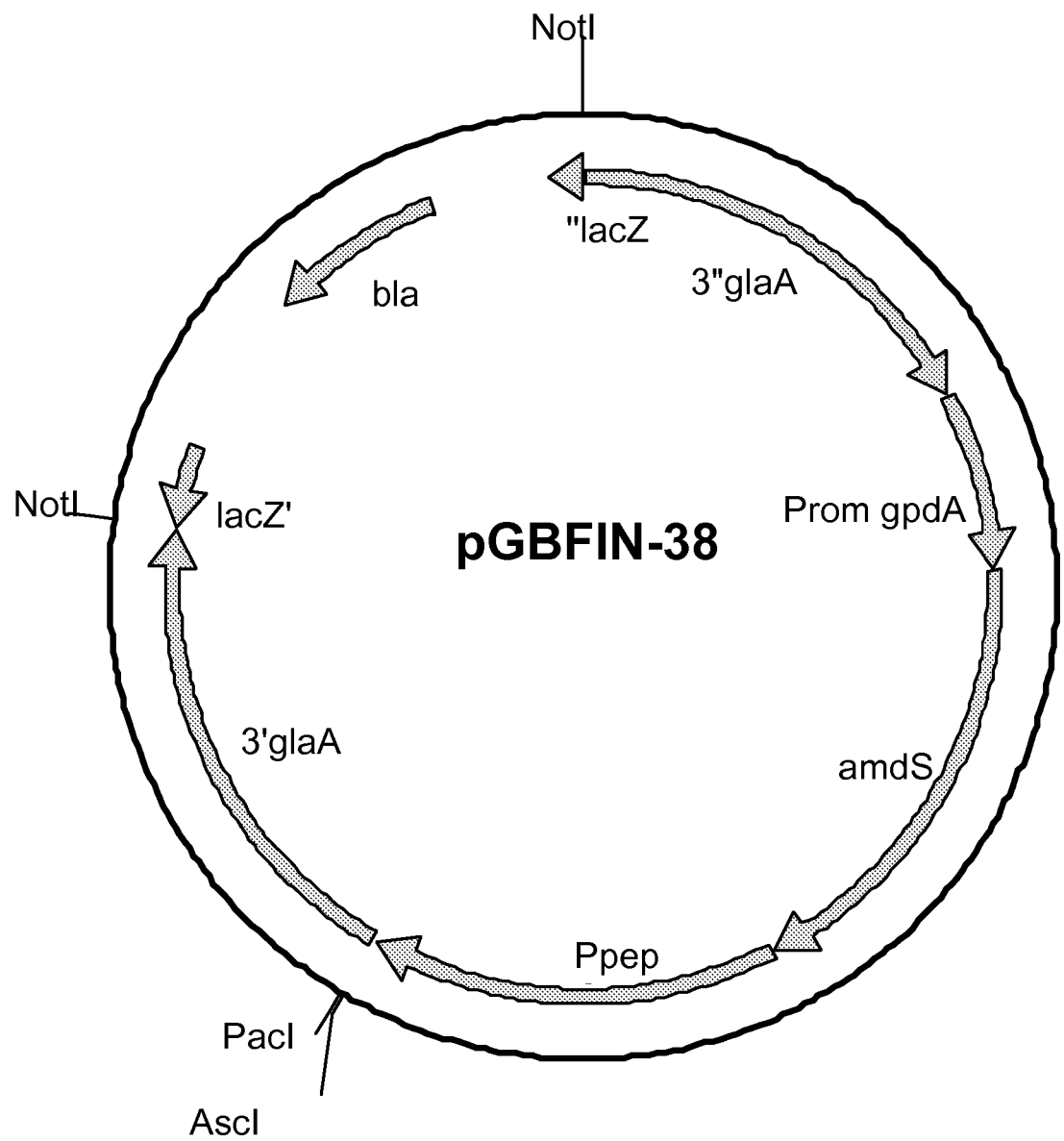
FIG. 2. pGBFIN23. Representation of the vector that is used for over expression of genes of interest. The genes of interest were cloned as PacI-AscI fragments, placing them under control of the pepC promoter (Ppep), AmdS is used as a selectable marker.

DNA sequences for all UPR-related genes, such as hacA, pdiA, tigA, cnxA, prpA, ostA, gptA, sstC were cloned in expression vector pGBFIN-38 (FIG. 2) resulting in for example pGBFINostA, pGBFINgptA and pGBFINsstC, etc., and as indicated in Table 2, of which the *E. coli* DNA can be removed by digestion and linearization with restriction enzyme NotI, prior to transformation of the *A. niger* strains.

Example 2

Disruption of Genes Involved in ERAD

Disruptants of the ERAD genes were obtained by disrupting the corresponding genomic sequence using the bi-directional amdS marker. The disruption construct was designed as depicted in FIG. 1 and linear DNA of deletion vector pGBDELdoaA, pGBDELderA and pGBDELhrdC (see also Example 1) was isolated and used to transform *A. niger* WT1, *A. niger* PLA1 and *A. niger* EPO1 using a method earlier described (Biotechnology of Filamentous fungi: Technology and Products. (1992) Reed Publishing (USA); Chapter 6: Transformation pages 113 to 156). This linear DNA integrated into the genome at the homologous locus by gene replacement as depicted in FIG. 1, thus substituting the endogenous ERAD gene by the amdS gene. Transformants were selected on acetamide media and colony purified according to standard procedures as described in EP635574B. Spores were plated on fluoro-acetamide media to select strains, which lost the amdS marker. Growing colonies were diagnosed by PCR for integration at the doaA, derA and hrdC locus and candidate strains tested by Southern analyses for deletion of the gene. Thus, the following recombinant strains were obtained having a lowered ERAD (ERAD-, see also Table 3): WT-DOA, WT-DER, WT-HRD and PLA-DOA, PLA-DER, PLA-HRD, EPO-DOA, etc.

Example 3

Overexpression of Genes Involved in UPR

The various resulting pGBFIN overexpression vectors for UPR-related genes (such as pGBFINhacA, pGBFINpdiA pGBFINsec61, pGBFINcnxA, pGBFINerdB and pGBFINeroA pGBFINostA, pGBFINgptA and pGBFINsstC, for example) were transformed as a pool using different *A. niger* strains. Recipient strains in transformation were WT1 and SEC1, EPO1 and PLA1 and also a number of ERAD strains described in Example 2 using the method earlier described. The amdS gene of *Aspergillus nidulans* was used as selection marker and induced growth on acetamide as sole N-source as described in Kelly, J. M., and Hynes, M. J. (1985) Transformation of *Aspergillus niger* by the amdS gene of *Aspergillus nidulans*. EMBO J. 4, 475-479. The AmdS gene was placed under control of the constitutive gpdA promoter of *A. nidulans*. Transformants were selected on acetamide media and colony purified according to standard procedures as described in EP635574B. Growing colonies were selected for increased expression of the respective reporter genes. Subsequently, strains with increased expression levels were diagnosed by PCR for integration of one or more of the respective genes of interest and candidate strains were tested by PCR for introduction of the respective genes.

Strains mentioned as UPR+ in Table 3 (Type) were selected as representative strains for overexpression of UPR-related genes. Strains mentioned as ERAD-/UPR+ in Table 3 (Type) were selected as representative strains for overexpression of UPR-related genes in a strain background with an ERAD gene disrupted or with a modified Sec61 translocation channel as described in WO2005/123763.

TABLE 3

Transformation scheme for strains and constructs indicated.

| Parental strain | Transforming plasmids | Type | New strain name |
|---|---|---|---|
| WT1 | pGBDELdoaA | ERAD- | WT-DOA |
| WT1 | pGBDELderA | ERAD- | WT-DER |
| WT1 | pGBDELhrdC | ERAD- | WT-HRD |
| PLA1 | pGBDELdoaA | ERAD- | PLA1-DOA |
| PLA1 | pGBDELderA | ERAD- | PLA1-DER |
| PLA1 | pGBDELhrdC | ERAD- | PLA1-HRD |
| EPO1 | pGBDELdoaA | ERAD- | EPO1-DOA |
| EPO1 | pGBDELderA | ERAD- | EPO1-DER |
| EPO1 | pGBDELhrdC | ERAD- | EPO1-HRD |
| WT1 | pGBFINostA pGBFINgptA pGBFINsstC | UPR+ | WT-UPR1 |
| WT1 | pGBFINostA | UPR+ | WT-UPR2 |
| WT1 | pGBFINgptA pGBFINsstC | UPR+ | WT-UPR3 |
| PLA1 | pGBFINostA pGBFINsstC | UPR+ | PLA-UPR1 |
| PLA1 | pGBFINgptA | UPR+ | PLA-UPR2 |
| PLA1 | pGBFINostA pGBFINgptA pGBFINsstC | UPR+ | PLA-UPR3 |
| EPO1 | pGBFINostA pGBFINsstC | UPR+ | EPO-UPR1 |
| EPO1 | pGBFINgptA | UPR+ | EPO-UPR2 |
| WT-DOA | pGBFINostA pGBFINgptA pGBFINsstC | ERAD-/UPR+ | WT-DOA-UPR1 |
| WT-DER | pGBFINgptA pGBFINsstC | ERAD-/UPR+ | WT-DER-UPR1 |
| WT-HRD | pGBFINostA pGBFINgptA pGBFINsstC | ERAD-/UPR+ | WT-HRD-UPR1 |
| PLA1-DOA | pGBFINprpA pGBFINgptA pGBFINsstC | ERAD-/UPR+ | PLA1-DOA-UPR1 |
| PLA1-DER | pGBFINpdiA pGBFINtigC | ERAD-/UPR+ | PLA1-DER-UPR1 |
| PLA1-HRD | pGBFINostA pGBFINeroA | ERAD-/UPR+ | PLA1-HRD-UPR1 |
| EPO1-DOA | pGBFINostA pGBFINsstC | ERAD-/UPR+ | EPO1-DOA-UPR1 |
| EPO1-DER | pGBFINostA pGBFINgptA pGBFINsstC | ERAD-/UPR+ | EPO1-DER-UPR1 |
| EPO1-HRD | pGBFINgptA pGBFINsstA | ERAD-/UPR+ | EPO1-HRD-UPR1 |
| SEC1 | pGBFINostA pGBFINgptA pGBFINsstC | SEC61/UPR+ | SEC1-UPR1 |

This resulted in a large number of *A. niger* strains over expressing various combinations of UPR-related genes, disruption of ERAD genes, a modified Sec61 translocation channel and combinations thereof in different strain backgrounds, all showing increased expression of their reporter protein in a screen. The expression levels of the above-described sequences were checked by Northern analysis as described in Molecular Cloning, supra.

Example 4

Improvement of the Secretion of the Homologous Proteins Glucoamylase and Endoprotease in the Respective ERAD and UPR *A. niger* Strains of the Invention.

Glycoamylase and proline specific endoprotease were used as examples of homologous secreted proteins. The endoprotease was overexpressed as described at the strains section above and the (endogenous) glucoamylase gene was expressed in the WT1 strain background.

Shake flask experiments of the UPR and ERAD strains of the EPO1 and PLA1 strains constructed in Example 2 and 3 were performed in media as described above in an incubator shaker using a 500 ml baffled shake flask. After four to six days of fermentation, samples were taken to determine either the proline specific endoprotease activity or the glucoamylase activity.

The proteolytic activity of the proline specific endoprotease is spectrophoto-metrically measured at 410 nm in time using CBZ-Gly(cine)-Pro(line)-pNA at 37° C. in a citrate/disodium phosphate buffer at pH 5. 1 U proline specific endoprotease is defined as the amount of enzyme which converts 1 μmol (micromol) CBZ-Gly(cine)-Pro(line)-pNA per min at pH 5 and 37° C. at the conditions described above.

Glucoamylase secretion was measured as the glucoamylase activity detected in the medium after 5 days of fermentation. Glucoamylase activity was measured as AGIU/ml by determining the liberation of paranitrofenol from the substrate p-nitrophenyl-a-D-glucopyranoside I. This resulted in a yellow colour, whose absorbance could be measured at 405 nm using a spectrophotometer. 1 AGIU is the quantity of enzyme, which produces 1 μmole of glucose per minute at pH 4.3 and 60° C. from a soluble starch substrate.

Figure 3:
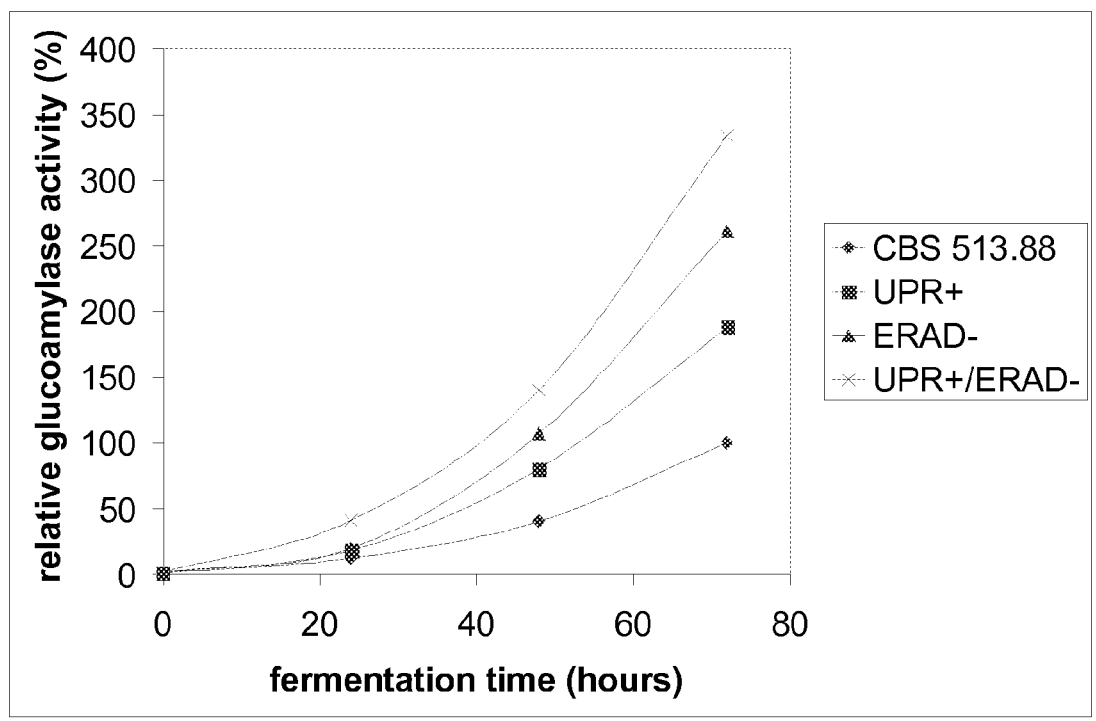
FIG. 3. Relative glucoamylase production in *Aspergillus niger* strains: CBS513.88, UPR+, ERAD−, and UPR+/ERAD−. Strain CBS 513.88, UPR+, ERAD−, and UPR+/ERAD−, over expressing glucoamylase, were cultured and analyzed for glucoamylase production (example 4). The amount of extracellular glucoamylase of strain CBS 513.88 and the average of the UPR+ strains, the average of the ERAD− strains, and the average of the UPR+/ERAD− strains is depicted versus fermentation time. The highest activity of strain CBS 513.88 was set at 100%.

The glucoamylase secretion level of all transformant strains was compared to the secretion level of *Aspergillus niger* WT1, which was used as a control strain. Glucoamylase production was increased in both UPR+ and in ERAD- strains compared to WT1 (Table 4 and FIG. 3). Glucoamylase production was especially increased in the ERAD-/UPR+ combination strain compared to WT1, UPR+ and ERAD- strains.

TABLE 4

Relative glucoamylase activities of ERAD– and UPR+ transformants

| New strain name | Glucoamylase activity |
|---|---|
| WT1 | 100% |
| WT-DOA | 260% |
| WT-DER | 250% |
| WT-HRD | 270% |
| WT-UPR1 | 190% |
| WT-UPR2 | 190% |
| WT-UPR3 | 180% |
| WT-DOA-UPR1 | 340% |
| WT-DER-UPR1 | 290% |
| WT-HRD-UPR1 | 370% |

The proline-specific endoprotease secretion level of all transformant strains was compared to the secretion level of *Aspergillus niger* EPO1, which was the recipient strain in transformation and the control strain in this experiment. Endoprotease production was increased in both UPR+ and in ERAD– strains compared to WT1 (Table 5). Also here, endoprotease production was especially increased in the ERAD–/UPR+ combination strain compared to WT1, UPR+ and ERAD– strains (Table 5). This demonstrated that the manipulation of genes involved in the UPR and/or in the ERAD lead to strains with improved protein secretion properties. Moreover, it is shown that combinatorial manipulation of down-regulation of ERAD and up-regulation of UPR has a synergetic effect on homologous protein production.

TABLE 5

Relative endoprotease activities of ERAD– and UPR+ transformants

| New strain name | Endoprotease activity |
|---|---|
| EPO1 | 100% |
| EPO1-DOA | 130% |
| EPO1-DER | 150% |
| EPO1-HRD | 140% |
| EPO-UPR1 | 150% |
| EPO-UPR2 | 170% |
| EPO1-DOA-UPR1 | 200% |
| EPO1-DER-UPR1 | 240% |
| EPO1-HRD-UPR1 | 300% |

Example 5

Improvement of the Secretion of a Heterologous Glucoamylase-Phospholipase A2 Fusion Protein Rich in Disulphide Bridges in the Respective ERAD and UPR *A. niger* Strains of the Invention Porcine phospholipase PLA2 was chosen as an example of a heterologous protein, which is rich in disulphide bridges. The glucoamylase-PLA2 fusion protein was over expressed under control of the glucoamylase promoter in several UPR+/ERAD– modulated strains (Table 3). The various PLA1 transformants, constructed in Example 2 and 3 and as depicted in Table 3, were fermented in media as described above in an incubator shaker using a 500 ml baffled shake flask. After four to six days of fermentation, samples were taken to determine the phospholipase activity in the fermentation medium.

To determine phospholipase PLA2 activity (PLA2) in *Aspergillus niger* culture broth spectrophotometrically, an artificial substrate is used: 1,2-dithiodioctanoyl phosphatidylcholine (diC8, substrate). PLA2 hydrolyses the sulphide bond at the A2 position, dissociating thio-octandïc acid. Thio-octandic acid reacts with 4,4 dithiopyridine (color reagent, 4-DTDP), forming 4-thiopyridone. 4-Thiopyridone is in tautomeric equilibrium with 4-mercaptopyridine, which absorbs radiation having a wavelength of 334 nm. The extinction change at that wavelength is measured. One unit is the amount of enzyme that liberates of 1 nmol thio-octandïc acid from 1,2-dithiodioctanoyl phosphatidylcholine per minute at 37° C. and pH 4.0. The substrate solution is prepared by dissolving 1 g diC8 crystals per 66 ml ethanol and add 264 ml acetate buffer. The acetate buffer comprises 0.1 M Acetate buffer pH 3.85 containing 0.2% Triton-X100. The colour reagent is a 11 mM 4,4-dithiodipyridine solution. It was prepared by weighting 5.0 mg 4,4-dithiodipyridine in a 2 ml eppendorf sample cup and dissolving in 1.00 ml ethanol. 1.00 ml of milli-Q water was added.

Figure 4:
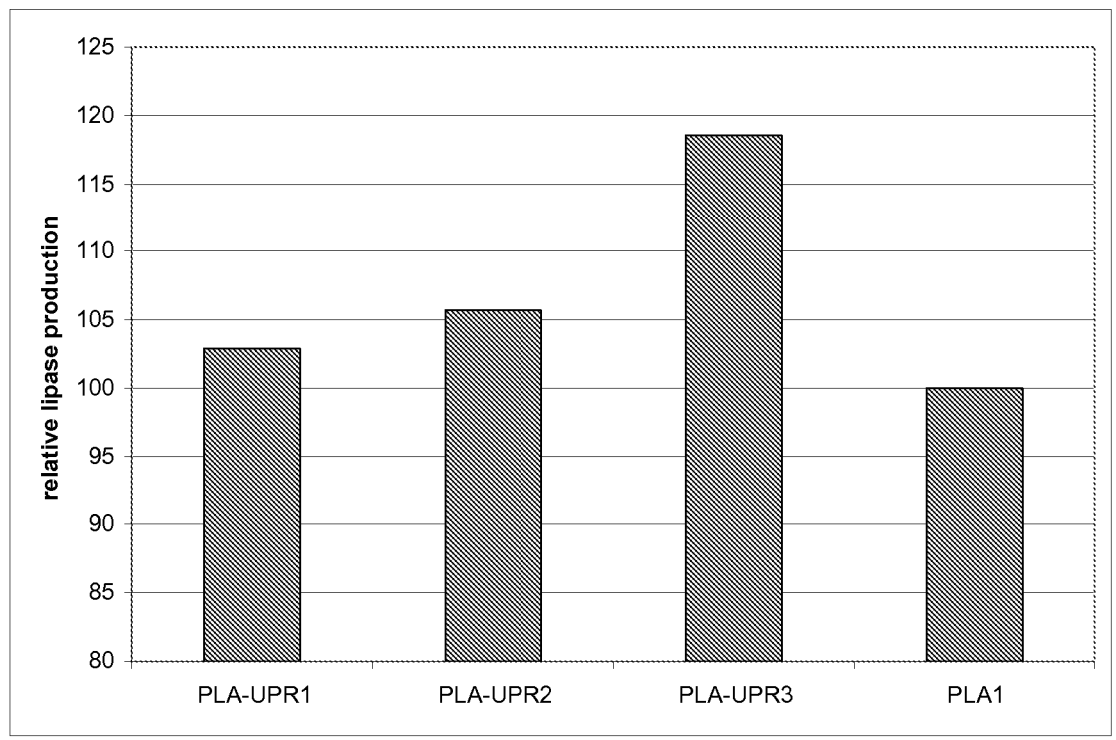
FIG. 4. Relative PLA2 production in *Aspergillus niger* strain PLA1 and three UPR+ strains. Strains PLA1, PLA-UPR1, PLA-UPR2 and PLA-UPR3, over expressing PLA2, were cultured and analyzed for PLA2 production (example 5). The amount of extracellular PLA2 is depicted, relative to strain PLA1, which was set at 100%.
Figure 5:
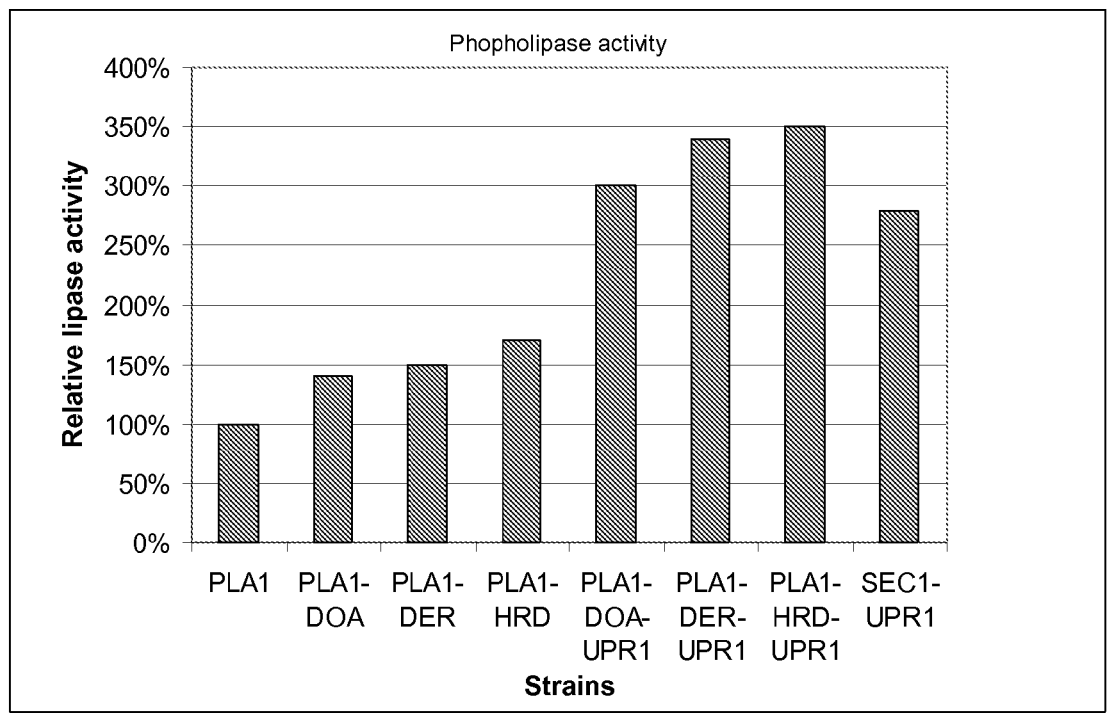
FIG. 5. Relative PLA2 production in *Aspergillus niger* strains: PLA1 and ERAD− and ERAD− UPR+ strains derived from PLA1. Strains PLA1, PLA1-DOA, PLA1-DER, PLA1-HRD, PLA1-DOA-UPR1, PLA1-DER-UPR1, PLA1-HRD-UPR-1 and SEC61-UPR1, over expressing PLA2, were cultured and analyzed for PLA2 production (example 5). The amount of extracellular PLA2 is depicted relative to strain PLA1, which was set at 100%.

The proline-specific PLA2 secretion level of all transformant strains was compared to the secretion level of *Aspergillus niger* PLA1, which was the recipient strain in transformation and the control strain in this experiment. PLA2 production was slightly increased in both UPR+ and in ERAD– strains compared to WT1 (FIGS. 4 and 5). PLA2 production was especially increased in the ERAD–/UPR+ and Sec61/UPR+ combination strains compared to WT1, UPR+ and ERAD– strains of PLA1 (FIGS. 4 and 5). This demonstrated that the manipulation of genes involved in the UPR and/or in the ERAD lead to strains with improved protein secretion properties. Moreover, it is shown that combinatorial manipulation of down-regulation of ERAD, modification of SEC61 and up-regulation of UPR has a synergetic effect on homologous protein production.

Example 6

Construction of an *Aspergillus niger* Strain with Improved Secretion Capacities for a Heterologous Protein Overexpression strains of WT3 were constructed using the methods as described in Example 3. These strains over expressed the hacA gene and pdiA and eroA genes (Table 2), respectively. The expression level of these genes was checked by Northern blot. The strains were designated HAC (hacA overexpression) and ERP (pdiA and eroA overexpression).

Figure 6:
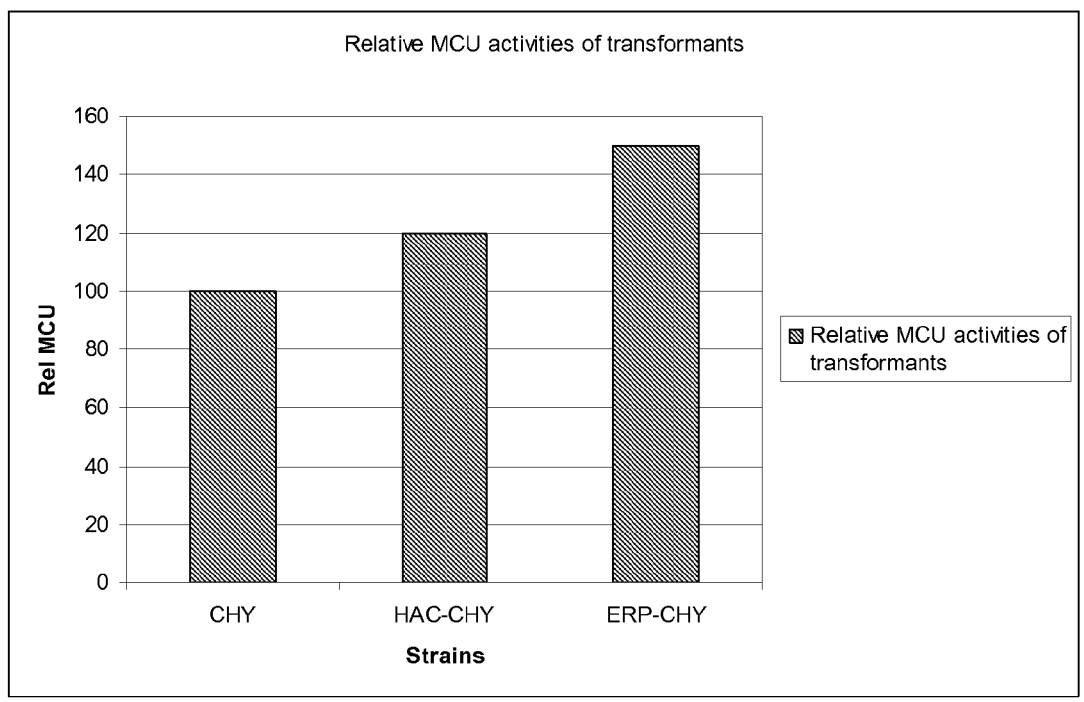
FIG. 6. Chymosin production in *Aspergillus niger* transformants. Strains CHY, HAC-CHY and ERP-CHY, over expressing chymosin were cultured and analyzed for chymosin production (example 6). After 6 days of fermentation the extracellular chymosin activity was determined and activities relative to strain CHY are depicted.

Calf chymosin was chosen as an example of a heterologous protein, containing disulphide bridges. This protein was over expressed under control of the glucoamylase promoter in both the WT3 strain and the obtained HAC and ERP strains using the same strategy as in Example 3, resulting in strains CHY, HAC-CHY and ERP-CHY, respectively. Transformants were selected using PCR. All transformed strains (CHY, HAC-CHY and ERP-CHY) were fermented according to the protocol as described in example 5. Chymosin concentration was determined in Milk Clotting Units (MCU) according to International Dairy Federation 157, Remcat method. The amount of extracellular chymosin activity was found to be 1.2 fold higher in the HAC-CHY strain compared to the parental strain CHY as shown in FIG. 6. The amount of extracellular chymosin activity was found to be 1.5 fold higher in the ERP-CHY strain compared to the parental strain CHY as shown in FIG. 6. Moreover if the medium was supplemented with 1 mM flavin adenine dinucleotide (FAD), the improvement in productivity for ERP-CHY was even 1.8 fold compared to the parental strain CHY (data not shown).

The invention claimed is:

1. An isolated filamentous fungus displaying a modulated expression of at least SEQ ID NO: 22.

2. The filamentous fungus according to claim 1, wherein the expression of SEQ ID NO: 22 is up regulated.

3. The filamentous fungus according to claim 1, wherein the expression level of SEQ ID NO: 22 is up regulated and wherein the expression level of SEQ ID NO: 55 is down regulated.

4. The filamentous fungus according to claim 1, wherein expression of a native sec61 gene is impaired, said filamentous fungus further synthesizing intracellularly:
(i) sec61 polypeptide having the sequence of SEQ ID NO: 63, and/or
(ii) sec61 polypeptide having the sequence of SEQ ID No: 63, wherein the amino acid at position 376 is replaced by phenylalanine, tyrosine, or histidine.

5. The filamentous fungus according to claim 1, transformed with a polynucleotide.

6. The filamentous fungus according to claim 1, wherein the filamentous fungus further comprises a DNA sequence encoding a protein of interest.

7. The filamentous fungus according to claim 6, wherein the DNA sequence encoding a protein of interest is operably linked to a promoter and to a secretion signal.

8. The filamentous fungus according to claim 1, wherein the expression level of a combination of at least SEQ ID NO: 22 and SEQ ID NO: 13 is up regulated, and wherein the expression level of SEQ ID NO: 55 is down regulated.

9. A method of making the filamentous fungus according to claim 1, said method comprising modulating expression of at least SEQ ID NOs: 22.

10. The method according to claim 9, wherein the expression of SEQ ID NO: 22 is up regulated.

11. The method according to claim 9, wherein the expression level of SEQ ID NO: 22 is up regulated and wherein the-expression level of SEQ ID NO: 55 is down regulated.

12. The method according to claim 9, wherein expression of a native sec61 gene is impaired, said method further comprising production in the filamentous fungal cell of:
(i) Sec 61 polypeptide having the sequence of SEQ ID NO:63, and/or
(ii) Sec 61 polypeptide having the sequence of SEQ ID NO: 63, wherein the amino acid at position 376 is replaced by phenylalanine, tyrosine or histidine.

13. The method according to claim 9, wherein the expression level of a DNA sequence which is up regulated is higher in the obtained filamentous fungus than the expression level of the corresponding DNA sequence in the parental filamentous fungus the filamentous fungus originates from.

14. The method according to claim 9, wherein the filamentous fungus is selected from the group consisting of *Aspergillus, Trichoderma*, and *Penicillium*.

15. The method according to claim 14, wherein the *Aspergillus* is selected from the group consisting of *Aspergillus niger, Aspergillus oryzae*, and *Aspergillus sojae* and the *Trichoderma* is *Trichoderma reesei*.

16. The method according to claim 11, wherein the expression level of a DNA sequence which is down regulated is lower in the obtained filamentous fungus than the expression level of the corresponding DNA sequence in the parental filamentous fungus the filamentous fungus originates from.

17. The method according to claim 11, wherein the expression level of a combination of at least SEQ ID NO: 22 and SEQ ID NO: 13 is up regulated, and wherein the expression level of SEQ ID NO: 55 is down regulated.

18. A method for production of a protein of interest, said method comprising culturing the filamentous fungus of claim 6 under conditions conducive to expression of the protein and optionally recovering the expressed protein.

* * * * *

SEQUENCE LISTING

<160> NUMBER OF SEQ ID NOS: 63

<210> SEQ ID NO 1
<211> LENGTH: 1510
<212> TYPE: DNA
<213> ORGANISM: Aspergillus niger

<400> SEQUENCE: 1

```
ccacttggcc aggcctggcc cccccagctt ccccccgttat gacacggtgg cctgtgttcc      60
tgtgacacgg gcaagcagac gtcctccaca agctgtgtcg acctacatca ccgtcctccc     120
ttgcagtgcg gttaagataa ggctcatagt aaatcgattg atccacaatt aaagatcaat     180
cacctgtcac gcttgaaatg atggaagaag cattctctcc agtcgactcc ctcgccggct     240
ccccgacgcc tgagttgcca ttgttgacag tgtccccggc ggacacgtcg cttgatgact     300
cgtcagtaca ggcaggggag accaaggcgg aagagaagaa gcctgtgaag aagagaaagt     360
catgggccca ggaattgcca gtcccgaaga ctaacttgcc cccaaggtaa gacatctata     420
tccataatag actatgtatg tatgtacacg atgctaattc gacataaaag gaaacgggcc     480
aagactgaag atgagaaaga gcaacgtcgt atcgagcgcg ttcttcgcaa tcgtgcggca     540
gcacaaacat cacgcgagcg caagaggctc gaaatggaga agttggaaaa tgagaagatt     600
cagatggaac agcaaaacca gttccttctg caacgactat cccagatgga agctgagaac     660
aatcgcttaa accaacaagt cgctcaacta tctgctgagg tccggggctc ccgtggcaac     720
actcccaagc ccggctcccc cgtctcagct tctcctaccc taactcctac cctatttaaa     780
caagaacgcg acgaaatccc tcttgaacgg attcctttcc ccacaccctc tatcaccgac     840
tactccccta ccttgaggcc ttccactctg gctgagtcct ccgacgtgac acaacatcct     900
gcagcggtgt tgtgcgacct gcagtgtccg tcgctggact cgaaggagaa ggaagtgccc     960
tctctctctt tgacgtcggc tcaaaccctg aacctcacgc tgccgatgat cttgcagctc    1020
ctctttctga cgatgacttc caccgcctat tcaacgttga ttcacccgtt gggtcagatt    1080
cttcagtcct tgaagacggg ttcgcctttg acgttctcga cggaggagat ctatcagcat    1140
ttccatttga ttctatggtt gatttcgacc ccgaatctgt tggcttcgaa ggcatcgagc    1200
cgccccacgg tcttccggat gagacttctc gccagacttc tagcgtgcaa cccagccttg    1260
gcgcgtccac ttcgcgatgc gacgggcagg gcattgcagc tggctgttag cgagcagttt    1320
cgccagggag atgcatcggc tgtcgatggt aacggagtcc aatggagctg ggagtctttg    1380
ttgaccttgg cgtggacgat agacctactc gaacagccgg gacgacgcaa acgaatcttg    1440
agcggtttga aatcagcgaa aactggacgg cgaagtaata ttggcaagtc tcaaaggagt    1500
acacggagtt                                                          1510
```

<210> SEQ ID NO 2
<211> LENGTH: 1026
<212> TYPE: DNA
<213> ORGANISM: Aspergillus niger
<220> FEATURE:
<221> NAME/KEY: CDS
<222> LOCATION: (1)..(1026)

<400> SEQUENCE: 2

```
atg gaa gaa gca ttc tct cca gtc gac tcc ctc gcc ggc tcc ccg acg        48
Met Glu Glu Ala Phe Ser Pro Val Asp Ser Leu Ala Gly Ser Pro Thr
1               5                   10                  15
```

| | | | | | | | | | | | | | | | | |
|---|---|---|---|---|---|---|---|---|---|---|---|---|---|---|---|---|
| cct | gag | ttg | cca | ttg | ttg | aca | gtg | tcc | ccg | gcg | gac | acg | tcg | ctt | gat | 96 |
| Pro | Glu | Leu | Pro | Leu | Leu | Thr | Val | Ser | Pro | Ala | Asp | Thr | Ser | Leu | Asp | |
| | 20 | | | | | 25 | | | | | 30 | | | | | |
| gac | tcg | tca | gta | cag | gca | ggg | gag | acc | aag | gcg | gaa | gag | aag | aag | cct | 144 |
| Asp | Ser | Ser | Val | Gln | Ala | Gly | Glu | Thr | Lys | Ala | Glu | Glu | Lys | Lys | Pro | |
| | | 35 | | | | | 40 | | | | | 45 | | | | |
| gtg | aag | aag | aga | aag | tca | tgg | ggc | cag | gaa | ttg | cca | gtc | ccg | aag | act | 192 |
| Val | Lys | Lys | Arg | Lys | Ser | Trp | Gly | Gln | Glu | Leu | Pro | Val | Pro | Lys | Thr | |
| 50 | | | | | 55 | | | | | 60 | | | | | | |
| aac | ttg | ccc | cca | agg | aaa | cgg | gcc | aag | act | gaa | gat | gag | aaa | gag | caa | 240 |
| Asn | Leu | Pro | Pro | Arg | Lys | Arg | Ala | Lys | Thr | Glu | Asp | Glu | Lys | Glu | Gln | |
| 65 | | | | | 70 | | | | | 75 | | | | | 80 | |
| cgt | cgt | atc | gag | cgc | gtt | ctt | cgc | aat | cgt | gcg | gca | gca | caa | aca | tca | 288 |
| Arg | Arg | Ile | Glu | Arg | Val | Leu | Arg | Asn | Arg | Ala | Ala | Ala | Gln | Thr | Ser | |
| | | | | 85 | | | | | 90 | | | | | 95 | | |
| cgc | gag | cgc | aag | agg | ctc | gaa | atg | gag | aag | ttg | gaa | aat | gag | aag | att | 336 |
| Arg | Glu | Arg | Lys | Arg | Leu | Glu | Met | Glu | Lys | Leu | Glu | Asn | Glu | Lys | Ile | |
| | | | 100 | | | | | 105 | | | | | 110 | | | |
| cag | atg | gaa | cag | caa | aac | cag | ttc | ctt | ctg | caa | cga | cta | tcc | cag | atg | 384 |
| Gln | Met | Glu | Gln | Gln | Asn | Gln | Phe | Leu | Leu | Gln | Arg | Leu | Ser | Gln | Met | |
| | 115 | | | | | 120 | | | | | 125 | | | | | |
| gaa | gct | gag | aac | aat | cgc | tta | aac | caa | caa | gtc | gct | caa | cta | tct | gct | 432 |
| Glu | Ala | Glu | Asn | Asn | Arg | Leu | Asn | Gln | Gln | Val | Ala | Gln | Leu | Ser | Ala | |
| 130 | | | | | 135 | | | | | 140 | | | | | | |
| gag | gtc | cgg | ggc | tcc | cgt | ggc | aac | act | ccc | aag | ccc | ggc | tcc | ccc | gtc | 480 |
| Glu | Val | Arg | Gly | Ser | Arg | Gly | Asn | Thr | Pro | Lys | Pro | Gly | Ser | Pro | Val | |
| 145 | | | | | 150 | | | | | 155 | | | | | 160 | |
| tca | gct | tct | cct | acc | cta | act | cct | acc | cta | ttt | aaa | caa | gaa | cgc | gac | 528 |
| Ser | Ala | Ser | Pro | Thr | Leu | Thr | Pro | Thr | Leu | Phe | Lys | Gln | Glu | Arg | Asp | |
| | | | | 165 | | | | | 170 | | | | | 175 | | |
| gaa | atc | cct | ctt | gaa | cgg | att | cct | ttc | ccc | aca | ccc | tct | atc | acc | gac | 576 |
| Glu | Ile | Pro | Leu | Glu | Arg | Ile | Pro | Phe | Pro | Thr | Pro | Ser | Ile | Thr | Asp | |
| | | | 180 | | | | | 185 | | | | | 190 | | | |
| tac | tcc | cct | acc | ttg | agg | cct | tcc | act | ctg | gct | gag | tcc | tcc | gac | gtg | 624 |
| Tyr | Ser | Pro | Thr | Leu | Arg | Pro | Ser | Thr | Leu | Ala | Glu | Ser | Ser | Asp | Val | |
| | 195 | | | | | 200 | | | | | 205 | | | | | |
| aca | caa | cat | cct | gca | gtg | tcc | gtc | gct | gga | ctc | gaa | gga | gaa | gga | agt | 672 |
| Thr | Gln | His | Pro | Ala | Val | Ser | Val | Ala | Gly | Leu | Glu | Gly | Glu | Gly | Ser | |
| 210 | | | | | 215 | | | | | 220 | | | | | | |
| gcc | ctc | tct | ctc | ttt | gac | gtc | ggc | tca | aac | cct | gaa | cct | cac | gct | gcc | 720 |
| Ala | Leu | Ser | Leu | Phe | Asp | Val | Gly | Ser | Asn | Pro | Glu | Pro | His | Ala | Ala | |
| 225 | | | | | 230 | | | | | 235 | | | | | 240 | |
| gat | gat | ctt | gca | gct | cct | ctt | tct | gac | gat | gac | ttc | cac | cgc | cta | ttc | 768 |
| Asp | Asp | Leu | Ala | Ala | Pro | Leu | Ser | Asp | Asp | Asp | Phe | His | Arg | Leu | Phe | |
| | | | | 245 | | | | | 250 | | | | | 255 | | |
| aac | gtt | gat | tca | ccc | gtt | ggg | tca | gat | tct | tca | gtc | ctt | gaa | gac | ggg | 816 |
| Asn | Val | Asp | Ser | Pro | Val | Gly | Ser | Asp | Ser | Ser | Val | Leu | Glu | Asp | Gly | |
| | | | 260 | | | | | 265 | | | | | 270 | | | |
| ttc | gcc | ttt | gac | gtt | ctc | gac | gga | gga | gat | cta | tca | gca | ttt | cca | ttt | 864 |
| Phe | Ala | Phe | Asp | Val | Leu | Asp | Gly | Gly | Asp | Leu | Ser | Ala | Phe | Pro | Phe | |
| | 275 | | | | | 280 | | | | | 285 | | | | | |
| gat | tct | atg | gtt | gat | ttc | gac | ccc | gaa | tct | gtt | ggc | ttc | gaa | ggc | atc | 912 |
| Asp | Ser | Met | Val | Asp | Phe | Asp | Pro | Glu | Ser | Val | Gly | Phe | Glu | Gly | Ile | |
| 290 | | | | | 295 | | | | | 300 | | | | | | |
| gag | ccg | ccc | cac | ggt | ctt | ccg | gat | gag | act | tct | cgc | cag | act | tct | agc | 960 |
| Glu | Pro | Pro | His | Gly | Leu | Pro | Asp | Glu | Thr | Ser | Arg | Gln | Thr | Ser | Ser | |
| 305 | | | | | 310 | | | | | 315 | | | | | 320 | |
| gtg | caa | ccc | agc | ctt | ggc | gcg | tcc | act | tcg | cga | tgc | gac | ggg | cag | ggc | 1008 |
| Val | Gln | Pro | Ser | Leu | Gly | Ala | Ser | Thr | Ser | Arg | Cys | Asp | Gly | Gln | Gly | |
| | | | | 325 | | | | | 330 | | | | | 335 | | |

```
att gca gct ggc tgt tag                                              1026
Ile Ala Ala Gly Cys
            340

<210> SEQ ID NO 3
<211> LENGTH: 341
<212> TYPE: PRT
<213> ORGANISM: Aspergillus niger

<400> SEQUENCE: 3

Met Glu Glu Ala Phe Ser Pro Val Asp Ser Leu Ala Gly Ser Pro Thr
1               5                   10                  15

Pro Glu Leu Pro Leu Leu Thr Val Ser Pro Ala Asp Thr Ser Leu Asp
            20                  25                  30

Asp Ser Ser Val Gln Ala Gly Glu Thr Lys Ala Glu Glu Lys Lys Pro
        35                  40                  45

Val Lys Lys Arg Lys Ser Trp Gly Gln Glu Leu Pro Val Pro Lys Thr
50                  55                  60

Asn Leu Pro Pro Arg Lys Arg Ala Lys Thr Glu Asp Glu Lys Glu Gln
65                  70                  75                  80

Arg Arg Ile Glu Arg Val Leu Arg Asn Arg Ala Ala Gln Thr Ser
                85                  90                  95

Arg Glu Arg Lys Arg Leu Glu Met Glu Lys Leu Glu Asn Glu Lys Ile
            100                 105                 110

Gln Met Glu Gln Gln Asn Gln Phe Leu Leu Gln Arg Leu Ser Gln Met
        115                 120                 125

Glu Ala Glu Asn Asn Arg Leu Asn Gln Gln Val Ala Gln Leu Ser Ala
    130                 135                 140

Glu Val Arg Gly Ser Arg Gly Asn Thr Pro Lys Pro Gly Ser Pro Val
145                 150                 155                 160

Ser Ala Ser Pro Thr Leu Thr Pro Thr Leu Phe Lys Gln Glu Arg Asp
                165                 170                 175

Glu Ile Pro Leu Glu Arg Ile Pro Phe Pro Thr Pro Ser Ile Thr Asp
            180                 185                 190

Tyr Ser Pro Thr Leu Arg Pro Ser Thr Leu Ala Glu Ser Ser Asp Val
        195                 200                 205

Thr Gln His Pro Ala Val Ser Val Ala Gly Leu Glu Gly Glu Gly Ser
    210                 215                 220

Ala Leu Ser Leu Phe Asp Val Gly Ser Asn Pro Glu Pro His Ala Ala
225                 230                 235                 240

Asp Asp Leu Ala Ala Pro Leu Ser Asp Asp Phe His Arg Leu Phe
                245                 250                 255

Asn Val Asp Ser Pro Val Gly Ser Asp Ser Ser Val Leu Glu Asp Gly
            260                 265                 270

Phe Ala Phe Asp Val Leu Asp Gly Gly Asp Leu Ser Ala Phe Pro Phe
        275                 280                 285

Asp Ser Met Val Asp Phe Asp Pro Glu Ser Val Gly Phe Glu Gly Ile
    290                 295                 300

Glu Pro Pro His Gly Leu Pro Asp Glu Thr Ser Arg Gln Thr Ser Ser
305                 310                 315                 320

Val Gln Pro Ser Leu Gly Ala Ser Thr Ser Arg Cys Asp Gly Gln Gly
                325                 330                 335

Ile Ala Ala Gly Cys
            340

<210> SEQ ID NO 4
```

<211> LENGTH: 1921
<212> TYPE: DNA
<213> ORGANISM: Aspergillus niger

<400> SEQUENCE: 4

```
gccgccattc caaatccata caattcaata ttacttctta agacatttcg cgtcacatgc      60
caagagcttc aggacacctt gcttctatct acttctttct gtcctctctt ctccctctct     120
tcttcctcga ttcatcccg ctgggtgatg ctttagctgc tactcttgga tcccctctcg      180
catcttcctt acccgcaatc atgctgcagc ccagctctgc gttgcttttc gtcacgtcgc     240
ttctggcggc gttgcccgtc aacgccgatg gattgtatac gaagaagtcc cccgtcttgc     300
aggtcaacca gaagaactac gaccagctca ttgcaaactc caatcacact tcggtaagta     360
cagctgtgca ggttattaca attgcctaca gacaagtcta ataagctctc ctagatcgta     420
gagtaagcca tcgatcaccc tacccatcta cctcccacaa tcctaaacct ccccgctctc     480
cctctagatt ctacgctccc tggtgcggcc actgccagaa cctaaagccc gcctacgaaa     540
aagccgcaac taatctcgac ggcctggcca agtcgccgc cgtcaattgc gactatgacg      600
acaacaaacc cttctgcggc cgcatgggcg tccagggctt ccctaccctc aagatcgtca     660
cccccggcaa gaaacccggc aagccccgcg tggaagacta caagggcgca cgaagtgcca     720
aagcgattgt cgaggcagtc gtcgaccgga ttcccaacca tgtgaagcgc gcaacagaca     780
aggaccttga cacttggctc gcgcaggatg aggaatcccc caaggccatc ctcttcacgg     840
agaaaggcac caccagccca ctcctccgcg ccctggccat cgacttcctc ggctccatcc     900
aagtcgctca agtccgcaac aaggaaaccg aagccgtcga gaaattcggc atcaccgagt     960
tcccaacctt cgtcctactc ccaggaggcg ccaagaccc catcgtctac gacggcgaac    1020
tgaagaagaa gcccatggtc gaattcctca gccaagccgc tgctcctaac ccggatcctg    1080
ctcccaaggg ctcgaccgcg ccccgcgata caacaagaa gaaatccacc gaaccttctc     1140
cagactccaa gattgtctcg gacgaggcca aaccgccag tgtgcccatt ccggctcccc     1200
ccattggtac cctgcccact gcggaagccc tcgaggctgc ttgtctgatg ccgaaatccg    1260
gtacctgtgt gctggctctc ctccctgaac cgagtgagcc ggacgcagag ctcccggctc    1320
cggccaagga cgccctcctc agtctcgctg agatctcgca caagcacgca gtccgtaaga    1380
gcaagctctt cccgttctac agtgtcccgg ctatcaatag cggagctaag accctccgcg    1440
ctgggcttgg tctgcctgag gataactcgg tggagatcgt tgctgtgaat ggacgccgtg    1500
gctggtggcg ccggtatgac tcggttgagg gcgcagagta cggccaggag cgtgtcgagg    1560
cttggattga tgcgatcagg ctgggtgagg gtgagaagca gaagttgcct gatggcgttg    1620
tcgttgaaga ggtagttgag gagaaggtcg aagagaaggt cgaggaagtg gttgaagaac    1680
ccgtcgagga gaagccggcg gtcgaccacg acgaattgta aaacatatgg tccgtatgga    1740
gtgcatgaat ttgtttatta gcacaggtgt ttatcaggtc aaataagtac tactagctgg    1800
tttcccatat cgagtatcaa aagcatacat atcatctact gtcagctact tcaattccac    1860
taatcgggat gaacttgtat tggaacactc atgtagaaat aagctctcta aagattcaat    1920
t                                                                   1921
```

<210> SEQ ID NO 5
<211> LENGTH: 1395
<212> TYPE: DNA
<213> ORGANISM: Aspergillus niger
<220> FEATURE:
<221> NAME/KEY: CDS
<222> LOCATION: (1)..(1395)

<400> SEQUENCE: 5

```
atg ctg cag ccc agc tct gcg ttg ctt ttc gtc acg tcg ctt ctg gcg      48
Met Leu Gln Pro Ser Ser Ala Leu Leu Phe Val Thr Ser Leu Leu Ala
1               5                   10                  15 gcg ttg ccc gtc aac gcc gat gga ttg tat acg aag aag tcc ccc gtc      96
Ala Leu Pro Val Asn Ala Asp Gly Leu Tyr Thr Lys Lys Ser Pro Val
            20                  25                  30 ttg cag gtc aac cag aag aac tac gac cag ctc att gca aac tcc aat     144
Leu Gln Val Asn Gln Lys Asn Tyr Asp Gln Leu Ile Ala Asn Ser Asn
        35                  40                  45 cac act tcg atc gta gaa ttc tac gct ccc tgg tgc ggc cac tgc cag     192
His Thr Ser Ile Val Glu Phe Tyr Ala Pro Trp Cys Gly His Cys Gln
    50                  55                  60 aac cta aag ccc gcc tac gaa aaa gcc gca act aat ctc gac ggc ctg     240
Asn Leu Lys Pro Ala Tyr Glu Lys Ala Ala Thr Asn Leu Asp Gly Leu
65                  70                  75                  80 gcc aaa gtc gcc gcc gtc aat tgc gac tat gac gac aac aaa ccc ttc     288
Ala Lys Val Ala Ala Val Asn Cys Asp Tyr Asp Asp Asn Lys Pro Phe
                85                  90                  95 tgc ggc cgc atg ggc gtc cag ggc ttc cct acc ctc aag atc gtc acc     336
Cys Gly Arg Met Gly Val Gln Gly Phe Pro Thr Leu Lys Ile Val Thr
            100                 105                 110 ccc ggc aag aaa ccc ggc aag ccc cgc gtg gaa gac tac aag ggc gca     384
Pro Gly Lys Lys Pro Gly Lys Pro Arg Val Glu Asp Tyr Lys Gly Ala
        115                 120                 125 cga agt gcc aaa gcg att gtc gag gca gtc gtc gac cgg att ccc aac     432
Arg Ser Ala Lys Ala Ile Val Glu Ala Val Val Asp Arg Ile Pro Asn
    130                 135                 140 cat gtg aag cgc gca aca gac aag gac ctt gac act tgg ctc gcg cag     480
His Val Lys Arg Ala Thr Asp Lys Asp Leu Asp Thr Trp Leu Ala Gln
145                 150                 155                 160 gat gag gaa tcc ccc aag gcc atc ctc ttc acg gag aaa ggc acc acc     528
Asp Glu Glu Ser Pro Lys Ala Ile Leu Phe Thr Glu Lys Gly Thr Thr
                165                 170                 175 agc cca ctc ctc cgc gcc ctg gcc atc gac ttc ctc ggc tcc atc caa     576
Ser Pro Leu Leu Arg Ala Leu Ala Ile Asp Phe Leu Gly Ser Ile Gln
            180                 185                 190 gtc gct caa gtc cgc aac aag gaa acc gaa gcc gtc gag aaa ttc ggc     624
Val Ala Gln Val Arg Asn Lys Glu Thr Glu Ala Val Glu Lys Phe Gly
        195                 200                 205 atc acc gag ttc cca acc ttc gtc cta ctc cca gga ggc ggc caa gac     672
Ile Thr Glu Phe Pro Thr Phe Val Leu Leu Pro Gly Gly Gly Gln Asp
    210                 215                 220 ccc atc gtc tac gac ggc gaa ctg aag aag aag ccc atg gtc gaa ttc     720
Pro Ile Val Tyr Asp Gly Glu Leu Lys Lys Lys Pro Met Val Glu Phe
225                 230                 235                 240 ctc agc caa gcc gct gct cct aac ccg gat cct gct ccc aag ggc tcg     768
Leu Ser Gln Ala Ala Ala Pro Asn Pro Asp Pro Ala Pro Lys Gly Ser
                245                 250                 255 acc gcg ccc cgc gat aac aac aag aag aaa tcc acc gaa cct tct cca     816
Thr Ala Pro Arg Asp Asn Asn Lys Lys Lys Ser Thr Glu Pro Ser Pro
            260                 265                 270 gac tcc aag att gtc tcg gac gag gcc aaa ccc gcc agt gtg ccc att     864
Asp Ser Lys Ile Val Ser Asp Glu Ala Lys Pro Ala Ser Val Pro Ile
        275                 280                 285 ccg gct ccc ccc att ggt acc ctg ccc act gcg gaa gcc ctc gag gct     912
Pro Ala Pro Pro Ile Gly Thr Leu Pro Thr Ala Glu Ala Leu Glu Ala
    290                 295                 300 gct tgt ctg atg ccg aaa tcc ggt acc tgt gtg ctg gct ctc ctc cct     960
Ala Cys Leu Met Pro Lys Ser Gly Thr Cys Val Leu Ala Leu Leu Pro
```

```
Ala Cys Leu Met Pro Lys Ser Gly Thr Cys Val Leu Ala Leu Leu Pro
305                 310                 315                 320 gaa ccg agt gag ccg gac gca gag ctc ccg gct ccg gcc aag gac gcc      1008
Glu Pro Ser Glu Pro Asp Ala Glu Leu Pro Ala Pro Ala Lys Asp Ala
                    325                 330                 335 ctc ctc agt ctc gct gag atc tcg cac aag cac gca gtc cgt aag agc      1056
Leu Leu Ser Leu Ala Glu Ile Ser His Lys His Ala Val Arg Lys Ser
                340                 345                 350 aag ctc ttc ccg ttc tac agt gtc ccg gct atc aat agc gga gct aag      1104
Lys Leu Phe Pro Phe Tyr Ser Val Pro Ala Ile Asn Ser Gly Ala Lys
            355                 360                 365 acc ctc cgc gct ggg ctt ggt ctg cct gag gat aac tcg gtg gag atc      1152
Thr Leu Arg Ala Gly Leu Gly Leu Pro Glu Asp Asn Ser Val Glu Ile
        370                 375                 380 gtt gct gtg aat gga cgc cgt ggc tgg tgg cgc cgg tat gac tcg gtt      1200
Val Ala Val Asn Gly Arg Arg Gly Trp Trp Arg Arg Tyr Asp Ser Val
385                 390                 395                 400 gag ggc gca gag tac ggc cag gag cgt gtc gag gct tgg att gat gcg      1248
Glu Gly Ala Glu Tyr Gly Gln Glu Arg Val Glu Ala Trp Ile Asp Ala
                    405                 410                 415 atc agg ctg ggt gag ggt gag aag cag aag ttg cct gat ggc gtt gtc      1296
Ile Arg Leu Gly Glu Gly Glu Lys Gln Lys Leu Pro Asp Gly Val Val
                420                 425                 430 gtt gaa gag gta gtt gag gag aag gtc gaa gag aag gtc gag gaa gtg      1344
Val Glu Glu Val Val Glu Glu Lys Val Glu Glu Lys Val Glu Glu Val
            435                 440                 445 gtt gaa gaa ccc gtc gag gag aag ccg gcg gtc gac cac gac gaa ttg      1392
Val Glu Glu Pro Val Glu Glu Lys Pro Ala Val Asp His Asp Glu Leu
        450                 455                 460 taa                                                                    1395

<210> SEQ ID NO 6
<211> LENGTH: 464
<212> TYPE: PRT
<213> ORGANISM: Aspergillus niger

<400> SEQUENCE: 6

Met Leu Gln Pro Ser Ser Ala Leu Leu Phe Val Thr Ser Leu Leu Ala
1               5                   10                  15

Ala Leu Pro Val Asn Ala Asp Gly Leu Tyr Thr Lys Lys Ser Pro Val
            20                  25                  30

Leu Gln Val Asn Gln Lys Asn Tyr Asp Gln Leu Ile Ala Asn Ser Asn
        35                  40                  45

His Thr Ser Ile Val Glu Phe Tyr Ala Pro Trp Cys Gly His Cys Gln
    50                  55                  60

Asn Leu Lys Pro Ala Tyr Glu Lys Ala Ala Thr Asn Leu Asp Gly Leu
65                  70                  75                  80

Ala Lys Val Ala Ala Val Asn Cys Asp Tyr Asp Asp Asn Lys Pro Phe
                85                  90                  95

Cys Gly Arg Met Gly Val Gln Gly Phe Pro Thr Leu Lys Ile Val Thr
            100                 105                 110

Pro Gly Lys Lys Pro Gly Lys Pro Arg Val Glu Asp Tyr Lys Gly Ala
        115                 120                 125

Arg Ser Ala Lys Ala Ile Val Glu Ala Val Val Asp Arg Ile Pro Asn
    130                 135                 140

His Val Lys Arg Ala Thr Asp Lys Asp Leu Asp Thr Trp Leu Ala Gln
145                 150                 155                 160

Asp Glu Glu Ser Pro Lys Ala Ile Leu Phe Thr Glu Lys Gly Thr Thr
```

```
                    165                 170                 175
Ser Pro Leu Leu Arg Ala Leu Ala Ile Asp Phe Leu Gly Ser Ile Gln
                180                 185                 190

Val Ala Gln Val Arg Asn Lys Glu Thr Glu Ala Val Glu Lys Phe Gly
            195                 200                 205

Ile Thr Glu Phe Pro Thr Phe Val Leu Leu Pro Gly Gly Gly Gln Asp
        210                 215                 220

Pro Ile Val Tyr Asp Gly Glu Leu Lys Lys Pro Met Val Glu Phe
225                 230                 235                 240

Leu Ser Gln Ala Ala Ala Pro Asn Pro Asp Pro Ala Pro Lys Gly Ser
                245                 250                 255

Thr Ala Pro Arg Asp Asn Asn Lys Lys Lys Ser Thr Glu Pro Ser Pro
            260                 265                 270

Asp Ser Lys Ile Val Ser Asp Glu Ala Lys Pro Ala Ser Val Pro Ile
        275                 280                 285

Pro Ala Pro Pro Ile Gly Thr Leu Pro Thr Ala Glu Ala Leu Glu Ala
    290                 295                 300

Ala Cys Leu Met Pro Lys Ser Gly Thr Cys Val Leu Ala Leu Leu Pro
305                 310                 315                 320

Glu Pro Ser Glu Pro Asp Ala Glu Leu Pro Ala Pro Lys Asp Ala
                325                 330                 335

Leu Leu Ser Leu Ala Glu Ile Ser His Lys His Ala Val Arg Lys Ser
            340                 345                 350

Lys Leu Phe Pro Phe Tyr Ser Val Pro Ala Ile Asn Ser Gly Ala Lys
        355                 360                 365

Thr Leu Arg Ala Gly Leu Gly Leu Pro Glu Asp Asn Ser Val Glu Ile
    370                 375                 380

Val Ala Val Asn Gly Arg Arg Gly Trp Trp Arg Arg Tyr Asp Ser Val
385                 390                 395                 400

Glu Gly Ala Glu Tyr Gly Gln Glu Arg Val Glu Ala Trp Ile Asp Ala
                405                 410                 415

Ile Arg Leu Gly Glu Gly Glu Lys Gln Lys Leu Pro Asp Gly Val Val
            420                 425                 430

Val Glu Glu Val Val Glu Glu Lys Val Glu Glu Lys Val Glu Glu Val
        435                 440                 445

Val Glu Glu Pro Val Glu Glu Lys Pro Ala Val Asp His Asp Glu Leu
    450                 455                 460

<210> SEQ ID NO 7
<211> LENGTH: 3891
<212> TYPE: DNA
<213> ORGANISM: Aspergillus niger

<400> SEQUENCE: 7
atccaattca tccattctat tccatcctat tcatccgctc aatgctgccc ttcaattgcc    60
catctgctct cgattcttct tccttctctt ttggttcctc ccacgcggat tttaccaact   120
gatgacacgc cccgtgccat cggatcccct actctccagc ttctctctcc atctggccca   180
ctgtattgga gtccctcagc atgcggtggc ggctgcctgg cgcccggtcg acccttcctg   240
ccagtgtcgc actcctcctg ctccccgttc ttgttgctcc gcagcagtgg catgaacatc   300
aacatgagct ctcctccacc gtttccgtcc ctctccgacc gactggtttc acctccggcg   360
tcgatacccc tccctctttc gacgtgaaat ccaacgatgc gagcgcccta gcaaccctgg   420
ctctggccgg ctctggccgc gccgttcgag cccctcctgc ccaagccagc agctctaccg   480
```

-continued

```
ctggcctggc tccgcagctt cacgcgcggt ccctgcagga ctgggaggtt gaggactttg    540
tcctgctggc gaccgtcgac ggttccattc acgcacgcga ccgcaagacc ggtgccgctc    600
gttgggccct cgaggtcccg agcagcccta tggtcgaaag cctctaccac cgagccaatc    660
gctccagctt cgaccgtgcc caaccagagg acgactttat ctggatcgtc gagccgagtc    720
agggcggaag cctctacatc tacagctcgg ggccagaggc aggcctccag aaattgggat    780
tgactgtgaa ggaacttgtt gacgaaacgc cttactcggg gactgacccg gccgttactt    840
atacggcacg aaaggaaacg acgctgtata ccatcgatgc tcgcaccgga aacattctgc    900
gggtgtttag ctctagaggt cccatttcgt caggtcagga atgtcgaaag gttgatggtc    960
tggatgtgga tatggaagaa tgcgaatccc cttcgggtac tctagtcctt ggtcgtgtcg   1020
aatacacggt agccatccag aacaccgaaa ccggtgatcc aatctgcact ctcaagtact   1080
cggagtggac ggccaacaac cgggatatgg acctccagag ccagtacctc cgcacgatgg   1140
atcaaagcca tatttacagc atgcatgatg gtgtagtctt aggcttcgat cattcacgga   1200
tggaccggcc acggtacacc cagcgattct cgagtccggt ggtccgcgtc ttcgatgttg   1260
ctcgtccggt cagcgccgac tcatctaacg accctactcc acttattcta ctctcgcagc   1320
ctctacagcc tcctgacccc gactacggta cgcttgacga tcgtgatgaa agagtattca   1380
ttgattacac cgagggtggt ggttggtatg ccatgtcgga ggccacctac ccgcttgtca   1440
ccgggagagc caagatggct caatgctacg aaaaagatta cctccgccat ggtcaaccc    1500
taacaagtct gaccccgagt cagcaacaag atgcactagc aggagtccat tctttgaacg   1560
gcccacgcgt cgtccgccgt cacatcccca gcatttctgg cccctcgtca gccgatatgt   1620
ccaatgacac gcctcgggag ttgatctata gctcatcgga cttggcactg cctccggctc   1680
tacgccacag caccattata cggaagggct gggacaatgc cattgatatt tttgtgacgc   1740
tcttgcttct gttttttcggc accttcatct ggttcaattc tcatcacatt caggagcttg   1800
ctaagcagaa gctggatctg aaaaatatca tggcctcgta cggacagccg cccatgtcta   1860
cccctcaac tccaatcgtg aagcccctc atttgaaacg cgaggctagc cctaatcgca    1920
tggcgaatct gactgtcgac atgaatgttt caggagagca gccgcagggt ggtgactcga   1980
cgccaaggcc caagaaatcc cagaactctc ttgcgcccga cacaactcca cgcgtacgca   2040
tccgggaacc gtctcaaggc ccagatggcg atgacgatgt ggacgagctc aatctacaag   2100
acggtgaaaa gcctaagaag aaggctcgcc gcggtcgtcg tggtggcaag aatcataggc   2160
ggggcaagaa gcccaatagc gacagcgaat ccagggaccc ggccgatcgc gttgttgatg   2220
aagtgaacaa gcttcaacct cagcctcgct tggaacccga tgtacagctg gcccggacgg   2280
tgtcgcatga gatcatggaa atggatgcg ttctccagat cggccgtctt agggtgttca    2340
ctgacgtggt cctgggacac ggcagccacg ggaccgtggt gtatcggggc tcgttcgatg   2400
gacgcgacgt ggctgtcaag cgcatgctgg tagaattcta tgatattgca tcccatgaag   2460
tgggcctgtt gcaagaaagt gatgaccatg gcaatgtgat ccggtactac tgccgagagc   2520
aggctgctgt tttcctctac attgctttgg agctctgccc ggcctctttg caggatgtgg   2580
ttgaacgtcc atcagatttc ccgcagttag tccagggcgg cttggacctg ccggacgttc   2640
tgcgccagat tgtggcaggt gttcgctatc ttcattctct taagattgtg caccgcgatc   2700
tgaagccaca gaacatcttg gtggcgatgc ctcgcgggcg tactggttca cgctccctgc   2760
ggttgctgat ctcggatttc ggcttgtgta agaagctcga agacaaccag agctccttcc   2820
gcgcaactac ggcacatgcc gcgggtacct caggctggcg agcccctgaa ttgctggtag   2880
```

-continued

```
acgacgacat gagcccggct atgcagggta gcgagtccca acacaccgaa tcatcagaac    2940
cagctgtggt ggatcctcaa accaaccggc gggctactcg agctatcgac atcttctctt    3000
tgggctgcgt cttttattac gttctgacgc ggggggtgcca tccttttgac aagaatggca   3060
agtttatgcg cgaggccaac attgtcaagg caaccacaa cctcgatgag ctgcagcgtc     3120
tgggcgacta tgcctacgag gctgaagatc taatccagtc catgttgtcg cttgatcctc    3180
gacgacggta agtcgatgct cattacgtgc catgcatagt actaactttt ctagacccga    3240
tgcgagcgct gtgttgacgc acccgttctt ttggcctcca tctgaccgtc ttagcttcct    3300
ctgcgatgtc tcggatcact ttgaatttga accgcgggat cctccttcgg acgcccttt     3360 gtgtctcgag tcggtcgctc cacgagtgat gggcccggac atggatttcc tgcgactact    3420
gccacgggac tttaaggata atctcggcaa gcagcgtaag tacacgggat cgaagatgtt    3480
agatttgctg cgagccctcc ggaacaagcg caaccattac aacgacatgc cggagcatct    3540
caaggcacac atcggcgggt tgcccgaggg gtatcttaat ttttggactg tgcgattccc    3600
cagtcttctc atgagctgcc actccgtcat tgtggagttg cgtttgacgc ggtccgaccg    3660
tttcaagcgc tacttcacgg cgactgacta ggtggtgttc acccacgtag acagtcattt    3720
acttgtatac atgcatatct agatgacata tgtcacaatc aataagttat acgagtctta    3780
cttatcattc tatcaatggg aattcatgct gcagagtcgt ccggtagtgt gggcggggta    3840
gtcacgtgtc tagtctagtg accggggaag ccctcagcga tgagtcatgg a             3891
```

<210> SEQ ID NO 8
<211> LENGTH: 3444
<212> TYPE: DNA
<213> ORGANISM: Aspergillus niger
<220> FEATURE:
<221> NAME/KEY: CDS
<222> LOCATION: (1)..(3444)

<400> SEQUENCE: 8

```
atg cgg tgg cgg ctg cct ggc gcc cgg tcg acc ctt cct gcc agt gtc     48
Met Arg Trp Arg Leu Pro Gly Ala Arg Ser Thr Leu Pro Ala Ser Val
1               5                   10                  15 gca ctc ctc ctg ctc ccc gtt ctt gtt gct ccg cag cag tgg cat gaa     96
Ala Leu Leu Leu Leu Pro Val Leu Val Ala Pro Gln Gln Trp His Glu
            20                  25                  30 cat caa cat gag ctc tcc tcc acc gtt tcc gtc cct ctc cga ccg act    144
His Gln His Glu Leu Ser Ser Thr Val Ser Val Pro Leu Arg Pro Thr
        35                  40                  45 ggt ttc acc tcc ggc gtc gat acc cct ccc tct ttc gac gtg aaa tcc    192
Gly Phe Thr Ser Gly Val Asp Thr Pro Pro Ser Phe Asp Val Lys Ser
    50                  55                  60 aac gat gcg agc gcc cta gca acc ctg gct ctg gcc ggc tct ggc cgc    240
Asn Asp Ala Ser Ala Leu Ala Thr Leu Ala Leu Ala Gly Ser Gly Arg
65                  70                  75                  80 gcc gtt cga gcc cct cct gcc caa gcc agc agc tct acc gct ggc ctg    288
Ala Val Arg Ala Pro Pro Ala Gln Ala Ser Ser Ser Thr Ala Gly Leu
                85                  90                  95 gct ccg cag ctt cac gcg cgg tcc ctg cag gac tgg gag gtt gag gac    336
Ala Pro Gln Leu His Ala Arg Ser Leu Gln Asp Trp Glu Val Glu Asp
            100                 105                 110 ttt gtc ctg ctg gcg acc gtc gac ggt tcc att cac gca cgc gac cgc    384
Phe Val Leu Leu Ala Thr Val Asp Gly Ser Ile His Ala Arg Asp Arg
        115                 120                 125 aag acc ggt gcc gct cgt tgg gcc ctc gag gtc ccg agc agc cct atg    432
Lys Thr Gly Ala Ala Arg Trp Ala Leu Glu Val Pro Ser Ser Pro Met
    130                 135                 140
```

```
gtc gaa agc ctc tac cac cga gcc aat cgc tcc agc ttc gac cgt gcc       480
Val Glu Ser Leu Tyr His Arg Ala Asn Arg Ser Ser Phe Asp Arg Ala
145                 150                 155                 160 caa cca gag gac gac ttt atc tgg atc gtc gag ccg agt cag ggc gga       528
Gln Pro Glu Asp Asp Phe Ile Trp Ile Val Glu Pro Ser Gln Gly Gly
                165                 170                 175 agc ctc tac atc tac agc tcg ggg cca gag gca ggc ctc cag aaa ttg       576
Ser Leu Tyr Ile Tyr Ser Ser Gly Pro Glu Ala Gly Leu Gln Lys Leu
            180                 185                 190 gga ttg act gtg aag gaa ctt gtt gac gaa acg cct tac tcg ggg act       624
Gly Leu Thr Val Lys Glu Leu Val Asp Glu Thr Pro Tyr Ser Gly Thr
        195                 200                 205 gac ccg gcc gtt act tat acg gca cga aag gaa acg acg ctg tat acc       672
Asp Pro Ala Val Thr Tyr Thr Ala Arg Lys Glu Thr Thr Leu Tyr Thr
    210                 215                 220 atc gat gct cgc acc gga aac att ctg cgg gtg ttt agc tct aga ggt       720
Ile Asp Ala Arg Thr Gly Asn Ile Leu Arg Val Phe Ser Ser Arg Gly
225                 230                 235                 240 ccc att tcg tca ggt cag gaa tgt cga aag gtt gat ggt ctg gat gtg       768
Pro Ile Ser Ser Gly Gln Glu Cys Arg Lys Val Asp Gly Leu Asp Val
                245                 250                 255 gat atg gaa gaa tgc gaa tcc cct tcg ggt act cta gtc ctt ggt cgt       816
Asp Met Glu Glu Cys Glu Ser Pro Ser Gly Thr Leu Val Leu Gly Arg
            260                 265                 270 gtc gaa tac acg gta gcc atc cag aac acc gaa acc ggt gat cca atc       864
Val Glu Tyr Thr Val Ala Ile Gln Asn Thr Glu Thr Gly Asp Pro Ile
        275                 280                 285 tgc act ctc aag tac tcg gag tgg acg gcc aac aac cgg gat atg gac       912
Cys Thr Leu Lys Tyr Ser Glu Trp Thr Ala Asn Asn Arg Asp Met Asp
    290                 295                 300 ctc cag agc cag tac ctc cgc acg atg gat caa agc cat att tac agc       960
Leu Gln Ser Gln Tyr Leu Arg Thr Met Asp Gln Ser His Ile Tyr Ser
305                 310                 315                 320 atg cat gat ggt gta gtc tta ggc ttc gat cat tca cgg atg gac cgg      1008
Met His Asp Gly Val Val Leu Gly Phe Asp His Ser Arg Met Asp Arg
                325                 330                 335 cca cgg tac acc cag cga ttc tcg agt ccg gtg gtc cgc gtc ttc gat      1056
Pro Arg Tyr Thr Gln Arg Phe Ser Ser Pro Val Val Arg Val Phe Asp
            340                 345                 350 gtt gct cgt ccg gtc agc gcc gac tca tct aac gac cct act cca ctt      1104
Val Ala Arg Pro Val Ser Ala Asp Ser Ser Asn Asp Pro Thr Pro Leu
        355                 360                 365 att cta ctc tcg cag cct cta cag cct cct gac ccc gac tac ggt acg      1152
Ile Leu Leu Ser Gln Pro Leu Gln Pro Pro Asp Pro Asp Tyr Gly Thr
    370                 375                 380 ctt gac gat cgt gat gaa aga gta ttc att gat tac acc gag ggt ggt      1200
Leu Asp Asp Arg Asp Glu Arg Val Phe Ile Asp Tyr Thr Glu Gly Gly
385                 390                 395                 400 ggt tgg tat gcc atg tcg gag gcc acc tac ccg ctt gtc acc ggg aga      1248
Gly Trp Tyr Ala Met Ser Glu Ala Thr Tyr Pro Leu Val Thr Gly Arg
                405                 410                 415 gcc aag atg gct caa tgc tac gaa aaa gat tac ctc cgc cat ggt caa      1296
Ala Lys Met Ala Gln Cys Tyr Glu Lys Asp Tyr Leu Arg His Gly Gln
            420                 425                 430 ccc cta aca agt ctg acc ccg agt cag caa caa gat gca cta gca gga      1344
Pro Leu Thr Ser Leu Thr Pro Ser Gln Gln Gln Asp Ala Leu Ala Gly
        435                 440                 445 gtc cat tct ttg aac ggc cca cgc gtc gtc cgc cgt cac atc ccc agc      1392
Val His Ser Leu Asn Gly Pro Arg Val Val Arg Arg His Ile Pro Ser
    450                 455                 460
```

```
att tct ggc ccc tcg tca gcc gat atg tcc aat gac acg cct cgg gag   1440
Ile Ser Gly Pro Ser Ser Ala Asp Met Ser Asn Asp Thr Pro Arg Glu
465                 470                 475                 480 ttg atc tat agc tca tcg gac ttg gca ctg cct ccg gct cta cgc cac   1488
Leu Ile Tyr Ser Ser Ser Asp Leu Ala Leu Pro Pro Ala Leu Arg His
            485                 490                 495 agc acc att ata cgg aag ggc tgg gac aat gcc att gat att ttt gtg   1536
Ser Thr Ile Ile Arg Lys Gly Trp Asp Asn Ala Ile Asp Ile Phe Val
        500                 505                 510 acg ctc ttg ctt ctg ttt ttc ggc acc ttc atc tgg ttc aat tct cat   1584
Thr Leu Leu Leu Leu Phe Phe Gly Thr Phe Ile Trp Phe Asn Ser His
    515                 520                 525 cac att cag gag ctt gct aag cag aag ctg gat ctg aaa aat atc atg   1632
His Ile Gln Glu Leu Ala Lys Gln Lys Leu Asp Leu Lys Asn Ile Met
530                 535                 540 gcc tcg tac gga cag ccg ccc atg tct acc ccc tca act cca atc gtg   1680
Ala Ser Tyr Gly Gln Pro Pro Met Ser Thr Pro Ser Thr Pro Ile Val
545                 550                 555                 560 gaa gcc cct cat ttg aaa cgc gag gct agc cct aat cgc atg gcg aat   1728
Glu Ala Pro His Leu Lys Arg Glu Ala Ser Pro Asn Arg Met Ala Asn
            565                 570                 575 ctg act gtc gac atg aat gtt tca gga gag cag ccg cag ggt ggt gac   1776
Leu Thr Val Asp Met Asn Val Ser Gly Glu Gln Pro Gln Gly Gly Asp
        580                 585                 590 tcg acg cca agg ccc aag aaa tcc cag aac tct ctt gcg ccc gac aca   1824
Ser Thr Pro Arg Pro Lys Lys Ser Gln Asn Ser Leu Ala Pro Asp Thr
    595                 600                 605 act cca cgc gta cgc atc cgg gaa ccg tct caa ggc cca gat ggc gat   1872
Thr Pro Arg Val Arg Ile Arg Glu Pro Ser Gln Gly Pro Asp Gly Asp
610                 615                 620 gac gat gtg gac gag ctc aat cta caa gac ggt gaa aag cct aag aag   1920
Asp Asp Val Asp Glu Leu Asn Leu Gln Asp Gly Glu Lys Pro Lys Lys
625                 630                 635                 640 aag gct cgc cgc ggt cgt cgt ggt ggc aag aat cat agg cgg ggc aag   1968
Lys Ala Arg Arg Gly Arg Arg Gly Gly Lys Asn His Arg Arg Gly Lys
            645                 650                 655 aag ccc aat agc gac agc gaa tcc agg gac ccg gcc gat cgc gtt gtt   2016
Lys Pro Asn Ser Asp Ser Glu Ser Arg Asp Pro Ala Asp Arg Val Val
        660                 665                 670 gat gaa gtg aac aag ctt caa cct cag cct cgc ttg gaa ccc gat gta   2064
Asp Glu Val Asn Lys Leu Gln Pro Gln Pro Arg Leu Glu Pro Asp Val
    675                 680                 685 cag ctg gcc cgg acg gtg tcg cat gag atc atg gaa atg gat ggc gtt   2112
Gln Leu Ala Arg Thr Val Ser His Glu Ile Met Glu Met Asp Gly Val
690                 695                 700 ctc cag atc ggc cgt ctt agg gtg ttc act gac gtg gtc ctg gga cac   2160
Leu Gln Ile Gly Arg Leu Arg Val Phe Thr Asp Val Val Leu Gly His
705                 710                 715                 720 ggc agc cac ggg acc gtg gtg tat cgg ggc tcg ttc gat gga cgc gac   2208
Gly Ser His Gly Thr Val Val Tyr Arg Gly Ser Phe Asp Gly Arg Asp
            725                 730                 735 gtg gct gtc aag cgc atg ctg gta gaa ttc tat gat att gca tcc cat   2256
Val Ala Val Lys Arg Met Leu Val Glu Phe Tyr Asp Ile Ala Ser His
        740                 745                 750 gaa gtg ggc ctg ttg caa gaa agt gat gac cat ggc aat gtg atc cgg   2304
Glu Val Gly Leu Leu Gln Glu Ser Asp Asp His Gly Asn Val Ile Arg
    755                 760                 765 tac tac tgc cga gag cag gct gct ggt ttc ctc tac att gct ttg gag   2352
Tyr Tyr Cys Arg Glu Gln Ala Ala Gly Phe Leu Tyr Ile Ala Leu Glu
770                 775                 780
```

|  |  |  |  |  |  |  |  |  |  |  |  |  |  |  |  |
|---|---|---|---|---|---|---|---|---|---|---|---|---|---|---|---|
| ctc | tgc | ccg | gcc | tct | ttg | cag | gat | gtg | gtt | gaa | cgt | cca | tca | gat | ttc | 2400 |
| Leu | Cys | Pro | Ala | Ser | Leu | Gln | Asp | Val | Val | Glu | Arg | Pro | Ser | Asp | Phe |
| 785 |  |  |  | 790 |  |  |  |  | 795 |  |  |  |  | 800 |

```
ctc tgc ccg gcc tct ttg cag gat gtg gtt gaa cgt cca tca gat ttc    2400
Leu Cys Pro Ala Ser Leu Gln Asp Val Val Glu Arg Pro Ser Asp Phe
785                 790                 795                 800 ccg cag tta gtc cag ggc ggc ttg gac ctg ccg gac gtt ctg cgc cag    2448
Pro Gln Leu Val Gln Gly Gly Leu Asp Leu Pro Asp Val Leu Arg Gln
                805                 810                 815 att gtg gca ggt gtt cgc tat ctt cat tct ctt aag att gtg cac cgc    2496
Ile Val Ala Gly Val Arg Tyr Leu His Ser Leu Lys Ile Val His Arg
            820                 825                 830 gat ctg aag cca cag aac atc ttg gtg gcg atg cct cgc ggg cgt act    2544
Asp Leu Lys Pro Gln Asn Ile Leu Val Ala Met Pro Arg Gly Arg Thr
        835                 840                 845 ggt tca cgc tcc ctg cgg ttg ctg atc tcg gat ttc ggc ttg tgt aag    2592
Gly Ser Arg Ser Leu Arg Leu Leu Ile Ser Asp Phe Gly Leu Cys Lys
    850                 855                 860 aag ctc gaa gac aac cag agc tcc ttc cgc gca act acg gca cat gcc    2640
Lys Leu Glu Asp Asn Gln Ser Ser Phe Arg Ala Thr Thr Ala His Ala
865                 870                 875                 880 gcg ggt acc tca ggc tgg cga gcc cct gaa ttg ctg gta gac gac gac    2688
Ala Gly Thr Ser Gly Trp Arg Ala Pro Glu Leu Leu Val Asp Asp Asp
                885                 890                 895 atg agc ccg gct atg cag ggt agc gag tcc caa cac acc gaa tca tca    2736
Met Ser Pro Ala Met Gln Gly Ser Glu Ser Gln His Thr Glu Ser Ser
            900                 905                 910 gaa cca gct gtg gtg gat cct caa acc aac cgg cgg gct act cga gct    2784
Glu Pro Ala Val Val Asp Pro Gln Thr Asn Arg Arg Ala Thr Arg Ala
        915                 920                 925 atc gac atc ttc tct ttg ggc tgc gtc ttt tat tac gtt ctg acg cgg    2832
Ile Asp Ile Phe Ser Leu Gly Cys Val Phe Tyr Tyr Val Leu Thr Arg
    930                 935                 940 ggg tgc cat cct ttt gac aag aat ggc aag ttt atg cgc gag gcc aac    2880
Gly Cys His Pro Phe Asp Lys Asn Gly Lys Phe Met Arg Glu Ala Asn
945                 950                 955                 960 att gtc aag ggc aac cac aac ctc gat gag ctg cag cgt ctg ggc gac    2928
Ile Val Lys Gly Asn His Asn Leu Asp Glu Leu Gln Arg Leu Gly Asp
                965                 970                 975 tat gcc tac gag gct gaa gat cta atc cag tcc atg ttg tcg ctt gat    2976
Tyr Ala Tyr Glu Ala Glu Asp Leu Ile Gln Ser Met Leu Ser Leu Asp
            980                 985                 990 cct cga cga cga ccc gat gcg agc gct gtg ttg acg cac ccg ttc ttt    3024
Pro Arg Arg Arg Pro Asp Ala Ser Ala Val Leu Thr His Pro Phe Phe
        995                 1000                1005 tgg cct cca tct gac cgt ctt agc ttc ctc tgc gat gtc tcg gat cac    3072
Trp Pro Pro Ser Asp Arg Leu Ser Phe Leu Cys Asp Val Ser Asp His
    1010                1015                1020 ttt gaa ttt gaa ccg cgg gat cct cct tcg gac gcc ctt ttg tgt ctc    3120
Phe Glu Phe Glu Pro Arg Asp Pro Pro Ser Asp Ala Leu Leu Cys Leu
1025                1030                1035                1040 gag tcg gtc gct cca cga gtg atg ggc ccg gac atg gat ttc ctg cga    3168
Glu Ser Val Ala Pro Arg Val Met Gly Pro Asp Met Asp Phe Leu Arg
                1045                1050                1055 cta ctg cca cgg gac ttt aag gat aat ctc ggc aag cag cgt aag tac    3216
Leu Leu Pro Arg Asp Phe Lys Asp Asn Leu Gly Lys Gln Arg Lys Tyr
            1060                1065                1070 acg gga tcg aag atg tta gat ttg ctg cga gcc ctc cgg aac aag cgc    3264
Thr Gly Ser Lys Met Leu Asp Leu Leu Arg Ala Leu Arg Asn Lys Arg
        1075                1080                1085 aac cat tac aac gac atg ccg gag cat ctc aag gca cac atc ggc ggg    3312
Asn His Tyr Asn Asp Met Pro Glu His Leu Lys Ala His Ile Gly Gly
    1090                1095                1100
```

```
ttg ccc gag ggg tat ctt aat ttt tgg act gtg cga ttc ccc agt ctt    3360
Leu Pro Glu Gly Tyr Leu Asn Phe Trp Thr Val Arg Phe Pro Ser Leu
1105                1110                1115                1120 ctc atg agc tgc cac tcc gtc att gtg gag ttg cgt ttg acg cgg tcc    3408
Leu Met Ser Cys His Ser Val Ile Val Glu Leu Arg Leu Thr Arg Ser
                1125                1130                1135 gac cgt ttc aag cgc tac ttc acg gcg act gac tag                    3444
Asp Arg Phe Lys Arg Tyr Phe Thr Ala Thr Asp
                1140                1145
```

<210> SEQ ID NO 9
<211> LENGTH: 1147
<212> TYPE: PRT
<213> ORGANISM: Aspergillus niger

<400> SEQUENCE: 9

```
Met Arg Trp Arg Leu Pro Gly Ala Arg Ser Thr Leu Pro Ala Ser Val
1               5                   10                  15

Ala Leu Leu Leu Leu Pro Val Leu Val Ala Pro Gln Gln Trp His Glu
                20                  25                  30

His Gln His Glu Leu Ser Ser Thr Val Ser Val Pro Leu Arg Pro Thr
            35                  40                  45

Gly Phe Thr Ser Gly Val Asp Thr Pro Pro Ser Phe Asp Val Lys Ser
        50                  55                  60

Asn Asp Ala Ser Ala Leu Ala Thr Leu Ala Leu Ala Gly Ser Gly Arg
65                  70                  75                  80

Ala Val Arg Ala Pro Pro Ala Gln Ala Ser Ser Thr Ala Gly Leu
                85                  90                  95

Ala Pro Gln Leu His Ala Arg Ser Leu Gln Asp Trp Glu Val Glu Asp
            100                 105                 110

Phe Val Leu Leu Ala Thr Val Asp Gly Ser Ile His Ala Arg Asp Arg
        115                 120                 125

Lys Thr Gly Ala Ala Arg Trp Ala Leu Glu Val Pro Ser Ser Pro Met
    130                 135                 140

Val Glu Ser Leu Tyr His Arg Ala Asn Arg Ser Ser Phe Asp Arg Ala
145                 150                 155                 160

Gln Pro Glu Asp Asp Phe Ile Trp Ile Val Glu Pro Ser Gln Gly Gly
                165                 170                 175

Ser Leu Tyr Ile Tyr Ser Ser Gly Pro Glu Ala Gly Leu Gln Lys Leu
            180                 185                 190

Gly Leu Thr Val Lys Glu Leu Val Asp Glu Thr Pro Tyr Ser Gly Thr
        195                 200                 205

Asp Pro Ala Val Thr Tyr Thr Ala Arg Lys Glu Thr Thr Leu Tyr Thr
    210                 215                 220

Ile Asp Ala Arg Thr Gly Asn Ile Leu Arg Val Phe Ser Ser Arg Gly
225                 230                 235                 240

Pro Ile Ser Ser Gly Gln Glu Cys Arg Lys Val Asp Gly Leu Asp Val
                245                 250                 255

Asp Met Glu Glu Cys Gly Ser Pro Ser Gly Thr Leu Val Leu Gly Arg
            260                 265                 270

Val Glu Tyr Thr Val Ala Ile Gln Asn Thr Glu Thr Gly Asp Pro Ile
        275                 280                 285

Cys Thr Leu Lys Tyr Ser Glu Trp Thr Ala Asn Asn Arg Asp Met Asp
    290                 295                 300

Leu Gln Ser Gln Tyr Leu Arg Thr Met Asp Gln Ser His Ile Tyr Ser
305                 310                 315                 320
```

-continued

Met His Asp Gly Val Val Leu Gly Phe Asp His Ser Arg Met Asp Arg
                325                 330                 335

Pro Arg Tyr Thr Gln Arg Phe Ser Ser Pro Val Val Arg Val Phe Asp
            340                 345                 350

Val Ala Arg Pro Val Ser Ala Asp Ser Ser Asn Asp Pro Thr Pro Leu
        355                 360                 365

Ile Leu Leu Ser Gln Pro Leu Gln Pro Pro Asp Pro Asp Tyr Gly Thr
    370                 375                 380

Leu Asp Asp Arg Asp Glu Arg Val Phe Ile Asp Tyr Thr Glu Gly Gly
385                 390                 395                 400

Gly Trp Tyr Ala Met Ser Glu Ala Thr Tyr Pro Leu Val Thr Gly Arg
                405                 410                 415

Ala Lys Met Ala Gln Cys Tyr Glu Lys Asp Tyr Leu Arg His Gly Gln
            420                 425                 430

Pro Leu Thr Ser Leu Thr Pro Ser Gln Gln Gln Asp Ala Leu Ala Gly
        435                 440                 445

Val His Ser Leu Asn Gly Pro Arg Val Val Arg His Ile Pro Ser
    450                 455                 460

Ile Ser Gly Pro Ser Ser Ala Asp Met Ser Asn Asp Thr Pro Arg Glu
465                 470                 475                 480

Leu Ile Tyr Ser Ser Ser Asp Leu Ala Leu Pro Pro Ala Leu Arg His
                485                 490                 495

Ser Thr Ile Ile Arg Lys Gly Trp Asp Asn Ala Ile Asp Ile Phe Val
            500                 505                 510

Thr Leu Leu Leu Leu Phe Phe Gly Thr Phe Ile Trp Phe Asn Ser His
        515                 520                 525

His Ile Gln Glu Leu Ala Lys Gln Lys Leu Asp Leu Lys Asn Ile Met
    530                 535                 540

Ala Ser Tyr Gly Gln Pro Pro Met Ser Thr Pro Ser Thr Pro Ile Val
545                 550                 555                 560

Glu Ala Pro His Leu Lys Arg Glu Ala Ser Pro Asn Arg Met Ala Asn
                565                 570                 575

Leu Thr Val Asp Met Asn Val Ser Gly Glu Gln Pro Gln Gly Gly Asp
            580                 585                 590

Ser Thr Pro Arg Pro Lys Lys Ser Gln Asn Ser Leu Ala Pro Asp Thr
        595                 600                 605

Thr Pro Arg Val Arg Ile Arg Glu Pro Ser Gln Gly Pro Asp Gly Asp
    610                 615                 620

Asp Asp Val Asp Glu Leu Asn Leu Gln Asp Gly Glu Lys Pro Lys Lys
625                 630                 635                 640

Lys Ala Arg Arg Gly Arg Arg Gly Gly Lys Asn His Arg Arg Gly Lys
                645                 650                 655

Lys Pro Asn Ser Asp Ser Glu Ser Arg Asp Pro Ala Asp Arg Val Val
            660                 665                 670

Asp Glu Val Asn Lys Leu Gln Pro Gln Pro Arg Leu Glu Pro Asp Val
        675                 680                 685

Gln Leu Ala Arg Thr Val Ser His Glu Ile Met Glu Met Asp Gly Val
    690                 695                 700

Leu Gln Ile Gly Arg Leu Arg Val Phe Thr Asp Val Val Leu Gly His
705                 710                 715                 720

Gly Ser His Gly Thr Val Val Tyr Arg Gly Ser Phe Asp Gly Arg Asp
                725                 730                 735

Val Ala Val Lys Arg Met Leu Val Glu Phe Tyr Asp Ile Ala Ser His

```
                    740                 745                 750
Glu Val Gly Leu Leu Gln Glu Ser Asp Asp His Gly Asn Val Ile Arg
            755                 760                 765
Tyr Tyr Cys Arg Glu Gln Ala Ala Gly Phe Leu Tyr Ile Ala Leu Glu
        770                 775                 780
Leu Cys Pro Ala Ser Leu Gln Asp Val Val Glu Arg Pro Ser Asp Phe
785                 790                 795                 800
Pro Gln Leu Val Gln Gly Gly Leu Asp Leu Pro Asp Val Leu Arg Gln
            805                 810                 815
Ile Val Ala Gly Val Arg Tyr Leu His Ser Leu Lys Ile Val His Arg
        820                 825                 830
Asp Leu Lys Pro Gln Asn Ile Leu Val Ala Met Pro Arg Gly Arg Thr
            835                 840                 845
Gly Ser Arg Ser Leu Arg Leu Leu Ile Ser Asp Phe Gly Leu Cys Lys
        850                 855                 860
Lys Leu Glu Asp Asn Gln Ser Ser Phe Arg Ala Thr Thr Ala His Ala
865                 870                 875                 880
Ala Gly Thr Ser Gly Trp Arg Ala Pro Glu Leu Leu Val Asp Asp Asp
            885                 890                 895
Met Ser Pro Ala Met Gln Gly Ser Glu Ser Gln His Thr Glu Ser Ser
        900                 905                 910
Glu Pro Ala Val Val Asp Pro Gln Thr Asn Arg Arg Ala Thr Arg Ala
            915                 920                 925
Ile Asp Ile Phe Ser Leu Gly Cys Val Phe Tyr Tyr Val Leu Thr Arg
        930                 935                 940
Gly Cys His Pro Phe Asp Lys Asn Gly Lys Phe Met Arg Glu Ala Asn
945                 950                 955                 960
Ile Val Lys Gly Asn His Asn Leu Asp Glu Leu Gln Arg Leu Gly Asp
            965                 970                 975
Tyr Ala Tyr Glu Ala Glu Asp Leu Ile Gln Ser Met Leu Ser Leu Asp
        980                 985                 990
Pro Arg Arg Arg Pro Asp Ala Ser Ala Val Leu Thr His Pro Phe Phe
            995                 1000                1005
Trp Pro Pro Ser Asp Arg Leu Ser Phe Leu Cys Asp Val Ser Asp His
        1010                1015                1020
Phe Glu Phe Glu Pro Arg Asp Pro Pro Ser Asp Ala Leu Leu Cys Leu
1025                1030                1035                1040
Glu Ser Val Ala Pro Arg Val Met Gly Pro Asp Met Asp Phe Leu Arg
            1045                1050                1055
Leu Leu Pro Arg Asp Phe Lys Asp Asn Leu Gly Lys Gln Arg Lys Tyr
        1060                1065                1070
Thr Gly Ser Lys Met Leu Asp Leu Leu Arg Ala Leu Arg Asn Lys Arg
        1075                1080                1085
Asn His Tyr Asn Asp Met Pro Glu His Leu Lys Ala His Ile Gly Gly
            1090                1095                1100
Leu Pro Glu Gly Tyr Leu Asn Phe Trp Thr Val Arg Phe Pro Ser Leu
1105                1110                1115                1120
Leu Met Ser Cys His Ser Val Ile Val Glu Leu Arg Leu Thr Arg Ser
            1125                1130                1135
Asp Arg Phe Lys Arg Tyr Phe Thr Ala Thr Asp
            1140                1145

<210> SEQ ID NO 10
<211> LENGTH: 2332
```

<212> TYPE: DNA
<213> ORGANISM: Aspergillus niger

<400> SEQUENCE: 10

```
tcccttcttc ctcttctccc tctcccttta ccttccccgt gcagctactt gactgttgag     60
cttgccttcc tctccctctt tgatccaccc ttaccctctc cggaggttca attgctggtg    120
cgctctgttc gcctttgttt gttttccttc ccttcctctc tcggacgttc tggttttaag    180
agcgccggtc gctatccacc atgcgtttca acgctgcttt gacttctgcc ctggtctcct    240
cggcttccat catgggctat gcccatgctg aggagaccga aagaagccc gagaccacct     300
ccttggccga aagcctacc ttcaccgtga gtaattctgc agaatgatat gaggtgctgc     360
ccgcgccctg ctaactgcgt gcttccagcc cacctccatc gaggctcctt tcttggagca    420
gttcaccgat gactgggact cccggtggac tccctctcac gctaagaagg aggactccaa    480
gtccgaggaa gactgggcct atgttggtga atggtccgtc gaggagccca ctgtcctcaa    540
gggtatggag ggtgacaagg gtctcgtcgt caagaacgtc gctgcccacc acgccatctc    600
ggctaagttt cccaagaaga tcgacaacaa ggacaagact ctggtcgtcc agtatgaggt    660
gaagccgcag agtaagtgtg acaattgctg cgcatgctgg gtgctgggac actaacgata    720
gtcacagact cccttgtctg cggtggtgcc tacctgaagc tcctccagga caacaagcag    780
ctccacctcg acgagttctc gaacgcgtct ccctacgtga tcatgttcgg tcccgacaag    840
tgtggtgcca ccaacaaggt aagatcttgc taaacgctgc ttagtgcagg tgactgcaac    900
agggactaac agctctatct ttttaggtt cacttcatct tccgtcacaa gaaccccaag     960
accggcgagt acgaggagaa gcaccttaag gcacctcccg ccgcccgtac ctccaaggtt   1020
acctccgttt acaccctggt cgtcaaccccc gatcagacct tccagatcct gattgatggc   1080
gagtccgtca aggaaggttc cctccttgag gacttcaacc ccctgtcaa ccccgagaag    1140
gagatcgacg acccccaagga caagaagccc gccgactggg ttgatgaggc caagatcccc   1200
gaccctgagg ctacgaagcc cgaggactgg gacgaggagg ctcccttcga gattgtcgac   1260
gaggaggcta ccattcccga ggactggctc gaggacgagc ccactagcat ccctgaccct   1320
gaggccgaga agcccgagga ctgggatgat gaggaggatg gcgactgggt tcctcccact   1380
gttcccaacc ccaagtgcca ggatgcctcc ggatgtggtc cttggtctcc ccctatgaag   1440
aagaaccctg actacaaggg caagtggtct gctcccttga ttgacaaccc ggcctacaag   1500
ggacctgggg cccccgcaa gattgccaac ccgcctact tcgaggacaa gactccctcc    1560
aactttgagc ccatgggcgc tgtaagtgta cctcttaatt ctaatgctaa ggctttggat   1620
gactaatgat gatgcagatt ggtttcgaga tttggaccat gcagaacgac atcctgttcg   1680
acaacatcta cgttggtcac tccgccgagg atgccgagaa gctgcgccag gagaccttcg   1740
atgtcaagca ccccattgag ctggctgagg aggaggccaa caagcccaag cctgaagaga   1800
aggccgccga acccagcgtt agcttcaagg aagacccccgt gggccacatc aaggagaagg   1860
tcgacaactt tgtccgcctc tccaagcagg accccatcaa cgccgtgaag caggttcctg   1920
acgttgccgg tggtcttgcc gctgttctcg tcacaatgat ccttgtcatc gtcggagccg   1980
ttggtgccag cacccggcc cctgcccccg ccaagaaggg caaggaggct gctggtgcta   2040
ccaaggagaa gactggtgcg gcctccagct cctccgcaga cactggcaag ggtggtgcta   2100
ccaagcgcac tacccgctct tctgccgagt aaagtggtgc agctatcggt ggaacagcac   2160
gcagggaaga aaggggggaga gtttaaaagg cgaaaaggtc aaacaaacaa acaaaccagg   2220
gatatcctaa ctacattgtg ttttattttt atacctctgt tgcagcgttc aatcaatgtt   2280
```

```
tcattctgat ccatggtga gaaggccagc tgggtatcag ctgccgccta ta        2332
```

<210> SEQ ID NO 11
<211> LENGTH: 1689
<212> TYPE: DNA
<213> ORGANISM: Aspergillus niger
<220> FEATURE:
<221> NAME/KEY: CDS
<222> LOCATION: (1)..(1689)

<400> SEQUENCE: 11

```
atg cgt ttc aac gct gct ttg act tct gcc ctg gtc tcc tcg gct tcc      48
Met Arg Phe Asn Ala Ala Leu Thr Ser Ala Leu Val Ser Ser Ala Ser
1               5                   10                  15 atc atg ggc tat gcc cat gct gag gag acc gag aag aag ccc gag acc      96
Ile Met Gly Tyr Ala His Ala Glu Glu Thr Glu Lys Lys Pro Glu Thr
            20                  25                  30 acc tcc ttg gcc gag aag cct acc ttc acc ccc acc tcc atc gag gct     144
Thr Ser Leu Ala Glu Lys Pro Thr Phe Thr Pro Thr Ser Ile Glu Ala
        35                  40                  45 cct ttc ttg gag cag ttc acc gat gac tgg gac tcc cgg tgg act ccc     192
Pro Phe Leu Glu Gln Phe Thr Asp Asp Trp Asp Ser Arg Trp Thr Pro
    50                  55                  60 tct cac gct aag aag gag gac tcc aag tcc gag gaa gac tgg gcc tat     240
Ser His Ala Lys Lys Glu Asp Ser Lys Ser Glu Glu Asp Trp Ala Tyr
65                  70                  75                  80 gtt ggt gaa tgg tcc gtc gag gag ccc act gtc ctc aag ggt atg gag     288
Val Gly Glu Trp Ser Val Glu Glu Pro Thr Val Leu Lys Gly Met Glu
                85                  90                  95 ggt gac aag ggt ctc gtc gtc aag aac gtc gct gcc cac cac gcc atc     336
Gly Asp Lys Gly Leu Val Val Lys Asn Val Ala Ala His His Ala Ile
            100                 105                 110 tcg gct aag ttt ccc aag aag atc gac aac aag gac aag act ctg gtc     384
Ser Ala Lys Phe Pro Lys Lys Ile Asp Asn Lys Asp Lys Thr Leu Val
        115                 120                 125 gtc cag tat gag gtg aag ccg cag aac tcc ctt gtc tgc ggt ggt gcc     432
Val Gln Tyr Glu Val Lys Pro Gln Asn Ser Leu Val Cys Gly Gly Ala
    130                 135                 140 tac ctg aag ctc ctc cag gac aac aag cag ctc cac ctc gac gag ttc     480
Tyr Leu Lys Leu Leu Gln Asp Asn Lys Gln Leu His Leu Asp Glu Phe
145                 150                 155                 160 tcg aac gcg tct ccc tac gtg atc atg ttc ggt ccc gac aag tgt ggt     528
Ser Asn Ala Ser Pro Tyr Val Ile Met Phe Gly Pro Asp Lys Cys Gly
                165                 170                 175 gcc acc aac aag gtt cac ttc atc ttc cgt cac aag aac ccc aag acc     576
Ala Thr Asn Lys Val His Phe Ile Phe Arg His Lys Asn Pro Lys Thr
            180                 185                 190 ggc gag tac gag gag aag cac ctt aag gca cct ccc gcc gcc cgt acc     624
Gly Glu Tyr Glu Glu Lys His Leu Lys Ala Pro Pro Ala Ala Arg Thr
        195                 200                 205 tcc aag gtt acc tcc gtt tac acc ctg gtc gtc aac ccc gat cag acc     672
Ser Lys Val Thr Ser Val Tyr Thr Leu Val Val Asn Pro Asp Gln Thr
    210                 215                 220 ttc cag atc ctg att gat ggc gag tcc gtc aag gaa ggt tcc ctc ctt     720
Phe Gln Ile Leu Ile Asp Gly Glu Ser Val Lys Glu Gly Ser Leu Leu
225                 230                 235                 240 gag gac ttc aac ccc cct gtc aac ccc gag aag gag atc gac gac ccc     768
Glu Asp Phe Asn Pro Pro Val Asn Pro Glu Lys Glu Ile Asp Asp Pro
                245                 250                 255 aag gac aag aag ccc gcc gac tgg gtt gat gag gcc aag atc ccc gac     816
Lys Asp Lys Lys Pro Ala Asp Trp Val Asp Glu Ala Lys Ile Pro Asp
```

```
                    260                 265                 270
cct gag gct acg aag ccc gag gac tgg gac gag gag gct ccc ttc gag    864
Pro Glu Ala Thr Lys Pro Glu Asp Trp Asp Glu Glu Ala Pro Phe Glu
        275                 280                 285 att gtc gac gag gag gct acc att ccc gag gac tgg ctc gag gac gag    912
Ile Val Asp Glu Glu Ala Thr Ile Pro Glu Asp Trp Leu Glu Asp Glu
    290                 295                 300 ccc act agc atc cct gac cct gag gcc gag aag ccc gag gac tgg gat    960
Pro Thr Ser Ile Pro Asp Pro Glu Ala Glu Lys Pro Glu Asp Trp Asp
305                 310                 315                 320 gat gag gag gat ggc gac tgg gtt cct ccc act gtt ccc aac ccc aag   1008
Asp Glu Glu Asp Gly Asp Trp Val Pro Pro Thr Val Pro Asn Pro Lys
                325                 330                 335 tgc cag gat gcc tcc gga tgt ggt cct tgg tct ccc cct atg aag aag   1056
Cys Gln Asp Ala Ser Gly Cys Gly Pro Trp Ser Pro Pro Met Lys Lys
            340                 345                 350 aac cct gac tac aag ggc aag tgg tct gct ccc ttg att gac aac ccg   1104
Asn Pro Asp Tyr Lys Gly Lys Trp Ser Ala Pro Leu Ile Asp Asn Pro
        355                 360                 365 gcc tac aag gga ccc tgg gcc ccc cgc aag att gcc aac ccc gcc tac   1152
Ala Tyr Lys Gly Pro Trp Ala Pro Arg Lys Ile Ala Asn Pro Ala Tyr
    370                 375                 380 ttc gag gac aag act ccc tcc aac ttt gag ccc atg ggc gct att ggt   1200
Phe Glu Asp Lys Thr Pro Ser Asn Phe Glu Pro Met Gly Ala Ile Gly
385                 390                 395                 400 ttc gag att tgg acc atg cag aac gac atc ctg ttc gac aac atc tac   1248
Phe Glu Ile Trp Thr Met Gln Asn Asp Ile Leu Phe Asp Asn Ile Tyr
                405                 410                 415 gtt ggt cac tcc gcc gag gat gcc gag aag ctg cgc cag gag acc ttc   1296
Val Gly His Ser Ala Glu Asp Ala Glu Lys Leu Arg Gln Glu Thr Phe
            420                 425                 430 gat gtc aag cac ccc att gag ctg gct gag gag gag gcc aac aag ccc   1344
Asp Val Lys His Pro Ile Glu Leu Ala Glu Glu Glu Ala Asn Lys Pro
        435                 440                 445 aag cct gaa gag aag gcc gcc gaa ccc agc gtt agc ttc aag gaa gac   1392
Lys Pro Glu Glu Lys Ala Ala Glu Pro Ser Val Ser Phe Lys Glu Asp
    450                 455                 460 ccc gtg ggc cac atc aag gag aag gtc gac aac ttt gtc cgc ctc tcc   1440
Pro Val Gly His Ile Lys Glu Lys Val Asp Asn Phe Val Arg Leu Ser
465                 470                 475                 480 aag cag gac ccc atc aac gcc gtg aag cag gtt cct gac gtt gcc ggt   1488
Lys Gln Asp Pro Ile Asn Ala Val Lys Gln Val Pro Asp Val Ala Gly
                485                 490                 495 ggt ctt gcc gct gtt ctc gtc aca atg atc ctt gtc atc gtc gga gcc   1536
Gly Leu Ala Ala Val Leu Val Thr Met Ile Leu Val Ile Val Gly Ala
            500                 505                 510 gtt ggt gcc agc acc ccg gcc cct gcc ccc gcc aag aag ggc aag gag   1584
Val Gly Ala Ser Thr Pro Ala Pro Ala Pro Ala Lys Lys Gly Lys Glu
        515                 520                 525 gct gct ggt gct acc aag gag aag act ggt gcg gcc tcc agc tcc tcc   1632
Ala Ala Gly Ala Thr Lys Glu Lys Thr Gly Ala Ala Ser Ser Ser Ser
    530                 535                 540 gca gac act ggc aag ggt ggt gct acc aag cgc act acc cgc tct tct   1680
Ala Asp Thr Gly Lys Gly Gly Ala Thr Lys Arg Thr Thr Arg Ser Ser
545                 550                 555                 560 gcc gag taa                                                        1689
Ala Glu

<210> SEQ ID NO 12
<211> LENGTH: 562
```

```
<212> TYPE: PRT
<213> ORGANISM: Aspergillus niger

<400> SEQUENCE: 12

Met Arg Phe Asn Ala Ala Leu Thr Ser Ala Leu Val Ser Ser Ala Ser
1               5                   10                  15

Ile Met Gly Tyr Ala His Ala Glu Glu Thr Glu Lys Lys Pro Glu Thr
            20                  25                  30

Thr Ser Leu Ala Glu Lys Pro Thr Phe Thr Pro Thr Ser Ile Glu Ala
        35                  40                  45

Pro Phe Leu Glu Gln Phe Thr Asp Asp Trp Asp Ser Arg Trp Thr Pro
    50                  55                  60

Ser His Ala Lys Lys Glu Asp Ser Lys Ser Glu Glu Asp Trp Ala Tyr
65                  70                  75                  80

Val Gly Glu Trp Ser Val Glu Glu Pro Thr Val Leu Lys Gly Met Glu
                85                  90                  95

Gly Asp Lys Gly Leu Val Val Lys Asn Val Ala Ala His His Ala Ile
            100                 105                 110

Ser Ala Lys Phe Pro Lys Lys Ile Asp Asn Lys Asp Lys Thr Leu Val
        115                 120                 125

Val Gln Tyr Glu Val Lys Pro Gln Asn Ser Leu Val Cys Gly Gly Ala
    130                 135                 140

Tyr Leu Lys Leu Leu Gln Asp Asn Lys Gln Leu His Leu Asp Glu Phe
145                 150                 155                 160

Ser Asn Ala Ser Pro Tyr Val Ile Met Phe Gly Pro Asp Lys Cys Gly
                165                 170                 175

Ala Thr Asn Lys Val His Phe Ile Phe Arg His Lys Asn Pro Lys Thr
            180                 185                 190

Gly Glu Tyr Glu Glu Lys His Leu Lys Ala Pro Pro Ala Ala Arg Thr
        195                 200                 205

Ser Lys Val Thr Ser Val Tyr Thr Leu Val Val Asn Pro Asp Gln Thr
    210                 215                 220

Phe Gln Ile Leu Ile Asp Gly Glu Ser Val Lys Glu Gly Ser Leu Leu
225                 230                 235                 240

Glu Asp Phe Asn Pro Pro Val Asn Pro Glu Lys Glu Ile Asp Asp Pro
                245                 250                 255

Lys Asp Lys Lys Pro Ala Asp Trp Val Asp Glu Ala Lys Ile Pro Asp
            260                 265                 270

Pro Glu Ala Thr Lys Pro Glu Asp Trp Asp Glu Ala Pro Phe Glu
        275                 280                 285

Ile Val Asp Glu Glu Ala Thr Ile Pro Glu Asp Trp Leu Glu Asp Glu
    290                 295                 300

Pro Thr Ser Ile Pro Asp Pro Glu Ala Glu Lys Pro Glu Asp Trp Asp
305                 310                 315                 320

Asp Glu Glu Asp Gly Asp Trp Val Pro Thr Val Pro Asn Pro Lys
                325                 330                 335

Cys Gln Asp Ala Ser Gly Cys Gly Pro Trp Ser Pro Met Lys Lys
            340                 345                 350

Asn Pro Asp Tyr Lys Gly Lys Trp Ser Ala Pro Leu Ile Asp Asn Pro
        355                 360                 365

Ala Tyr Lys Gly Pro Trp Ala Pro Arg Lys Ile Ala Asn Pro Ala Tyr
    370                 375                 380

Phe Glu Asp Lys Thr Pro Ser Asn Phe Glu Pro Met Gly Ala Ile Gly
385                 390                 395                 400
```

```
Phe Glu Ile Trp Thr Met Gln Asn Asp Ile Leu Phe Asp Asn Ile Tyr
            405                 410                 415

Val Gly His Ser Ala Glu Asp Ala Glu Lys Leu Arg Gln Glu Thr Phe
        420                 425                 430

Asp Val Lys His Pro Ile Glu Leu Ala Glu Glu Glu Ala Asn Lys Pro
                435                 440                 445

Lys Pro Glu Glu Lys Ala Ala Glu Pro Ser Val Ser Phe Lys Glu Asp
    450                 455                 460

Pro Val Gly His Ile Lys Glu Lys Val Asp Asn Phe Val Arg Leu Ser
465                 470                 475                 480

Lys Gln Asp Pro Ile Asn Ala Val Lys Gln Val Pro Val Ala Gly
            485                 490                 495

Gly Leu Ala Ala Val Leu Val Thr Met Ile Leu Val Ile Val Gly Ala
                500                 505                 510

Val Gly Ala Ser Thr Pro Ala Pro Ala Pro Ala Lys Lys Gly Lys Glu
        515                 520                 525

Ala Ala Gly Ala Thr Lys Glu Lys Thr Gly Ala Ala Ser Ser Ser Ser
    530                 535                 540

Ala Asp Thr Gly Lys Gly Gly Ala Thr Lys Arg Thr Thr Arg Ser Ser
545                 550                 555                 560

Ala Glu

<210> SEQ ID NO 13
<211> LENGTH: 2097
<212> TYPE: DNA
<213> ORGANISM: Aspergillus niger

<400> SEQUENCE: 13
gccgcggcgg tcgccgtacg taattcgtaa tcccgcatcg ggacacctca gcatctccgc      60
gcgtctttct cccctcgac tatcgccaat tcttccacct tccgtccatc ctctcgctca     120
tttctttctc cttgggacta tctcctggtg agtgtatagg tcctaggcgc ggtcgttgag     180
agaccgccca tctgcccact atgaggccgt ttaccgcact tgctgcgctg tgcggcttgt     240
tcctgtccag caacagcttg gtctatgccg actcggctcc ctcgagctcc cctgtagctc     300
tccctcgcga tttcaagcct ccccaagtgt ttaagaacgc caatcttgtc cgcaacacca     360
atttggagaa gggatacccta cgtgagaccg tcaatgttgt cgttgagaat gtggacaaga     420
agccgcagtc cgactactac ttgtccttcc catccgacct ttacgacaag gtcggtgccc     480
tagaagtccg tgataaatcg gctcctgaac agggacgctt cgaagtggaa gctactgagt     540
tcgactcaag caggtaagtc gaccacaatg gcggccaatg gctggttggt ggagcacgaa     600
gccacggttg cttgatctat gcatggtgga tgtatcccgg gcggtttgct gatctcctct     660
ctttctttac acagggactt ccagtacttc gttgttcacc tccccaagcc tctcgcccct     720
tcgtcgcaga tcactctggg catctcctac tccgccctca cacccctgaa gccccgtcct     780
gcggccatca gccagaatga tcgccagtac ctcgcctatg ccttctctgc ctacgctccc     840
tcggcttaca cgacaacgac ccagaagacc aagatcaagt tccccagcac caatgttccc     900
gactacacct ccacggacct gacgtcgggc gcggatccag agcgccaggg tgccacctac     960
acctacggac cctacgccga cgtcgctccc gagaccacct cccggccag tgtccggtac    1020 gagttcacca agcccgtcat cactgccact cttctggagc gtgacctgga agtgtcccac    1080
tggggcggca acctggcgac ggaagagcgc tactggctgc gcaacaacgg ctccaagctc    1140
accgacaact tcaaccgcgt ggaatggacc atcagcagct accagcagct gccgtcctcc    1200
```

-continued

```
gctatccgcg agctgaagat ccccctcaag cccggctccg tggacccota cttcaccgac      1260 gacattggca acgtttccac gagccgctac cgtcccggaa aggtcccgaa ccgtgacgcc      1320
tccctggagc ttcgtccccg gttccccatc ttcggcggat ggaactacag cttccgcatt      1380
ggctggaaca acgacctctc tgccttcctt cgcaaggctg tcaccggcgc tgattcctac      1440
gtcctcaagg tccccttcat cgagggcccc aaggtttccg agggtattca gtatgagaag      1500
gccgtcgtgc gcatcatcct ccccgagggt gcccggaacg tccgctacga gctcctcgag      1560
aaggcgacta gcaatggtct ccccggtgcg aaccagatcc agactgagct caccagccac      1620
aagactttca tggatcccct aggacgcacg gcgctgactt tgaccgtgga ggagttgact      1680
gatgaggccc gtgactcgca gatagtggta agtaactacc tccatacgcc ggatagatat      1740
cgggaatagt ccagctcatt tttggatata ggtcacttac gactactctc tgtgggatgg      1800
attgcgcaag cccgtgacca tcacggcggg gctgttcacc gtgtttgttg ccgcgtgggc      1860
gattggaaat attgacgtga gtattaagaa gcggtagatg gaggttgtat catattgttt      1920
cagttatacc agccagacag acagacagaa ttcaatagta gctgtttgta gacgactaga      1980
attctgatag tgtgatttcg aatgattccc tccttgaata atatggagac agtctgatgc      2040
agagtggtct ttgcaccagg tagtaagtgg gctatcggtt gtcagcgtca cctgaca        2097
```

<210> SEQ ID NO 14
<211> LENGTH: 1512
<212> TYPE: DNA
<213> ORGANISM: Aspergillus niger
<220> FEATURE:
<221> NAME/KEY: CDS
<222> LOCATION: (1)..(1512)

<400> SEQUENCE: 14

```
atg agg ccg ttt acc gca ctt gct gcg ctg tgc ggc ttg ttc ctg tcc        48
Met Arg Pro Phe Thr Ala Leu Ala Ala Leu Cys Gly Leu Phe Leu Ser
1               5                   10                  15 agc aac agc ttg gtc tat gcc gac tcg gct ccc tcg agc tcc cct gta        96
Ser Asn Ser Leu Val Tyr Ala Asp Ser Ala Pro Ser Ser Ser Pro Val
            20                  25                  30 gct ctc cct cgc gat ttc aag cct ccc caa gtg ttt aag aac gcc aat       144
Ala Leu Pro Arg Asp Phe Lys Pro Pro Gln Val Phe Lys Asn Ala Asn
        35                  40                  45 ctt gtc cgc aac acc aat ttg gag aag gga tac cta cgt gag acc gtc       192
Leu Val Arg Asn Thr Asn Leu Glu Lys Gly Tyr Leu Arg Glu Thr Val
    50                  55                  60 aat gtt gtc gtt gag aat gtg gac aag aag ccg cag tcc gac tac tac       240
Asn Val Val Val Glu Asn Val Asp Lys Lys Pro Gln Ser Asp Tyr Tyr
65                  70                  75                  80 ttg tcc ttc cca tcc gac ctt tac gac aag gtc ggt gcc cta gaa gtc       288
Leu Ser Phe Pro Ser Asp Leu Tyr Asp Lys Val Gly Ala Leu Glu Val
                85                  90                  95 cgt gat aaa tcg gct cct gaa cag gga cgc ttc gaa gtg gaa gct act       336
Arg Asp Lys Ser Ala Pro Glu Gln Gly Arg Phe Glu Val Glu Ala Thr
            100                 105                 110 gag ttc gac tca agc agg gac ttc cag tac ttc gtt gtt cac ctc ccc       384
Glu Phe Asp Ser Ser Arg Asp Phe Gln Tyr Phe Val Val His Leu Pro
        115                 120                 125 aag cct ctc gcc cct tcg tcg cag atc act ctg ggc atc tcc tac tcc       432
Lys Pro Leu Ala Pro Ser Ser Gln Ile Thr Leu Gly Ile Ser Tyr Ser
    130                 135                 140 gcc ctc aac acc ctg aag ccc cgt cct gcg gcc atc agc cag aat gat       480
Ala Leu Asn Thr Leu Lys Pro Arg Pro Ala Ala Ile Ser Gln Asn Asp
145                 150                 155                 160
```

```
cgc cag tac ctc gcc tat gcc ttc tct gcc tac gct ccc tcg gct tac    528
Arg Gln Tyr Leu Ala Tyr Ala Phe Ser Ala Tyr Ala Pro Ser Ala Tyr
            165                 170                 175 acg aca acg acc cag aag acc aag atc aag ttc ccc agc acc aat gtt    576
Thr Thr Thr Thr Gln Lys Thr Lys Ile Lys Phe Pro Ser Thr Asn Val
        180                 185                 190 ccc gac tac acc tcc acg gac ctg acg tcg ggc gcg gat cca gag cgc    624
Pro Asp Tyr Thr Ser Thr Asp Leu Thr Ser Gly Ala Asp Pro Glu Arg
            195                 200                 205 cag ggt gcc acc tac acc tac gga ccc tac gcc gac gtc gct ccc gag    672
Gln Gly Ala Thr Tyr Thr Tyr Gly Pro Tyr Ala Asp Val Ala Pro Glu
        210                 215                 220 acc acc tac ccg gcc agt gtc cgg tac gag ttc acc aag ccc gtc atc    720
Thr Thr Tyr Pro Ala Ser Val Arg Tyr Glu Phe Thr Lys Pro Val Ile
225                 230                 235                 240 act gcc act ctt ctg gag cgt gac ctg gaa gtg tcc cac tgg ggc ggc    768
Thr Ala Thr Leu Leu Glu Arg Asp Leu Glu Val Ser His Trp Gly Gly
            245                 250                 255 aac ctg gcg acg gaa gag cgc tac tgg ctg cgc aac aac ggc tcc aag    816
Asn Leu Ala Thr Glu Glu Arg Tyr Trp Leu Arg Asn Asn Gly Ser Lys
        260                 265                 270 ctc acc gac aac ttc aac cgc gtg gaa tgg acc atc agc agc tac cag    864
Leu Thr Asp Asn Phe Asn Arg Val Glu Trp Thr Ile Ser Ser Tyr Gln
            275                 280                 285 cag ctg ccg tcc tcc gct atc cgc gag ctg aag atc ccc ctc aag ccc    912
Gln Leu Pro Ser Ser Ala Ile Arg Glu Leu Lys Ile Pro Leu Lys Pro
        290                 295                 300 ggc tcc gtg gac ccc tac ttc acc gac gac att ggc aac gtt tcc acg    960
Gly Ser Val Asp Pro Tyr Phe Thr Asp Asp Ile Gly Asn Val Ser Thr
305                 310                 315                 320 agc cgc tac cgt ccc gga aag gtc ccg aac cgt gac gcc tcc ctg gag   1008
Ser Arg Tyr Arg Pro Gly Lys Val Pro Asn Arg Asp Ala Ser Leu Glu
            325                 330                 335 ctt cgt ccc cgg ttc ccc atc ttc ggc gga tgg aac tac agc ttc cgc   1056
Leu Arg Pro Arg Phe Pro Ile Phe Gly Gly Trp Asn Tyr Ser Phe Arg
        340                 345                 350 att ggc tgg aac aac gac ctc tct gcc ttc ctt cgc aag gct gtc acc   1104
Ile Gly Trp Asn Asn Asp Leu Ser Ala Phe Leu Arg Lys Ala Val Thr
            355                 360                 365 ggc gct gat tcc tac gtc ctc aag gtc ccc ttc atc gag ggc ccc aag   1152
Gly Ala Asp Ser Tyr Val Leu Lys Val Pro Phe Ile Glu Gly Pro Lys
        370                 375                 380 gtt tcc gag ggt att cag tat gag aag gcc gtc gtg cgc atc atc ctc   1200
Val Ser Glu Gly Ile Gln Tyr Glu Lys Ala Val Val Arg Ile Ile Leu
385                 390                 395                 400 ccc gag ggt gcc cgg aac gtc cgc tac gag ctc ctc gag aag gcg act   1248
Pro Glu Gly Ala Arg Asn Val Arg Tyr Glu Leu Leu Glu Lys Ala Thr
            405                 410                 415 agc aat ggt ctc ccc ggt gcg aac cag atc cag act gag ctc acc agc   1296
Ser Asn Gly Leu Pro Gly Ala Asn Gln Ile Gln Thr Glu Leu Thr Ser
        420                 425                 430 cac aag act ttc atg gat acc cta gga cgc acg gcg ctg act ttg acc   1344
His Lys Thr Phe Met Asp Thr Leu Gly Arg Thr Ala Leu Thr Leu Thr
            435                 440                 445 gtg gag gag ttg act gat gag gcc cgt gac tcg cag ata gtg gtc act   1392
Val Glu Glu Leu Thr Asp Glu Ala Arg Asp Ser Gln Ile Val Val Thr
        450                 455                 460 tac gac tac tct ctg tgg gat gga ttg cgc aag ccc gtg acc atc acg   1440
Tyr Asp Tyr Ser Leu Trp Asp Gly Leu Arg Lys Pro Val Thr Ile Thr
465                 470                 475                 480
```

```
gcg ggg ctg ttc acc gtg ttt gtt gcc gcg tgg gcg att gga aat att    1488
Ala Gly Leu Phe Thr Val Phe Val Ala Ala Trp Ala Ile Gly Asn Ile
                    485                 490                 495 gac gtg agt att aag aag cgg tag                                    1512
Asp Val Ser Ile Lys Lys Arg
                500
```

<210> SEQ ID NO 15
<211> LENGTH: 503
<212> TYPE: PRT
<213> ORGANISM: Aspergillus niger

<400> SEQUENCE: 15

```
Met Arg Pro Phe Thr Ala Leu Ala Ala Leu Cys Gly Leu Phe Leu Ser
1               5                   10                  15

Ser Asn Ser Leu Val Tyr Ala Asp Ser Ala Pro Ser Ser Pro Val
            20                  25                  30

Ala Leu Pro Arg Asp Phe Lys Pro Pro Gln Val Phe Lys Asn Ala Asn
        35                  40                  45

Leu Val Arg Asn Thr Asn Leu Glu Lys Gly Tyr Leu Arg Glu Thr Val
50                  55                  60

Asn Val Val Glu Asn Val Asp Lys Lys Pro Gln Ser Asp Tyr Tyr
65              70                  75                  80

Leu Ser Phe Pro Ser Asp Leu Tyr Asp Lys Val Gly Ala Leu Glu Val
                85                  90                  95

Arg Asp Lys Ser Ala Pro Glu Gln Gly Arg Phe Glu Val Glu Ala Thr
            100                 105                 110

Glu Phe Asp Ser Ser Arg Asp Phe Gln Tyr Phe Val Val His Leu Pro
        115                 120                 125

Lys Pro Leu Ala Pro Ser Ser Gln Ile Thr Leu Gly Ile Ser Tyr Ser
130                 135                 140

Ala Leu Asn Thr Leu Lys Pro Arg Pro Ala Ala Ile Ser Gln Asn Asp
145                 150                 155                 160

Arg Gln Tyr Leu Ala Tyr Ala Phe Ser Ala Tyr Ala Pro Ser Ala Tyr
                165                 170                 175

Thr Thr Thr Thr Gln Lys Thr Lys Ile Lys Phe Pro Ser Thr Asn Val
            180                 185                 190

Pro Asp Tyr Thr Ser Thr Asp Leu Thr Ser Gly Ala Asp Pro Glu Arg
        195                 200                 205

Gln Gly Ala Thr Tyr Thr Tyr Gly Pro Tyr Ala Asp Val Ala Pro Glu
    210                 215                 220

Thr Thr Tyr Pro Ala Ser Val Arg Tyr Glu Phe Thr Lys Pro Val Ile
225                 230                 235                 240

Thr Ala Thr Leu Leu Glu Arg Asp Leu Glu Val Ser His Trp Gly Gly
                245                 250                 255

Asn Leu Ala Thr Glu Glu Arg Tyr Trp Leu Arg Asn Asn Gly Ser Lys
            260                 265                 270

Leu Thr Asp Asn Phe Asn Arg Val Glu Trp Thr Ile Ser Ser Tyr Gln
        275                 280                 285

Gln Leu Pro Ser Ser Ala Ile Arg Glu Leu Lys Ile Pro Leu Lys Pro
    290                 295                 300

Gly Ser Val Asp Pro Tyr Phe Thr Asp Ile Gly Asn Val Ser Thr
305                 310                 315                 320

Ser Arg Tyr Arg Pro Gly Lys Val Pro Asn Arg Asp Ala Ser Leu Glu
                325                 330                 335
```

Leu Arg Pro Arg Phe Pro Ile Phe Gly Gly Trp Asn Tyr Ser Phe Arg
        340                 345                 350

Ile Gly Trp Asn Asn Asp Leu Ser Ala Phe Leu Arg Lys Ala Val Thr
            355                 360                 365

Gly Ala Asp Ser Tyr Val Leu Lys Val Pro Phe Ile Glu Gly Pro Lys
        370                 375                 380

Val Ser Glu Gly Ile Gln Tyr Glu Lys Ala Val Arg Ile Ile Leu
385                 390                 395                 400

Pro Glu Gly Ala Arg Asn Val Arg Tyr Glu Leu Leu Glu Lys Ala Thr
                405                 410                 415

Ser Asn Gly Leu Pro Gly Ala Asn Gln Ile Gln Thr Glu Leu Thr Ser
            420                 425                 430

His Lys Thr Phe Met Asp Thr Leu Gly Arg Thr Ala Leu Thr Leu Thr
        435                 440                 445

Val Glu Glu Leu Thr Asp Glu Ala Arg Asp Ser Gln Ile Val Val Thr
450                 455                 460

Tyr Asp Tyr Ser Leu Trp Asp Gly Leu Arg Lys Pro Val Thr Ile Thr
465                 470                 475                 480

Ala Gly Leu Phe Thr Val Phe Val Ala Ala Trp Ala Ile Gly Asn Ile
            485                 490                 495

Asp Val Ser Ile Lys Lys Arg
            500

<210> SEQ ID NO 16
<211> LENGTH: 2212
<212> TYPE: DNA
<213> ORGANISM: Aspergillus niger

<400> SEQUENCE: 16
cttttctctt tcggtagctt ctgctctacg cgtcacctgc cttcctctct ctccccaccc        60
ctctccctcc aaacgggccg gtctattatt tgttttcatt gactttcgag gatctccccg       120
gaagccactg gaaaagcaga tatccattta ataccctct cccatcgtcc tctattccgc       180
tgctgcttct ttattacaag atgcgctcct tcgcgcttg gctcgttagc cttctcggag       240
catccgcggt ggttgcggct gctgataccg agtctgatgt tatttcactg gatcaggaca       300
catttgagag cttcatgaac gagcacggtc tcgtgcttgc cgaattcttt gctccttggt       360
gtggccactg taaagccctc gcaccaaagt atgaggaagc agctacggag ctcaaggcga       420
agaatatccc tctggtgaag gttgactgca ccgccgagga ggatctctgc cggagtcagg       480
gcgttgaagg ctaccctacc ctcaagatct tcggggtgt tgactctagc aagccttacc       540
agggcgctag gcaaacagaa tcgtgagtcc tcttggtttt gactggacga agaaatgga       600 tatgcatcaa aaggctatcg tgtatgtgat gtgctactga cccatcggac ggtttcccag       660
aatcgtttcc tacatgatta agcagtcact cctgcagta tcctccgtga acgaggagaa       720
tttagaagag atcaagacca tggacaagat tgtcgtgatc ggttatatcc cgtccgagga       780
ccaggaaact tatcaagcat tcgaaaaata tgctgagtct cagcgggata actacctctt       840
tgctgccacg gacgatgccg ccattgcgaa atcggaaggt gtcgagcagc cctccatcgt       900
gctctataag gacttcgatg agaagaaggc tgtttacgat ggcgagatcg aacaggaggc       960
tattcacagc tgggtgaaat ccgctagtac tccccttgtg ggcgagattg gcctgagac      1020 ctactctggc tatattgggg taagttgaat ctatacgtcg acgtgacatc tctttgcatt      1080
tcggcttgag tttcgatacc aatttgctgg ctgaactggc taaccacttt tcttataggc      1140
tggagtccca ttggcctata tctttgccga gaccaaggag gagcgcgaaa agtacaccga      1200

-continued

```
agacttcaag cctattgccc agaagcacaa gggtgctatc aacattgcta ctattgacgc   1260
caagatgttc ggtgcccacg ctggaaacct caacctagac tctcagaagt tcccggcatt   1320
cgccatccag gatcccgcaa agaacgccaa ataccctat gaccaggcca aggaattgaa    1380
tgccgacgag gttgaaaagt tcatccagga tgttctggat gggaaggtcg agcctagcat   1440
caagtcggaa cctgttcccg aatctcagga gggccccgtc acggttgtag tggcccattc   1500
ctacaaggat ctcgtcattg acaatgacaa ggatgtcttg ctcgaattct acgcaccttg   1560
gtgtggacac tgcaaagcgt atgtctcttc gatccctaa gtacactagg tgttggagca    1620
caatcaacta acagcaaatc tatagtcttg ctccgaagta cgatgagctc gcagctctct   1680
atgctgacca ccccgatttg gcggctaagg tcaccatcgc taagatcgat gcgacggcca   1740
acgatgttcc ggacccgatt accggattcc ctaccctcag actctacccg gccggtgcca   1800
aggactcccc cattgagtac tctggctcgc gcactgtcga ggatcttgcc aactttgtga   1860
aggagaatgg caaacacaac gttgacgccc tcaatgtcgc ttccgaggaa acacaggagg   1920
gtggtgatgt gactgaggct gctccctccg ctacggaggc cgagaccccg gctgccacag   1980
atgacgagaa ggcagaacat gacgaactgt aaacagtctc ccaattgaga tcccgcttag   2040
tgctgtgccg tatcaatcac taattatttg gaacttcgtt tctctattgt taacttttgt   2100
aatctctgga ccaatctgtt gttggttgaa ttagctaaat tggaccagtt tctatatggc   2160
cagacaatgt gatgaatata aatttgctc cacgcatgtc tacctcgttc ca            2212

<210> SEQ ID NO 17
<211> LENGTH: 1548
<212> TYPE: DNA
<213> ORGANISM: Aspergillus niger
<220> FEATURE:
<221> NAME/KEY: CDS
<222> LOCATION: (1)..(1548)

<400> SEQUENCE: 17 atg cgc tcc ttc gcg cct tgg ctc gtt agc ctt ctc gga gca tcc gcg      48
Met Arg Ser Phe Ala Pro Trp Leu Val Ser Leu Leu Gly Ala Ser Ala
1               5                   10                  15 gtg gtt gcg gct gct gat acc gag tct gat gtt att tca ctg gat cag      96
Val Val Ala Ala Ala Asp Thr Glu Ser Asp Val Ile Ser Leu Asp Gln
            20                  25                  30 gac aca ttt gag agc ttc atg aac gag cac ggt ctc gtg ctt gcc gaa     144
Asp Thr Phe Glu Ser Phe Met Asn Glu His Gly Leu Val Leu Ala Glu
        35                  40                  45 ttc ttt gct cct tgg tgt ggc cac tgt aaa gcc ctc gca cca aag tat     192
Phe Phe Ala Pro Trp Cys Gly His Cys Lys Ala Leu Ala Pro Lys Tyr
    50                  55                  60 gag gaa gca gct acg gag ctc aag gcg aag aat atc cct ctg gtg aag     240
Glu Glu Ala Ala Thr Glu Leu Lys Ala Lys Asn Ile Pro Leu Val Lys
65                  70                  75                  80 gtt gac tgc acc gcc gag gag gat ctc tgc cgg agt cag ggc gtt gaa     288
Val Asp Cys Thr Ala Glu Glu Asp Leu Cys Arg Ser Gln Gly Val Glu
                85                  90                  95 ggc tac cct acc ctc aag atc ttt cgg ggt gtt gac tct agc aag cct     336
Gly Tyr Pro Thr Leu Lys Ile Phe Arg Gly Val Asp Ser Ser Lys Pro
            100                 105                 110 tac cag ggc gct agg caa aca gaa tca atc gtt tcc tac atg att aag     384
Tyr Gln Gly Ala Arg Gln Thr Glu Ser Ile Val Ser Tyr Met Ile Lys
        115                 120                 125 cag tca ctt cct gca gta tcc tcc gtg aac gag gag aat tta gaa gag     432
Gln Ser Leu Pro Ala Val Ser Ser Val Asn Glu Glu Asn Leu Glu Glu
```

```
                130                 135                 140
atc aag acc atg gac aag att gtc gtg atc ggt tat atc ccg tcc gag    480
Ile Lys Thr Met Asp Lys Ile Val Val Ile Gly Tyr Ile Pro Ser Glu
145                 150                 155                 160 gac cag gaa act tat caa gca ttc gaa aaa tat gct gag tct cag cgg    528
Asp Gln Glu Thr Tyr Gln Ala Phe Glu Lys Tyr Ala Glu Ser Gln Arg
                165                 170                 175 gat aac tac ctc ttt gct gcc acg gac gat gcc gcc att gcg aaa tcg    576
Asp Asn Tyr Leu Phe Ala Ala Thr Asp Asp Ala Ala Ile Ala Lys Ser
            180                 185                 190 gaa ggt gtc gag cag ccc tcc atc gtg ctc tat aag gac ttc gat gag    624
Glu Gly Val Glu Gln Pro Ser Ile Val Leu Tyr Lys Asp Phe Asp Glu
        195                 200                 205 aag aag gct gtt tac gat ggc gag atc gaa cag gag gct att cac agc    672
Lys Lys Ala Val Tyr Asp Gly Glu Ile Glu Gln Glu Ala Ile His Ser
    210                 215                 220 tgg gtg aaa tcc gct agt act ccc ctt gtg ggc gag att ggc cct gag    720
Trp Val Lys Ser Ala Ser Thr Pro Leu Val Gly Glu Ile Gly Pro Glu
225                 230                 235                 240 acc tac tct ggc tat att ggg gct gga gtc cca ttg gcc tat atc ttt    768
Thr Tyr Ser Gly Tyr Ile Gly Ala Gly Val Pro Leu Ala Tyr Ile Phe
                245                 250                 255 gcc gag acc aag gag gag cgc gaa aag tac acc gaa gac ttc aag cct    816
Ala Glu Thr Lys Glu Glu Arg Glu Lys Tyr Thr Glu Asp Phe Lys Pro
            260                 265                 270 att gcc cag aag cac aag ggt gct atc aac att gct act att gac gcc    864
Ile Ala Gln Lys His Lys Gly Ala Ile Asn Ile Ala Thr Ile Asp Ala
        275                 280                 285 aag atg ttc ggt gcc cac gct gga aac ctc aac cta gac tct cag aag    912
Lys Met Phe Gly Ala His Ala Gly Asn Leu Asn Leu Asp Ser Gln Lys
    290                 295                 300 ttc ccg gca ttc gcc atc cag gat ccc gca aag aac gcc aaa tac ccc    960
Phe Pro Ala Phe Ala Ile Gln Asp Pro Ala Lys Asn Ala Lys Tyr Pro
305                 310                 315                 320 tat gac cag gcc aag gaa ttg aat gcc gac gag gtt gaa aag ttc atc    1008
Tyr Asp Gln Ala Lys Glu Leu Asn Ala Asp Glu Val Glu Lys Phe Ile
                325                 330                 335 cag gat gtt ctg gat ggg aag gtc gag cct agc atc aag tcg gaa cct    1056
Gln Asp Val Leu Asp Gly Lys Val Glu Pro Ser Ile Lys Ser Glu Pro
            340                 345                 350 gtt ccc gaa tct cag gag ggc ccc gtc acg gtt gta gtg gcc cat tcc    1104
Val Pro Glu Ser Gln Glu Gly Pro Val Thr Val Val Val Ala His Ser
        355                 360                 365 tac aag gat ctc gtc att gac aat gac aag gat gtc ttg ctc gaa ttc    1152
Tyr Lys Asp Leu Val Ile Asp Asn Asp Lys Asp Val Leu Leu Glu Phe
    370                 375                 380 tac gca cct tgg tgt gga cac tgc aaa gct ctt gct ccg aag tac gat    1200
Tyr Ala Pro Trp Cys Gly His Cys Lys Ala Leu Ala Pro Lys Tyr Asp
385                 390                 395                 400 gag ctc gca gct ctc tat gct gac cac ccc gat ttg gcg gct aag gtc    1248
Glu Leu Ala Ala Leu Tyr Ala Asp His Pro Asp Leu Ala Ala Lys Val
                405                 410                 415 acc atc gct aag atc gat gcg acg gcc aac gat gtt ccg gac ccg att    1296
Thr Ile Ala Lys Ile Asp Ala Thr Ala Asn Asp Val Pro Asp Pro Ile
            420                 425                 430 acc gga ttc cct acc ctc aga ctc tac ccg gcc ggt gcc aag gac tcc    1344
Thr Gly Phe Pro Thr Leu Arg Leu Tyr Pro Ala Gly Ala Lys Asp Ser
        435                 440                 445 ccc att gag tac tct ggc tcg cgc act gtc gag gat ctt gcc aac ttt    1392
Pro Ile Glu Tyr Ser Gly Ser Arg Thr Val Glu Asp Leu Ala Asn Phe
```

```
                450                 455                 460
gtg aag gag aat ggc aaa cac aac gtt gac gcc ctc aat gtc gct tcc      1440
Val Lys Glu Asn Gly Lys His Asn Val Asp Ala Leu Asn Val Ala Ser
465                 470                 475                 480 gag gaa aca cag gag ggt ggt gat gtg act gag gct gct ccc tcc gct      1488
Glu Glu Thr Gln Glu Gly Gly Asp Val Thr Glu Ala Ala Pro Ser Ala
                485                 490                 495 acg gag gcc gag acc ccg gct gcc aca gat gac gag aag gca gaa cat      1536
Thr Glu Ala Glu Thr Pro Ala Ala Thr Asp Asp Glu Lys Ala Glu His
            500                 505                 510 gac gaa ctg taa                                                      1548
Asp Glu Leu
        515

<210> SEQ ID NO 18
<211> LENGTH: 515
<212> TYPE: PRT
<213> ORGANISM: Aspergillus niger

<400> SEQUENCE: 18

Met Arg Ser Phe Ala Pro Trp Leu Val Ser Leu Leu Gly Ala Ser Ala
1               5                   10                  15

Val Val Ala Ala Ala Asp Thr Glu Ser Asp Val Ile Ser Leu Asp Gln
                20                  25                  30

Asp Thr Phe Glu Ser Phe Met Asn Glu His Gly Leu Val Leu Ala Glu
            35                  40                  45

Phe Phe Ala Pro Trp Cys Gly His Cys Lys Ala Leu Ala Pro Lys Tyr
        50                  55                  60

Glu Glu Ala Ala Thr Glu Leu Lys Ala Lys Asn Ile Pro Leu Val Lys
65                  70                  75                  80

Val Asp Cys Thr Ala Glu Glu Asp Leu Cys Arg Ser Gln Gly Val Glu
                85                  90                  95

Gly Tyr Pro Thr Leu Lys Ile Phe Arg Gly Val Asp Ser Ser Lys Pro
            100                 105                 110

Tyr Gln Gly Ala Arg Gln Thr Glu Ser Ile Val Ser Tyr Met Ile Lys
        115                 120                 125

Gln Ser Leu Pro Ala Val Ser Ser Val Asn Glu Glu Asn Leu Glu Glu
    130                 135                 140

Ile Lys Thr Met Asp Lys Ile Val Val Ile Gly Tyr Ile Pro Ser Glu
145                 150                 155                 160

Asp Gln Glu Thr Tyr Gln Ala Phe Glu Lys Tyr Ala Glu Ser Gln Arg
                165                 170                 175

Asp Asn Tyr Leu Phe Ala Ala Thr Asp Asp Ala Ala Ile Ala Lys Ser
            180                 185                 190

Glu Gly Val Glu Gln Pro Ser Ile Val Leu Tyr Lys Asp Phe Asp Glu
        195                 200                 205

Lys Lys Ala Val Tyr Asp Gly Glu Ile Glu Gln Glu Ala Ile His Ser
    210                 215                 220

Trp Val Lys Ser Ala Ser Thr Pro Leu Val Gly Glu Ile Gly Pro Glu
225                 230                 235                 240

Thr Tyr Ser Gly Tyr Ile Gly Ala Gly Val Pro Leu Ala Tyr Ile Phe
                245                 250                 255

Ala Glu Thr Lys Glu Glu Arg Glu Lys Tyr Thr Glu Asp Phe Lys Pro
            260                 265                 270

Ile Ala Gln Lys His Lys Gly Ala Ile Asn Ile Ala Thr Ile Asp Ala
        275                 280                 285
```

```
Lys Met Phe Gly Ala His Ala Gly Asn Leu Asn Leu Asp Ser Gln Lys
        290                 295                 300
Phe Pro Ala Phe Ala Ile Gln Asp Pro Ala Lys Asn Ala Lys Tyr Pro
305                 310                 315                 320
Tyr Asp Gln Ala Lys Glu Leu Asn Ala Asp Glu Val Glu Lys Phe Ile
                325                 330                 335
Gln Asp Val Leu Asp Gly Lys Val Glu Pro Ser Ile Lys Ser Glu Pro
            340                 345                 350
Val Pro Glu Ser Gln Glu Gly Pro Val Thr Val Val Ala His Ser
        355                 360                 365
Tyr Lys Asp Leu Val Ile Asp Asn Asp Lys Asp Val Leu Leu Glu Phe
    370                 375                 380
Tyr Ala Pro Trp Cys Gly His Cys Lys Ala Leu Ala Pro Lys Tyr Asp
385                 390                 395                 400
Glu Leu Ala Ala Leu Tyr Ala Asp His Pro Asp Leu Ala Ala Lys Val
                405                 410                 415
Thr Ile Ala Lys Ile Asp Ala Thr Ala Asn Asp Val Pro Asp Pro Ile
            420                 425                 430
Thr Gly Phe Pro Thr Leu Arg Leu Tyr Pro Ala Gly Ala Lys Asp Ser
        435                 440                 445
Pro Ile Glu Tyr Ser Gly Ser Arg Thr Val Glu Asp Leu Ala Asn Phe
    450                 455                 460
Val Lys Glu Asn Gly Lys His Asn Val Asp Ala Leu Asn Val Ala Ser
465                 470                 475                 480
Glu Glu Thr Gln Glu Gly Gly Asp Val Thr Ala Ala Pro Ser Ala
                485                 490                 495
Thr Glu Ala Glu Thr Pro Ala Ala Thr Asp Asp Glu Lys Ala Glu His
            500                 505                 510
Asp Glu Leu
        515

<210> SEQ ID NO 19
<211> LENGTH: 2113
<212> TYPE: DNA
<213> ORGANISM: Aspergillus niger

<400> SEQUENCE: 19
cccgcaatcc ccgtcgacct catcgcttcc tccctttctc ctccatcctc tctctcttcc      60
gtcgtctttt cttcttctcc ttctcctttt gtacttcccc tccattcctt cagctggttc     120
tcgcctccag ctttcctttc tttctttccc tcccctttta ttcgagtaat cctgcagctc     180
tgggaggtgc aacagtcaca atgagcggac gtgagtcttg cacgcgatcg ctgccatctc     240
cgcgacagcg ttccatcctt tacctcaatg gatcagcaaa tgctgatact cgattctagt     300
ccggtttctc gatctcatca agcccttcac gcccctcctc ccggaggtgg ccgcccggga     360
aaccaaggtt cccttcaacc agaagttgat gtggacgggg gtacgtgata cttgtccagc     420
tcgacatgag cttctaagct aatggattac ccctgcagtt gacccctattg atcttcctgg    480
tcatgagcca gatgcccttg tacgaattg tctcctctga cacctccgac cctctgtact      540
ggctccgtat gatgttggcc agtaaccggg taccctgat ggaactgggt atcacccca       600
tcatctcctc tggcatggtt ttccaggtat gtaatgggaa aattgcaatc tgatcacgga     660
tatcgggcat ttgctaatat gtggcttttg tctgatagct tctcgctggt acccacctca    720
tcgatgtcaa cctggacctg aagaccgacc gtgaactgta tcagaccgct cagaagctct     780
tcgctatcat cctgtccttc ggtcaggcct gcgtctacgt cctcactggt ctttacggcc     840
```

```
agcccagtga ccttggtgcc ggtatctgtg ttctgctgat tgttcagctg gtcgttgctg      900
gcttggttgt catcctgctg gatgagctgc tccagaaggg ctatggtctt ggtagcggta      960
tctctctgtt catcgcgacc aacatctgcg agtcgatcgt ctggaaggct ttctctccta     1020
cgaccatcaa cactggccgt ggtcccgagt ttgagggtgc catcattgcc ctcttccacc     1080
ttctgttgac ctggtccgac aagcagcgcg ctctccgcga ggctttctac cgccagaacc     1140
tccccaacat catgaacctg ctggctactc tcctcgtttt cgccgctgtg atctacctcc     1200
agggcttccg tgttgagatc cctgtcaagt cctcccgcca gcgtggcatg cgtggttcct     1260
accctgttcg cctgttctac acctccaaca tgcccatcat gcttcagtct gctctgtgct     1320
ccaacatctt cctcatcagt cagatgctgt actctcgctt ctctgacaac ctccttgtca     1380
agcttctcgg tgtttgggag cctcgtgagg ttctgccca gctccacgcc gctccggca     1440 ttgcctacta catgtctcct cccctgaact tcaaggaggc ccttcttgac cccattcaca     1500
ccgccgttta catcacctc atgctggttg cttgtgctct cttctccaag acctggattg     1560
aggtttccgg ctctgctccc cgcgatgttg ccaagcagct caaggaccag gtctcgtga     1620 tggctggtca ccgtgagcag agcatgtaca aggagctcaa cgcgcgtcatc cctactgctg     1680 ctgctttcgg tggtgcctgc attggtgccc tgtccgtcgc ttctgacctg cttggtgctc     1740
ttggcagcga tactggtatc ctccttgccg ttacgtaagt cttcactttg gtctcagatt     1800
ttctgaagtg gatactaaca ttcaaatgca ggattatata cggatacttt gaaattgccg     1860
cccgtgaggc cgacattgga tcgggcctca agggccttgt tccgggtaac tagataaggc     1920 ccccttttg atgaaagcat gagaagaagt ttgagggctt atgtttgttc ttgcaacttt     1980
ctgtttcttc tcaggtagtg tgctgttgtg gctgggatct ggattattta gtttcttgat     2040
ggatgtatgg ctagttttaa caatttgcag gaggggaaga tcttctctac ggagatacgt     2100
ccacgccaca gct                                                       2113
```

<210> SEQ ID NO 20
<211> LENGTH: 1437
<212> TYPE: DNA
<213> ORGANISM: Aspergillus niger
<220> FEATURE:
<221> NAME/KEY: CDS
<222> LOCATION: (1)..(1437)

<400> SEQUENCE: 20

```
atg agc gga ctc cgg ttt ctc gat ctc atc aag ccc ttc acg ccc ctc       48
Met Ser Gly Leu Arg Phe Leu Asp Leu Ile Lys Pro Phe Thr Pro Leu
1               5                   10                  15 ctc ccg gag gtg gcc gcc ccg gaa acc aag gtt ccc ttc aac cag aag       96
Leu Pro Glu Val Ala Ala Pro Glu Thr Lys Val Pro Phe Asn Gln Lys
            20                  25                  30 ttg atg tgg acg ggg ttg acc cta ttg atc ttc ctg gtc atg agc cag      144
Leu Met Trp Thr Gly Leu Thr Leu Leu Ile Phe Leu Val Met Ser Gln
        35                  40                  45 atg ccc ttg tac gga att gtc tcc tct gac acc tcc gac cct ctg tac      192
Met Pro Leu Tyr Gly Ile Val Ser Ser Asp Thr Ser Asp Pro Leu Tyr
    50                  55                  60 tgg ctc cgt atg atg ttg gcc agt aac cgg ggt acc ctg atg gaa ctg      240
Trp Leu Arg Met Met Leu Ala Ser Asn Arg Gly Thr Leu Met Glu Leu
65                  70                  75                  80 ggt atc acc ccc atc atc tcc tct ggc atg gtt ttc cag ctt ctc gct      288
Gly Ile Thr Pro Ile Ile Ser Ser Gly Met Val Phe Gln Leu Leu Ala
                85                  90                  95
```

| | | |
|---|---|---|
| ggt acc cac ctc atc gat gtc aac ctg gac ctg aag acc gac cgt gaa<br>Gly Thr His Leu Ile Asp Val Asn Leu Asp Leu Lys Thr Asp Arg Glu<br>                100                    105                    110 | | 336 |
| ctg tat cag acc gct cag aag ctc ttc gct atc atc ctg tcc ttc ggt<br>Leu Tyr Gln Thr Ala Gln Lys Leu Phe Ala Ile Ile Leu Ser Phe Gly<br>        115                    120                    125 | | 384 |
| cag gcc tgc gtc tac gtc ctc act ggt ctt tac ggc cag ccc agt gac<br>Gln Ala Cys Val Tyr Val Leu Thr Gly Leu Tyr Gly Gln Pro Ser Asp<br>130                    135                    140 | | 432 |
| ctt ggt gcc ggt atc tgt gtt ctg ctg att gtt cag ctg gtc gtt gct<br>Leu Gly Ala Gly Ile Cys Val Leu Leu Ile Val Gln Leu Val Val Ala<br>145                    150                    155                    160 | | 480 |
| ggc ttg gtt gtc atc ctg ctg gat gag ctg ctc cag aag ggc tat ggt<br>Gly Leu Val Val Ile Leu Leu Asp Glu Leu Leu Gln Lys Gly Tyr Gly<br>                165                    170                    175 | | 528 |
| ctt ggt agc ggt atc tct ctg ttc atc gcg acc aac atc tgc gag tcg<br>Leu Gly Ser Gly Ile Ser Leu Phe Ile Ala Thr Asn Ile Cys Glu Ser<br>        180                    185                    190 | | 576 |
| atc gtc tgg aag gct ttc tct cct acg acc atc aac act ggc cgt ggt<br>Ile Val Trp Lys Ala Phe Ser Pro Thr Thr Ile Asn Thr Gly Arg Gly<br>                195                    200                    205 | | 624 |
| ccc gag ttt gag ggt gcc atc att gcc ctc ttc cac ctt ctg ttg acc<br>Pro Glu Phe Glu Gly Ala Ile Ile Ala Leu Phe His Leu Leu Leu Thr<br>210                    215                    220 | | 672 |
| tgg tcc gac aag cag cgc gct ctc cgc gag gct ttc tac cgc cag aac<br>Trp Ser Asp Lys Gln Arg Ala Leu Arg Glu Ala Phe Tyr Arg Gln Asn<br>225                    230                    235                    240 | | 720 |
| ctc ccc aac atc atg aac ctg ctg gct act ctc ctc gtt ttc gcc gct<br>Leu Pro Asn Ile Met Asn Leu Leu Ala Thr Leu Leu Val Phe Ala Ala<br>                    245                    250                    255 | | 768 |
| gtg atc tac ctc cag ggc ttc cgt gtt gag atc cct gtc aag tcc tcc<br>Val Ile Tyr Leu Gln Gly Phe Arg Val Glu Ile Pro Val Lys Ser Ser<br>        260                    265                    270 | | 816 |
| cgc cag cgt ggc atg cgt ggt tcc tac cct gtt cgc ctg ttc tac acc<br>Arg Gln Arg Gly Met Arg Gly Ser Tyr Pro Val Arg Leu Phe Tyr Thr<br>                275                    280                    285 | | 864 |
| tcc aac atg ccc atc atg ctt cag tct gct ctg tgc tcc aac atc ttc<br>Ser Asn Met Pro Ile Met Leu Gln Ser Ala Leu Cys Ser Asn Ile Phe<br>290                    295                    300 | | 912 |
| ctc atc agt cag atg ctg tac tct cgc ttc tct gac aac ctc ctt gtc<br>Leu Ile Ser Gln Met Leu Tyr Ser Arg Phe Ser Asp Asn Leu Leu Val<br>305                    310                    315                    320 | | 960 |
| aag ctt ctc ggt gtt tgg gag cct cgt gag ggt tct gcc cag ctc cac<br>Lys Leu Leu Gly Val Trp Glu Pro Arg Glu Gly Ser Ala Gln Leu His<br>        325                    330                    335 | | 1008 |
| gcc gcc tcc ggc att gcc tac tac atg tct cct ccc ctg aac ttc aag<br>Ala Ala Ser Gly Ile Ala Tyr Tyr Met Ser Pro Pro Leu Asn Phe Lys<br>                340                    345                    350 | | 1056 |
| gag gcc ctt ctt gac ccc att cac acc gcc gtt tac atc acc ttc atg<br>Glu Ala Leu Leu Asp Pro Ile His Thr Ala Val Tyr Ile Thr Phe Met<br>                    355                    360                    365 | | 1104 |
| ctg gtt gct tgt gct ctc ttc tcc aag acc tgg att gag gtt tcc ggc<br>Leu Val Ala Cys Ala Leu Phe Ser Lys Thr Trp Ile Glu Val Ser Gly<br>370                    375                    380 | | 1152 |
| tct gct ccc cgc gat gtt gcc aag cag ctc aag gac cag ggt ctc gtg<br>Ser Ala Pro Arg Asp Val Ala Lys Gln Leu Lys Asp Gln Gly Leu Val<br>385                    390                    395                    400 | | 1200 |
| atg gct ggt cac cgt gag cag agc atg tac aag gag ctc aag cgc gtc<br>Met Ala Gly His Arg Glu Gln Ser Met Tyr Lys Glu Leu Lys Arg Val<br>                    405                    410                    415 | | 1248 |

-continued

```
atc cct act gct gct gct ttc ggt ggt gcc tgc att ggt gcc ctg tcc    1296
Ile Pro Thr Ala Ala Ala Phe Gly Gly Ala Cys Ile Gly Ala Leu Ser
            420                 425                 430 gtc gct tct gac ctg ctt ggt gct ctt ggc agc ggt act ggt atc ctc    1344
Val Ala Ser Asp Leu Leu Gly Ala Leu Gly Ser Gly Thr Gly Ile Leu
        435                 440                 445 ctt gcc gtt acg att ata tac gga tac ttt gaa att gcc gcc cgt gag    1392
Leu Ala Val Thr Ile Ile Tyr Gly Tyr Phe Glu Ile Ala Ala Arg Glu
    450                 455                 460 ggc gac att gga tcg ggc ctc aag ggc ctt gtt ccg ggt aac tag        1437
Gly Asp Ile Gly Ser Gly Leu Lys Gly Leu Val Pro Gly Asn
465                 470                 475
```

<210> SEQ ID NO 21
<211> LENGTH: 478
<212> TYPE: PRT
<213> ORGANISM: Aspergillus niger

<400> SEQUENCE: 21

```
Met Ser Gly Leu Arg Phe Leu Asp Leu Ile Lys Pro Phe Thr Pro Leu
1               5                   10                  15

Leu Pro Glu Val Ala Ala Pro Glu Thr Lys Val Pro Phe Asn Gln Lys
            20                  25                  30

Leu Met Trp Thr Gly Leu Thr Leu Leu Ile Phe Leu Val Met Ser Gln
        35                  40                  45

Met Pro Leu Tyr Gly Ile Val Ser Asp Thr Ser Asp Pro Leu Tyr
    50                  55                  60

Trp Leu Arg Met Met Leu Ala Ser Asn Arg Gly Thr Leu Met Glu Leu
65                  70                  75                  80

Gly Ile Thr Pro Ile Ile Ser Ser Gly Met Val Phe Gln Leu Leu Ala
                85                  90                  95

Gly Thr His Leu Ile Asp Val Asn Leu Asp Leu Lys Thr Asp Arg Glu
            100                 105                 110

Leu Tyr Gln Thr Ala Gln Lys Leu Phe Ala Ile Ile Leu Ser Phe Gly
        115                 120                 125

Gln Ala Cys Val Tyr Val Leu Thr Gly Leu Tyr Gly Gln Pro Ser Asp
    130                 135                 140

Leu Gly Ala Gly Ile Cys Val Leu Leu Ile Val Gln Leu Val Val Ala
145                 150                 155                 160

Gly Leu Val Val Ile Leu Leu Asp Glu Leu Leu Gln Lys Gly Tyr Gly
                165                 170                 175

Leu Gly Ser Gly Ile Ser Leu Phe Ile Ala Thr Asn Ile Cys Glu Ser
            180                 185                 190

Ile Val Trp Lys Ala Phe Ser Pro Thr Thr Ile Asn Thr Gly Arg Gly
        195                 200                 205

Pro Glu Phe Glu Gly Ala Ile Ile Ala Leu Phe His Leu Leu Leu Thr
    210                 215                 220

Trp Ser Asp Lys Gln Arg Ala Leu Arg Glu Ala Phe Tyr Arg Gln Asn
225                 230                 235                 240

Leu Pro Asn Ile Met Asn Leu Leu Ala Thr Leu Leu Val Phe Ala Ala
                245                 250                 255

Val Ile Tyr Leu Gln Gly Phe Arg Val Glu Ile Pro Val Lys Ser Ser
            260                 265                 270

Arg Gln Arg Gly Met Arg Gly Ser Tyr Pro Val Arg Leu Phe Tyr Thr
        275                 280                 285

Ser Asn Met Pro Ile Met Leu Gln Ser Ala Leu Cys Ser Asn Ile Phe
    290                 295                 300
```

```
Leu Ile Ser Gln Met Leu Tyr Ser Arg Phe Ser Asp Asn Leu Leu Val
305                 310                 315                 320

Lys Leu Leu Gly Val Trp Glu Pro Arg Glu Gly Ser Ala Gln Leu His
            325                 330                 335

Ala Ala Ser Gly Ile Ala Tyr Tyr Met Ser Pro Pro Leu Asn Phe Lys
        340                 345                 350

Glu Ala Leu Leu Asp Pro Ile His Thr Ala Val Tyr Ile Thr Phe Met
    355                 360                 365

Leu Val Ala Cys Ala Leu Phe Ser Lys Thr Trp Ile Glu Val Ser Gly
370                 375                 380

Ser Ala Pro Arg Asp Val Ala Lys Gln Leu Lys Asp Gln Gly Leu Val
385                 390                 395                 400

Met Ala Gly His Arg Glu Gln Ser Met Tyr Lys Glu Leu Lys Arg Val
            405                 410                 415

Ile Pro Thr Ala Ala Ala Phe Gly Gly Ala Cys Ile Gly Ala Leu Ser
        420                 425                 430

Val Ala Ser Asp Leu Leu Gly Ala Leu Gly Ser Gly Thr Gly Ile Leu
    435                 440                 445

Leu Ala Val Thr Ile Ile Tyr Gly Tyr Phe Glu Ile Ala Ala Arg Glu
    450                 455                 460

Gly Asp Ile Gly Ser Gly Leu Lys Gly Leu Val Pro Gly Asn
465                 470                 475

<210> SEQ ID NO 22
<211> LENGTH: 5117
<212> TYPE: DNA
<213> ORGANISM: Aspergillus niger

<400> SEQUENCE: 22
agctcgactg ggcatcttta atgcctcatt ggtctataca ttaattatac tgaattggta      60
attacattgt tgccattgat cacctcgagc ttatccgccg cccgttatgt gtgcttgcta     120
gctagcttat cgggaacagc tagctagtca acaccgctgc catcagctct aggtatcatt     180
tcccgtggtg ggctgtgacg atggtatctg gactggcaaa tttcgcctca tggcgacttg     240
catctgtatt gattgccggc tgctggcta tccagggacg cgctagtcca tcagtcaatg      300
ttgctctcca agcttcgttt gattccccac cttatctgat agagctactg taagtgaaat     360
tcagacagat ctagttggat gctcttgatt cctgggctga cctctatgta gcgaatccgc     420
tgcggaggag aactccacct catacttccc gttactcgat cggatcgccg acggtatttt     480
cgatgacgct gttacggata aggacctata tgatcgcttc ctggaggttg tgcgtgagga     540
tggacactta cggaccccctg aaagtctctc atctttcaag ctgtcgctgg cgatgagatc     600
cgccagtccg cggatcacgg ctcactacca gtactacaat gcttcggttc aatattcgtt     660
aatgccgcg caggatgcgg tctgtcctgt ttgggtgcac tccgaaggaa agcaatactg      720
ctcgtctact atggaacgcg cccagcagga tgttacgggt tctgagtgag tggtaatctc     780
aaatttgtgt ctacatgctg gtgactaacc gctacaatgt agtgacccac gagaactccc     840
tttcgatcgt gtcttcggag atccctctct gcctccagcg attttgtatg cggatatagc     900
gtccccgatg ttcaaggaat tcaccagtc actgagtacg atggcgaaag aaggacaagt      960
ctcgtatcgc gtgcgataca gacctcctca acattggtct ccacgtcctg ttttttgtgtc   1020
tggatacggt gtcgagctgg cgttaaagcg gacggactat attgtgattg atgatagaga    1080
cgcggaagaa agagggaccg gcagcattga gtccggaaag tctgatgaga cagaagatga    1140
```

```
tttggatgac ctgagacccc tgtcatcatc cgaagtttct cggcttgggc tgaacacggt    1200
cgggtatgtg ttggatagcg atgacccgtt tgacacactt gtgaagctgt cacaggattt    1260
ccccaaatac tccgcacgtg ttgcggctca caacgtttcc accgagctgt tgcaagatgt    1320
tcggtccagc agattgcgta tgcttccgcc ggggctcaac gtgctctgga tcaacggtgt    1380
tcagattgaa cctcgacaag tggacgcatt cactcttctg gatcacttgc gtcgcgaaag    1440
gaaattgatc gagaagttcc gaaacttagg cctgtccgct acagatgctg tagagctttt    1500
gtcacaccct ctgcttggag aggccttggc acgggatggc cctcagcgtt acaactaccg    1560
tgatgacatt gagggaggtg gtgtcatcat gtggctgaac aatctcgaaa aggatgcgcg    1620
ctatgaatcg tggcctagcg aactcgcagg agtaggtaca tccgggattc tttattgcgg    1680
agatgctaat gtctggtagt ttatgcaacg cacatatcca ggccagcttc cggcagtccg    1740
ccgcgattcc aacaatattg tctttcctgt cgacttgacg agcactgaag atgctgatat    1800
tgttgtcaag acaatccagg tctttgtgaa gaacaaaatt cccgtcagat ttggtttgat    1860
tccggtcaca ttctcagacg gagcaattgc tcagctcaag gtcgctcatt accttcaaga    1920
gacttttggt ctggccagtt ttatggatta ccttgaagcg gtaaggacta actttcccgt    1980
aaccaaattc cgctattgtt tgtcagttac taattggagc agtcggcgtc caaaaataag    2040
ttggcttctc cggataaggc ctgcttccag gctgcaactc aggaccggag tcctcgtctg    2100
gagaaggtgt ctctatctct agatgaagtc ttgaataatg ctgtatatga cgcaacggta    2160
tcaaagacaa ctgcgtacct aaaccgtctg gggatgaagc acgagccatc acatgctttt    2220
gttaacggca ttcctgtcac ccgcaatgac aaatgggcgc aggaaatgag cacaaaaata    2280
agcaaagata ctcagctaat tcagcagaag attgctgatg ccgaggtcga tgaagatacc    2340
tggttgccag aattgtttct ctcgcaggct ttcgataggc gcaatccggc gatcgttcca    2400
gaggacccga aagagatccg ggctgtggac ttggtgcagc ttgcggactc ccaagagaag    2460
ctcttcagtc agattccacg tttagggcta gatgaaagca atgccttgga gagtgcccat    2520
gccatcgttg ttggcaactt tgatgagaaa tccggttacg agctactcag cgcggccctt    2580
gagagccgaa aaacacatgg tgaagttgag atgcttttcc tacacaatcc taagctcgag    2640
gcgtcccccg catctaggtc tgtcgctgtt cgtcgattgt tgaatggtgg caaagaggta    2700
gatgccagcc agattttgga ggcgatcgcc tcttccgcct cgccagcaga tgaggaagct    2760
ggggatgcgg cactcttctg ggaggctcag cgagctgtag tagaagagct tggactcgct    2820
ccgggcgaaa gggcacttgt catcaacgga agggtcgttg gaccgattgc agaagacacc    2880
gccctgacct cagaggacct ggaccagcta ctgatatatg agaagcaaaa gcggattact    2940
ccggtagcaa aggcggtcaa agcccttgaa ttcgacgaga agctttctga tccgctagac    3000
tttgccaagc ttacctcgct caccacgctg tccacgatct cggatgtgcc agagggcata    3060
tatgagtcga cttcggacat tcggttgaat ttgttcaaca gatggaacga ctcacaatca    3120
gctatcactg tctccaattc cgatgatcca gcaattacca ttgtagcatc tatcgatccg    3180
acttcggaag ttgctcagaa gtggctacca attctaaaag tactgtcgga gctggcaagt    3240
gtcagagtga gattggtcct gaacccgcgc gaggagatca agagctgcc caccaagcgc    3300 ttctatcgtt atgttctcga ttcggagcca tcgttcaacg aagatgggtc ggtttcccgg    3360
cccacagcct ccttctcggg cgttcccgtc gaggcactcc tcaccctggg catggatgtt    3420
ccctcttctt ggcttgtggc tcccaaggat tctatccacg atcttgacaa tatcaagtta    3480
agttccgtca aggacggctc gaatgtcgat gctatttacg cattggaaca catcttgatc    3540
```

```
gagggccact cccgggatat gaccacgaag tccccaccta gaggagttca gcttgtcctt    3600
ggaactgaga acaaccctca cttctcggat acaatcatca tggccaatct cggatacttc    3660
caattcaaag cccaacctgg actgtggaac atcaacctca aaccgggccg tagcgaacgc    3720
atcttcaccc tcgacagcgt aggcagcctc ggctacaacc cccaacctgg cgacgaaaac    3780
aacgaagtgg ccctcctctc cttccaaggc cgcacccttt tcccgcgtgt ctcccgtaag    3840
aagggctacg agaccgaaga cgtcctcgag accaacccca accaggttc tgcgatggac    3900 tacatgaata agggggttcaa cttcgcctcc ggtatcctct ccagcgtcgg agtcggcacc    3960
aaaggcagca ctagcggcaa acaggctgac attaacatct tctccgtcgc cagtggacac    4020
ctctacgagc gcatgctcaa cattatgatg gtctcagtga tgcgcaacac caaccacagc    4080
gtgaaattct ggttcatcga acaattcctc tccccgtcct tcaagtcctt cctgcctcac    4140
cttgcgaagg agtataactt ctcttacgaa atggtcacct acaaatggcc acactggctc    4200
cgggcccaga aagaaaagca acgtgaaatc tggggctaca agatcctctt cctggacgtt    4260
ctcttccctc tcgacctcga caaagtcatc tttgtcgacg ccgaccagat agtccgcaca    4320
gatatgtacg acctcgtcag ccttgacctc gaaggcgctc cgtacggctt tactcccatg    4380
tgcgactccc gccacgagat ggaaggcttc cgcttctgga agcaggggta ctggaagaac    4440
ttcctccgtg gtcaacccta ccatatctcc gcgctttacg ttgtcgacct gaaccgcttc    4500
cgtgccatcg ccgccggcga tcgcctgcgt ggacagtacc agatgctgtc agctgacccc    4560
gagagtttga gcaacctgga ccaggatctg ccgaaccaca tgcagcatca tatcccgatc    4620
aagagtctgc cgcaggagtg gctgtggtgt gagacttggt gctcggatga gtcgcagtca    4680
caggctcgga cgatcgacct gtgcaataac ccgatgacga aggagccgaa gttggatcgt    4740
gccaggaggc aggtacctga gtggacggag tatgatgatg agattgcggc cttgtcgaag    4800
agagttgccg ctgagaagca gcaggggcag gtggaggaag aaagggccgg tgaatcgtac    4860
cctgacgagg atgaggaggg cgagacttcc tctggctggg ataaggatga gctttagcgg    4920
gtttcgtttc aattatagcg tgtatacata gatcagtttg gtctccaata gggaatagat    4980
tgttcgcttt acaagtcttg gtatcgtttc gtgcatgata ttcttttagt tgactgacct    5040
aggatcgtaa tgccttggct tctcaatcct ataagaccta cattgggaaa cacaagcatt    5100
ctcttactcg agaaaca                                                   5117
```

<210> SEQ ID NO 23
<211> LENGTH: 4488
<212> TYPE: DNA
<213> ORGANISM: Aspergillus niger
<220> FEATURE:
<221> NAME/KEY: CDS
<222> LOCATION: (1)..(4488)

<400> SEQUENCE: 23

```
atg gta tct gga ctg gca aat ttc gcc tca tgg cga ctt gca tct gta     48
Met Val Ser Gly Leu Ala Asn Phe Ala Ser Trp Arg Leu Ala Ser Val
1               5                   10                  15 ttg att gcc ggc ctg ctg gct atc cag gga cgc gct agt cca tca gtc     96
Leu Ile Ala Gly Leu Leu Ala Ile Gln Gly Arg Ala Ser Pro Ser Val
            20                  25                  30 aat gtt gct ctc caa gct tcg ttt gat tcc cca cct tat ctg ata gag    144
Asn Val Ala Leu Gln Ala Ser Phe Asp Ser Pro Pro Tyr Leu Ile Glu
        35                  40                  45 cta ctc gaa tcc gct gcg gag gag aac tcc acc tca tac ttc ccg tta    192
Leu Leu Glu Ser Ala Ala Glu Glu Asn Ser Thr Ser Tyr Phe Pro Leu
    50                  55                  60
```

-continued

| | | |
|---|---|---|
| ctc gat cgg atc gcc gac ggt att ttc gat gac gct gtt acg gat aag<br>Leu Asp Arg Ile Ala Asp Gly Ile Phe Asp Asp Ala Val Thr Asp Lys<br>65                        70                        75                       80 | 240 |
| gac cta tat gat cgc ttc ctg gag gtt gtg cgt gag gat gga cac tta<br>Asp Leu Tyr Asp Arg Phe Leu Glu Val Val Arg Glu Asp Gly His Leu<br>                    85                        90                       95 | 288 |
| cgg acc cct gaa agt ctc tca tct ttc aag ctg tcg ctg gcg atg aga<br>Arg Thr Pro Glu Ser Leu Ser Ser Phe Lys Leu Ser Leu Ala Met Arg<br>              100                      105                      110 | 336 |
| tcc gcc agt ccg cgg atc acg gct cac tac cag tac tac aat gct tcg<br>Ser Ala Ser Pro Arg Ile Thr Ala His Tyr Gln Tyr Tyr Asn Ala Ser<br>        115                      120                      125 | 384 |
| gtt caa tat tcg tta atg gcc gcg cag gat gcg gtc tgt cct gtt tgg<br>Val Gln Tyr Ser Leu Met Ala Ala Gln Asp Ala Val Cys Pro Val Trp<br>130                        135                      140 | 432 |
| gtg cac tcc gaa gga aag caa tac tgc tcg tct act atg gaa cgc gcc<br>Val His Ser Glu Gly Lys Gln Tyr Cys Ser Ser Thr Met Glu Arg Ala<br>145                      150                      155                      160 | 480 |
| cag cag gat gtt acg ggt tct gat gac cca cga gaa ctc cct ttc gat<br>Gln Gln Asp Val Thr Gly Ser Asp Asp Pro Arg Glu Leu Pro Phe Asp<br>                    165                      170                      175 | 528 |
| cgt gtc ttc gga gat ccc tct ctg cct cca gcg att ttg tat gcg gat<br>Arg Val Phe Gly Asp Pro Ser Leu Pro Pro Ala Ile Leu Tyr Ala Asp<br>              180                      185                      190 | 576 |
| ata gcg tcc ccg atg ttc aag gaa ttt cac cag tca ctg agt acg atg<br>Ile Ala Ser Pro Met Phe Lys Glu Phe His Gln Ser Leu Ser Thr Met<br>        195                      200                      205 | 624 |
| gcg aaa gaa gga caa gtc tcg tat cgc gtg cga tac aga cct cct caa<br>Ala Lys Glu Gly Gln Val Ser Tyr Arg Val Arg Tyr Arg Pro Pro Gln<br>210                        215                      220 | 672 |
| cat tgg tct cca cgt cct gtt ttt gtg tct gga tac ggt gtc gag ctg<br>His Trp Ser Pro Arg Pro Val Phe Val Ser Gly Tyr Gly Val Glu Leu<br>225                        230                      235                      240 | 720 |
| gcg tta aag cgg acg gac tat att gtg att gat gat aga gac gcg gaa<br>Ala Leu Lys Arg Thr Asp Tyr Ile Val Ile Asp Asp Arg Asp Ala Glu<br>                    245                      250                      255 | 768 |
| gaa aga ggg acc ggc agc att gag tcc gga aag tct gat gag aca gaa<br>Glu Arg Gly Thr Gly Ser Ile Glu Ser Gly Lys Ser Asp Glu Thr Glu<br>              260                      265                      270 | 816 |
| gat gat ttg gat gac ctg aga ccc ctg tca tca tcc gaa gtt tct cgg<br>Asp Asp Leu Asp Asp Leu Arg Pro Leu Ser Ser Ser Glu Val Ser Arg<br>        275                      280                      285 | 864 |
| ctt ggg ctg aac acg gtc ggg tat gtg ttg gat agc gat gac ccg ttt<br>Leu Gly Leu Asn Thr Val Gly Tyr Val Leu Asp Ser Asp Asp Pro Phe<br>290                        295                      300 | 912 |
| gac aca ctt gtg aag ctg tca cag gat ttc ccc aaa tac tcc gca cgt<br>Asp Thr Leu Val Lys Leu Ser Gln Asp Phe Pro Lys Tyr Ser Ala Arg<br>305                        310                      315                      320 | 960 |
| gtt gcg gct cac aac gtt tcc acc gag ctg ttg caa gat gtt cgg tcc<br>Val Ala Ala His Asn Val Ser Thr Glu Leu Leu Gln Asp Val Arg Ser<br>                    325                      330                      335 | 1008 |
| agc aga ttg cgt atg ctt ccg ccg ggg ctc aac gtg ctc tgg atc aac<br>Ser Arg Leu Arg Met Leu Pro Pro Gly Leu Asn Val Leu Trp Ile Asn<br>              340                      345                      350 | 1056 |
| ggt gtt cag att gaa cct cga caa gtg gac gca ttc act ctt ctg gat<br>Gly Val Gln Ile Glu Pro Arg Gln Val Asp Ala Phe Thr Leu Leu Asp<br>        355                      360                      365 | 1104 |
| cac ttg cgt cgc gaa agg aaa ttg atc gag aag ttc cga aac tta ggc<br>His Leu Arg Arg Glu Arg Lys Leu Ile Glu Lys Phe Arg Asn Leu Gly<br>370                        375                      380 | 1152 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ctg | tcc | gct | aca | gat | gct | gta | gag | ctt | ttg | tca | cac | cct | ctg | ctt | gga | 1200 |
| Leu | Ser | Ala | Thr | Asp | Ala | Val | Glu | Leu | Leu | Ser | His | Pro | Leu | Leu | Gly |      |
| 385 |     |     |     | 390 |     |     |     |     | 395 |     |     |     |     | 400 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gag | gcc | ttg | gca | cgg | gat | ggc | cct | cag | cgt | tac | aac | tac | cgt | gat | gac | 1248 |
| Glu | Ala | Leu | Ala | Arg | Asp | Gly | Pro | Gln | Arg | Tyr | Asn | Tyr | Arg | Asp | Asp |      |
|     |     |     |     | 405 |     |     |     |     | 410 |     |     |     |     | 415 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| att | gag | gga | ggt | ggt | gtc | atc | atg | tgg | ctg | aac | aat | ctc | gaa | aag | gat | 1296 |
| Ile | Glu | Gly | Gly | Gly | Val | Ile | Met | Trp | Leu | Asn | Asn | Leu | Glu | Lys | Asp |      |
|     |     |     | 420 |     |     |     |     | 425 |     |     |     |     | 430 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcg | cgc | tat | gaa | tcg | tgg | cct | agc | gaa | ctc | gca | gga | ttt | atg | caa | cgc | 1344 |
| Ala | Arg | Tyr | Glu | Ser | Trp | Pro | Ser | Glu | Leu | Ala | Gly | Phe | Met | Gln | Arg |      |
|     |     | 435 |     |     |     |     | 440 |     |     |     |     | 445 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| aca | tat | cca | ggc | cag | ctt | ccg | gca | gtc | cgc | cgc | gat | tcc | aac | aat | att | 1392 |
| Thr | Tyr | Pro | Gly | Gln | Leu | Pro | Ala | Val | Arg | Arg | Asp | Ser | Asn | Asn | Ile |      |
|     | 450 |     |     |     |     | 455 |     |     |     |     | 460 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gtc | ttt | cct | gtc | gac | ttg | acg | agc | act | gaa | gat | gct | gat | att | gtt | gtc | 1440 |
| Val | Phe | Pro | Val | Asp | Leu | Thr | Ser | Thr | Glu | Asp | Ala | Asp | Ile | Val | Val |      |
| 465 |     |     |     |     | 470 |     |     |     |     | 475 |     |     |     |     | 480 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| aag | aca | atc | cag | gtc | ttt | gtg | aag | aac | aaa | att | ccc | gtc | aga | ttt | ggt | 1488 |
| Lys | Thr | Ile | Gln | Val | Phe | Val | Lys | Asn | Lys | Ile | Pro | Val | Arg | Phe | Gly |      |
|     |     |     |     | 485 |     |     |     |     | 490 |     |     |     |     | 495 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ttg | att | ccg | gtc | aca | ttc | tca | gac | gga | gca | att | gct | cag | ctc | aag | gtc | 1536 |
| Leu | Ile | Pro | Val | Thr | Phe | Ser | Asp | Gly | Ala | Ile | Ala | Gln | Leu | Lys | Val |      |
|     |     |     | 500 |     |     |     |     | 505 |     |     |     |     | 510 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gct | cat | tac | ctt | caa | gag | act | ttt | ggt | ctg | gcc | agt | ttt | atg | gat | tac | 1584 |
| Ala | His | Tyr | Leu | Gln | Glu | Thr | Phe | Gly | Leu | Ala | Ser | Phe | Met | Asp | Tyr |      |
|     |     | 515 |     |     |     |     | 520 |     |     |     |     | 525 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ctt | gaa | gcg | tcg | gcg | tcc | aaa | aat | aag | ttg | gct | tct | ccg | gat | aag | gcc | 1632 |
| Leu | Glu | Ala | Ser | Ala | Ser | Lys | Asn | Lys | Leu | Ala | Ser | Pro | Asp | Lys | Ala |      |
|     | 530 |     |     |     |     | 535 |     |     |     |     | 540 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tgc | ttc | cag | gct | gca | act | cag | gac | cgg | agt | cct | cgt | ctg | gag | aag | gtg | 1680 |
| Cys | Phe | Gln | Ala | Ala | Thr | Gln | Asp | Arg | Ser | Pro | Arg | Leu | Glu | Lys | Val |      |
| 545 |     |     |     |     | 550 |     |     |     |     | 555 |     |     |     |     | 560 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tct | cta | tct | cta | gat | gaa | gtc | ttg | aat | aat | gct | gta | tat | gac | gca | acg | 1728 |
| Ser | Leu | Ser | Leu | Asp | Glu | Val | Leu | Asn | Asn | Ala | Val | Tyr | Asp | Ala | Thr |      |
|     |     |     |     | 565 |     |     |     |     | 570 |     |     |     |     | 575 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gta | tca | aag | aca | act | gcg | tac | cta | aac | cgt | ctg | ggg | atg | aag | cac | gag | 1776 |
| Val | Ser | Lys | Thr | Thr | Ala | Tyr | Leu | Asn | Arg | Leu | Gly | Met | Lys | His | Glu |      |
|     |     |     | 580 |     |     |     |     | 585 |     |     |     |     | 590 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cca | tca | cat | gct | ttt | gtt | aac | ggc | att | cct | gtc | acc | cgc | aat | gac | aaa | 1824 |
| Pro | Ser | His | Ala | Phe | Val | Asn | Gly | Ile | Pro | Val | Thr | Arg | Asn | Asp | Lys |      |
|     |     | 595 |     |     |     |     | 600 |     |     |     |     | 605 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tgg | gcg | cag | gaa | atg | agc | aca | aaa | ata | agc | aaa | gat | act | cag | cta | att | 1872 |
| Trp | Ala | Gln | Glu | Met | Ser | Thr | Lys | Ile | Ser | Lys | Asp | Thr | Gln | Leu | Ile |      |
|     | 610 |     |     |     |     | 615 |     |     |     |     | 620 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cag | cag | aag | att | gct | gat | gcc | gag | gtc | gat | gaa | gat | acc | tgg | ttg | cca | 1920 |
| Gln | Gln | Lys | Ile | Ala | Asp | Ala | Glu | Val | Asp | Glu | Asp | Thr | Trp | Leu | Pro |      |
| 625 |     |     |     |     | 630 |     |     |     |     | 635 |     |     |     |     | 640 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gaa | ttg | ttt | ctc | tcg | cag | gct | ttc | gat | agg | cgc | aat | ccg | gcg | atc | gtt | 1968 |
| Glu | Leu | Phe | Leu | Ser | Gln | Ala | Phe | Asp | Arg | Arg | Asn | Pro | Ala | Ile | Val |      |
|     |     |     |     | 645 |     |     |     |     | 650 |     |     |     |     | 655 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cca | gag | gac | ccg | aaa | gag | atc | cgg | gct | gtg | gac | ttg | gtg | cag | ctt | gcg | 2016 |
| Pro | Glu | Asp | Pro | Lys | Glu | Ile | Arg | Ala | Val | Asp | Leu | Val | Gln | Leu | Ala |      |
|     |     |     | 660 |     |     |     |     | 665 |     |     |     |     | 670 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gac | tcc | caa | gag | aag | ctc | ttc | agt | cag | att | cca | cgt | tta | ggg | cta | gat | 2064 |
| Asp | Ser | Gln | Glu | Lys | Leu | Phe | Ser | Gln | Ile | Pro | Arg | Leu | Gly | Leu | Asp |      |
|     |     |     | 675 |     |     |     |     | 680 |     |     |     |     | 685 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gaa | agc | aat | gcc | ttg | gag | agt | gcc | cat | gcc | atc | gtt | gtt | ggc | aac | ttt | 2112 |
| Glu | Ser | Asn | Ala | Leu | Glu | Ser | Ala | His | Ala | Ile | Val | Val | Gly | Asn | Phe |      |
|     | 690 |     |     |     |     | 695 |     |     |     |     | 700 |     |     |     |     |      |

```
                                                        -continued gat gag aaa tcc ggt tac gag cta ctc agc gcg gcc ctt gag agc cga    2160
Asp Glu Lys Ser Gly Tyr Glu Leu Leu Ser Ala Ala Leu Glu Ser Arg
705             710                 715                 720 aaa aca cat ggt gaa gtt gag atg ctt ttc cta cac aat cct aag ctc    2208
Lys Thr His Gly Glu Val Glu Met Leu Phe Leu His Asn Pro Lys Leu
            725                 730                 735 gag gcg tcc ccc gca tct agg tct gtc gct gtt cgt cga ttg ttg aat    2256
Glu Ala Ser Pro Ala Ser Arg Ser Val Ala Val Arg Arg Leu Leu Asn
740                 745                 750 ggt ggc aaa gag gta gat gcc agc cag att ttg gag gcg atc gcc tct    2304
Gly Gly Lys Glu Val Asp Ala Ser Gln Ile Leu Glu Ala Ile Ala Ser
        755                 760                 765 tcc gcc tcg cca gca gat gag gaa gct ggg gat gcg gca ctc ttc tgg    2352
Ser Ala Ser Pro Ala Asp Glu Glu Ala Gly Asp Ala Ala Leu Phe Trp
770                 775                 780 gag gct cag cga gct gta gta gaa gag ctt gga ctc gct ccg ggc gaa    2400
Glu Ala Gln Arg Ala Val Val Glu Glu Leu Gly Leu Ala Pro Gly Glu
785             790                 795                 800 agg gca ctt gtc atc aac gga agg gtc gtt gga ccg att gca gaa gac    2448
Arg Ala Leu Val Ile Asn Gly Arg Val Val Gly Pro Ile Ala Glu Asp
                805                 810                 815 acc gcc ctg acc tca gag gac ctg gac cag cta ctg ata tat gag aag    2496
Thr Ala Leu Thr Ser Glu Asp Leu Asp Gln Leu Leu Ile Tyr Glu Lys
            820                 825                 830 caa aag cgg att act ccg gta gca aag gcg gtc aaa gcc ctt gaa ttc    2544
Gln Lys Arg Ile Thr Pro Val Ala Lys Ala Val Lys Ala Leu Glu Phe
        835                 840                 845 gac gag aag ctt tct gat ccg cta gac ttt gcc aag ctt acc tcg ctc    2592
Asp Glu Lys Leu Ser Asp Pro Leu Asp Phe Ala Lys Leu Thr Ser Leu
850                 855                 860 acc acg ctg tcc acg atc tcg gat gtg cca gag ggc ata tat gag tcg    2640
Thr Thr Leu Ser Thr Ile Ser Asp Val Pro Glu Gly Ile Tyr Glu Ser
865             870                 875                 880 act tcg gac att cgg ttg aat ttg ttc aac aga tgg aac gac tca caa    2688
Thr Ser Asp Ile Arg Leu Asn Leu Phe Asn Arg Trp Asn Asp Ser Gln
                885                 890                 895 tca gct atc act gtc tcc aat tcc gat gat cca gca att acc att gta    2736
Ser Ala Ile Thr Val Ser Asn Ser Asp Asp Pro Ala Ile Thr Ile Val
            900                 905                 910 gca tct atc gat ccg act tcg gaa gtt gct cag aag tgg cta cca att    2784
Ala Ser Ile Asp Pro Thr Ser Glu Val Ala Gln Lys Trp Leu Pro Ile
        915                 920                 925 cta aaa gta ctg tcg gag ctg gca agt gtc aga gtg aga ttg gtc ctg    2832
Leu Lys Val Leu Ser Glu Leu Ala Ser Val Arg Val Arg Leu Val Leu
930                 935                 940 aac ccg cgc gag gag atc aaa gag ctg ccc acc aag cgc ttc tat cgt    2880
Asn Pro Arg Glu Glu Ile Lys Glu Leu Pro Thr Lys Arg Phe Tyr Arg
945             950                 955                 960 tat gtt ctc gat tcg gag cca tcg ttc aac gaa gat ggg tcg gtt tcc    2928
Tyr Val Leu Asp Ser Glu Pro Ser Phe Asn Glu Asp Gly Ser Val Ser
                965                 970                 975 cgg ccc aca gcc tcc ttc tcg ggc gtt ccc gtc gag gca ctc ctc acc    2976
Arg Pro Thr Ala Ser Phe Ser Gly Val Pro Val Glu Ala Leu Leu Thr
            980                 985                 990 ctg ggc atg gat gtt ccc tct tct tgg ctt gtg gct ccc aag gat tct    3024
Leu Gly Met Asp Val Pro Ser Ser Trp Leu Val Ala Pro Lys Asp Ser
        995                 1000                1005 atc cac gat ctt gac aat atc aag tta agt tcc gtc aag gac ggc tcg    3072
Ile His Asp Leu Asp Asn Ile Lys Leu Ser Ser Val Lys Asp Gly Ser
1010                1015                1020
```

```
aat gtc gat gct att tac gca ttg gaa cac atc ttg atc gag ggc cac    3120
Asn Val Asp Ala Ile Tyr Ala Leu Glu His Ile Leu Ile Glu Gly His
1025                1030                1035                1040 tcc cgg gat atg acc acg aag tcc cca cct aga gga gtt cag ctt gtc    3168
Ser Arg Asp Met Thr Thr Lys Ser Pro Pro Arg Gly Val Gln Leu Val
            1045                1050                1055 ctt gga act gag aac aac cct cac ttc tcg gat aca atc atc atg gcc    3216
Leu Gly Thr Glu Asn Asn Pro His Phe Ser Asp Thr Ile Ile Met Ala
        1060                1065                1070 aat ctc gga tac ttc caa ttc aaa gcc caa cct gga ctg tgg aac atc    3264
Asn Leu Gly Tyr Phe Gln Phe Lys Ala Gln Pro Gly Leu Trp Asn Ile
    1075                1080                1085 aac ctc aaa ccg ggc cgt agc gaa cgc atc ttc acc ctc gac agc gta    3312
Asn Leu Lys Pro Gly Arg Ser Glu Arg Ile Phe Thr Leu Asp Ser Val
1090                1095                1100 ggc agc ctc ggc tac aac ccc caa cct ggc gac gaa aac aac gaa gtg    3360
Gly Ser Leu Gly Tyr Asn Pro Gln Pro Gly Asp Glu Asn Asn Glu Val
1105                1110                1115                1120 gcc ctc ctc tcc ttc caa ggc cgc acc ctt ttc ccg cgt gtc tcc cgt    3408
Ala Leu Leu Ser Phe Gln Gly Arg Thr Leu Phe Pro Arg Val Ser Arg
            1125                1130                1135 aag aag ggc tac gag acc gaa gac gtc ctc gag acc aac ccc aaa cca    3456
Lys Lys Gly Tyr Glu Thr Glu Asp Val Leu Glu Thr Asn Pro Lys Pro
        1140                1145                1150 ggt tct gcg atg gac tac atg aat aag ggg ttc aac ttc gcc tcc ggt    3504
Gly Ser Ala Met Asp Tyr Met Asn Lys Gly Phe Asn Phe Ala Ser Gly
    1155                1160                1165 atc ctc tcc agc gtc gga gtc ggc acc aaa ggc agc act agc ggc aaa    3552
Ile Leu Ser Ser Val Gly Val Gly Thr Lys Gly Ser Thr Ser Gly Lys
1170                1175                1180 cag gct gac att aac atc ttc tcc gtc gcc agt gga cac ctc tac gag    3600
Gln Ala Asp Ile Asn Ile Phe Ser Val Ala Ser Gly His Leu Tyr Glu
1185                1190                1195                1200 cgc atg ctc aac att atg atg gtc tca gtg atg cgc aac acc aac cac    3648
Arg Met Leu Asn Ile Met Met Val Ser Val Met Arg Asn Thr Asn His
            1205                1210                1215 agc gtg aaa ttc tgg ttc atc gaa caa ttc ctc tcc ccg tcc ttc aag    3696
Ser Val Lys Phe Trp Phe Ile Glu Gln Phe Leu Ser Pro Ser Phe Lys
        1220                1225                1230 tcc ttc ctg cct cac ctt gcg aag gag tat aac ttc tct tac gaa atg    3744
Ser Phe Leu Pro His Leu Ala Lys Glu Tyr Asn Phe Ser Tyr Glu Met
    1235                1240                1245 gtc acc tac aaa tgg cca cac tgg ctc cgg gcc cag aaa gaa aag caa    3792
Val Thr Tyr Lys Trp Pro His Trp Leu Arg Ala Gln Lys Glu Lys Gln
1250                1255                1260 cgt gaa atc tgg ggc tac aag atc ctc ttc ctg gac gtt ctc ttc cct    3840
Arg Glu Ile Trp Gly Tyr Lys Ile Leu Phe Leu Asp Val Leu Phe Pro
1265                1270                1275                1280 ctc gac ctc gac aaa gtc atc ttt gtc gac gcc gac cag ata gtc cgc    3888
Leu Asp Leu Asp Lys Val Ile Phe Val Asp Ala Asp Gln Ile Val Arg
            1285                1290                1295 aca gat atg tac gac ctc gtc agc ctt gac ctc gaa ggc gct ccg tac    3936
Thr Asp Met Tyr Asp Leu Val Ser Leu Asp Leu Glu Gly Ala Pro Tyr
        1300                1305                1310 ggc ttt act ccc atg tgc gac tcc cgc cac gag atg gaa ggc ttc cgc    3984
Gly Phe Thr Pro Met Cys Asp Ser Arg His Glu Met Glu Gly Phe Arg
    1315                1320                1325 ttc tgg aag cag ggg tac tgg aag aac ttc ctc cgt ggt caa ccc tac    4032
Phe Trp Lys Gln Gly Tyr Trp Lys Asn Phe Leu Arg Gly Gln Pro Tyr
1330                1335                1340
```

```
cat atc tcc gcg ctt tac gtt gtc gac ctg aac cgc ttc cgt gcc atc    4080
His Ile Ser Ala Leu Tyr Val Val Asp Leu Asn Arg Phe Arg Ala Ile
1345                1350                1355                1360 gcc gcc ggc gat cgc ctg cgt gga cag tac cag atg ctg tca gct gac    4128
Ala Ala Gly Asp Arg Leu Arg Gly Gln Tyr Gln Met Leu Ser Ala Asp
                1365                1370                1375 ccc gag agt ttg agc aac ctg gac cag gat ctg ccg aac cac atg cag    4176
Pro Glu Ser Leu Ser Asn Leu Asp Gln Asp Leu Pro Asn His Met Gln
1380                1385                1390 cat cat atc ccg atc aag agt ctg ccg cag gag tgg ctg tgg tgt gag    4224
His His Ile Pro Ile Lys Ser Leu Pro Gln Glu Trp Leu Trp Cys Glu
                1395                1400                1405 act tgg tgc tcg gat gag tcg cag tca cag gct cgg acg atc gac ctg    4272
Thr Trp Cys Ser Asp Glu Ser Gln Ser Gln Ala Arg Thr Ile Asp Leu
1410                1415                1420 tgc aat aac ccg atg acg aag gag ccg aag ttg gat cgt gcc agg agg    4320
Cys Asn Asn Pro Met Thr Lys Glu Pro Lys Leu Asp Arg Ala Arg Arg
1425                1430                1435                1440 cag gta cct gag tgg acg gag tat gat gat gag att gcg gcc ttg tcg    4368
Gln Val Pro Glu Trp Thr Glu Tyr Asp Asp Glu Ile Ala Ala Leu Ser
                1445                1450                1455 aag aga gtt gcc gct gag aag cag cag ggg cag gtg gag gaa gaa agg    4416
Lys Arg Val Ala Ala Glu Lys Gln Gln Gly Gln Val Glu Glu Glu Arg
                1460                1465                1470 gcc ggt gaa tcg tac cct gac gag gat gag gag ggc gag act tcc tct    4464
Ala Gly Glu Ser Tyr Pro Asp Glu Asp Glu Glu Gly Glu Thr Ser Ser
                1475                1480                1485 ggc tgg gat aag gat gag ctt tag                                     4488
Gly Trp Asp Lys Asp Glu Leu
                1490                1495

<210> SEQ ID NO 24
<211> LENGTH: 1495
<212> TYPE: PRT
<213> ORGANISM: Aspergillus niger

<400> SEQUENCE: 24

Met Val Ser Gly Leu Ala Asn Phe Ala Ser Trp Arg Leu Ala Ser Val
1               5                   10                  15

Leu Ile Ala Gly Leu Leu Ala Ile Gln Gly Arg Ala Ser Pro Ser Val
                20                  25                  30

Asn Val Ala Leu Gln Ala Ser Phe Asp Ser Pro Pro Tyr Leu Ile Glu
            35                  40                  45

Leu Leu Glu Ser Ala Ala Glu Glu Asn Ser Thr Ser Tyr Phe Pro Leu
        50                  55                  60

Leu Asp Arg Ile Ala Asp Gly Ile Phe Asp Asp Ala Val Thr Asp Lys
65                  70                  75                  80

Asp Leu Tyr Asp Arg Phe Leu Glu Val Val Arg Glu Asp Gly His Leu
                85                  90                  95

Arg Thr Pro Glu Ser Leu Ser Ser Phe Lys Leu Ser Leu Ala Met Arg
            100                 105                 110

Ser Ala Ser Pro Arg Ile Thr Ala His Tyr Gln Tyr Asn Ala Ser
        115                 120                 125

Val Gln Tyr Ser Leu Met Ala Ala Gln Asp Ala Val Cys Pro Val Trp
    130                 135                 140

Val His Ser Glu Gly Lys Gln Tyr Cys Ser Ser Thr Met Glu Arg Ala
145                 150                 155                 160

Gln Gln Asp Val Thr Gly Ser Asp Asp Pro Arg Glu Leu Pro Phe Asp
```

```
                    165                 170                 175
Arg Val Phe Gly Asp Pro Ser Leu Pro Pro Ala Ile Leu Tyr Ala Asp
                180                 185                 190

Ile Ala Ser Pro Met Phe Lys Glu Phe His Gln Ser Leu Ser Thr Met
            195                 200                 205

Ala Lys Glu Gly Gln Val Ser Tyr Arg Val Arg Tyr Arg Pro Pro Gln
        210                 215                 220

His Trp Ser Pro Arg Pro Val Phe Val Ser Gly Tyr Gly Val Glu Leu
225                 230                 235                 240

Ala Leu Lys Arg Thr Asp Tyr Ile Val Ile Asp Asp Arg Asp Ala Glu
                245                 250                 255

Glu Arg Gly Thr Gly Ser Ile Glu Ser Gly Lys Ser Asp Glu Thr Glu
            260                 265                 270

Asp Asp Leu Asp Asp Leu Arg Pro Leu Ser Ser Ser Glu Val Ser Arg
        275                 280                 285

Leu Gly Leu Asn Thr Val Gly Tyr Val Leu Asp Ser Asp Pro Phe
    290                 295                 300

Asp Thr Leu Val Lys Leu Ser Gln Asp Phe Pro Lys Tyr Ser Ala Arg
305                 310                 315                 320

Val Ala Ala His Asn Val Ser Thr Glu Leu Leu Gln Asp Val Arg Ser
                325                 330                 335

Ser Arg Leu Arg Met Leu Pro Pro Gly Leu Asn Val Leu Trp Ile Asn
            340                 345                 350

Gly Val Gln Ile Glu Pro Arg Gln Val Asp Ala Phe Thr Leu Leu Asp
        355                 360                 365

His Leu Arg Arg Glu Arg Lys Leu Ile Glu Lys Phe Arg Asn Leu Gly
    370                 375                 380

Leu Ser Ala Thr Asp Ala Val Glu Leu Leu Ser His Pro Leu Leu Gly
385                 390                 395                 400

Glu Ala Leu Ala Arg Asp Gly Pro Gln Arg Tyr Asn Tyr Arg Asp Asp
                405                 410                 415

Ile Glu Gly Gly Gly Val Ile Met Trp Leu Asn Asn Leu Glu Lys Asp
            420                 425                 430

Ala Arg Tyr Glu Ser Trp Pro Ser Glu Leu Ala Gly Phe Met Gln Arg
        435                 440                 445

Thr Tyr Pro Gly Gln Leu Pro Ala Val Arg Arg Asp Ser Asn Asn Ile
    450                 455                 460

Val Phe Pro Val Asp Leu Thr Ser Thr Glu Asp Ala Asp Ile Val Val
465                 470                 475                 480

Lys Thr Ile Gln Val Phe Val Lys Asn Lys Ile Pro Val Arg Phe Gly
                485                 490                 495

Leu Ile Pro Val Thr Phe Ser Asp Gly Ala Ile Ala Gln Leu Lys Val
            500                 505                 510

Ala His Tyr Leu Gln Glu Thr Phe Gly Leu Ala Ser Phe Met Asp Tyr
        515                 520                 525

Leu Glu Ala Ser Ala Ser Lys Asn Lys Leu Ala Ser Pro Asp Lys Ala
    530                 535                 540

Cys Phe Gln Ala Ala Thr Gln Asp Arg Ser Pro Arg Leu Glu Lys Val
545                 550                 555                 560

Ser Leu Ser Leu Asp Glu Val Leu Asn Asn Ala Val Tyr Asp Ala Thr
                565                 570                 575

Val Ser Lys Thr Thr Ala Tyr Leu Asn Arg Leu Gly Met Lys His Glu
            580                 585                 590
```

-continued

```
Pro Ser His Ala Phe Val Asn Gly Ile Pro Val Thr Arg Asn Asp Lys
    595                 600                 605

Trp Ala Gln Glu Met Ser Thr Lys Ile Ser Lys Asp Thr Gln Leu Ile
610                 615                 620

Gln Gln Lys Ile Ala Asp Ala Glu Val Asp Glu Asp Thr Trp Leu Pro
625                 630                 635                 640

Glu Leu Phe Leu Ser Gln Ala Phe Asp Arg Arg Asn Pro Ala Ile Val
                645                 650                 655

Pro Glu Asp Pro Lys Glu Ile Arg Ala Val Asp Leu Val Gln Leu Ala
                660                 665                 670

Asp Ser Gln Glu Lys Leu Phe Ser Gln Ile Pro Arg Leu Gly Leu Asp
                675                 680                 685

Glu Ser Asn Ala Leu Glu Ser Ala His Ala Ile Val Val Gly Asn Phe
690                 695                 700

Asp Glu Lys Ser Gly Tyr Glu Leu Leu Ser Ala Ala Leu Glu Ser Arg
705                 710                 715                 720

Lys Thr His Gly Glu Val Glu Met Leu Phe Leu His Asn Pro Lys Leu
                725                 730                 735

Glu Ala Ser Pro Ala Ser Arg Ser Val Ala Val Arg Arg Leu Leu Asn
                740                 745                 750

Gly Gly Lys Glu Val Asp Ala Ser Gln Ile Leu Glu Ala Ile Ala Ser
            755                 760                 765

Ser Ala Ser Pro Ala Asp Glu Glu Ala Gly Asp Ala Ala Leu Phe Trp
770                 775                 780

Glu Ala Gln Arg Ala Val Val Glu Glu Leu Gly Leu Ala Pro Gly Glu
785                 790                 795                 800

Arg Ala Leu Val Ile Asn Gly Arg Val Val Gly Pro Ile Ala Glu Asp
                805                 810                 815

Thr Ala Leu Thr Ser Glu Asp Leu Asp Gln Leu Leu Ile Tyr Glu Lys
                820                 825                 830

Gln Lys Arg Ile Thr Pro Val Ala Lys Ala Val Lys Ala Leu Glu Phe
                835                 840                 845

Asp Glu Lys Leu Ser Asp Pro Leu Asp Phe Ala Lys Leu Thr Ser Leu
850                 855                 860

Thr Thr Leu Ser Thr Ile Ser Asp Val Pro Glu Gly Ile Tyr Glu Ser
865                 870                 875                 880

Thr Ser Asp Ile Arg Leu Asn Leu Phe Asn Arg Trp Asn Asp Ser Gln
                885                 890                 895

Ser Ala Ile Thr Val Ser Asn Ser Asp Pro Ala Ile Thr Ile Val
                900                 905                 910

Ala Ser Ile Asp Pro Thr Ser Glu Val Ala Gln Lys Trp Leu Pro Ile
            915                 920                 925

Leu Lys Val Leu Ser Glu Leu Ala Ser Val Arg Val Arg Leu Val Leu
930                 935                 940

Asn Pro Arg Glu Glu Ile Lys Glu Leu Pro Thr Lys Arg Phe Tyr Arg
945                 950                 955                 960

Tyr Val Leu Asp Ser Glu Pro Ser Phe Asn Asp Gly Ser Val Ser
                965                 970                 975

Arg Pro Thr Ala Ser Phe Ser Gly Val Pro Val Glu Ala Leu Leu Thr
            980                 985                 990

Leu Gly Met Asp Val Pro Ser Ser Trp Leu Val Ala Pro Lys Asp Ser
        995                 1000                1005

Ile His Asp Leu Asp Asn Ile Lys Leu Ser Ser Val Lys Asp Gly Ser
    1010                1015                1020
```

```
Asn Val Asp Ala Ile Tyr Ala Leu Glu His Ile Leu Ile Glu Gly His
1025                1030                1035                1040

Ser Arg Asp Met Thr Thr Lys Ser Pro Pro Arg Gly Val Gln Leu Val
                1045                1050                1055

Leu Gly Thr Glu Asn Asn Pro His Phe Ser Asp Thr Ile Ile Met Ala
            1060                1065                1070

Asn Leu Gly Tyr Phe Gln Phe Lys Ala Gln Pro Gly Leu Trp Asn Ile
        1075                1080                1085

Asn Leu Lys Pro Gly Arg Ser Glu Arg Ile Phe Thr Leu Asp Ser Val
    1090                1095                1100

Gly Ser Leu Gly Tyr Asn Pro Gln Pro Gly Asp Glu Asn Asn Glu Val
1105                1110                1115                1120

Ala Leu Leu Ser Phe Gln Gly Arg Thr Leu Phe Pro Arg Val Ser Arg
                1125                1130                1135

Lys Lys Gly Tyr Glu Thr Glu Asp Val Leu Glu Thr Asn Pro Lys Pro
            1140                1145                1150

Gly Ser Ala Met Asp Tyr Met Asn Lys Gly Phe Asn Phe Ala Ser Gly
        1155                1160                1165

Ile Leu Ser Ser Val Gly Val Gly Thr Lys Gly Ser Thr Ser Gly Lys
    1170                1175                1180

Gln Ala Asp Ile Asn Ile Phe Ser Val Ala Ser Gly His Leu Tyr Glu
1185                1190                1195                1200

Arg Met Leu Asn Ile Met Met Val Ser Val Met Arg Asn Thr Asn His
                1205                1210                1215

Ser Val Lys Phe Trp Phe Ile Glu Gln Phe Leu Ser Pro Ser Phe Lys
            1220                1225                1230

Ser Phe Leu Pro His Leu Ala Lys Glu Tyr Asn Phe Ser Tyr Glu Met
        1235                1240                1245

Val Thr Tyr Lys Trp Pro His Trp Leu Arg Ala Gln Lys Glu Lys Gln
    1250                1255                1260

Arg Glu Ile Trp Gly Tyr Lys Ile Leu Phe Leu Asp Val Leu Phe Pro
1265                1270                1275                1280

Leu Asp Leu Asp Lys Val Ile Phe Val Asp Ala Asp Gln Ile Val Arg
                1285                1290                1295

Thr Asp Met Tyr Asp Leu Val Ser Leu Asp Leu Glu Gly Ala Pro Tyr
            1300                1305                1310

Gly Phe Thr Pro Met Cys Asp Ser Arg His Glu Met Glu Gly Phe Arg
        1315                1320                1325

Phe Trp Lys Gln Gly Tyr Trp Lys Asn Phe Leu Arg Gly Gln Pro Tyr
    1330                1335                1340

His Ile Ser Ala Leu Tyr Val Val Asp Leu Asn Arg Phe Arg Ala Ile
1345                1350                1355                1360

Ala Ala Gly Asp Arg Leu Arg Gly Gln Tyr Gln Met Leu Ser Ala Asp
                1365                1370                1375

Pro Glu Ser Leu Ser Asn Leu Asp Gln Asp Leu Pro Asn His Met Gln
            1380                1385                1390

His His Ile Pro Ile Lys Ser Leu Pro Gln Glu Trp Leu Trp Cys Glu
        1395                1400                1405

Thr Trp Cys Ser Asp Glu Ser Gln Ser Gln Ala Arg Thr Ile Asp Leu
    1410                1415                1420

Cys Asn Asn Pro Met Thr Lys Glu Pro Lys Leu Asp Arg Ala Arg Arg
1425                1430                1435                1440

Gln Val Pro Glu Trp Thr Glu Tyr Asp Asp Glu Ile Ala Ala Leu Ser
```

Lys Arg Val Ala Ala Glu Lys Gln Gln Gly Gln Val Glu Glu Glu Arg
                1445                1450                1455
                                1460                1465                1470

Ala Gly Glu Ser Tyr Pro Asp Glu Asp Glu Glu Gly Glu Thr Ser Ser
        1475                1480                1485

Gly Trp Asp Lys Asp Glu Leu
        1490            1495

<210> SEQ ID NO 25
<211> LENGTH: 1531
<212> TYPE: DNA
<213> ORGANISM: Aspergillus niger

<400> SEQUENCE: 25

| | | |
|---|---|---|
| attgtcatac agtggccgac aacctacgtt acccgaccgg gtctctgggt tgattaactg | 60 |
| agcacggtcc acacgaggac cattgaggac catctctcgc gaacttactg ggctatcttg | 120 |
| atggtactct agaagtgggt tgcaggacaa ttccacagtg aaagctgcgt gtcaagcttt | 180 |
| ctatatatac actattgacc atgctgaacc tcaatatctt ccggctactg gccgatctct | 240 |
| cccatatctc ctccaaatgt gtcttgatat gggctatcca tcgcaataag agcgcagaag | 300 |
| gtccgtataa taacttgcat tgttgcagtg tgctgcgagc taagcatcgt ttcaaataat | 360 |
| aggagtctcc cttctgacgc agatgctcta tgctttggtg ttcgtgactc gttatctcga | 420 |
| ccttttctcg aaggcaggat ggaagcactt ctacctcgta ttcttcaagc tattttatat | 480 |
| catctcctcg ttctacgtta tatacctgat gatgagagta tttccccgga cacgggaaag | 540 |
| ggagcgagcc tggaagatgg ctataatatc ggtcgctcta tctctggttc tggctcctat | 600 |
| atctattgtc atcttctatc gtggttatcc cgatagatgg ttcacggagg taagtgggat | 660 |
| ggctcgcatt ggcctgcaga cgtcgctaac caaaccgtga tgatatgcag acttgctgga | 720 |
| ctttctcgat tatattagag tccgtctgtg ttctccctca attgttgctc ttgcgccaaa | 780 |
| cgaccgttcc gacagtcatc gattcatact acctgcttat gctgggatcc taccgtgcct | 840 |
| tctatattct caattggctt gtgcggggac tgggctctga gggtcattgg gacgtaattg | 900 |
| cagacctcta cggtgtcatc cagacggctt tctacgtcga tttcgcctgg gtttactact | 960 |
| cccgccaacg cgtgaagctc cgaaacggcg gtgtcgttga ctcggaagat ttccgccata | 1020 |
| gctggctagt gagcaagata ctgaatttcc ggcagcgaag gagtgcagat gaggagcaga | 1080 |
| atttgaacga cgaggacgtg gaggatgagg aagttgctgg tggcggtaga cccaggaaca | 1140 |
| accgctgggg agcaatgggg atctccgtct cggccgacga tacgctagga aaccatcgtg | 1200 |
| ggacaagcca agacgagagt ctggaagggt tcttagaaga tgaagaagac gacgaggaca | 1260 |
| ataacgggta ccctgtgaac ggggcgttc gtccgaagca gtcaaccggg gtaacgggca | 1320 |
| gtcacgaatg aactatctgc ccttaaaccc catatataga aatcctgctg cagatcagcc | 1380 |
| ggttttggtt acacgattca actgccctcg gggcattata tacatcccta gggctcgttc | 1440 |
| tccccctttc gcttccttca tggtctgttt ctttattgct cgggtctttg tttgcatgga | 1500 |
| tttctctcac gtcatcaagt tttcacaatc t | 1531 |

<210> SEQ ID NO 26
<211> LENGTH: 1008
<212> TYPE: DNA
<213> ORGANISM: Aspergillus niger
<220> FEATURE:
<221> NAME/KEY: CDS
<222> LOCATION: (1)..(1008)

<400> SEQUENCE: 26

```
atg ctg aac ctc aat atc ttc cgg cta ctg gcc gat ctc tcc cat atc      48
Met Leu Asn Leu Asn Ile Phe Arg Leu Leu Ala Asp Leu Ser His Ile
 1               5                  10                  15 tcc tcc aaa tgt gtc ttg ata tgg gct atc cat cgc aat aag agc gca      96
Ser Ser Lys Cys Val Leu Ile Trp Ala Ile His Arg Asn Lys Ser Ala
             20                  25                  30 gaa gga gtc tcc ctt ctg acg cag atg ctc tat gct ttg gtg ttc gtg     144
Glu Gly Val Ser Leu Leu Thr Gln Met Leu Tyr Ala Leu Val Phe Val
         35                  40                  45 act cgt tat ctc gac ctt ttc tcg aag gca gga tgg aag cac ttc tac     192
Thr Arg Tyr Leu Asp Leu Phe Ser Lys Ala Gly Trp Lys His Phe Tyr
 50                  55                  60 ctc gta ttc ttc aag cta ttt tat atc atc tcc tcg ttc tac gtt ata     240
Leu Val Phe Phe Lys Leu Phe Tyr Ile Ile Ser Ser Phe Tyr Val Ile
 65                  70                  75                  80 tac ctg atg atg aga gta ttt ccc cgg aca cgg gaa agg gag cga gcc     288
Tyr Leu Met Met Arg Val Phe Pro Arg Thr Arg Glu Arg Glu Arg Ala
                 85                  90                  95 tgg aag atg gct ata ata tcg gtc gct cta tct ctg gtt ctg gct cct     336
Trp Lys Met Ala Ile Ile Ser Val Ala Leu Ser Leu Val Leu Ala Pro
            100                 105                 110 ata tct att gtc atc ttc tat cgt ggt tat ccc gat aga tgg ttc acg     384
Ile Ser Ile Val Ile Phe Tyr Arg Gly Tyr Pro Asp Arg Trp Phe Thr
        115                 120                 125 gag act tgc tgg act ttc tcg att ata tta gag tcc gtc tgt gtt ctc     432
Glu Thr Cys Trp Thr Phe Ser Ile Ile Leu Glu Ser Val Cys Val Leu
    130                 135                 140 cct caa ttg ttg ctc ttg cgc caa acg acc gtt ccg aca gtc atc gat     480
Pro Gln Leu Leu Leu Leu Arg Gln Thr Thr Val Pro Thr Val Ile Asp
145                 150                 155                 160 tca tac tac ctg ctt atg ctg gga tcc tac cgt gcc ttc tat att ctc     528
Ser Tyr Tyr Leu Leu Met Leu Gly Ser Tyr Arg Ala Phe Tyr Ile Leu
                165                 170                 175 aat tgg ctt gtg cgg gga ctg ggc tct gag ggt cat tgg gac gta att     576
Asn Trp Leu Val Arg Gly Leu Gly Ser Glu Gly His Trp Asp Val Ile
            180                 185                 190 gca gac ctc tac ggt gtc atc cag acg gct ttc tac gtc gat ttc gcc     624
Ala Asp Leu Tyr Gly Val Ile Gln Thr Ala Phe Tyr Val Asp Phe Ala
        195                 200                 205 tgg gtt tac tac tcc cgc caa cgc gtg aag ctc cga aac ggc ggt gtc     672
Trp Val Tyr Tyr Ser Arg Gln Arg Val Lys Leu Arg Asn Gly Gly Val
    210                 215                 220 gtt gac tcg gaa gat ttc cgc cat agc tgg cta gtg agc aag ata ctg     720
Val Asp Ser Glu Asp Phe Arg His Ser Trp Leu Val Ser Lys Ile Leu
225                 230                 235                 240 aat ttc cgg cag cga agg agt gca gat gag gag cag aat ttg aac gac     768
Asn Phe Arg Gln Arg Arg Ser Ala Asp Glu Glu Gln Asn Leu Asn Asp
                245                 250                 255 gag gac gtg gag gat gag gaa gtt gct ggt ggc ggt aga ccc agg aac     816
Glu Asp Val Glu Asp Glu Glu Val Ala Gly Gly Gly Arg Pro Arg Asn
            260                 265                 270 aac cgc tgg gga gca atg ggg atc tcc gtc tcg gcc gac gat acg cta     864
Asn Arg Trp Gly Ala Met Gly Ile Ser Val Ser Ala Asp Asp Thr Leu
        275                 280                 285 gga aac cat cgt ggg aca agc caa gac gag agt ctg gaa ggg ttc tta     912
Gly Asn His Arg Gly Thr Ser Gln Asp Glu Ser Leu Glu Gly Phe Leu
    290                 295                 300 gaa gat gaa gaa gac gac gag gac aat aac ggg tac cct gtg aac ggg     960
Glu Asp Glu Glu Asp Asp Glu Asp Asn Asn Gly Tyr Pro Val Asn Gly
```

```
               305                 310                 315                 320
    ggc gtt cgt ccg aag cag tca acc ggg gta acg ggc agt cac gaa tga           1008
    Gly Val Arg Pro Lys Gln Ser Thr Gly Val Thr Gly Ser His Glu
                    325                 330                 335
```

<210> SEQ ID NO 27
<211> LENGTH: 335
<212> TYPE: PRT
<213> ORGANISM: Aspergillus niger

<400> SEQUENCE: 27

Met Leu Asn Leu Asn Ile Phe Arg Leu Leu Ala Asp Leu Ser His Ile
1               5                   10                  15

Ser Ser Lys Cys Val Leu Ile Trp Ala Ile His Arg Asn Lys Ser Ala
            20                  25                  30

Glu Gly Val Ser Leu Leu Thr Gln Met Leu Tyr Ala Leu Val Phe Val
        35                  40                  45

Thr Arg Tyr Leu Asp Leu Phe Ser Lys Ala Gly Trp Lys His Phe Tyr
    50                  55                  60

Leu Val Phe Phe Lys Leu Phe Tyr Ile Ile Ser Ser Phe Tyr Val Ile
65                  70                  75                  80

Tyr Leu Met Met Arg Val Phe Pro Arg Thr Arg Glu Arg Glu Arg Ala
                85                  90                  95

Trp Lys Met Ala Ile Ile Ser Val Ala Leu Ser Leu Val Leu Ala Pro
            100                 105                 110

Ile Ser Ile Val Ile Phe Tyr Arg Gly Tyr Pro Asp Arg Trp Phe Thr
        115                 120                 125

Glu Thr Cys Trp Thr Phe Ser Ile Ile Leu Glu Ser Val Cys Val Leu
    130                 135                 140

Pro Gln Leu Leu Leu Leu Arg Gln Thr Thr Val Pro Thr Val Ile Asp
145                 150                 155                 160

Ser Tyr Tyr Leu Leu Met Leu Gly Ser Tyr Arg Ala Phe Tyr Ile Leu
                165                 170                 175

Asn Trp Leu Val Arg Gly Leu Gly Ser Glu Gly His Trp Asp Val Ile
            180                 185                 190

Ala Asp Leu Tyr Gly Val Ile Gln Thr Ala Phe Tyr Val Asp Phe Ala
        195                 200                 205

Trp Val Tyr Tyr Ser Arg Gln Arg Val Lys Leu Arg Asn Gly Val
    210                 215                 220

Val Asp Ser Glu Asp Phe Arg His Ser Trp Leu Val Ser Lys Ile Leu
225                 230                 235                 240

Asn Phe Arg Gln Arg Ser Ala Asp Glu Glu Gln Asn Leu Asn Asp
                245                 250                 255

Glu Asp Val Glu Asp Glu Val Ala Gly Gly Arg Pro Arg Asn
            260                 265                 270

Asn Arg Trp Gly Ala Met Gly Ile Ser Val Ser Ala Asp Asp Thr Leu
        275                 280                 285

Gly Asn His Arg Gly Thr Ser Gln Asp Glu Ser Leu Glu Gly Phe Leu
    290                 295                 300

Glu Asp Glu Glu Asp Asp Glu Asp Asn Asn Gly Tyr Pro Val Asn Gly
305                 310                 315                 320

Gly Val Arg Pro Lys Gln Ser Thr Gly Val Thr Gly Ser His Glu
                325                 330                 335

<210> SEQ ID NO 28
<211> LENGTH: 3392

<212> TYPE: DNA
<213> ORGANISM: Aspergillus niger

<400> SEQUENCE: 28

```
gcccttgttg tactactttc attatcgtat ctagttgcat tttccttctt ctatcccagc    60
acataacagc tttgtgtgtg ggaccttcac ctctggtaga tgcaggtcga cacactagtg   120
gttgctgata gttcttcttt cagaggttga gtgtctctga ttgactactg agctctccca   180
tcatggccgg aactcggcca atgtccaacc gttggaccct actgctgtcc ttggtgatcc   240
tactcggatg ccttgtcatc cccggaggta agcctatcca atcacactcc tactggtgag   300
gctctccttg acatctaaca atgacgcata gtcaccgtga acacgagaa cttcaagaca    360
tgttctcaat cgggcttctg taagcggaac agagcattcg ccgacgatgc tgccgcccaa   420
ggttcctcct gggcctcccc atacgaactc gactcatcct ccatccagtt caaggatggc   480
caattgcacg gaaccattct caagtccgtc tcccccaacg agaaagtcaa gctgcctctc   540
gttgtctcct tcctcgagtc cggcgccgcc cgagttgttg tcgatgagga aaagcgcatg   600
aacggtgaca tccagcttcg acacgatagc aaagcacgca aggaacgcta caatgaggca   660
gagaaatggg tgttggttgg tggcctggag ttgagcaaaa ccgcgacctt gagacctgaa   720
accgagtctg gctttaccag agtcttgtac ggtccggaca accagttcga ggctgtcatc   780
cgccacgccc cctttagcgc cgacttcaag agggatggcc aaacccacgt tcaattgaac   840
aacaagggct accttaacat ggagcattgg cgccctaagg tagaggtcga aggcgagggc   900
gagcagcaaa cccaggaaga tgaaagcact tggtgggatg agagctttgg tggaaacacg   960
gacaccaagc ccaggggtcc cgagagtgtg ggattggata tcaccttccc tggctacaag  1020
catgttttg gaattcctga gcatgctgac tctctctcct taaaggaaac tcggtaagct  1080
agtcgcgcag tgacattttc catctcgcag aactgacagc gtcccagagg tggtgaaggg  1140
aatcacgaag agccctaccg catgtacaat gcggatgtat ttgagtacga gctgagcagt  1200
cccatgacct tgtatggtgc tattccattc atgcaggcac atcgcaagga ctccaccgtc  1260
ggtgtcttct ggctgaatgc tgcagagacc tgggtggaca ttgtcaagtc tacctcatct  1320
cctaacccctc ttgctctcgg cgtgggcgcc accactgaca cccagagtca ttggttttcg  1380
gagtccggcc agctcgacgt gttcgttttc cttggtccta ccccacagga aatcagcaag  1440
acctatggtg aactcaccgg ctacactcag ttgcctcaac attttgccat tgcttatcac  1500
cagtgccgct ggaactacat cactgatgag gatgtcaagg aggtcgatcg caactttgac  1560
aagtaccaga tccctacga tgtcatctgg ctggacatcg aatataccga tgacagaaag  1620
tatttcacct gggatccact cagtttcccc gatccgatca gcatggagga gcagctcgat  1680
gagtcggagc gcaaactcgt cgttatcatt gacccgcaca tcaagaacca ggacaagtac  1740
agcatcgtcc aagaaatgaa gagcaaagac ttggccacta gaacaagga cggtgagatc  1800
tacgacgggt ggtgttggcc tggctcttct cactggatcg ataccttcaa ccccgccgcc  1860
atcaaatggt gggtcagctt attcaagttt gacaagttca aggggacgct gtccaatgtc  1920
ttcatttgga acgacatgaa cgagccctcg gttttcaacg gtcccgaaac cacgatgccc  1980
aaggataacc ttcatcatgg caactgggag caccgtgaca tccataacgt tcatggaatc  2040
accctggtca atgccaccta cgatgccctt ctagagcgca agagggcga gatccgtcgg  2100
cctttcattc tgacacggtc atattatgct ggtgctcaac ggatgtctgc tatgtggacg  2160
ggtgataacc aggctacttg ggaacacttg gccgcttcca tccctatggt tctgaacaac  2220
ggcattgcgg gcttcccctt tgccggtgct gacgtgggcg gtttcttcca gaaccctagc  2280
```

-continued

```
aaggagctct tgaccagatg gtaccaagct ggtatttggt accccttctt ccgggcccac    2340
gcgcatattg acacgcgccg gagagagccg tatctgattg ccgagccaca ccggtctatc    2400
atctcccagg ctatccgcct gaggtatcag cttctccccg cctggtacac tgccttccac    2460
gaagcttccg tgaacggaat gccgatcgtg aggccgcagt actacgctca cccttgggat    2520
gaggctggct ttgccattga cgaccagctt tatctcggct ccaccggtct tcttgctaag    2580
cctgttgtct ccgaggaggc caccacggcc gacatttacc ttgctgacga cgaaaagtac    2640
tatgactact ttgactacac cgtctaccag ggagccggaa agcggcatac ggtgcctgct    2700
cctatggaga ctgtgccatt gctgatgcag ggtggccatg taatcccccg caaggaccgt    2760
cctcgccgca gtagcgcctt gatgagatgg gatccgtaca ctcttgttgt ggtcttggat    2820
aagaacggtc aagccgatgg ctctctctac gtggatgacg tgagacgtt cgactatgag    2880 cgtggagctt atatccaccg ccgtttccgc ttccaggagt ctgccctggt ctcggaggat    2940
gttggcacca agggtcctaa gacggccgag tacttgaaga ccatggccaa cgttcgtgtt    3000
gagcgggtgg tggtagttga tcctcctaag gaatggcagg gtaagaccag tgtgactgtc    3060
attgaggatg gagcttcggc ggcttcgaca gcctctatgc agtaccacag ccagcccgat    3120
ggcaaggccg catatgcggt ggtgaagaac cccaatgtcg gcattggaaa gacatggcgg    3180
attgagtttt agactagacg aggatatgga ttgagcaccc atacatatat gcaagaggct    3240
catatatcaa acatcaatgg tatttagtta tgacgctttc agatgcccct acaccctagt    3300
tgagcaccac ccgtagtaga atcgtagtga agggtggaac cccaaccctg aagaggaaaa    3360
agggaaggca actcccggag tggggctgag tc                                  3392
```

<210> SEQ ID NO 29
<211> LENGTH: 2874
<212> TYPE: DNA
<213> ORGANISM: Aspergillus niger
<220> FEATURE:
<221> NAME/KEY: CDS
<222> LOCATION: (1)..(2874)

<400> SEQUENCE: 29

```
atg tcc aac cgt tgg acc cta ctg ctg tcc ttg gtg atc cta ctc gga     48
Met Ser Asn Arg Trp Thr Leu Leu Leu Ser Leu Val Ile Leu Leu Gly
1               5                   10                  15 tgc ctt gtc atc ccc gga gtc acc gtg aaa cac gag aac ttc aag aca     96
Cys Leu Val Ile Pro Gly Val Thr Val Lys His Glu Asn Phe Lys Thr
            20                  25                  30 tgt tct caa tcg ggc ttc tgt aag cgg aac aga gca ttc gcc gac gat    144
Cys Ser Gln Ser Gly Phe Cys Lys Arg Asn Arg Ala Phe Ala Asp Asp
        35                  40                  45 gct gcc gcc caa ggt tcc tcc tgg gcc tcc cca tac gaa ctc gac tca    192
Ala Ala Ala Gln Gly Ser Ser Trp Ala Ser Pro Tyr Glu Leu Asp Ser
    50                  55                  60 tcc tcc atc cag ttc aag gat ggc caa ttg cac gga acc att ctc aag    240
Ser Ser Ile Gln Phe Lys Asp Gly Gln Leu His Gly Thr Ile Leu Lys
65                  70                  75                  80 tcc gtc tcc ccc aac gag aaa gtc aag ctg cct ctc gtt gtc tcc ttc    288
Ser Val Ser Pro Asn Glu Lys Val Lys Leu Pro Leu Val Val Ser Phe
                85                  90                  95 ctc gag tcc ggc gcc gcc cga gtt gtt gtc gat gag gaa aag cgc atg    336
Leu Glu Ser Gly Ala Ala Arg Val Val Val Asp Glu Glu Lys Arg Met
            100                 105                 110 aac ggt gac atc cag ctt cga cac gat agc aaa gca cgc aag gaa cgc    384
Asn Gly Asp Ile Gln Leu Arg His Asp Ser Lys Ala Arg Lys Glu Arg
```

```
                    115                 120                 125
tac aat gag gca gag aaa tgg gtg ttg gtt ggt ggc ctg gag ttg agc      432
Tyr Asn Glu Ala Glu Lys Trp Val Leu Val Gly Gly Leu Glu Leu Ser
    130                 135                 140 aaa acc gcg acc ttg aga cct gaa acc gag tct ggc ttt acc aga gtc      480
Lys Thr Ala Thr Leu Arg Pro Glu Thr Glu Ser Gly Phe Thr Arg Val
145                 150                 155                 160 ttg tac ggt ccg gac aac cag ttc gag gct gtc atc cgc cac gcc ccc      528
Leu Tyr Gly Pro Asp Asn Gln Phe Glu Ala Val Ile Arg His Ala Pro
                165                 170                 175 ttt agc gcc gac ttc aag agg gat ggc caa acc cac gtt caa ttg aac      576
Phe Ser Ala Asp Phe Lys Arg Asp Gly Gln Thr His Val Gln Leu Asn
            180                 185                 190 aac aag ggc tac ctt aac atg gag cat tgg cgc cct aag gta gag gtc      624
Asn Lys Gly Tyr Leu Asn Met Glu His Trp Arg Pro Lys Val Glu Val
        195                 200                 205 gaa ggc gag ggc gag cag caa acc cag gaa gat gaa agc act tgg tgg      672
Glu Gly Glu Gly Glu Gln Gln Thr Gln Glu Asp Glu Ser Thr Trp Trp
    210                 215                 220 gat gag agc ttt ggt gga aac acg gac acc aag ccc agg ggt ccc gag      720
Asp Glu Ser Phe Gly Gly Asn Thr Asp Thr Lys Pro Arg Gly Pro Glu
225                 230                 235                 240 agt gtg gga ttg gat atc acc ttc cct ggc tac aag cat gtt ttt gga      768
Ser Val Gly Leu Asp Ile Thr Phe Pro Gly Tyr Lys His Val Phe Gly
                245                 250                 255 att cct gag cat gct gac tct ctc tcc tta aag gaa act cga ggt ggt      816
Ile Pro Glu His Ala Asp Ser Leu Ser Leu Lys Glu Thr Arg Gly Gly
            260                 265                 270 gaa ggg aat cac gaa gag ccc tac cgc atg tac aat gcg gat gta ttt      864
Glu Gly Asn His Glu Glu Pro Tyr Arg Met Tyr Asn Ala Asp Val Phe
        275                 280                 285 gag tac gag ctg agc agt ccc atg acc ttg tat ggt gct att cca ttc      912
Glu Tyr Glu Leu Ser Ser Pro Met Thr Leu Tyr Gly Ala Ile Pro Phe
    290                 295                 300 atg cag gca cat cgc aag gac tcc acc gtc ggt gtc ttc tgg ctg aat      960
Met Gln Ala His Arg Lys Asp Ser Thr Val Gly Val Phe Trp Leu Asn
305                 310                 315                 320 gct gca gag acc tgg gtg gac att gtc aag tct acc tca tct cct aac     1008
Ala Ala Glu Thr Trp Val Asp Ile Val Lys Ser Thr Ser Ser Pro Asn
                325                 330                 335 cct ctt gct ctc ggc gtg ggc gcc acc act gac acc cag agt cat tgg     1056
Pro Leu Ala Leu Gly Val Gly Ala Thr Thr Asp Thr Gln Ser His Trp
            340                 345                 350 ttt tcg gag tcc ggc cag ctc gac gtg ttc gtt ttc ctt ggt cct acc     1104
Phe Ser Glu Ser Gly Gln Leu Asp Val Phe Val Phe Leu Gly Pro Thr
        355                 360                 365 cca cag gaa atc agc aag acc tat ggt gaa ctc acc ggc tac act cag     1152
Pro Gln Glu Ile Ser Lys Thr Tyr Gly Glu Leu Thr Gly Tyr Thr Gln
    370                 375                 380 ttg cct caa cat ttt gcc att gct tat cac cag tgc cgc tgg aac tac     1200
Leu Pro Gln His Phe Ala Ile Ala Tyr His Gln Cys Arg Trp Asn Tyr
385                 390                 395                 400 atc act gat gag gat gtc aag gag gtc gat cgc aac ttt gac aag tac     1248
Ile Thr Asp Glu Asp Val Lys Glu Val Asp Arg Asn Phe Asp Lys Tyr
                405                 410                 415 cag atc ccc tac gat gtc atc tgg ctg gac atc gaa tat acc gat gac     1296
Gln Ile Pro Tyr Asp Val Ile Trp Leu Asp Ile Glu Tyr Thr Asp Asp
            420                 425                 430 aga aag tat ttc acc tgg gat cca ctc agt ttc ccc gat ccg atc agc     1344
Arg Lys Tyr Phe Thr Trp Asp Pro Leu Ser Phe Pro Asp Pro Ile Ser
```

```
                  435                 440                 445
atg gag gag cag ctc gat gag tcg gag cgc aaa ctc gtc gtt atc att   1392
Met Glu Glu Gln Leu Asp Glu Ser Glu Arg Lys Leu Val Val Ile Ile
450                 455                 460 gac ccg cac atc aag aac cag gac aag tac agc atc gtc caa gaa atg   1440
Asp Pro His Ile Lys Asn Gln Asp Lys Tyr Ser Ile Val Gln Glu Met
465                 470                 475                 480 aag agc aaa gac ttg gcc act aag aac aag gac ggt gag atc tac gac   1488
Lys Ser Lys Asp Leu Ala Thr Lys Asn Lys Asp Gly Glu Ile Tyr Asp
                485                 490                 495 ggg tgg tgt tgg cct ggc tct tct cac tgg atc gat acc ttc aac ccc   1536
Gly Trp Cys Trp Pro Gly Ser Ser His Trp Ile Asp Thr Phe Asn Pro
            500                 505                 510 gcc gcc atc aaa tgg tgg gtc agc tta ttc aag ttt gac aag ttc aag   1584
Ala Ala Ile Lys Trp Trp Val Ser Leu Phe Lys Phe Asp Lys Phe Lys
            515                 520                 525 ggg acg ctg tcc aat gtc ttc att tgg aac gac atg aac gag ccc tcg   1632
Gly Thr Leu Ser Asn Val Phe Ile Trp Asn Asp Met Asn Glu Pro Ser
530                 535                 540 gtt ttc aac ggt ccc gaa acc acg atg ccc aag gat aac ctt cat cat   1680
Val Phe Asn Gly Pro Glu Thr Thr Met Pro Lys Asp Asn Leu His His
545                 550                 555                 560 ggc aac tgg gag cac cgt gac atc cat aac gtt cat gga atc acc ctg   1728
Gly Asn Trp Glu His Arg Asp Ile His Asn Val His Gly Ile Thr Leu
                565                 570                 575 gtc aat gcc acc tac gat gcc ctt cta gag cgc aag aag ggc gag atc   1776
Val Asn Ala Thr Tyr Asp Ala Leu Leu Glu Arg Lys Lys Gly Glu Ile
                580                 585                 590 cgt cgg cct ttc att ctg aca cgg tca tat tat gct ggt gct caa cgg   1824
Arg Arg Pro Phe Ile Leu Thr Arg Ser Tyr Tyr Ala Gly Ala Gln Arg
            595                 600                 605 atg tct gct atg tgg acg ggt gat aac cag gct act tgg gaa cac ttg   1872
Met Ser Ala Met Trp Thr Gly Asp Asn Gln Ala Thr Trp Glu His Leu
610                 615                 620 gcc gct tcc atc cct atg gtt ctg aac aac ggc att gcg ggc ttc ccc   1920
Ala Ala Ser Ile Pro Met Val Leu Asn Asn Gly Ile Ala Gly Phe Pro
625                 630                 635                 640 ttt gcc ggt gct gac gtg ggc ggt ttc ttc cag aac cct agc aag gag   1968
Phe Ala Gly Ala Asp Val Gly Gly Phe Phe Gln Asn Pro Ser Lys Glu
                645                 650                 655 ctc ttg acc aga tgg tac caa gct ggt att tgg tac ccc ttc ttc cgg   2016
Leu Leu Thr Arg Trp Tyr Gln Ala Gly Ile Trp Tyr Pro Phe Phe Arg
            660                 665                 670 gcc cac gcg cat att gac acg cgc cgg aga gag ccg tat ctg att gcc   2064
Ala His Ala His Ile Asp Thr Arg Arg Arg Glu Pro Tyr Leu Ile Ala
            675                 680                 685 gag cca cac cgg tct atc atc tcc cag gct atc cgc ctg agg tat cag   2112
Glu Pro His Arg Ser Ile Ile Ser Gln Ala Ile Arg Leu Arg Tyr Gln
690                 695                 700 ctt ctc ccc gcc tgg tac act gcc ttc cac gaa gct tcc gtg aac gga   2160
Leu Leu Pro Ala Trp Tyr Thr Ala Phe His Glu Ala Ser Val Asn Gly
705                 710                 715                 720 atg ccg atc gtg agg ccg cag tac tac gct cac cct tgg gat gag gct   2208
Met Pro Ile Val Arg Pro Gln Tyr Tyr Ala His Pro Trp Asp Glu Ala
                725                 730                 735 ggc ttt gcc att gac gac cag ctt tat ctc ggc tcc acc ggt ctt ctt   2256
Gly Phe Ala Ile Asp Asp Gln Leu Tyr Leu Gly Ser Thr Gly Leu Leu
            740                 745                 750 gct aag cct gtt gtc tcc gag gag gcc acc acg gcc gac att tac ctt   2304
Ala Lys Pro Val Val Ser Glu Glu Ala Thr Thr Ala Asp Ile Tyr Leu
```

```
                    755                  760                   765
gct gac gac gaa aag tac tat gac tac ttt gac tac acc gtc tac cag      2352
Ala Asp Asp Glu Lys Tyr Tyr Asp Tyr Phe Asp Tyr Thr Val Tyr Gln
770                 775                   780 gga gcc gga aag cgg cat acg gtg cct gct cct atg gag act gtg cca      2400
Gly Ala Gly Lys Arg His Thr Val Pro Ala Pro Met Glu Thr Val Pro
785                 790                   795                 800 ttg ctg atg cag ggt ggc cat gta atc ccc cgc aag gac cgt cct cgc      2448
Leu Leu Met Gln Gly Gly His Val Ile Pro Arg Lys Asp Arg Pro Arg
                    805                   810                 815 cgc agt agc gcc ttg atg aga tgg gat ccg tac act ctt gtt gtg gtc      2496
Arg Ser Ser Ala Leu Met Arg Trp Asp Pro Tyr Thr Leu Val Val Val
                820                   825                  830 ttg gat aag aac ggt caa gcc gat ggc tct ctc tac gtg gat gac ggt      2544
Leu Asp Lys Asn Gly Gln Ala Asp Gly Ser Leu Tyr Val Asp Asp Gly
            835                   840                  845 gag acg ttc gac tat gag cgt gga gct tat atc cac cgc gtt ttc cgc      2592
Glu Thr Phe Asp Tyr Glu Arg Gly Ala Tyr Ile His Arg Val Phe Arg
850                 855                   860 ttc cag gag tct gcc ctg gtc tcg gag gat gtt ggc acc aag ggt cct      2640
Phe Gln Glu Ser Ala Leu Val Ser Glu Asp Val Gly Thr Lys Gly Pro
865                 870                   875                 880 aag acg gcc gag tac ttg aag acc atg gcc aac gtt cgt gtt gag cgg      2688
Lys Thr Ala Glu Tyr Leu Lys Thr Met Ala Asn Val Arg Val Glu Arg
                    885                   890                 895 gtg gtg gta gtt gat cct cct aag gaa tgg cag ggt aag acc agt gtg      2736
Val Val Val Val Asp Pro Pro Lys Glu Trp Gln Gly Lys Thr Ser Val
                900                   905                  910 act gtc att gag gat gga gct tcg gcg gct tcg aca gcc tct atg cag      2784
Thr Val Ile Glu Asp Gly Ala Ser Ala Ala Ser Thr Ala Ser Met Gln
            915                   920                  925 tac cac agc cag ccc gat ggc aag gcc gca tat gcg gtg gtg aag aac      2832
Tyr His Ser Gln Pro Asp Gly Lys Ala Ala Tyr Ala Val Val Lys Asn
930                 935                   940 ccc aat gtc ggc att gga aag aca tgg cgg att gag ttt tag              2874
Pro Asn Val Gly Ile Gly Lys Thr Trp Arg Ile Glu Phe
945                 950                   955

<210> SEQ ID NO 30
<211> LENGTH: 957
<212> TYPE: PRT
<213> ORGANISM: Aspergillus niger

<400> SEQUENCE: 30

Met Ser Asn Arg Trp Thr Leu Leu Ser Leu Val Ile Leu Leu Gly
1               5                   10                  15

Cys Leu Val Ile Pro Gly Val Thr Val Lys His Glu Asn Phe Lys Thr
                20                  25                  30

Cys Ser Gln Ser Gly Phe Cys Lys Arg Asn Arg Ala Phe Ala Asp Asp
            35                  40                  45

Ala Ala Ala Gln Gly Ser Ser Trp Ala Ser Pro Tyr Glu Leu Asp Ser
        50                  55                  60

Ser Ser Ile Gln Phe Lys Asp Gly Gln Leu His Gly Thr Ile Leu Lys
65                  70                  75                  80

Ser Val Ser Pro Asn Glu Lys Val Lys Leu Pro Leu Val Ser Phe
                85                  90                  95

Leu Glu Ser Gly Ala Ala Arg Val Val Val Asp Glu Glu Lys Arg Met
            100                 105                 110

Asn Gly Asp Ile Gln Leu Arg His Asp Ser Lys Ala Arg Lys Glu Arg
```

```
                    115                 120                 125
Tyr Asn Glu Ala Glu Lys Trp Val Leu Val Gly Gly Leu Glu Leu Ser
                130                 135                 140

Lys Thr Ala Thr Leu Arg Pro Glu Thr Glu Ser Gly Phe Thr Arg Val
145                 150                 155                 160

Leu Tyr Gly Pro Asp Asn Gln Phe Glu Ala Val Ile Arg His Ala Pro
                165                 170                 175

Phe Ser Ala Asp Phe Lys Arg Asp Gly Gln Thr His Val Gln Leu Asn
                180                 185                 190

Asn Lys Gly Tyr Leu Asn Met Glu His Trp Arg Pro Lys Val Glu Val
                195                 200                 205

Glu Gly Glu Gly Glu Gln Gln Thr Gln Glu Asp Glu Ser Thr Trp Trp
210                 215                 220

Asp Glu Ser Phe Gly Gly Asn Thr Asp Thr Lys Pro Arg Gly Pro Glu
225                 230                 235                 240

Ser Val Gly Leu Asp Ile Thr Phe Pro Gly Tyr Lys His Val Phe Gly
                245                 250                 255

Ile Pro Glu His Ala Asp Ser Leu Ser Leu Lys Glu Thr Arg Gly Gly
                260                 265                 270

Glu Gly Asn His Glu Glu Pro Tyr Arg Met Tyr Asn Ala Asp Val Phe
                275                 280                 285

Glu Tyr Glu Leu Ser Ser Pro Met Thr Leu Tyr Gly Ala Ile Pro Phe
                290                 295                 300

Met Gln Ala His Arg Lys Asp Ser Thr Val Gly Val Phe Trp Leu Asn
305                 310                 315                 320

Ala Ala Glu Thr Trp Val Asp Ile Val Lys Ser Thr Ser Ser Pro Asn
                325                 330                 335

Pro Leu Ala Leu Gly Val Gly Ala Thr Thr Asp Thr Gln Ser His Trp
                340                 345                 350

Phe Ser Glu Ser Gly Gln Leu Asp Val Phe Val Phe Leu Gly Pro Thr
                355                 360                 365

Pro Gln Glu Ile Ser Lys Thr Tyr Gly Glu Leu Thr Gly Tyr Thr Gln
370                 375                 380

Leu Pro Gln His Phe Ala Ile Ala Tyr His Gln Cys Arg Trp Asn Tyr
385                 390                 395                 400

Ile Thr Asp Glu Asp Val Lys Glu Val Asp Arg Asn Phe Asp Lys Tyr
                405                 410                 415

Gln Ile Pro Tyr Asp Val Ile Trp Leu Asp Ile Glu Tyr Thr Asp Asp
                420                 425                 430

Arg Lys Tyr Phe Thr Trp Asp Pro Leu Ser Phe Pro Asp Pro Ile Ser
                435                 440                 445

Met Glu Glu Gln Leu Asp Glu Ser Glu Arg Lys Leu Val Val Ile Ile
                450                 455                 460

Asp Pro His Ile Lys Asn Gln Asp Lys Tyr Ser Ile Val Gln Glu Met
465                 470                 475                 480

Lys Ser Lys Asp Leu Ala Thr Lys Asn Lys Asp Gly Glu Ile Tyr Asp
                485                 490                 495

Gly Trp Cys Trp Pro Gly Ser Ser His Trp Ile Asp Thr Phe Asn Pro
                500                 505                 510

Ala Ala Ile Lys Trp Trp Val Ser Leu Phe Lys Phe Asp Lys Phe Lys
                515                 520                 525

Gly Thr Leu Ser Asn Val Phe Ile Trp Asn Asp Met Asn Glu Pro Ser
                530                 535                 540
```

-continued

Val Phe Asn Gly Pro Glu Thr Thr Met Pro Lys Asp Asn Leu His His
545                 550                 555                 560

Gly Asn Trp Glu His Arg Asp Ile His Asn Val His Gly Ile Thr Leu
            565                 570                 575

Val Asn Ala Thr Tyr Asp Ala Leu Leu Glu Arg Lys Lys Gly Glu Ile
        580                 585                 590

Arg Arg Pro Phe Ile Leu Thr Arg Ser Tyr Tyr Ala Gly Ala Gln Arg
    595                 600                 605

Met Ser Ala Met Trp Thr Gly Asp Asn Gln Ala Thr Trp Glu His Leu
610                 615                 620

Ala Ala Ser Ile Pro Met Val Leu Asn Asn Gly Ile Ala Gly Phe Pro
625                 630                 635                 640

Phe Ala Gly Ala Asp Val Gly Gly Phe Phe Gln Asn Pro Ser Lys Glu
                645                 650                 655

Leu Leu Thr Arg Trp Tyr Gln Ala Gly Ile Trp Tyr Pro Phe Phe Arg
            660                 665                 670

Ala His Ala His Ile Asp Thr Arg Arg Glu Pro Tyr Leu Ile Ala
        675                 680                 685

Glu Pro His Arg Ser Ile Ile Ser Gln Ala Ile Arg Leu Arg Tyr Gln
    690                 695                 700

Leu Leu Pro Ala Trp Tyr Thr Ala Phe His Glu Ala Ser Val Asn Gly
705                 710                 715                 720

Met Pro Ile Val Arg Pro Gln Tyr Tyr Ala His Pro Trp Asp Glu Ala
                725                 730                 735

Gly Phe Ala Ile Asp Asp Gln Leu Tyr Leu Gly Ser Thr Gly Leu Leu
            740                 745                 750

Ala Lys Pro Val Val Ser Glu Glu Ala Thr Thr Ala Asp Ile Tyr Leu
        755                 760                 765

Ala Asp Asp Glu Lys Tyr Tyr Asp Tyr Phe Asp Tyr Thr Val Tyr Gln
    770                 775                 780

Gly Ala Gly Lys Arg His Thr Val Pro Ala Pro Met Glu Thr Val Pro
785                 790                 795                 800

Leu Leu Met Gln Gly Gly His Val Ile Pro Arg Lys Asp Arg Pro Arg
                805                 810                 815

Arg Ser Ser Ala Leu Met Arg Trp Asp Pro Tyr Thr Leu Val Val Val
            820                 825                 830

Leu Asp Lys Asn Gly Gln Ala Asp Gly Ser Leu Tyr Val Asp Asp Gly
        835                 840                 845

Glu Thr Phe Asp Tyr Glu Arg Gly Ala Tyr Ile His Arg Arg Phe Arg
    850                 855                 860

Phe Gln Glu Ser Ala Leu Val Ser Glu Asp Val Gly Thr Lys Gly Pro
865                 870                 875                 880

Lys Thr Ala Glu Tyr Leu Lys Thr Met Ala Asn Val Arg Val Glu Arg
                885                 890                 895

Val Val Val Val Asp Pro Pro Lys Glu Trp Gln Gly Lys Thr Ser Val
            900                 905                 910

Thr Val Ile Glu Asp Gly Ala Ser Ala Ala Ser Thr Ala Ser Met Gln
        915                 920                 925

Tyr His Ser Gln Pro Asp Gly Lys Ala Ala Tyr Ala Val Val Lys Asn
    930                 935                 940

Pro Asn Val Gly Ile Gly Lys Thr Trp Arg Ile Glu Phe
945                 950                 955

<210> SEQ ID NO 31

<211> LENGTH: 2303
<212> TYPE: DNA
<213> ORGANISM: Aspergillus niger

<400> SEQUENCE: 31

| | | | | | |
|---|---|---|---|---|---|
| agcggcaggc | cgataaggag | ctgagtcagc | gagccccaga | atgggcgggc | gattatcacc | 60 |
| agctggccag | aagctctctc | cgcattcctg | atggtggatt | gattgatgaa | ttgattgctt | 120 |
| ttttgtcttg | ctcttgttag | tttgttctct | agtgccccta | cacagcattg | gtcagggagc | 180 |
| tcaatgctgc | cactgccacc | atgatacttc | ctcagggatc | gctcttcttg | gtgagcatag | 240 |
| ctgcttgctc | gaccgtcgtg | gctgcggcgg | gtgatgcctc | ctctcgtccc | cggggtgtag | 300 |
| gtcccgaatg | taagtgccac | ttatatacct | acttaggctg | aggcggtgct | acacgcaacc | 360 |
| attctattcc | aacttgcatc | ctcgccataa | tcttgttttt | ttgtcggcat | tggtcatgct | 420 |
| aactggtttc | gtctaatggt | tggcagtcgc | caagttctac | aaggatacca | ccaccttcac | 480 |
| gtgcatctcc | cacccagcca | tccagatccc | cttctccgcc | gtgaacgatg | attactgtga | 540 |
| ctgtccggat | ggcagtgatg | agcctggcac | atctgcctgt | gccttcctgt | ctcgcaactc | 600 |
| cgccctaaca | ccgggtgagc | gccccggcag | cgacgatctc | gagctgacat | ccgccctgcc | 660 |
| gggtttctac | tgcaagaaca | agggccacaa | gcccggctac | gtccccttcc | agcgggtcaa | 720 |
| tgacggcatc | tgtgactatg | agctctgctg | cgacggcagt | gacgagtggg | cccgccctgg | 780 |
| cggcaccaag | tgtgaagaca | agtgcaagga | gatcggcaag | gaatggcgga | agaaggagga | 840 |
| gaagagacag | aagtccatga | ctgcggcttt | gaagaagaag | aaggatctgc | ttgtggaggc | 900 |
| tggtagacag | cagaaggagg | tcgaggacaa | tatcaagcgt | ctggaagttg | aaattcaggc | 960 |
| ccaggagctg | aaggtcaatg | atcttcaggc | ggagctggag | gaggtggagc | agcaggaggc | 1020 |
| gagcaaggtc | gtgaagggca | agacggcggg | caaggttaat | gtgcttgctg | ggttggctaa | 1080 |
| gagccgggtt | gaggagcttc | gaaacgccct | gatggacgtc | cgcaaggagc | gtgatgatac | 1140 |
| ccgtgcccgt | gtgaaggagc | tcgaagagat | tctgtctaag | ttcaaggtgg | aatacaaccc | 1200 |
| taacttcaac | gatgagggcg | ttaagcgcgc | tgtgcgcagc | tgggaagact | acgccgccaa | 1260 |
| gggcacccct | gagggcgccg | tgaacaacgc | tcaggaccgt | gatttggatg | aaattgctaa | 1320 |
| gcccgatgat | gagaaggcgg | gcatcaactg | gaacagtgg | gagaatgaag | aggatgggtg | 1380 |
| tgaggctggt | cttggtatgt | aaatcatttc | agagtgaggg | ttatcgatgt | tcccgcgcta | 1440 |
| acatcagatt | tagtctacca | gctggcagcc | taccttccgc | cttctttggt | cgagtttatc | 1500 |
| gaaggcaagg | tgctcttcgt | cagaggtctc | ttggaagata | acggaattct | acccaaggcg | 1560 |
| gccgagactt | ctacgtccga | atccaaggtt | gtgtcagaag | cccgagaagc | cgtgaagtca | 1620 |
| gcagagaagg | agcttggaga | caagcagaag | cagctgaagg | atcacaagtc | cgatcttgag | 1680 |
| acggactatg | gtgtcggatc | catcttccgt | gccctcaagg | gcgtttgcat | ctccaaggac | 1740 |
| tcgggtgagt | acacgtatga | gcactgcttc | ctggaccaga | caaaacagat | tccaaagaag | 1800 |
| ggcggcggat | ccacacgcat | gggcaagtac | accggcattg | ggtcggtcag | tgttgatgtg | 1860 |
| ctcaacgagg | cgggcgagat | tgtccccgaa | gacagggtca | ctcttcagta | cgccaacgga | 1920 |
| caaggctgct | ggaatggacc | ggcccgctcg | acgacggtca | tcctgacatg | cggcgaagag | 1980 |
| gatgcgatcc | tgaaggtggc | cgaagacgag | aagtgcgtgt | actcgatgca | tgtcacgtcg | 2040 |
| ccggccgtgt | gtcccggagg | cgatgagggc | gcaactgccc | cgaaccgcaa | ggatgagctg | 2100 |
| tgagcagtga | tgggaccata | tttagggtta | tatcagagcg | ctacaagtct | ataggttttg | 2160 |
| cttatttgaa | ttgcatacac | agcatctgtt | gttctgacag | caatcatgag | ctactgacct | 2220 |

```
<210> SEQ ID NO 32
<211> LENGTH: 1707
<212> TYPE: DNA
<213> ORGANISM: Aspergillus niger
<220> FEATURE:
<221> NAME/KEY: CDS
<222> LOCATION: (1)..(1707)

<400> SEQUENCE: 32 atg ata ctt cct cag gga tcg ctc ttc ttg gtg agc ata gct gct tgc      48
Met Ile Leu Pro Gln Gly Ser Leu Phe Leu Val Ser Ile Ala Ala Cys
1               5                   10                  15 tcg acc gtc gtg gct gcg gcg ggt gat gcc tcc tct cgt ccc cgg ggt      96
Ser Thr Val Val Ala Ala Ala Gly Asp Ala Ser Ser Arg Pro Arg Gly
            20                  25                  30 gta ggt ccc gaa ttc gcc aag ttc tac aag gat acc acc acc ttc acg     144
Val Gly Pro Glu Phe Ala Lys Phe Tyr Lys Asp Thr Thr Thr Phe Thr
        35                  40                  45 tgc atc tcc cac cca gcc atc cag atc ccc ttc tcc gcc gtg aac gat     192
Cys Ile Ser His Pro Ala Ile Gln Ile Pro Phe Ser Ala Val Asn Asp
    50                  55                  60 gat tac tgt gac tgt ccg gat ggc agt gat gag cct ggc aca tct gcc     240
Asp Tyr Cys Asp Cys Pro Asp Gly Ser Asp Glu Pro Gly Thr Ser Ala
65                  70                  75                  80 tgt gcc ttc ctg tct cgc aac tcc gcc cta aca ccg ggt gag cgc ccc     288
Cys Ala Phe Leu Ser Arg Asn Ser Ala Leu Thr Pro Gly Glu Arg Pro
                85                  90                  95 ggc agc gac gat ctc gag ctg aca tcc gcc ctg ccg ggt ttc tac tgc     336
Gly Ser Asp Asp Leu Glu Leu Thr Ser Ala Leu Pro Gly Phe Tyr Cys
            100                 105                 110 aag aac aag ggc cac aag ccc ggc tac gtc ccc ttc cag cgg gtc aat     384
Lys Asn Lys Gly His Lys Pro Gly Tyr Val Pro Phe Gln Arg Val Asn
        115                 120                 125 gac ggc atc tgt gac tat gag ctc tgc tgc gac ggc agt gac gag tgg     432
Asp Gly Ile Cys Asp Tyr Glu Leu Cys Cys Asp Gly Ser Asp Glu Trp
    130                 135                 140 gcc cgc cct ggc ggc acc aag tgt gaa gac aag tgc aag gag atc ggc     480
Ala Arg Pro Gly Gly Thr Lys Cys Glu Asp Lys Cys Lys Glu Ile Gly
145                 150                 155                 160 aag gaa tgg cgg aag aag gag gag aag aga cag aag tcc atg act gcg     528
Lys Glu Trp Arg Lys Lys Glu Glu Lys Arg Gln Lys Ser Met Thr Ala
                165                 170                 175 gct ttg aag aag aag aag gat ctg ctt gtg gag gct ggt aga cag cag     576
Ala Leu Lys Lys Lys Lys Asp Leu Leu Val Glu Ala Gly Arg Gln Gln
            180                 185                 190 aag gag gtc gag gac aat atc aag cgt ctg gaa gtt gaa att cag gcc     624
Lys Glu Val Glu Asp Asn Ile Lys Arg Leu Glu Val Glu Ile Gln Ala
        195                 200                 205 cag gag ctg aag gtc aat gat ctt cag gcg gag ctg gag gag gtg gag     672
Gln Glu Leu Lys Val Asn Asp Leu Gln Ala Glu Leu Glu Glu Val Glu
    210                 215                 220 cag cag gag gcg agc aag gtc gtg aag ggc aag acg gcg ggc aag gtt     720
Gln Gln Glu Ala Ser Lys Val Val Lys Gly Lys Thr Ala Gly Lys Val
225                 230                 235                 240 aat gtg ctt gct ggg ttg gct aag agc cgg gtt gag gag ctt cga aac     768
Asn Val Leu Ala Gly Leu Ala Lys Ser Arg Val Glu Glu Leu Arg Asn
                245                 250                 255 gcc ctg atg gac gtc cgc aag gag cgt gat gat acc cgt gcc cgt gtg     816
Ala Leu Met Asp Val Arg Lys Glu Arg Asp Asp Thr Arg Ala Arg Val
```

```
                Ala Leu Met Asp Val Arg Lys Glu Arg Asp Thr Arg Ala Arg Val
                                260                 265                 270 aag gag ctc gaa gag att ctg tct aag ttc aag gtg gaa tac aac cct         864
Lys Glu Leu Glu Glu Ile Leu Ser Lys Phe Lys Val Glu Tyr Asn Pro
            275                 280                 285 aac ttc aac gat gag ggc gtt aag cgc gct gtg cgc agc tgg gaa gac         912
Asn Phe Asn Asp Glu Gly Val Lys Arg Ala Val Arg Ser Trp Glu Asp
    290                 295                 300 tac gcc gcc aag ggc acc ctt gag ggc gcc gtg aac aac gct cag gac         960
Tyr Ala Ala Lys Gly Thr Leu Glu Gly Ala Val Asn Asn Ala Gln Asp
305                 310                 315                 320 cgt gat ttg gat gaa att gct aag ccc gat gat gag aag gcg ggc atc        1008
Arg Asp Leu Asp Glu Ile Ala Lys Pro Asp Asp Glu Lys Ala Gly Ile
                325                 330                 335 aac tgg gaa cag tgg gag aat gaa gag gat ggg tgt gag gct ggt ctt        1056
Asn Trp Glu Gln Trp Glu Asn Glu Glu Asp Gly Cys Glu Ala Gly Leu
            340                 345                 350 gtc tac cag ctg gca gcc tac ctt ccg cct tct ttg gtc gag ttt atc        1104
Val Tyr Gln Leu Ala Ala Tyr Leu Pro Pro Ser Leu Val Glu Phe Ile
    355                 360                 365 gaa ggc aag gtg ctc ttc gtc aga ggt ctc ttg gaa gat aac gga att        1152
Glu Gly Lys Val Leu Phe Val Arg Gly Leu Leu Glu Asp Asn Gly Ile
370                 375                 380 cta ccc aag gcg gcc gag act tct acg tcc gaa tcc aag gtt gtg tca        1200
Leu Pro Lys Ala Ala Glu Thr Ser Thr Ser Glu Ser Lys Val Val Ser
385                 390                 395                 400 gaa gcc cga gaa gcc gtg aag tca gca gag aag gag ctt gga gac aag        1248
Glu Ala Arg Glu Ala Val Lys Ser Ala Glu Lys Glu Leu Gly Asp Lys
                405                 410                 415 cag aag cag ctg aag gat cac aag tcc gat ctt gag acg gac tat ggt        1296
Gln Lys Gln Leu Lys Asp His Lys Ser Asp Leu Glu Thr Asp Tyr Gly
            420                 425                 430 gtc gga tcc atc ttc cgt gcc ctc aag ggc gtt tgc atc tcc aag gac        1344
Val Gly Ser Ile Phe Arg Ala Leu Lys Gly Val Cys Ile Ser Lys Asp
    435                 440                 445 tcg ggt gag tac acg tat gag cac tgc ttc ctg gac cag aca aaa cag        1392
Ser Gly Glu Tyr Thr Tyr Glu His Cys Phe Leu Asp Gln Thr Lys Gln
450                 455                 460 att cca aag aag ggc ggc gga tcc aca cgc atg ggc aag tac acc ggc        1440
Ile Pro Lys Lys Gly Gly Gly Ser Thr Arg Met Gly Lys Tyr Thr Gly
465                 470                 475                 480 att ggg tcg gtc agt gtt gat gtg ctc aac gag gcg ggc gag att gtc        1488
Ile Gly Ser Val Ser Val Asp Val Leu Asn Glu Ala Gly Glu Ile Val
                485                 490                 495 ccc gaa gac agg gtc act ctt cag tac gcc aac gga caa ggc tgc tgg        1536
Pro Glu Asp Arg Val Thr Leu Gln Tyr Ala Asn Gly Gln Gly Cys Trp
            500                 505                 510 aat gga ccg gcc cgc tcg acg acg gtc atc ctg aca tgc ggc gaa gag        1584
Asn Gly Pro Ala Arg Ser Thr Thr Val Ile Leu Thr Cys Gly Glu Glu
    515                 520                 525 gat gcg atc ctg aag gtg gcc gaa gac gag aag tgc gtg tac tcg atg        1632
Asp Ala Ile Leu Lys Val Ala Glu Asp Glu Lys Cys Val Tyr Ser Met
530                 535                 540 cat gtc acg tcg ccg gcc gtg tgt ccc gga ggc gat gag ggc gca act        1680
His Val Thr Ser Pro Ala Val Cys Pro Gly Gly Asp Glu Gly Ala Thr
545                 550                 555                 560 gcc ccg aac cgc aag gat gag ctg tga                                    1707
Ala Pro Asn Arg Lys Asp Glu Leu
                565
```

```
<210> SEQ ID NO 33
<211> LENGTH: 568
<212> TYPE: PRT
<213> ORGANISM: Aspergillus niger

<400> SEQUENCE: 33

Met Ile Leu Pro Gln Gly Ser Leu Phe Leu Val Ser Ile Ala Ala Cys
1               5                   10                  15

Ser Thr Val Val Ala Ala Gly Asp Ala Ser Ser Arg Pro Arg Gly
            20                  25                  30

Val Gly Pro Glu Phe Ala Lys Phe Tyr Lys Asp Thr Thr Phe Thr
        35                  40                  45

Cys Ile Ser His Pro Ala Ile Gln Ile Pro Phe Ser Ala Val Asn Asp
    50                  55                  60

Asp Tyr Cys Asp Cys Pro Asp Gly Ser Asp Glu Pro Gly Thr Ser Ala
65                  70                  75                  80

Cys Ala Phe Leu Ser Arg Asn Ser Ala Leu Thr Pro Gly Glu Arg Pro
                85                  90                  95

Gly Ser Asp Asp Leu Glu Leu Thr Ser Ala Leu Pro Gly Phe Tyr Cys
                100                 105                 110

Lys Asn Lys Gly His Lys Pro Gly Tyr Val Pro Phe Gln Arg Val Asn
            115                 120                 125

Asp Gly Ile Cys Asp Tyr Glu Leu Cys Cys Asp Gly Ser Asp Glu Trp
    130                 135                 140

Ala Arg Pro Gly Gly Thr Lys Cys Glu Asp Lys Cys Lys Glu Ile Gly
145                 150                 155                 160

Lys Glu Trp Arg Lys Lys Glu Lys Arg Gln Lys Ser Met Thr Ala
            165                 170                 175

Ala Leu Lys Lys Lys Lys Asp Leu Leu Val Glu Ala Gly Arg Gln Gln
                180                 185                 190

Lys Glu Val Glu Asp Asn Ile Lys Arg Leu Glu Val Glu Ile Gln Ala
            195                 200                 205

Gln Glu Leu Lys Val Asn Asp Leu Gln Ala Glu Leu Glu Glu Val Glu
    210                 215                 220

Gln Gln Glu Ala Ser Lys Val Val Lys Gly Lys Thr Ala Gly Lys Val
225                 230                 235                 240

Asn Val Leu Ala Gly Leu Ala Lys Ser Arg Val Glu Glu Leu Arg Asn
                245                 250                 255

Ala Leu Met Asp Val Arg Lys Glu Arg Asp Asp Thr Arg Ala Arg Val
                260                 265                 270

Lys Glu Leu Glu Glu Ile Leu Ser Lys Phe Lys Val Glu Tyr Asn Pro
            275                 280                 285

Asn Phe Asn Asp Glu Gly Val Lys Arg Ala Val Arg Ser Trp Glu Asp
    290                 295                 300

Tyr Ala Ala Lys Gly Thr Leu Glu Gly Ala Val Asn Asn Ala Gln Asp
305                 310                 315                 320

Arg Asp Leu Asp Glu Ile Ala Lys Pro Asp Asp Glu Lys Ala Gly Ile
                325                 330                 335

Asn Trp Glu Gln Trp Glu Asn Glu Glu Asp Gly Cys Glu Ala Gly Leu
                340                 345                 350

Val Tyr Gln Leu Ala Ala Tyr Leu Pro Pro Ser Leu Val Glu Phe Ile
            355                 360                 365

Glu Gly Lys Val Leu Phe Val Arg Gly Leu Leu Glu Asp Asn Gly Ile
    370                 375                 380

Leu Pro Lys Ala Ala Glu Thr Ser Thr Ser Glu Ser Lys Val Val Ser
```

```
                385                 390                 395                 400
Glu Ala Arg Glu Ala Val Lys Ser Ala Glu Lys Glu Leu Gly Asp Lys
                    405                 410                 415
Gln Lys Gln Leu Lys Asp His Lys Ser Asp Leu Glu Thr Asp Tyr Gly
                420                 425                 430
Val Gly Ser Ile Phe Arg Ala Leu Lys Gly Val Cys Ile Ser Lys Asp
            435                 440                 445
Ser Gly Glu Tyr Thr Tyr Glu His Cys Phe Leu Asp Gln Thr Lys Gln
        450                 455                 460
Ile Pro Lys Lys Gly Gly Ser Thr Arg Met Gly Lys Tyr Thr Gly
465                 470                 475                 480
Ile Gly Ser Val Ser Val Asp Val Leu Asn Glu Ala Gly Glu Ile Val
            485                 490                 495
Pro Glu Asp Arg Val Thr Leu Gln Tyr Ala Asn Gly Gln Gly Cys Trp
                500                 505                 510
Asn Gly Pro Ala Arg Ser Thr Thr Val Ile Leu Thr Cys Gly Glu Glu
            515                 520                 525
Asp Ala Ile Leu Lys Val Ala Glu Asp Glu Lys Cys Val Tyr Ser Met
        530                 535                 540
His Val Thr Ser Pro Ala Val Cys Pro Gly Gly Asp Glu Gly Ala Thr
545                 550                 555                 560
Ala Pro Asn Arg Lys Asp Glu Leu
                565

<210> SEQ ID NO 34
<211> LENGTH: 2343
<212> TYPE: DNA
<213> ORGANISM: Aspergillus niger

<400> SEQUENCE: 34
gcctgaccac gatcgaccgt tgacaatcca ggcttcccett ccgtcgctga tcttcatgtg      60
aaggaccctg ttttcttgct tacctaccat agaccttcat tgcatagctt cactctatac     120
tctcttggtt tctgtcatac actccaattc cttcctccgt ccttgtccac tcgtttccgc     180
cggtctccgg ctattccaag atgcgctccg cagccaaatt tttctatttg gcggtatttg     240
ccctgtcgag gctttccaat gccgagactg ggctgcacca taaccaggac aagtgtgcgg     300
taagtcgata caacgctcgg gcatacgctt ggactgcatg ttgtagaccg gacttggctg     360
attcattctc atctctacca gattgacccc actgccatgg tgtccgacgc ttgtgtctcc     420
tacgccacta tcgatcatct gaacgatcaa gtctacaccc tcctccaatc cattacgcaa     480
gataccgatt tcttctcgta ctaccgtctt aatctcttca acaaagtctg tccattctgg     540
tccgatgcga atagtatgtg cgggaacatt gcatgctccg tcaacacaat cgaatctgaa     600
gacgacattc cgttaacatg gcgcgcggag gagctcagta aactcgaggg acccaaagca     660
ggccatccgg gccgcaatca acgaaaggag cgacctctta atcgaccgct ccaaggaatg     720
ctaggcgaaa atgttggaga gagctgtgtg gtggagtatg acgatgaatg tgatgaacgg     780
gactactgtg ttcccgaaga tgagggtgct agcggcaagg gagactatgt cagtctcgtt     840
gataatccag aacggttcac agggtatgcc ggtatgggcg cccatcaggt ttgggatgca     900
atctatcggg agaattgctt cctcaaaccg gtgcccgagc tatcacccgt tactcctcag     960
ctgggtggtc ttcaagctgt caacgatttc cgtcatgtgc ttcagcagga gttgaagcgc    1020
cctgacctgc ttccattgga caatgaatgc cttgagaagc gagtgttcca tcgtctcatc    1080
agcggaatgc atgcgtctat ctcgacccac ctttgctggg actacctaaa ccagacgacg    1140
```

-continued

```
ggacaatggc atcctaacct tcaatgcttc aaagatcgtc tccacgatca ccccgagcgc    1200
atctcgaacc tgtacttcaa ctacgcgctg gtctcgcgcg ccgtggcgaa gctgcagaaa    1260
cacctacaca actacaacta ctgcgtcggt gatccggtcc aggatgccat gactagggag    1320
aaggtctcca agttgacctc gaccttggct gaccgcccct aaattttcga cgagaacgtc    1380
atgttccagg atcccagctc cgctggcctg aaggaagact tccgcaaccg attccgcaac    1440
gtcagtcgcc tgatggactg cgtcgggtgc gacaaatgcc gcctctgggg caagctccag    1500
gtcaacggat atggcaccgc tctgaaagtg ctgttcgagt acgacgagac taagaacggc    1560
gagaacccgt tgctgcgccg gactgagctg gtggcactga tcaataccct tggtcgcatt    1620
tctcacagca ttgccgccgt ccggagtttc accgggcca tggatgtggg cgatggggag    1680
gtcttcacca tccccgcgag cattgcgtcc aaggagcgcg gtggcaagaa gaagacccga    1740
cgacttctca agacggtgg ctcaaccttc tattatgagg atggcgatga tgacaacttt    1800
gtctacatca ccgagaaact tccgtgggag aaggtccggg tacgccgcga cacggatacg    1860
gtctgggatg atattaaggc cgagttttct atgatctggg acatttacgt ctatgtgctg    1920
aagagctggg tcaatgcacc aaagacattg taagtgatgg catacgatga cctccacagt    1980
ttcctatata ctaactgggc attgcagctt cgagatcgcc gtcctggagg ttgctcgggt    2040
atggaactac tggctgggtc tgcctgtgcc gccacggtcc tggaggatcc agcttcccaa    2100
gcgacccacc cctccaacac ccccgaccca tgaggagctc tagacggtag aagtgggcaa    2160
ggcgacgtgg tggaagatgg cggtgactgg gattgtattg tataactagc gtcgttgagg    2220
actaatcttt ttccgatctg tttgggccgg cgttgttgac gatgcctgtt gggaaatcgc    2280
atctcgggag ttctgggagc attttaggcc gctgtacata tttcaagcaa tgggcctgag    2340
cat                                                                 2343
```

<210> SEQ ID NO 35
<211> LENGTH: 1803
<212> TYPE: DNA
<213> ORGANISM: Aspergillus niger
<220> FEATURE:
<221> NAME/KEY: CDS
<222> LOCATION: (1)..(1803)

<400> SEQUENCE: 35

```
atg cgc tcc gca gcc aaa ttt ttc tat ttg gcg gta ttt gcc ctg tcg      48
Met Arg Ser Ala Ala Lys Phe Phe Tyr Leu Ala Val Phe Ala Leu Ser
1               5                   10                  15 agg ctt tcc aat gcc gag act ggg ctg cac cat aac cag gac aag tgt      96
Arg Leu Ser Asn Ala Glu Thr Gly Leu His His Asn Gln Asp Lys Cys
            20                  25                  30 gcg att gac ccc act gcc atg gtg tcc gac gct tgt gtc tcc tac gcc     144
Ala Ile Asp Pro Thr Ala Met Val Ser Asp Ala Cys Val Ser Tyr Ala
        35                  40                  45 act atc gat cat ctg aac gat caa gtc tac acc ctc ctc caa tcc att     192
Thr Ile Asp His Leu Asn Asp Gln Val Tyr Thr Leu Leu Gln Ser Ile
    50                  55                  60 acg caa gat acc gat ttc ttc tcg tac tac cgt ctt aat ctc ttc aac     240
Thr Gln Asp Thr Asp Phe Phe Ser Tyr Tyr Arg Leu Asn Leu Phe Asn
65                  70                  75                  80 aaa gtc tgt cca ttc tgg tcc gat gcg aat agt atg tgc ggg aac att     288
Lys Val Cys Pro Phe Trp Ser Asp Ala Asn Ser Met Cys Gly Asn Ile
                85                  90                  95 gca tgc tcc gtc aac aca atc gaa tct gaa gac gac att ccg tta aca     336
Ala Cys Ser Val Asn Thr Ile Glu Ser Glu Asp Asp Ile Pro Leu Thr
```

-continued

```
               100                 105                 110
tgg cgc gcg gag gag ctc agt aaa ctc gag gga ccc aaa gca ggc cat      384
Trp Arg Ala Glu Glu Leu Ser Lys Leu Glu Gly Pro Lys Ala Gly His
    115                 120                 125 ccg ggc cgc aat caa cga aag gag cga cct ctt aat cga ccg ctc caa      432
Pro Gly Arg Asn Gln Arg Lys Glu Arg Pro Leu Asn Arg Pro Leu Gln
130                 135                 140 gga atg cta ggc gaa aat gtt gga gag agc tgt gtg gtg gag tat gac      480
Gly Met Leu Gly Glu Asn Val Gly Glu Ser Cys Val Val Glu Tyr Asp
145                 150                 155                 160 gat gaa tgt gat gaa cgg gac tac tgt gtt ccc gaa gat gag ggt gct      528
Asp Glu Cys Asp Glu Arg Asp Tyr Cys Val Pro Glu Asp Glu Gly Ala
                165                 170                 175 agc ggc aag gga gac tat gtc agt ctc gtt gat aat cca gaa cgg ttc      576
Ser Gly Lys Gly Asp Tyr Val Ser Leu Val Asp Asn Pro Glu Arg Phe
            180                 185                 190 aca ggg tat gcc ggt atg ggc gcc cat cag gtt tgg gat gca atc tat      624
Thr Gly Tyr Ala Gly Met Gly Ala His Gln Val Trp Asp Ala Ile Tyr
        195                 200                 205 cgg gag aat tgc ttc ctc aaa ccg gtg ccc gag cta tca ccc gtt act      672
Arg Glu Asn Cys Phe Leu Lys Pro Val Pro Glu Leu Ser Pro Val Thr
210                 215                 220 cct cag ctg ggt ggt ctt caa gct gtc aac gat ttc cgt cat gtg ctt      720
Pro Gln Leu Gly Gly Leu Gln Ala Val Asn Asp Phe Arg His Val Leu
225                 230                 235                 240 cag cag gag ttg aag cgc cct gac ctg ctt cca ttg gac aat gaa tgc      768
Gln Gln Glu Leu Lys Arg Pro Asp Leu Leu Pro Leu Asp Asn Glu Cys
                245                 250                 255 ctt gag aag cga gtg ttc cat cgt ctc atc agc gga atg cat gcg tct      816
Leu Glu Lys Arg Val Phe His Arg Leu Ile Ser Gly Met His Ala Ser
            260                 265                 270 atc tcg acc cac ctt tgc tgg gac tac cta aac cag acg acg gga caa      864
Ile Ser Thr His Leu Cys Trp Asp Tyr Leu Asn Gln Thr Thr Gly Gln
        275                 280                 285 tgg cat cct aac ctt caa tgc ttc aaa gat cgt ctc cac gat cac ccc      912
Trp His Pro Asn Leu Gln Cys Phe Lys Asp Arg Leu His Asp His Pro
290                 295                 300 gag cgc atc tcg aac ctg tac ttc aac tac gcg ctg gtc tcg cgc gcc      960
Glu Arg Ile Ser Asn Leu Tyr Phe Asn Tyr Ala Leu Val Ser Arg Ala
305                 310                 315                 320 gtg gcg aag ctg cag aaa cac cta cac aac tac aac tac tgc gtc ggt     1008
Val Ala Lys Leu Gln Lys His Leu His Asn Tyr Asn Tyr Cys Val Gly
                325                 330                 335 gat ccg gtc cag gat gcc atg act agg gag aag gtc tcc aag ttg acc     1056
Asp Pro Val Gln Asp Ala Met Thr Arg Glu Lys Val Ser Lys Leu Thr
            340                 345                 350 tcg acc ttg gct gac cgc cct caa att ttc gac gag aac gtc atg ttc     1104
Ser Thr Leu Ala Asp Arg Pro Gln Ile Phe Asp Glu Asn Val Met Phe
        355                 360                 365 cag gat ccc agc tcc gct ggc ctg aag gaa gac ttc cgc aac cga ttc     1152
Gln Asp Pro Ser Ser Ala Gly Leu Lys Glu Asp Phe Arg Asn Arg Phe
370                 375                 380 cgc aac gtc agt cgc ctg atg gac tgc gtc ggg tgc gac aaa tgc cgc     1200
Arg Asn Val Ser Arg Leu Met Asp Cys Val Gly Cys Asp Lys Cys Arg
385                 390                 395                 400 ctc tgg ggc aag ctc cag gtc aac gga tat ggc acc gct ctg aaa gtg     1248
Leu Trp Gly Lys Leu Gln Val Asn Gly Tyr Gly Thr Ala Leu Lys Val
                405                 410                 415 ctg ttc gag tac gac gag act aag aac ggc gag aac ccg ttg ctg cgc     1296
Leu Phe Glu Tyr Asp Glu Thr Lys Asn Gly Glu Asn Pro Leu Leu Arg
```

-continued

```
                420                 425                 430
cgg act gag ctg gtg gca ctg atc aat acc ctt ggt cgc att tct cac     1344
Arg Thr Glu Leu Val Ala Leu Ile Asn Thr Leu Gly Arg Ile Ser His
        435                 440                 445 agc att gcc gcc gtc cgg agt ttc cac cgg gcc atg gat gtg ggc gat     1392
Ser Ile Ala Ala Val Arg Ser Phe His Arg Ala Met Asp Val Gly Asp
450                 455                 460 ggg gag gtc ttc acc atc ccc gcg agc att gcg tcc aag gag cgc ggt     1440
Gly Glu Val Phe Thr Ile Pro Ala Ser Ile Ala Ser Lys Glu Arg Gly
465                 470                 475                 480 ggc aag aag aag acc cga cga ctt ctc aaa gac ggt ggc tca acc ttc     1488
Gly Lys Lys Lys Thr Arg Arg Leu Leu Lys Asp Gly Gly Ser Thr Phe
            485                 490                 495 tat tat gag gat ggc gat gat gac aac ttt gtc tac atc acc gag aaa     1536
Tyr Tyr Glu Asp Gly Asp Asp Asp Asn Phe Val Tyr Ile Thr Glu Lys
            500                 505                 510 ctt ccg tgg gag aag gtc cgg gta cgc cgc gac acg gat acg gtc tgg     1584
Leu Pro Trp Glu Lys Val Arg Val Arg Arg Asp Thr Asp Thr Val Trp
            515                 520                 525 gat gat att aag gcc gag ttt tct atg atc tgg gac att tac gtc tat     1632
Asp Asp Ile Lys Ala Glu Phe Ser Met Ile Trp Asp Ile Tyr Val Tyr
530                 535                 540 gtg ctg aag agc tgg gtc aat gca cca aag aca ttc ttc gag atc gcc     1680
Val Leu Lys Ser Trp Val Asn Ala Pro Lys Thr Phe Phe Glu Ile Ala
545                 550                 555                 560 gtc ctg gag gtt gct cgg gta tgg aac tac tgg ctg ggt ctg cct gtg     1728
Val Leu Glu Val Ala Arg Val Trp Asn Tyr Trp Leu Gly Leu Pro Val
                565                 570                 575 ccg cca cgg tcc tgg agg atc cag ctt ccc aag cga ccc acc cct cca     1776
Pro Pro Arg Ser Trp Arg Ile Gln Leu Pro Lys Arg Pro Thr Pro Pro
            580                 585                 590 aca ccc ccg acc cat gag gag ctc tag                                 1803
Thr Pro Pro Thr His Glu Glu Leu
            595                 600

<210> SEQ ID NO 36
<211> LENGTH: 600
<212> TYPE: PRT
<213> ORGANISM: Aspergillus niger

<400> SEQUENCE: 36

Met Arg Ser Ala Ala Lys Phe Phe Tyr Leu Ala Val Phe Ala Leu Ser
1               5                   10                  15

Arg Leu Ser Asn Ala Glu Thr Gly Leu His His Asn Gln Asp Lys Cys
                20                  25                  30

Ala Ile Asp Pro Thr Ala Met Val Ser Asp Ala Cys Val Ser Tyr Ala
            35                  40                  45

Thr Ile Asp His Leu Asn Asp Gln Val Tyr Thr Leu Leu Gln Ser Ile
        50                  55                  60

Thr Gln Asp Thr Asp Phe Ser Tyr Tyr Arg Leu Asn Leu Phe Asn
65                  70                  75                  80

Lys Val Cys Pro Phe Trp Ser Asp Ala Asn Ser Met Cys Gly Asn Ile
                85                  90                  95

Ala Cys Ser Val Asn Thr Ile Glu Ser Glu Asp Asp Ile Pro Leu Thr
            100                 105                 110

Trp Arg Ala Glu Glu Leu Ser Lys Leu Glu Gly Pro Lys Ala Gly His
        115                 120                 125

Pro Gly Arg Asn Gln Arg Lys Glu Arg Pro Leu Asn Arg Pro Leu Gln
    130                 135                 140
```

```
Gly Met Leu Gly Glu Asn Val Gly Glu Ser Cys Val Glu Tyr Asp
145                 150                 155                 160

Asp Glu Cys Asp Glu Arg Asp Tyr Cys Val Pro Glu Asp Gly Ala
                165                 170                 175

Ser Gly Lys Gly Asp Tyr Val Ser Leu Val Asp Asn Pro Glu Arg Phe
                180                 185                 190

Thr Gly Tyr Ala Gly Met Gly Ala His Gln Val Trp Asp Ala Ile Tyr
                195                 200                 205

Arg Glu Asn Cys Phe Leu Lys Pro Val Pro Glu Leu Ser Pro Val Thr
                210                 215                 220

Pro Gln Leu Gly Gly Leu Gln Ala Val Asn Asp Phe Arg His Val Leu
225                 230                 235                 240

Gln Gln Glu Leu Lys Arg Pro Asp Leu Pro Leu Asp Asn Glu Cys
                245                 250                 255

Leu Glu Lys Arg Val Phe His Arg Leu Ile Ser Gly Met His Ala Ser
                260                 265                 270

Ile Ser Thr His Leu Cys Trp Asp Tyr Leu Asn Gln Thr Thr Gly Gln
                275                 280                 285

Trp His Pro Asn Leu Gln Cys Phe Lys Asp Arg Leu His Asp His Pro
                290                 295                 300

Glu Arg Ile Ser Asn Leu Tyr Phe Asn Tyr Ala Leu Val Ser Arg Ala
305                 310                 315                 320

Val Ala Lys Leu Gln Lys His Leu His Asn Tyr Asn Tyr Cys Val Gly
                325                 330                 335

Asp Pro Val Gln Asp Ala Met Thr Arg Glu Lys Val Ser Lys Leu Thr
                340                 345                 350

Ser Thr Leu Ala Asp Arg Pro Gln Ile Phe Asp Glu Asn Val Met Phe
                355                 360                 365

Gln Asp Pro Ser Ser Ala Gly Leu Lys Glu Asp Phe Arg Asn Arg Phe
                370                 375                 380

Arg Asn Val Ser Arg Leu Met Asp Cys Val Gly Cys Asp Lys Cys Arg
385                 390                 395                 400

Leu Trp Gly Lys Leu Gln Val Asn Gly Tyr Gly Thr Ala Leu Lys Val
                405                 410                 415

Leu Phe Glu Tyr Asp Glu Thr Lys Asn Gly Glu Asn Pro Leu Leu Arg
                420                 425                 430

Arg Thr Glu Leu Val Ala Leu Ile Asn Thr Leu Gly Arg Ile Ser His
                435                 440                 445

Ser Ile Ala Ala Val Arg Ser Phe His Arg Ala Met Asp Val Gly Asp
450                 455                 460

Gly Glu Val Phe Thr Ile Pro Ala Ser Ile Ala Ser Lys Glu Arg Gly
465                 470                 475                 480

Gly Lys Lys Thr Arg Arg Leu Leu Lys Asp Gly Gly Ser Thr Phe
                485                 490                 495

Tyr Tyr Glu Asp Gly Asp Asp Asn Phe Val Tyr Ile Thr Glu Lys
                500                 505                 510

Leu Pro Trp Glu Lys Val Arg Val Arg Arg Asp Thr Asp Thr Val Trp
                515                 520                 525

Asp Asp Ile Lys Ala Glu Phe Ser Met Ile Trp Asp Ile Tyr Val Tyr
                530                 535                 540

Val Leu Lys Ser Trp Val Asn Ala Pro Lys Thr Phe Phe Glu Ile Ala
545                 550                 555                 560

Val Leu Glu Val Ala Arg Val Trp Asn Tyr Trp Leu Gly Leu Pro Val
```

Pro Pro Arg Ser Trp Arg Ile Gln Leu Pro Lys Arg Pro Thr Pro Pro
            580                 585                 590

Thr Pro Pro Thr His Glu Glu Leu
        595                 600

<210> SEQ ID NO 37
<211> LENGTH: 2977
<212> TYPE: DNA
<213> ORGANISM: Aspergillus niger

<400> SEQUENCE: 37

```
gtggttgact tgggtgactt acgtacctgg cgccaagccc cagaagagac caccttgcga      60
agctctcgac actcttcaat tcattccccc gttcacgaca cctcccaacc cttccctctc     120
atcagctccc gggacaggtc gagggctgtt tgctcatctt ctttcccatt ggatcttgat     180
tcttttctcc cctggccatt atggccgaat caccccctcga tgtcctcttg aagggtaact     240
ccggcagaac aacacgcggc cttctgcgga ttatcattct agctaccatt gccgctgctg     300
ctgtgtccag tcgtctgttc agtgtgatcc gtatgtctct taacttatat gatcgggtca     360
attgaattat cgttactgac agttgccctc taggattcga gagtattatc cacgagtgta     420
tgttttgata ccgatcctcc cgtctatacc ttcaagctac cgcggattcg gcattcgaca     480
ccgtgtgcag ccaacttcac ttccaaaacc aatcaatgct aatgtagctc actcctacag     540
tcgacccctg gttcaacttc cgcgcaacaa aatacctggt ctcccatggc tttgagagct     600
tctgggactg gttcgacgac cgtacgttcc tcttgccaag cctgccttaa cctacatata     660
ctgatctaag atgctgctca ggaacatggc accctctggg acgtgtcact ggtggcacgc     720
tataccccgg tctcatggtg accagcggtg ttatttacca cgtcttgcgg ttcctcacta     780
tccctgtcga catccgtaac atctgtgtct tgcttgcccc gggtttctcc ggtttgaccg     840
cgctggcaat gtacttcctg actcgcgaga tggcgacatc cccctccgct ggtctcctcg     900
cggctgcttt catgggtatc gtccctggat acatctctcg ttccgtcgca ggcagctacg     960
ataacgaggc catcgccatt ttcctgctgg tattcaccctt cttcctgtgg atcaaggctg    1020
ttaagaatgg ctccatcatg tggggttctc tggcggcctt gttctacggc tacatggtgt    1080
ctgcctgggg tggttatgtc ttcatcacta acttgatccc tctgcacgtt ttcgttcttc    1140
tgtgcatggg cagatacagc tcgcgtatct atatcagtta taccacttgg tatgctctgg    1200
gaactctggc cagtatgcag attccttttcg tcggattcct gccgattcgc aacagtgacc    1260
acatgtccgc acttggtatg tactctcatt aaccgtagtg aagagcgttt gtactgacct    1320
tgccaggtgt cttcggcctc attcagctcg tggcctttgc tgacttcgtc cggggtttca    1380
ttccgggcag gcacttccag agacttctga ccaccatgat catcgtcgta tttggcatcg    1440
ctttcgtcgg actcgtcgtc ctcaccgtgt ccggagtgat cgccccttgg agtggtcgtt    1500
tctactctct gtgggatacc ggctatgcca agatccacat ccctatcatt cgtccgtct    1560
ccgagcacca gcccactgct tggcccgcct tcttctttga cctgaacttc ttgatctggc    1620
tcttccctgc cggtgtctac atgtgcttcc gggatctcaa ggatgagcac gttttttgtca    1680
tcatctactc ggtgcttgcc agttacttcg caggtgtcat ggttcgtctg atgttgactt    1740
tgacccctat tgtttgtgtt gcggctgctc tggccctctc caccatcctc gacacgtatg    1800
tgttcgcaaa gaatgccccc aaccccgcgc caaggcgaa cgacgacacc tcggacggtc    1860
ttcgttccac caggaagccc gatgttggtg tcacgtccta cctgtccaag gctgttatga    1920
```

```
cttcctccgt tgtcatctat cttcttctct tcgttgcgca ctgcacctgg gtcacctcga    1980
acgcatactc ctccccgtct gtggttctcg caagccgctt gcctgatgga agccagcaca    2040
tcatcgacga ctaccgtgag gcgtactact ggcttcgtca gaacaccgag cacaacgcca    2100
agatcatgtc ctggtgggat tacgctacc  agattggtgg tatggcggac cgccctaccc    2160
tggttgacaa caacacgtgg aacaacaccc acattgccac tgtcggtaag gcgatgagct    2220
ctcgtgagga agtcagttac cccatcctcc gtcagcacga tgttgattac gtgctggtgg    2280
tgtttggtgg attgctgggc tactccggtg acgacatcaa caagttcctg tggatggtcc    2340
gtatcgctga aggtatctgg cccgacgagg tcaaggagcg tgacttcttc actgcccggg    2400
gtgaataccg ggttgatgac ggagccaccc cgactatgcg taacagcttg atgtaagatt    2460 taccectgct tgccatggca gtgatatgat actaacagcg acccaggtac aaaatgtcct    2520
actacaactt caactcgttg ttcggtcccg gccaggccgt tgaccgcgtg cgtggatcga    2580
gactccccgc ggaaggccct cagctgaaca cgctcgagga ggcattcacc agtgagaact    2640
ggatcatccg catctacaag gtcaaggatc tcgacaacct tggccgtgac acaacaacg     2700 cggtggcctt tgacaagggc cacaagcgca agcgcgctac caagcgcaag ggccctcgtg    2760
tcctgcggac cgagtaaagg tccaggtgtc gttgatagat accaggttgg gtgtaaaatt    2820
gatcccttct tcttcttcat ttcttagcat gtcattttca attccatgtt cttgtacgtg    2880
tcatcaccat ataggcggaa tcatagaagt tgtccatctg gttagaggct gtagactgta    2940
cattttaccc caagcaccaa atatgaacct tgagtga                             2977

<210> SEQ ID NO 38
<211> LENGTH: 2226
<212> TYPE: DNA
<213> ORGANISM: Aspergillus niger
<220> FEATURE:
<221> NAME/KEY: CDS
<222> LOCATION: (1)..(2226)

<400> SEQUENCE: 38 atg gcc gaa tca ccc ctc gat gtc ctc ttg aag ggt aac tcc ggc aga      48
Met Ala Glu Ser Pro Leu Asp Val Leu Leu Lys Gly Asn Ser Gly Arg
1               5                   10                  15 aca aca cgc ggc ctt ctg cgg att atc att cta gct acc att gcc gct      96
Thr Thr Arg Gly Leu Leu Arg Ile Ile Ile Leu Ala Thr Ile Ala Ala
            20                  25                  30 gct gct gtg tcc agt cgt ctg ttc agt gtg atc cga ttc gag agt att     144
Ala Ala Val Ser Ser Arg Leu Phe Ser Val Ile Arg Phe Glu Ser Ile
        35                  40                  45 atc cac gag ttc gac ccc tgg ttc aac ttc cgc gca aca aaa tac ctg     192
Ile His Glu Phe Asp Pro Trp Phe Asn Phe Arg Ala Thr Lys Tyr Leu
    50                  55                  60 gtc tcc cat ggc ttt gag agc ttc tgg gac tgg ttc gac gac cga aca     240
Val Ser His Gly Phe Glu Ser Phe Trp Asp Trp Phe Asp Asp Arg Thr
65                  70                  75                  80 tgg cac cct ctg gga cgt gtc act ggt ggc acg cta tac ccc ggt ctc     288
Trp His Pro Leu Gly Arg Val Thr Gly Gly Thr Leu Tyr Pro Gly Leu
                85                  90                  95 atg gtg acc agc ggt gtt att tac cac gtc ttg cgg ttc ctc act atc     336
Met Val Thr Ser Gly Val Ile Tyr His Val Leu Arg Phe Leu Thr Ile
            100                 105                 110 cct gtc gac atc cgt aac atc tgt gtc ttg ctt gcc ccg ggt ttc tcc     384
Pro Val Asp Ile Arg Asn Ile Cys Val Leu Leu Ala Pro Gly Phe Ser
        115                 120                 125 ggt ttg acc gcg ctg gca atg tac ttc ctg act cgc gag atg gcg aca     432
Gly Leu Thr Ala Leu Ala Met Tyr Phe Leu Thr Arg Glu Met Ala Thr
```

|  |  |  |  |  |  |  |  |  |  |  |  |  |  |
|---|---|---|---|---|---|---|---|---|---|---|---|---|---|
| Gly | Leu | Thr | Ala | Leu | Ala | Met | Tyr | Phe | Leu | Thr | Arg | Glu | Met | Ala | Thr |
|  | 130 |  |  |  | 135 |  |  |  | 140 |  |  |  |  |  |  |

```
tcc ccc tcc gct ggt ctc ctc gcg gct gct ttc atg ggt atc gtc cct    480
Ser Pro Ser Ala Gly Leu Leu Ala Ala Ala Phe Met Gly Ile Val Pro
145             150                 155                 160 gga tac atc tct cgt tcc gtc gca ggc agc tac gat aac gag gcc atc    528
Gly Tyr Ile Ser Arg Ser Val Ala Gly Ser Tyr Asp Asn Glu Ala Ile
                165                 170                 175 gcc att ttc ctg ctg gta ttc acc ttc ttc ctg tgg atc aag gct gtt    576
Ala Ile Phe Leu Leu Val Phe Thr Phe Phe Leu Trp Ile Lys Ala Val
            180                 185                 190 aag aat ggc tcc atc atg tgg ggt tct ctg gcg gcc ttg ttc tac ggc    624
Lys Asn Gly Ser Ile Met Trp Gly Ser Leu Ala Ala Leu Phe Tyr Gly
        195                 200                 205 tac atg gtg tct gcc tgg ggt ggt tat gtc ttc atc act aac ttg atc    672
Tyr Met Val Ser Ala Trp Gly Gly Tyr Val Phe Ile Thr Asn Leu Ile
210                 215                 220 cct ctg cac gtt ttc gtt ctt ctg tgc atg ggc aga tac agc tcg cgt    720
Pro Leu His Val Phe Val Leu Leu Cys Met Gly Arg Tyr Ser Ser Arg
225                 230                 235                 240 atc tat atc agt tat acc act tgg tat gct ctg gga act ctg gcc agt    768
Ile Tyr Ile Ser Tyr Thr Thr Trp Tyr Ala Leu Gly Thr Leu Ala Ser
                245                 250                 255 atg cag att cct ttc gtc gga ttc ctg ccg att cgc aac agt gac cac    816
Met Gln Ile Pro Phe Val Gly Phe Leu Pro Ile Arg Asn Ser Asp His
            260                 265                 270 atg tcc gca ctt ggt gtc ttc ggc ctc att cag ctc gtg gcc ttt gct    864
Met Ser Ala Leu Gly Val Phe Gly Leu Ile Gln Leu Val Ala Phe Ala
        275                 280                 285 gac ttc gtc cgg ggt ttc att ccg ggc agg cac ttc cag aga ctt ctg    912
Asp Phe Val Arg Gly Phe Ile Pro Gly Arg His Phe Gln Arg Leu Leu
    290                 295                 300 acc acc atg atc atc gtc gta ttt ggc atc gct ttc gtc gga ctc gtc    960
Thr Thr Met Ile Ile Val Val Phe Gly Ile Ala Phe Val Gly Leu Val
305                 310                 315                 320 gtc ctc acc gtg tcc gga gtg atc gcc cct tgg agt ggt cgt ttc tac    1008
Val Leu Thr Val Ser Gly Val Ile Ala Pro Trp Ser Gly Arg Phe Tyr
                325                 330                 335 tct ctg tgg gat acc ggc tat gcc aag atc cac atc cct atc att gcg    1056
Ser Leu Trp Asp Thr Gly Tyr Ala Lys Ile His Ile Pro Ile Ile Ala
            340                 345                 350 tcc gtc tcc gag cac cag ccc act gct tgg ccc gcc ttc ttc ttt gac    1104
Ser Val Ser Glu His Gln Pro Thr Ala Trp Pro Ala Phe Phe Phe Asp
        355                 360                 365 ctg aac ttc ttg atc tgg ctc ttc cct gcc ggt gtc tac atg tgc ttc    1152
Leu Asn Phe Leu Ile Trp Leu Phe Pro Ala Gly Val Tyr Met Cys Phe
    370                 375                 380 cgg gat ctc aag gat gag cac gtt ttt gtc atc atc tac tcg gtg ctt    1200
Arg Asp Leu Lys Asp Glu His Val Phe Val Ile Ile Tyr Ser Val Leu
385                 390                 395                 400 gcc agt tac ttc gca ggt gtc atg gtt cgt ctg atg ttg act ttg acc    1248
Ala Ser Tyr Phe Ala Gly Val Met Val Arg Leu Met Leu Thr Leu Thr
                405                 410                 415 cct att gtt tgt gtt gcg gct gct ctg gcc ctc tcc acc atc ctc gac    1296
Pro Ile Val Cys Val Ala Ala Ala Leu Ala Leu Ser Thr Ile Leu Asp
            420                 425                 430 acg tat gtg ttc gca aag aat ggc ccc aac ccc cgc gcc aag gcg aac    1344
Thr Tyr Val Phe Ala Lys Asn Gly Pro Asn Pro Arg Ala Lys Ala Asn
        435                 440                 445 gac gac acc tcg gac ggt ctt cgt tcc acc agg aag ccc gat gtt ggt    1392
```

-continued

```
Asp Asp Thr Ser Asp Gly Leu Arg Ser Thr Arg Lys Pro Asp Val Gly
    450             455                 460 gtc acg tcc tac ctg tcc aag gct gtt atg act tcc tcc gtt gtc atc     1440
Val Thr Ser Tyr Leu Ser Lys Ala Val Met Thr Ser Ser Val Val Ile
465                 470                 475                 480 tat ctt ctt ctc ttc gtt gcg cac tgc acc tgg gtc acc tcg aac gca     1488
Tyr Leu Leu Leu Phe Val Ala His Cys Thr Trp Val Thr Ser Asn Ala
                485                 490                 495 tac tcc tcc ccg tct gtg gtt ctc gca agc cgc ttg cct gat gga agc     1536
Tyr Ser Ser Pro Ser Val Val Leu Ala Ser Arg Leu Pro Asp Gly Ser
            500                 505                 510 cag cac atc atc gac gac tac cgt gag gcg tac tac tgg ctt cgt cag     1584
Gln His Ile Ile Asp Asp Tyr Arg Glu Ala Tyr Tyr Trp Leu Arg Gln
        515                 520                 525 aac acc gag cac aac gcc aag atc atg tcc tgg tgg gat tac ggc tac     1632
Asn Thr Glu His Asn Ala Lys Ile Met Ser Trp Trp Asp Tyr Gly Tyr
    530                 535                 540 cag att ggt ggt atg gcg gac cgc cct acc ctg gtt gac aac aac acg     1680
Gln Ile Gly Gly Met Ala Asp Arg Pro Thr Leu Val Asp Asn Asn Thr
545                 550                 555                 560 tgg aac aac acc cac att gcc act gtc ggt aag gcg atg agc tct cgt     1728
Trp Asn Asn Thr His Ile Ala Thr Val Gly Lys Ala Met Ser Ser Arg
                565                 570                 575 gag gaa gtc agt tac ccc atc ctc cgt cag cac gat gtt gat tac gtg     1776
Glu Glu Val Ser Tyr Pro Ile Leu Arg Gln His Asp Val Asp Tyr Val
            580                 585                 590 ctg gtg gtg ttt ggt gga ttg ctg ggc tac tcc ggt gac gac atc aac     1824
Leu Val Val Phe Gly Gly Leu Leu Gly Tyr Ser Gly Asp Asp Ile Asn
        595                 600                 605 aag ttc ctg tgg atg gtc cgt atc gct gaa ggt atc tgg ccc gac gag     1872
Lys Phe Leu Trp Met Val Arg Ile Ala Glu Gly Ile Trp Pro Asp Glu
    610                 615                 620 gtc aag gag cgt gac ttc ttc act gcc cgg ggt gaa tac cgg gtt gat     1920
Val Lys Glu Arg Asp Phe Phe Thr Ala Arg Gly Glu Tyr Arg Val Asp
625                 630                 635                 640 gac gga gcc acc ccg act atg cgt aac agc ttg atg tac aaa atg tcc     1968
Asp Gly Ala Thr Pro Thr Met Arg Asn Ser Leu Met Tyr Lys Met Ser
                645                 650                 655 tac tac aac ttc aac tcg ttg ttc ggt ccc ggc cag gcc gtt gac cgc     2016
Tyr Tyr Asn Phe Asn Ser Leu Phe Gly Pro Gly Gln Ala Val Asp Arg
            660                 665                 670 gtg cgt gga tcg aga ctc ccc gcg gaa ggc cct cag ctg aac acg ctc     2064
Val Arg Gly Ser Arg Leu Pro Ala Glu Gly Pro Gln Leu Asn Thr Leu
        675                 680                 685 gag gag gca ttc acc agt gag aac tgg atc atc cgc atc tac aag gtc     2112
Glu Glu Ala Phe Thr Ser Glu Asn Trp Ile Ile Arg Ile Tyr Lys Val
    690                 695                 700 aag gat ctc gac aac ctt ggc cgt gac cac aac aac gcg gtg gcc ttt     2160
Lys Asp Leu Asp Asn Leu Gly Arg Asp His Asn Asn Ala Val Ala Phe
705                 710                 715                 720 gac aag ggc cac aag cgc aag cgc gct acc aag cgc aag ggc cct cgt     2208
Asp Lys Gly His Lys Arg Lys Arg Ala Thr Lys Arg Lys Gly Pro Arg
                725                 730                 735 gtc ctg cgg acc gag taa                                             2226
Val Leu Arg Thr Glu
            740

<210> SEQ ID NO 39
<211> LENGTH: 741
<212> TYPE: PRT
<213> ORGANISM: Aspergillus niger
```

```
<400> SEQUENCE: 39

Met Ala Glu Ser Pro Leu Asp Val Leu Leu Lys Gly Asn Ser Gly Arg
1               5                   10                  15

Thr Thr Arg Gly Leu Leu Arg Ile Ile Ile Leu Ala Thr Ile Ala Ala
            20                  25                  30

Ala Ala Val Ser Ser Arg Leu Phe Ser Val Ile Arg Phe Glu Ser Ile
        35                  40                  45

Ile His Glu Phe Asp Pro Trp Phe Asn Phe Arg Ala Thr Lys Tyr Leu
    50                  55                  60

Val Ser His Gly Phe Glu Ser Phe Trp Asp Trp Phe Asp Asp Arg Thr
65                  70                  75                  80

Trp His Pro Leu Gly Arg Val Thr Gly Gly Thr Leu Tyr Pro Gly Leu
                85                  90                  95

Met Val Thr Ser Gly Val Ile Tyr His Val Leu Arg Phe Leu Thr Ile
            100                 105                 110

Pro Val Asp Ile Arg Asn Ile Cys Val Leu Leu Ala Pro Gly Phe Ser
        115                 120                 125

Gly Leu Thr Ala Leu Ala Met Tyr Phe Leu Thr Arg Glu Met Ala Thr
    130                 135                 140

Ser Pro Ser Ala Gly Leu Leu Ala Ala Ala Phe Met Gly Ile Val Pro
145                 150                 155                 160

Gly Tyr Ile Ser Arg Ser Val Ala Gly Ser Tyr Asp Asn Glu Ala Ile
                165                 170                 175

Ala Ile Phe Leu Leu Val Phe Thr Phe Leu Trp Ile Lys Ala Val
            180                 185                 190

Lys Asn Gly Ser Ile Met Trp Gly Ser Leu Ala Ala Leu Phe Tyr Gly
                195                 200                 205

Tyr Met Val Ser Ala Trp Gly Gly Tyr Val Phe Ile Thr Asn Leu Ile
            210                 215                 220

Pro Leu His Val Phe Val Leu Cys Met Gly Arg Tyr Ser Ser Arg
225                 230                 235                 240

Ile Tyr Ile Ser Tyr Thr Thr Trp Tyr Ala Leu Gly Thr Leu Ala Ser
                245                 250                 255

Met Gln Ile Pro Phe Val Gly Phe Leu Pro Ile Arg Asn Ser Asp His
            260                 265                 270

Met Ser Ala Leu Gly Val Phe Gly Leu Ile Gln Leu Val Ala Phe Ala
    275                 280                 285

Asp Phe Val Arg Gly Phe Ile Pro Gly Arg His Phe Gln Arg Leu Leu
    290                 295                 300

Thr Thr Met Ile Ile Val Val Phe Gly Ile Ala Phe Val Gly Leu Val
305                 310                 315                 320

Val Leu Thr Val Ser Gly Val Ile Ala Pro Trp Ser Gly Arg Phe Tyr
            325                 330                 335

Ser Leu Trp Asp Thr Gly Tyr Ala Lys Ile His Ile Pro Ile Ile Ala
                340                 345                 350

Ser Val Ser Glu His Gln Pro Thr Ala Trp Pro Ala Phe Phe Asp
    355                 360                 365

Leu Asn Phe Leu Ile Trp Leu Phe Pro Ala Gly Val Tyr Met Cys Phe
    370                 375                 380

Arg Asp Leu Lys Asp Glu His Val Phe Val Ile Ile Tyr Ser Val Leu
385                 390                 395                 400

Ala Ser Tyr Phe Ala Gly Val Met Val Arg Leu Met Leu Thr Leu Thr
                405                 410                 415
```

```
Pro Ile Val Cys Val Ala Ala Leu Ala Leu Ser Thr Ile Leu Asp
            420                 425                 430
Thr Tyr Val Phe Ala Lys Asn Gly Pro Asn Pro Arg Ala Lys Ala Asn
            435                 440                 445
Asp Asp Thr Ser Asp Gly Leu Arg Ser Thr Arg Lys Pro Asp Val Gly
            450                 455                 460
Val Thr Ser Tyr Leu Ser Lys Ala Val Met Thr Ser Ser Val Val Ile
465                 470                 475                 480
Tyr Leu Leu Leu Phe Val Ala His Cys Thr Trp Val Thr Ser Asn Ala
                485                 490                 495
Tyr Ser Ser Pro Ser Val Val Leu Ala Ser Arg Leu Pro Asp Gly Ser
            500                 505                 510
Gln His Ile Ile Asp Asp Tyr Arg Glu Ala Tyr Tyr Trp Leu Arg Gln
            515                 520                 525
Asn Thr Glu His Asn Ala Lys Ile Met Ser Trp Trp Asp Tyr Gly Tyr
            530                 535                 540
Gln Ile Gly Gly Met Ala Asp Arg Pro Thr Leu Val Asp Asn Asn Thr
545                 550                 555                 560
Trp Asn Asn Thr His Ile Ala Thr Val Gly Lys Ala Met Ser Ser Arg
                565                 570                 575
Glu Glu Val Ser Tyr Pro Ile Leu Arg Gln His Asp Val Asp Tyr Val
            580                 585                 590
Leu Val Val Phe Gly Gly Leu Leu Gly Tyr Ser Gly Asp Asp Ile Asn
            595                 600                 605
Lys Phe Leu Trp Met Val Arg Ile Ala Glu Gly Ile Trp Pro Asp Glu
            610                 615                 620
Val Lys Glu Arg Asp Phe Phe Thr Ala Arg Gly Glu Tyr Arg Val Asp
625                 630                 635                 640
Asp Gly Ala Thr Pro Thr Met Arg Asn Ser Leu Met Tyr Lys Met Ser
                645                 650                 655
Tyr Tyr Asn Phe Asn Ser Leu Phe Gly Pro Gly Gln Ala Val Asp Arg
            660                 665                 670
Val Arg Gly Ser Arg Leu Pro Ala Glu Gly Pro Gln Leu Asn Thr Leu
            675                 680                 685
Glu Glu Ala Phe Thr Ser Glu Asn Trp Ile Ile Arg Ile Tyr Lys Val
            690                 695                 700
Lys Asp Leu Asp Asn Leu Gly Arg Asp His Asn Asn Ala Val Ala Phe
705                 710                 715                 720
Asp Lys Gly His Lys Arg Lys Arg Ala Thr Lys Arg Lys Gly Pro Arg
                725                 730                 735
Val Leu Arg Thr Glu
            740

<210> SEQ ID NO 40
<211> LENGTH: 1546
<212> TYPE: DNA
<213> ORGANISM: Aspergillus niger

<400> SEQUENCE: 40
ttaccaagtg tcctctttga cccgctcggt ctccgcagcg cttccgcctt ccacgccggg    60
agctcatacg actatatcta cactccgccc agcaacaacc ccttccctcg ctgaacggac   120
aggaccattt gctattgaca agtaacattg tcaatcgccc tgcttctact tctccctaaa   180
ccaaaaccac accatccatc atggtccgtc tcagcaatct cgtgagctgc ctcggcctgg   240
```

-continued

```
cctccgcggt caccgcagca gtggtcgatc tcgtccccaa gaacttcgac gacgtcgtcc      300
tcaagtccgg caagcccgct ctggttgaat tcttcgctcc ctggtgcggc cactgcaaga      360
acctcgcgcc cgtgtatgaa gagctgggcc aggcattcgc ccatgcctcc gacaaggtca      420
ccgtcggcaa ggttgatgcg gacgagcacc gcgacttggg ccgcaagttc ggtgtccagg      480
gattccccac gctaaagtgg ttcgacggaa agagtgacga gccggaggat tacaagggtg      540
gtcgtgattt ggagagtctg tcttcgttca tctctgagaa gacgggcgtc aagcccgtg       600 gtcctaagaa ggagcccagc aaggtggaga tgctgaacga cgcgactttc aagggcgctg      660
ttggtggcga taatgatgtt ctggttgcgt tcaccgcgcc gtggtgtgga cgtgagtatc      720
ctcgtttcat cgttcccgct ctagaagcaa atcactaact acggcctttt aaaacagact      780
gcaagaacct cgctcctacc tgggaagccc tggccaacga cttcgtcctc gagcccaacg      840
ttgtgatcgc caaggtcgac gccgacgctg agaacggcaa ggccaccgcc agagagcagg      900
gcgtgtccgg atacccccacc atcaagttct tccccaaggg ctctacggaa tctgttccct      960
atgagggtgc ccgctctgag caggccttca ttgacttcct caacgagaag accggcaccc     1020
accgtaccgt tggcggcgga ctcgacacca aggccggcac cattgctagc ctggacgagc     1080
tgattgccag cacttctgct gctgacctgg ccgccgcagt caagaaggct gctacggagc     1140
ttaaggacaa gtacgctcag tactacgtca aggttgcgga caagctgagc cagaacgccg     1200
agtatgccgc taaggagctt gctcgtctgg agaagatcct ggccaagggt ggatcggccc     1260
ctgagaaggt ggatgacctt atctcccgca gcaacatcct tcgcaagttt gttggtgagg     1320
agaaggaggc caaggatgag ctgtagatat tgtatggatt atgacttgtt tagctagggt     1380
ataggcacct agtttctgtt actctgtatg atatcaagag gcagttatga gaatgctatc     1440
gatgcgaaca gtaaaccatc catttcccat tcccatgtat gtatacacaa gaacataaga     1500
gtatatagta gatgtaaatt gacagtaaaa agcgtatctt cacatt                    1546
```

<210> SEQ ID NO 41
<211> LENGTH: 1080
<212> TYPE: DNA
<213> ORGANISM: Aspergillus niger
<220> FEATURE:
<221> NAME/KEY: CDS
<222> LOCATION: (1)..(1080)

<400> SEQUENCE: 41

```
atg gtc cgt ctc agc aat ctc gtg agc tgc ctc ggc ctg gcc tcc gcg       48
Met Val Arg Leu Ser Asn Leu Val Ser Cys Leu Gly Leu Ala Ser Ala
1               5                   10                  15 gtc acc gca gca gtg gtc gat ctc gtc ccc aag aac ttc gac gac gtc       96
Val Thr Ala Ala Val Val Asp Leu Val Pro Lys Asn Phe Asp Asp Val
            20                  25                  30 gtc ctc aag tcc ggc aag ccc gct ctg gtt gaa ttc ttc gct ccc tgg      144
Val Leu Lys Ser Gly Lys Pro Ala Leu Val Glu Phe Phe Ala Pro Trp
        35                  40                  45 tgc ggc cac tgc aag aac ctc gcg ccc gtg tat gaa gag ctg ggc cag      192
Cys Gly His Cys Lys Asn Leu Ala Pro Val Tyr Glu Glu Leu Gly Gln
    50                  55                  60 gca ttc gcc cat gcc tcc gac aag gtc acc gtc ggc aag gtt gat gcg      240
Ala Phe Ala His Ala Ser Asp Lys Val Thr Val Gly Lys Val Asp Ala
65                  70                  75                  80 gac gag cac cgc gac ttg ggc cgc aag ttc ggt gtc cag gga ttc ccc      288
Asp Glu His Arg Asp Leu Gly Arg Lys Phe Gly Val Gln Gly Phe Pro
                85                  90                  95 acg cta aag tgg ttc gac gga aag agt gac gag ccg gag gat tac aag      336
```

```
Thr Leu Lys Trp Phe Asp Gly Lys Ser Asp Glu Pro Glu Asp Tyr Lys
            100                 105                 110 ggt ggt cgt gat ttg gag agt ctg tct tcg ttc atc tct gag aag acg       384
Gly Gly Arg Asp Leu Glu Ser Leu Ser Ser Phe Ile Ser Glu Lys Thr
            115                 120                 125 ggc gtc aag ccc cgt ggt cct aag aag gag ccc agc aag gtg gag atg       432
Gly Val Lys Pro Arg Gly Pro Lys Lys Glu Pro Ser Lys Val Glu Met
130                 135                 140 ctg aac gac gcg act ttc aag ggc gct gtt ggt ggc gat aat gat gtt       480
Leu Asn Asp Ala Thr Phe Lys Gly Ala Val Gly Gly Asp Asn Asp Val
145                 150                 155                 160 ctg gtt gcg ttc acc gcg ccg tgg tgt gga cac tgc aag aac ctc gct       528
Leu Val Ala Phe Thr Ala Pro Trp Cys Gly His Cys Lys Asn Leu Ala
                165                 170                 175 cct acc tgg gaa gcc ctg gcc aac gac ttc gtc ctc gag ccc aac gtt       576
Pro Thr Trp Glu Ala Leu Ala Asn Asp Phe Val Leu Glu Pro Asn Val
            180                 185                 190 gtg atc gcc aag gtc gac gcc gac gct gag aac ggc aag gcc acc gcc       624
Val Ile Ala Lys Val Asp Ala Asp Ala Glu Asn Gly Lys Ala Thr Ala
        195                 200                 205 aga gag cag ggc gtg tcc gga tac ccc acc atc aag ttc ttc ccc aag       672
Arg Glu Gln Gly Val Ser Gly Tyr Pro Thr Ile Lys Phe Phe Pro Lys
    210                 215                 220 ggc tct acg gaa tct gtt ccc tat gag ggt gcc cgc tct gag cag gcc       720
Gly Ser Thr Glu Ser Val Pro Tyr Glu Gly Ala Arg Ser Glu Gln Ala
225                 230                 235                 240 ttc att gac ttc ctc aac gag aag acc ggc acc cac cgt acc gtt ggc       768
Phe Ile Asp Phe Leu Asn Glu Lys Thr Gly Thr His Arg Thr Val Gly
                245                 250                 255 ggc gga ctc gac acc aag gcc ggc acc att gct agc ctg gac gag ctg       816
Gly Gly Leu Asp Thr Lys Ala Gly Thr Ile Ala Ser Leu Asp Glu Leu
            260                 265                 270 att gcc agc act tct gct gct gac ctg gcc gcc gca gtc aag aag gct       864
Ile Ala Ser Thr Ser Ala Ala Asp Leu Ala Ala Ala Val Lys Lys Ala
        275                 280                 285 gct acg gag ctt aag gac aag tac gct cag tac tac gtc aag gtt gcg       912
Ala Thr Glu Leu Lys Asp Lys Tyr Ala Gln Tyr Tyr Val Lys Val Ala
    290                 295                 300 gac aag ctg agc cag aac gcc gag tat gcc gct aag gag ctt gct cgt       960
Asp Lys Leu Ser Gln Asn Ala Glu Tyr Ala Ala Lys Glu Leu Ala Arg
305                 310                 315                 320 ctg gag aag atc ctg gcc aag ggt gga tcg gcc cct gag aag gtg gat      1008
Leu Glu Lys Ile Leu Ala Lys Gly Gly Ser Ala Pro Glu Lys Val Asp
                325                 330                 335 gac ctt atc tcc cgc agc aac atc ctt cgc aag ttt gtt ggt gag gag      1056
Asp Leu Ile Ser Arg Ser Asn Ile Leu Arg Lys Phe Val Gly Glu Glu
            340                 345                 350 aag gag gcc aag gat gag ctg tag                                      1080
Lys Glu Ala Lys Asp Glu Leu
            355

<210> SEQ ID NO 42
<211> LENGTH: 359
<212> TYPE: PRT
<213> ORGANISM: Aspergillus niger

<400> SEQUENCE: 42

Met Val Arg Leu Ser Asn Leu Val Ser Cys Leu Gly Leu Ala Ser Ala
1               5                   10                  15

Val Thr Ala Ala Val Val Asp Leu Val Pro Lys Asn Phe Asp Asp Val
            20                  25                  30
```

Val Leu Lys Ser Gly Lys Pro Ala Leu Val Glu Phe Phe Ala Pro Trp
         35                  40                  45

Cys Gly His Cys Lys Asn Leu Ala Pro Val Tyr Glu Glu Leu Gly Gln
     50                  55                  60

Ala Phe Ala His Ala Ser Asp Lys Val Thr Val Gly Lys Val Asp Ala
 65                  70                  75                  80

Asp Glu His Arg Asp Leu Gly Arg Lys Phe Gly Val Gln Gly Phe Pro
                 85                  90                  95

Thr Leu Lys Trp Phe Asp Gly Lys Ser Asp Glu Pro Glu Asp Tyr Lys
                100                 105                 110

Gly Gly Arg Asp Leu Glu Ser Leu Ser Ser Phe Ile Ser Glu Lys Thr
            115                 120                 125

Gly Val Lys Pro Arg Gly Pro Lys Lys Glu Pro Ser Lys Val Glu Met
        130                 135                 140

Leu Asn Asp Ala Thr Phe Lys Gly Ala Val Gly Gly Asp Asn Asp Val
145                 150                 155                 160

Leu Val Ala Phe Thr Ala Pro Trp Cys Gly His Cys Lys Asn Leu Ala
                165                 170                 175

Pro Thr Trp Glu Ala Leu Ala Asn Asp Phe Val Leu Glu Pro Asn Val
            180                 185                 190

Val Ile Ala Lys Val Asp Ala Asp Ala Glu Asn Gly Lys Ala Thr Ala
        195                 200                 205

Arg Glu Gln Gly Val Ser Gly Tyr Pro Thr Ile Lys Phe Phe Pro Lys
    210                 215                 220

Gly Ser Thr Glu Ser Val Pro Tyr Glu Gly Ala Arg Ser Glu Gln Ala
225                 230                 235                 240

Phe Ile Asp Phe Leu Asn Glu Lys Thr Gly Thr His Arg Thr Val Gly
                245                 250                 255

Gly Gly Leu Asp Thr Lys Ala Gly Thr Ile Ala Ser Leu Asp Glu Leu
            260                 265                 270

Ile Ala Ser Thr Ser Ala Ala Asp Leu Ala Ala Val Lys Lys Ala
        275                 280                 285

Ala Thr Glu Leu Lys Asp Lys Tyr Ala Gln Tyr Tyr Val Lys Val Ala
    290                 295                 300

Asp Lys Leu Ser Gln Asn Ala Glu Tyr Ala Ala Lys Glu Leu Ala Arg
305                 310                 315                 320

Leu Glu Lys Ile Leu Ala Lys Gly Gly Ser Ala Pro Glu Lys Val Asp
                325                 330                 335

Asp Leu Ile Ser Arg Ser Asn Ile Leu Arg Lys Phe Val Gly Glu Glu
            340                 345                 350

Lys Glu Ala Lys Asp Glu Leu
        355

<210> SEQ ID NO 43
<211> LENGTH: 2673
<212> TYPE: DNA
<213> ORGANISM: Aspergillus niger

<400> SEQUENCE: 43
gccaagaacg tcggcgaaat gaagctccgc aacgccaggt ggcccgttcc gcatcggggc    60
cgagcaagca actcccccg agtctcaagt gctcatcttc actatcagct cctctcccct    120
ctcttacttt atcggaagct cgagcacaga gtcgccatgc cctctcact gttcacttct    180 attcaacttt ctcacacaac atgaagaact ggtggctgtg gcgtttcctg ccgttggcgc    240

-continued

```
ttcgtgagtc ctcttactgt ggagcttagc cgcatcacgc gatagcaact gacctccaag    300
catcactttc cagtgcttct gcaggcgctt gcggatgaat acaatggaca gcacgacaca    360
caaaaaccct taacagatgt tgttcctgaa tcatatgcac atgctgagtc ctcgagcggg    420
cccgagggct ctgacgttct accgggacac ggtaagcggc cctgtgcatg acgccagcgc    480
acccatcctt gctaacaact agtgatttga tgtgccaata gtacacgtcg aaaatgccct    540
tcaaatcctc cgagagagca agatccccat tgtcgctcac gagaaaccgt ccggccttct    600
ggggtacacc tggcattacg cccaagaagc cttccgactc ctatttatga atggaccaca    660
gccggatgga acacacaagc aaaagctcga tccaaatgtt gcaaaggctg cgaatgaact    720
taaggttgcg gcgcaagaac accaaaaccc cgatgcaatg ttcctcttag cggaaatgaa    780
cttctacgga aacttcaccc acccgagaga tttcaagcag gcgtttcatt ggtaccaaac    840
tctggcgtca tcgactggaa acagtacggc gcaatatatg cttgggttta tgtatgcaac    900
gggtgtcggg ggtgcggtgg agcgcgacca ggctaaggcc ctgttatacc acacctttgc    960
ggctgaagcg ggcaatacga agtcggaaat gaccctcgcg tatcgctacc acgctggaat   1020
tggggctcct agagattgcg atcaagcgac ttactactat aagaaggtgg ctgataaggc   1080
tattgaatac ttccgatcgg gaccgcccgg tggccataac atgatccgcg agtcctaccg   1140
ttgggcggac gaagagggtg gtgtttatgg tgaaggcgct agtgtatcga ctgccgtacg   1200
cgatggaacg cattcgagca cggaagccag cttggaagac gtcttggagt acctggattt   1260
gatgtcgaga aagggcgaac tgaaggctac tttcagcttg ggcaagatgc attacgaagg   1320
gggccgcggc ttgcctcgga atttccgaaa gtcgatgaat tacttccgac aggtcgccaa   1380
gcggtattgg aataaagatg gatcggtgaa ccccaaccat cctgttggtg ttgaaaagct   1440
cgcttcgaaa gcagcaggcc atattggcat gatgtacctg cgtggcgagg gggtggaaca   1500
gaactttgca accgctcaga cttggtttag gcgtggactc gcgaatggtg atgctctctg   1560
tcagcatgag ctaggactga tgtacctgca tggctatggt gtgacaccag atgcgttcag   1620
agctgcatca caatttaagg ctgcggctga gcaggacttc ccggcggctg aaacgagact   1680
gggtgccctg tttctagacc agggtgatgt ccagaccgcc acccgttatt cgaactggc   1740
tgcgcgctgg ggatggatgg aggccttcta ctacctggca gaattgtcca acaatggggt   1800
tggtcggaaa cgacactgcg ggatggccgc gtcttactac aagatggtcg cagagcgggc   1860
ggaagtcatc cattcatctt ttgaggaagc aaatacggcg tatgagaacg gagacaagga   1920
acgggctctc attccggcgc tgatggctgc ggagcagggt tacgagcatg cacagtccaa   1980
tgttgcgttc ctgctggacg agcagcggtc cttattcgcc attgacacta tcctcccagg   2040
agctaagaag agcagaccgg ctttgctgcg gaatgcagcg ctggctctta tctattggac   2100
acgttccgcc aaacaggcga acatcgactc cttgctcaag atgggcgatt actacctggc   2160
gggcatggga attgctgcgg atgcggagaa ggcctcgacc tgctaccaca cagcagccga   2220
agtgcactat agcgcacagg cgtactggaa tctgggatgg atgcatgaga atggcgttgc   2280
ggtggaccaa gacttccaca tggccaagcg atactacgat ctagcgctgg agactagctc   2340
cgaggcatat ctgcccgtga agctcagtct gcttaaactg cggatgcggg gatactggaa   2400
ctggctcacg aacggagaca tcaaccctat ccgagaggaa gaaggtaagg accccaaca    2460
tccttttcgc tgagaaaccc gaacaatcac acttacacac taatgcagaa gtgaggtcgc   2520
atcgcacctt gaaggaattc atcgccactt ttatccagaa caacgaggaa gaagaggccg   2580
ccttccgcgc ccagatgtac aaacaggacg aggaggacga actcatgtcg aataatcgcc   2640
```

-continued

| | | |
|---|---|---|
| ttgacgacca ccgcgaagac ggctactatg atg | | 2673 |

<210> SEQ ID NO 44
<211> LENGTH: 2070
<212> TYPE: DNA
<213> ORGANISM: Aspergillus niger
<220> FEATURE:
<221> NAME/KEY: CDS
<222> LOCATION: (1)..(2070)

<400> SEQUENCE: 44

| | | |
|---|---|---|
| atg aag aac tgg tgg ctg tgg cgt ttc ctg ccg ttg gcg ctt cat gtt<br>Met Lys Asn Trp Trp Leu Trp Arg Phe Leu Pro Leu Ala Leu His Val<br>1               5                   10                  15 | | 48 |
| gtt cct gaa tca tat gca cat gct gag tcc tcg agc ggg ccc gag ggc<br>Val Pro Glu Ser Tyr Ala His Ala Glu Ser Ser Ser Gly Pro Glu Gly<br>            20                  25                  30 | | 96 |
| tct gac gtt cta ccg gga cac gta cac gtc gaa aat gcc ctt caa atc<br>Ser Asp Val Leu Pro Gly His Val His Val Glu Asn Ala Leu Gln Ile<br>        35                  40                  45 | | 144 |
| ctc cga gag agc aag atc ccc att gtc gct cac gag aaa ccg tcc ggc<br>Leu Arg Glu Ser Lys Ile Pro Ile Val Ala His Glu Lys Pro Ser Gly<br>    50                  55                  60 | | 192 |
| ctt ctg ggg tac acc tgg cat tac gcc caa gaa gcc ttc cga ctc cta<br>Leu Leu Gly Tyr Thr Trp His Tyr Ala Gln Glu Ala Phe Arg Leu Leu<br>65                  70                  75                  80 | | 240 |
| ttt atg aat gga cca cag ccg gat gga aca cac aag caa aag ctc gat<br>Phe Met Asn Gly Pro Gln Pro Asp Gly Thr His Lys Gln Lys Leu Asp<br>                85                  90                  95 | | 288 |
| cca aat gtt gca aag gct gcg aat gaa ctt aag gtt gcg gcg caa gaa<br>Pro Asn Val Ala Lys Ala Ala Asn Glu Leu Lys Val Ala Ala Gln Glu<br>            100                 105                 110 | | 336 |
| cac caa aac ccc gat gca atg ttc ctc tta gcg gaa atg aac ttc tac<br>His Gln Asn Pro Asp Ala Met Phe Leu Leu Ala Glu Met Asn Phe Tyr<br>        115                 120                 125 | | 384 |
| ggc aac ttc acc cac ccg aga gat ttc aag cag gcg ttt cat tgg tac<br>Gly Asn Phe Thr His Pro Arg Asp Phe Lys Gln Ala Phe His Trp Tyr<br>    130                 135                 140 | | 432 |
| caa act ctg gcg tca tcg act gga aac agt acg gcg caa tat atg ctt<br>Gln Thr Leu Ala Ser Ser Thr Gly Asn Ser Thr Ala Gln Tyr Met Leu<br>145                 150                 155                 160 | | 480 |
| ggg ttt atg tat gca acg ggt gtc ggg ggt gcg gtg gag cgc gac cag<br>Gly Phe Met Tyr Ala Thr Gly Val Gly Gly Ala Val Glu Arg Asp Gln<br>                165                 170                 175 | | 528 |
| gct aag gcc ctg tta tac cac acc ttt gcg gct gaa gcg ggc aat acg<br>Ala Lys Ala Leu Leu Tyr His Thr Phe Ala Ala Glu Ala Gly Asn Thr<br>            180                 185                 190 | | 576 |
| aag tcg gaa atg acc ctc gcg tat cgc tac cac gct gga att ggg gct<br>Lys Ser Glu Met Thr Leu Ala Tyr Arg Tyr His Ala Gly Ile Gly Ala<br>        195                 200                 205 | | 624 |
| cct aga gat tgc gat caa gcg act tac tac tat aag aag gtg gct gat<br>Pro Arg Asp Cys Asp Gln Ala Thr Tyr Tyr Tyr Lys Lys Val Ala Asp<br>    210                 215                 220 | | 672 |
| aag gct att gaa tac ttc cga tcg gga ccg ccc ggt ggc cat aac atg<br>Lys Ala Ile Glu Tyr Phe Arg Ser Gly Pro Pro Gly Gly His Asn Met<br>225                 230                 235                 240 | | 720 |
| atc cgc gag tcc tac cgt tgg gcg gac gaa gag ggt ggt gtt tat ggt<br>Ile Arg Glu Ser Tyr Arg Trp Ala Asp Glu Glu Gly Gly Val Tyr Gly<br>                245                 250                 255 | | 768 |
| gaa ggc gct agt gta tcg act gcc gta cgc gat gga acg cat tcg agc<br>Glu Gly Ala Ser Val Ser Thr Ala Val Arg Asp Gly Thr His Ser Ser<br>            260                 265                 270 | | 816 |

| | | |
|---|---|---|
| acg gaa gcc agc ttg gaa gac gtc ttg gag tac ctg gat ttg atg tcg<br>Thr Glu Ala Ser Leu Glu Asp Val Leu Glu Tyr Leu Asp Leu Met Ser<br>275 280 285 | | 864 |
| aga aag ggc gaa ctg aag gct act ttc agc ttg ggc aag atg cat tac<br>Arg Lys Gly Glu Leu Lys Ala Thr Phe Ser Leu Gly Lys Met His Tyr<br>290 295 300 | | 912 |
| gaa ggg ggc cgc ggc ttg cct cgg aat ttc cga aag tcg atg aat tac<br>Glu Gly Gly Arg Gly Leu Pro Arg Asn Phe Arg Lys Ser Met Asn Tyr<br>305 310 315 320 | | 960 |
| ttc cga cag gtc gcc aag cgg tat tgg aat aaa gat gga tcg gtg aac<br>Phe Arg Gln Val Ala Lys Arg Tyr Trp Asn Lys Asp Gly Ser Val Asn<br>325 330 335 | | 1008 |
| ccc aac cat cct gtt ggt gtt gaa aag ctc gct tcg aaa gca gca ggc<br>Pro Asn His Pro Val Gly Val Glu Lys Leu Ala Ser Lys Ala Ala Gly<br>340 345 350 | | 1056 |
| cat att ggc atg atg tac ctg cgt ggc gag ggg gtg gaa cag aac ttt<br>His Ile Gly Met Met Tyr Leu Arg Gly Glu Gly Val Glu Gln Asn Phe<br>355 360 365 | | 1104 |
| gca acc gct cag act tgg ttt agg cgt gga ctc gcg aat ggt gat gct<br>Ala Thr Ala Gln Thr Trp Phe Arg Arg Gly Leu Ala Asn Gly Asp Ala<br>370 375 380 | | 1152 |
| ctc tgt cag cat gag cta gga ctg atg tac ctg cat ggc tat ggt gtg<br>Leu Cys Gln His Glu Leu Gly Leu Met Tyr Leu His Gly Tyr Gly Val<br>385 390 395 400 | | 1200 |
| aca cca gat gcg ttc aga gct gca tca caa ttt aag gct gcg gct gag<br>Thr Pro Asp Ala Phe Arg Ala Ala Ser Gln Phe Lys Ala Ala Ala Glu<br>405 410 415 | | 1248 |
| cag gac ttc ccg gcg gct gaa acg aga ctg ggt gcc ctg ttt cta gac<br>Gln Asp Phe Pro Ala Ala Glu Thr Arg Leu Gly Ala Leu Phe Leu Asp<br>420 425 430 | | 1296 |
| cag ggt gat gtc cag acc gcc acc cgt tat ttc gaa ctg gct gcg cgc<br>Gln Gly Asp Val Gln Thr Ala Thr Arg Tyr Phe Glu Leu Ala Ala Arg<br>435 440 445 | | 1344 |
| tgg gga tgg atg gag gcc ttc tac tac ctg gca gaa ttg tcc aac aat<br>Trp Gly Trp Met Glu Ala Phe Tyr Tyr Leu Ala Glu Leu Ser Asn Asn<br>450 455 460 | | 1392 |
| ggg gtt ggt cgg aaa cga cac tgc ggg atg gcc gcg tct tac tac aag<br>Gly Val Gly Arg Lys Arg His Cys Gly Met Ala Ala Ser Tyr Tyr Lys<br>465 470 475 480 | | 1440 |
| atg gtc gca gag cgg gcg gaa gtc atc cat tca tct ttt gag gaa gca<br>Met Val Ala Glu Arg Ala Glu Val Ile His Ser Ser Phe Glu Glu Ala<br>485 490 495 | | 1488 |
| aat acg gcg tat gag aac gga gac aag gaa cgg gct ctc att ccg gcg<br>Asn Thr Ala Tyr Glu Asn Gly Asp Lys Glu Arg Ala Leu Ile Pro Ala<br>500 505 510 | | 1536 |
| ctg atg gct gcg gag cag ggt tac gag cat gca cag tcc aat gtt gcg<br>Leu Met Ala Ala Glu Gln Gly Tyr Glu His Ala Gln Ser Asn Val Ala<br>515 520 525 | | 1584 |
| ttc ctg ctg gac gag cag cgg tcc tta ttc gcc att gac act atc ctc<br>Phe Leu Leu Asp Glu Gln Arg Ser Leu Phe Ala Ile Asp Thr Ile Leu<br>530 535 540 | | 1632 |
| cca gga gct aag aag agc aga ccg gct ttg ctg cgg aat gca gcg ctg<br>Pro Gly Ala Lys Lys Ser Arg Pro Ala Leu Leu Arg Asn Ala Ala Leu<br>545 550 555 560 | | 1680 |
| gct ctt atc tat tgg aca cgt tcc gcc aaa cag gcg aac atc gac tcc<br>Ala Leu Ile Tyr Trp Thr Arg Ser Ala Lys Gln Ala Asn Ile Asp Ser<br>565 570 575 | | 1728 |
| ttg ctc aag atg ggc gat tac tac ctg gcg ggc atg gga att gct gcg<br>Leu Leu Lys Met Gly Asp Tyr Tyr Leu Ala Gly Met Gly Ile Ala Ala<br>580 585 590 | | 1776 |

```
gat gcg gag aag gcc tcg acc tgc tac cac aca gca gcc gaa gtg cac    1824
Asp Ala Glu Lys Ala Ser Thr Cys Tyr His Thr Ala Ala Glu Val His
            595                 600                 605 tat agc gca cag gcg tac tgg aat ctg gga tgg atg cat gag aat ggc    1872
Tyr Ser Ala Gln Ala Tyr Trp Asn Leu Gly Trp Met His Glu Asn Gly
610                 615                 620 gtt gcg gtg gac caa gac ttc cac atg gcc aag cga tac tac gat cta    1920
Val Ala Val Asp Gln Asp Phe His Met Ala Lys Arg Tyr Tyr Asp Leu
625                 630                 635                 640 gcg ctg gag act agc tcc gag gca tat ctg ccc gtg aag ctc agt ctg    1968
Ala Leu Glu Thr Ser Ser Glu Ala Tyr Leu Pro Val Lys Leu Ser Leu
            645                 650                 655 ctt aaa ctg cgg atg cgg gga tac tgg aac tgg ctc acg aac gga gac    2016
Leu Lys Leu Arg Met Arg Gly Tyr Trp Asn Trp Leu Thr Asn Gly Asp
            660                 665                 670 atc aac cct atc cga gag gaa gaa ggt aag gaa ccc caa cat cct ttt    2064
Ile Asn Pro Ile Arg Glu Glu Glu Gly Lys Glu Pro Gln His Pro Phe
                675                 680                 685 cgc tga                                                             2070
Arg

<210> SEQ ID NO 45
<211> LENGTH: 689
<212> TYPE: PRT
<213> ORGANISM: Aspergillus niger

<400> SEQUENCE: 45

Met Lys Asn Trp Trp Leu Trp Arg Phe Leu Pro Leu Ala Leu His Val
1               5                   10                  15

Val Pro Glu Ser Tyr Ala His Ala Glu Ser Ser Gly Pro Glu Gly
            20                  25                  30

Ser Asp Val Leu Pro Gly His Val His Val Glu Asn Ala Leu Gln Ile
        35                  40                  45

Leu Arg Glu Ser Lys Ile Pro Ile Val Ala His Glu Lys Pro Ser Gly
    50                  55                  60

Leu Leu Gly Tyr Thr Trp His Tyr Ala Gln Glu Ala Phe Arg Leu Leu
65                  70                  75                  80

Phe Met Asn Gly Pro Gln Pro Asp Gly Thr His Lys Gln Lys Leu Asp
                85                  90                  95

Pro Asn Val Ala Lys Ala Ala Asn Glu Leu Lys Val Ala Ala Gln Glu
            100                 105                 110

His Gln Asn Pro Asp Ala Met Phe Leu Leu Ala Glu Met Asn Phe Tyr
        115                 120                 125

Gly Asn Phe Thr His Pro Arg Asp Phe Lys Gln Ala Phe His Trp Tyr
    130                 135                 140

Gln Thr Leu Ala Ser Ser Thr Gly Asn Ser Thr Ala Gln Tyr Met Leu
145                 150                 155                 160

Gly Phe Met Tyr Ala Thr Gly Val Gly Gly Ala Val Glu Arg Asp Gln
                165                 170                 175

Ala Lys Ala Leu Leu Tyr His Thr Phe Ala Ala Glu Ala Gly Asn Thr
            180                 185                 190

Lys Ser Glu Met Thr Leu Ala Tyr Arg Tyr His Ala Gly Ile Gly Ala
        195                 200                 205

Pro Arg Asp Cys Asp Gln Ala Thr Tyr Tyr Lys Lys Val Ala Asp
    210                 215                 220

Lys Ala Ile Glu Tyr Phe Arg Ser Gly Pro Pro Gly Gly His Asn Met
225                 230                 235                 240
```

-continued

```
Ile Arg Glu Ser Tyr Arg Trp Ala Asp Glu Glu Gly Val Tyr Gly
            245                 250                 255

Glu Gly Ala Ser Val Ser Thr Ala Val Arg Asp Gly Thr His Ser Ser
        260                 265                 270

Thr Glu Ala Ser Leu Glu Asp Val Leu Glu Tyr Leu Asp Leu Met Ser
            275                 280                 285

Arg Lys Gly Glu Leu Lys Ala Thr Phe Ser Leu Gly Lys Met His Tyr
    290                 295                 300

Glu Gly Gly Arg Gly Leu Pro Arg Asn Phe Arg Lys Ser Met Asn Tyr
305                 310                 315                 320

Phe Arg Gln Val Ala Lys Arg Tyr Trp Asn Lys Asp Gly Ser Val Asn
                325                 330                 335

Pro Asn His Pro Val Gly Val Glu Lys Leu Ala Ser Lys Ala Ala Gly
                340                 345                 350

His Ile Gly Met Met Tyr Leu Arg Gly Glu Gly Val Glu Gln Asn Phe
            355                 360                 365

Ala Thr Ala Gln Thr Trp Phe Arg Arg Gly Leu Ala Asn Gly Asp Ala
    370                 375                 380

Leu Cys Gln His Glu Leu Gly Leu Met Tyr Leu His Gly Tyr Gly Val
385                 390                 395                 400

Thr Pro Asp Ala Phe Arg Ala Ala Ser Gln Phe Lys Ala Ala Ala Glu
                405                 410                 415

Gln Asp Phe Pro Ala Ala Glu Thr Arg Leu Gly Ala Leu Phe Leu Asp
                420                 425                 430

Gln Gly Asp Val Gln Thr Ala Thr Arg Tyr Phe Glu Leu Ala Ala Arg
            435                 440                 445

Trp Gly Trp Met Glu Ala Phe Tyr Tyr Leu Ala Glu Leu Ser Asn Asn
    450                 455                 460

Gly Val Gly Arg Lys Arg His Cys Gly Met Ala Ala Ser Tyr Tyr Lys
465                 470                 475                 480

Met Val Ala Glu Arg Ala Glu Val Ile His Ser Ser Phe Glu Glu Ala
                485                 490                 495

Asn Thr Ala Tyr Glu Asn Gly Asp Lys Glu Arg Ala Leu Ile Pro Ala
            500                 505                 510

Leu Met Ala Ala Glu Gln Gly Tyr Glu His Ala Gln Ser Asn Val Ala
    515                 520                 525

Phe Leu Leu Asp Glu Gln Arg Ser Leu Phe Ala Ile Asp Thr Ile Leu
    530                 535                 540

Pro Gly Ala Lys Lys Ser Arg Pro Ala Leu Leu Arg Asn Ala Ala Leu
545                 550                 555                 560

Ala Leu Ile Tyr Trp Thr Arg Ser Ala Lys Gln Ala Asn Ile Asp Ser
            565                 570                 575

Leu Leu Lys Met Gly Asp Tyr Tyr Leu Ala Gly Met Gly Ile Ala Ala
            580                 585                 590

Asp Ala Glu Lys Ala Ser Thr Cys Tyr His Thr Ala Ala Glu Val His
            595                 600                 605

Tyr Ser Ala Gln Ala Tyr Trp Asn Leu Gly Trp Met His Glu Asn Gly
        610                 615                 620

Val Ala Val Asp Gln Asp Phe His Met Ala Lys Arg Tyr Tyr Asp Leu
625                 630                 635                 640

Ala Leu Glu Thr Ser Ser Glu Ala Tyr Leu Pro Val Lys Leu Ser Leu
            645                 650                 655

Leu Lys Leu Arg Met Arg Gly Tyr Trp Asn Trp Leu Thr Asn Gly Asp
```

```
                    660               665                670
Ile Asn Pro Ile Arg Glu Glu Glu Gly Lys Glu Pro Gln His Pro Phe
            675                 680                 685
Arg

<210> SEQ ID NO 46
<211> LENGTH: 2326
<212> TYPE: DNA
<213> ORGANISM: Aspergillus niger

<400> SEQUENCE: 46
ctgtctggtt catgcacatc acttactagt tagcacttgt tcatattgtc attgtgtcaa      60
ttttactcga ctgatcccaa ctttatcatt ctcctctgct ttacgccatt gtttctcttg     120
cagtgagcat tgcgacttcg attatgcgcc cgtgattgtc tacgcccaac atccctccgc     180
aaggacagaa caatcccagg atgaccgcgt cttcagaaac ccagtccgct ctggcggaat     240
ctccacagag catagtatta catgtgctat gtccatcttt acctcctcct aaccgattca     300
ctctccacga catctctcca tccaccacca tctccactct caaagctcga atcgcccaga     360
ccattccgag tgaaccatcc cctgaaactc agaggctgat ataccggggg aagccctta     420
cgaacgacgc cgtggcgcta atgatgtgt tagagtcatc aaatgtgcgt atgatcttat     480
tcctatgccc cttgtagtc ggcagatact aacagtgata cttgacccag gataccgagt     540
attccatcca cctcgtcctt cctcctgccc cagttcccca tgcttcaact tctgccagag     600
ctcctgctcc aatgccgcgg ggagcttcag gtaaccccgc gcctcagagt ccattctcat     660
cgaaccgatt cacgccgcaa cacctgcctc acggacaaga gatcaggtat cgaggtcccg     720
cattgcccgc tgttccccat gaggcagaga tcggactcgc cttgaggcgg aatatcgagg     780
ctattcgtcg acagattgat atgcaggaac ggggcgggcc gttgggaggc gtcgcggcag     840
gcaccgcggg ggctacttcc cactcgacca catccacgac tacgacagct tcgttcgctc     900
agcaacctgc atggccacac gtaacacctg gtctatcgca cccaggacat tcgtccatct     960
catctgattt cacaatggct tccggctcat cgggaacagc caatgtccat agcaacctcc    1020
ccgaagaagt ccgattgcgc ctacaaatac tcagaaatca gattgcgttt ggcgaagagc    1080
aactgaaccg gggggttgcg cccccaatgg accatataat tcgcatacgt acacaattgt    1140
tcgctttgct cgacgaccaa tatcagaacc cacatgctga gcgcgacggc tcgattgaat    1200
ctttgctcac tcgcgtcttt aatatctata cccgcgctga tcagctccgc gtctcacaag    1260
ctagaaccat gcccacacct gttctatctg gacctcccaa tcccgcacca gggcaggctc    1320
ctctgtacct tctctcgtca ccaaacggct atcaagccct ggttgcatct ccccgcggtg    1380
cagaaacgat gcagtcttct ctcgatacac tccgagccat gcactccccg accggagcct    1440
ctgcgcctcg tacaggtgct ccaccggaga ttcacaatgc gaacgcagtt gtcatggaga    1500
acattgtccg acaggccgta ctcaaccaac gcatcgaaaa caacgggcaa ttgagcttca    1560
cacgcaatct ccgacgcatg tggctatttg tgcgcttgta tttcttctgc tacatgttca    1620
gcgaaccggg cacatggtct cgcgtggtgt atgtaaccct agccgtcctt gtctcactcc    1680
tgtcagaaac cggatccca cagcagttgt accgaatgct tgtggcgcca gtgcaacgac    1740
acctggaagg actggttcat ttcgctccgg acgaaccgac tccagcacca cctggcacgc    1800
agtcaactgg gcaagggaac gttcccactg ctcagccaac cggaatgcga caccagctgc    1860
gccgcgtaga acgtccttg gcgcttttca ttgcaagctt ggttccgggc gtgggcgaga    1920
gacacgtgga agtgcgcaat gccgcagaag cggcccggaa cgcagagcgt gcaagagagg    1980
```

```
aagaagagcg acgtcgacag gaggaagagg ccaccaacgc aggcacgact ggtgaggctc    2040
aggcacaggc acaggagagc agcgagaacg aacagagaga aacgggtgag aatgcaccca    2100
acacgatacc ccaaactgag aattagccat agcggagcta ttagacttgt actgagtata    2160
ctcggtgatt tgaaacttgt gttcatgatg tattgatagc tgcgatcata tttccatacc    2220
gcttagtgcg gcaagatatc ttagtctatt agcgcaacat atatctactg cagtgtacct    2280
tcaagtaatc tatccacatc cacccacaca taatccactc tatcta                  2326
```

<210> SEQ ID NO 47
<211> LENGTH: 1860
<212> TYPE: DNA
<213> ORGANISM: Aspergillus niger
<220> FEATURE:
<221> NAME/KEY: CDS
<222> LOCATION: (1)..(1860)

<400> SEQUENCE: 47

```
atg acc gcg tct tca gaa acc cag tcc gct ctg gcg gaa tct cca cag      48
Met Thr Ala Ser Ser Glu Thr Gln Ser Ala Leu Ala Glu Ser Pro Gln
1               5                   10                  15 agc ata gta tta cat gtg cta tgt cca tct tta cct cct cct aac cga      96
Ser Ile Val Leu His Val Leu Cys Pro Ser Leu Pro Pro Pro Asn Arg
                20                  25                  30 ttc act ctc cac gac atc tct cca tcc acc acc atc tcc act ctc aaa     144
Phe Thr Leu His Asp Ile Ser Pro Ser Thr Thr Ile Ser Thr Leu Lys
            35                  40                  45 gct cga atc gcc cag acc att ccg agt gaa cca tcc cct gaa act cag     192
Ala Arg Ile Ala Gln Thr Ile Pro Ser Glu Pro Ser Pro Glu Thr Gln
        50                  55                  60 agg ctg ata tac cgg ggg aag ccc ctt acg aac gac gcc gtg gcg cta     240
Arg Leu Ile Tyr Arg Gly Lys Pro Leu Thr Asn Asp Ala Val Ala Leu
65                  70                  75                  80 aat gat gtg tta gag tca tca aat gat acc gag tat tcc atc cac ctc     288
Asn Asp Val Leu Glu Ser Ser Asn Asp Thr Glu Tyr Ser Ile His Leu
                85                  90                  95 gtc ctt cct cct gcc cca gtt ccc cat gct tca act tct gcc aga gct     336
Val Leu Pro Pro Ala Pro Val Pro His Ala Ser Thr Ser Ala Arg Ala
                100                 105                 110 cct gct cca atg ccg cgg gga gct tca ggt aac ccc gcg cct cag agt     384
Pro Ala Pro Met Pro Arg Gly Ala Ser Gly Asn Pro Ala Pro Gln Ser
            115                 120                 125 cca ttc tca tcg aac cga ttc acg ccg caa cac ctg cct cac gga caa     432
Pro Phe Ser Ser Asn Arg Phe Thr Pro Gln His Leu Pro His Gly Gln
        130                 135                 140 gag atc agg tat cga ggt ccc gca ttg ccc gct gtt ccc cat gag gca     480
Glu Ile Arg Tyr Arg Gly Pro Ala Leu Pro Ala Val Pro His Glu Ala
145                 150                 155                 160 gag atc gga ctc gcc ttg agg cgg aat atc gag gct att cgt cga cag     528
Glu Ile Gly Leu Ala Leu Arg Arg Asn Ile Glu Ala Ile Arg Arg Gln
                165                 170                 175 att gat atg cag gaa cgg ggc ggg ccg ttg gga ggc gtc gcg gca ggc     576
Ile Asp Met Gln Glu Arg Gly Gly Pro Leu Gly Gly Val Ala Ala Gly
            180                 185                 190 acc gcg ggg gct act tcc cac tcg acc aca tcc acg act acg aca gct     624
Thr Ala Gly Ala Thr Ser His Ser Thr Thr Ser Thr Thr Thr Thr Ala
        195                 200                 205 tcg ttc gct cag caa cct gca tgg cca cac gta aca cct ggt cta tcg     672
Ser Phe Ala Gln Gln Pro Ala Trp Pro His Val Thr Pro Gly Leu Ser
    210                 215                 220
```

```
                                      -continued cac cca gga cat tcg tcc atc tca tct gat ttc aca atg gct tcc ggc    720
His Pro Gly His Ser Ser Ile Ser Ser Asp Phe Thr Met Ala Ser Gly
225             230                 235                 240 tca tcg gga aca gcc aat gtc cat agc aac ctc ccc gaa gaa gtc cga    768
Ser Ser Gly Thr Ala Asn Val His Ser Asn Leu Pro Glu Glu Val Arg
            245                 250                 255 ttg cgc cta caa ata ctc aga aat cag att gcg ttt ggc gaa gag caa    816
Leu Arg Leu Gln Ile Leu Arg Asn Gln Ile Ala Phe Gly Glu Glu Gln
        260                 265                 270 ctg aac cgg ggg gtt gcg ccc cca atg gac cat ata att cgc ata cgt    864
Leu Asn Arg Gly Val Ala Pro Pro Met Asp His Ile Ile Arg Ile Arg
    275                 280                 285 aca caa ttg ttc gct ttg ctc gac gac caa tat cag aac cca cat gct    912
Thr Gln Leu Phe Ala Leu Leu Asp Asp Gln Tyr Gln Asn Pro His Ala
290                 295                 300 gag cgc gac ggc tcg att gaa tct ttg ctc act cgc gtc ttt aat atc    960
Glu Arg Asp Gly Ser Ile Glu Ser Leu Leu Thr Arg Val Phe Asn Ile
305             310                 315                 320 tat acc cgc gct gat cag ctc cgc gtc tca caa gct aga acc atg ccc   1008
Tyr Thr Arg Ala Asp Gln Leu Arg Val Ser Gln Ala Arg Thr Met Pro
            325                 330                 335 aca cct gtt cta tct gga cct ccc aat ccc gca cca ggg cag gct cct   1056
Thr Pro Val Leu Ser Gly Pro Pro Asn Pro Ala Pro Gly Gln Ala Pro
        340                 345                 350 ctg tac ctt ctc tcg tca cca aac ggc tat caa gcc ctg gtt gca tct   1104
Leu Tyr Leu Leu Ser Ser Pro Asn Gly Tyr Gln Ala Leu Val Ala Ser
    355                 360                 365 ccc cgc ggt gca gaa acg atg cag tct tct ctc gat aca ctc cga gcc   1152
Pro Arg Gly Ala Glu Thr Met Gln Ser Ser Leu Asp Thr Leu Arg Ala
370                 375                 380 atg cac tcc ccg acc gga gcc tct gcg cct cgt aca ggt gct cca ccg   1200
Met His Ser Pro Thr Gly Ala Ser Ala Pro Arg Thr Gly Ala Pro Pro
385             390                 395                 400 gag att cac aat gcg aac gca gtt gtc atg gag aac att gtc cga cag   1248
Glu Ile His Asn Ala Asn Ala Val Val Met Glu Asn Ile Val Arg Gln
            405                 410                 415 gcc gta ctc aac caa cgc atc gaa aac aac ggg caa ttg agc ttc aca   1296
Ala Val Leu Asn Gln Arg Ile Glu Asn Asn Gly Gln Leu Ser Phe Thr
        420                 425                 430 cgc aat ctc cga cgc atg tgg cta ttt gtg cgc ttg tat ttc ttc tgc   1344
Arg Asn Leu Arg Arg Met Trp Leu Phe Val Arg Leu Tyr Phe Phe Cys
    435                 440                 445 tac atg ttc agc gaa ccg ggc aca tgg tct cgc gtg gtg tat gta acc   1392
Tyr Met Phe Ser Glu Pro Gly Thr Trp Ser Arg Val Val Tyr Val Thr
450                 455                 460 cta gcc gtc ctt gtc tca ctc ctg tca gaa acc ggg atc cca cag cag   1440
Leu Ala Val Leu Val Ser Leu Leu Ser Glu Thr Gly Ile Pro Gln Gln
465             470                 475                 480 ttg tac cga atg ctt gtg gcg cca gtg caa cga cac ctg gaa gga ctg   1488
Leu Tyr Arg Met Leu Val Ala Pro Val Gln Arg His Leu Glu Gly Leu
            485                 490                 495 gtt cat ttc gct ccg gac gaa ccg act cca gca cca cct ggc acg cag   1536
Val His Phe Ala Pro Asp Glu Pro Thr Pro Ala Pro Pro Gly Thr Gln
        500                 505                 510 tca act ggg caa ggg aac gtt ccc act gct cag cca acc gga atg cga   1584
Ser Thr Gly Gln Gly Asn Val Pro Thr Ala Gln Pro Thr Gly Met Arg
    515                 520                 525 cac cag ctg cgc cgc gta gaa cgg tcc ttg gcg ctt ttc att gca agc   1632
His Gln Leu Arg Arg Val Glu Arg Ser Leu Ala Leu Phe Ile Ala Ser
530                 535                 540
```

-continued

```
ttg gtt ccg ggc gtg ggc gag aga cac gtg gaa gtg cgc aat gcc gca     1680
Leu Val Pro Gly Val Gly Glu Arg His Val Glu Val Arg Asn Ala Ala
545                 550                 555                 560 gaa gcg gcc cgg aac gca gag cgt gca aga gag gaa gag cga cgt         1728
Glu Ala Ala Arg Asn Ala Glu Arg Ala Arg Glu Glu Glu Arg Arg
                565                 570                 575 cga cag gag gaa gag gcc acc aac gca ggc acg act ggt gag gct cag     1776
Arg Gln Glu Glu Glu Ala Thr Asn Ala Gly Thr Thr Gly Glu Ala Gln
                580                 585                 590 gca cag gca cag gag agc agc gag aac gaa cag aga gaa acg ggt gag     1824
Ala Gln Ala Gln Glu Ser Ser Glu Asn Glu Gln Arg Glu Thr Gly Glu
            595                 600                 605 aat gca ccc aac acg ata ccc caa act gag aat tag                     1860
Asn Ala Pro Asn Thr Ile Pro Gln Thr Glu Asn
610                 615
```

<210> SEQ ID NO 48
<211> LENGTH: 619
<212> TYPE: PRT
<213> ORGANISM: Aspergillus niger

<400> SEQUENCE: 48

```
Met Thr Ala Ser Ser Glu Thr Gln Ser Ala Leu Ala Glu Ser Pro Gln
1               5                   10                  15

Ser Ile Val Leu His Val Leu Cys Pro Ser Leu Pro Pro Asn Arg
            20                  25                  30

Phe Thr Leu His Asp Ile Ser Pro Ser Thr Ile Ser Thr Leu Lys
        35                  40                  45

Ala Arg Ile Ala Gln Thr Ile Pro Ser Glu Pro Ser Pro Glu Thr Gln
50                  55                  60

Arg Leu Ile Tyr Arg Gly Lys Pro Leu Thr Asn Asp Ala Val Ala Leu
65                  70                  75                  80

Asn Asp Val Leu Glu Ser Ser Asn Asp Thr Glu Tyr Ser Ile His Leu
                85                  90                  95

Val Leu Pro Pro Ala Pro Val Pro His Ala Ser Thr Ser Ala Arg Ala
            100                 105                 110

Pro Ala Pro Met Pro Arg Gly Ala Ser Gly Asn Pro Ala Pro Gln Ser
        115                 120                 125

Pro Phe Ser Ser Asn Arg Phe Thr Pro Gln His Leu Pro His Gly Gln
    130                 135                 140

Glu Ile Arg Tyr Arg Gly Pro Ala Leu Pro Ala Val Pro His Glu Ala
145                 150                 155                 160

Glu Ile Gly Leu Ala Leu Arg Arg Asn Ile Glu Ala Ile Arg Arg Gln
                165                 170                 175

Ile Asp Met Gln Glu Arg Gly Gly Pro Leu Gly Val Ala Ala Gly
            180                 185                 190

Thr Ala Gly Ala Thr Ser His Ser Thr Thr Ser Thr Thr Thr Ala
        195                 200                 205

Ser Phe Ala Gln Gln Pro Ala Trp Pro His Val Thr Pro Gly Leu Ser
    210                 215                 220

His Pro Gly His Ser Ser Ile Ser Ser Asp Phe Thr Met Ala Ser Gly
225                 230                 235                 240

Ser Ser Gly Thr Ala Asn Val His Ser Asn Leu Pro Glu Glu Val Arg
                245                 250                 255

Leu Arg Leu Gln Ile Leu Arg Asn Gln Ile Ala Phe Gly Glu Glu Gln
            260                 265                 270

Leu Asn Arg Gly Val Ala Pro Pro Met Asp His Ile Ile Arg Ile Arg
```

```
                    275                 280                 285
Thr Gln Leu Phe Ala Leu Leu Asp Asp Gln Tyr Gln Asn Pro His Ala
            290                 295                 300
Glu Arg Asp Gly Ser Ile Glu Ser Leu Leu Thr Arg Val Phe Asn Ile
305                 310                 315                 320
Tyr Thr Arg Ala Asp Gln Leu Arg Val Ser Gln Ala Arg Thr Met Pro
                325                 330                 335
Thr Pro Val Leu Ser Gly Pro Pro Asn Pro Ala Pro Gly Gln Ala Pro
                340                 345                 350
Leu Tyr Leu Leu Ser Ser Pro Asn Gly Tyr Gln Ala Leu Val Ala Ser
                355                 360                 365
Pro Arg Gly Ala Glu Thr Met Gln Ser Ser Leu Asp Thr Leu Arg Ala
            370                 375                 380
Met His Ser Pro Thr Gly Ala Ser Ala Pro Arg Thr Gly Ala Pro Pro
385                 390                 395                 400
Glu Ile His Asn Ala Asn Ala Val Val Met Glu Asn Ile Val Arg Gln
                405                 410                 415
Ala Val Leu Asn Gln Arg Ile Glu Asn Asn Gly Gln Leu Ser Phe Thr
            420                 425                 430
Arg Asn Leu Arg Arg Met Trp Leu Phe Val Arg Leu Tyr Phe Phe Cys
        435                 440                 445
Tyr Met Phe Ser Glu Pro Gly Thr Trp Ser Arg Val Val Tyr Val Thr
    450                 455                 460
Leu Ala Val Leu Val Ser Leu Leu Ser Glu Thr Gly Ile Pro Gln Gln
465                 470                 475                 480
Leu Tyr Arg Met Leu Val Ala Pro Val Gln Arg His Leu Glu Gly Leu
                485                 490                 495
Val His Phe Ala Pro Asp Glu Pro Thr Pro Ala Pro Pro Gly Thr Gln
            500                 505                 510
Ser Thr Gly Gln Gly Asn Val Pro Thr Ala Gln Pro Thr Gly Met Arg
        515                 520                 525
His Gln Leu Arg Arg Val Glu Arg Ser Leu Ala Leu Phe Ile Ala Ser
    530                 535                 540
Leu Val Pro Gly Val Gly Glu Arg His Val Glu Val Arg Asn Ala Ala
545                 550                 555                 560
Glu Ala Ala Arg Asn Ala Glu Arg Ala Arg Glu Glu Glu Arg Arg
                565                 570                 575
Arg Gln Glu Glu Glu Ala Thr Asn Ala Gly Thr Thr Gly Glu Ala Gln
            580                 585                 590
Ala Gln Ala Gln Glu Ser Ser Glu Asn Glu Gln Arg Glu Thr Gly Glu
        595                 600                 605
Asn Ala Pro Asn Thr Ile Pro Gln Thr Glu Asn
610                 615

<210> SEQ ID NO 49
<211> LENGTH: 2941
<212> TYPE: DNA
<213> ORGANISM: Aspergillus niger

<400> SEQUENCE: 49
tcaggtactc caggtgaact agttggtact actaagcagg aactcccccc ctctctctct      60
tcccaaaggt gccttgaaac cctcccggcc atctttggtg cctccatctc atccttttgg     120
ctcttgccag ttcccctct tcatctctaa ccttccctac tgggatctat atttccctac      180
ttctctccac tggtctatgt atgcctgagt tcaagatctc cgcttctttg gagggccacg     240
```

```
gcgatgatgt aagaacatcc cggctgttga cgctggccac ctttcacctt caaccccct      300
ccattgtcgc ccactgacgc ctctttctct cactctcagg ttcgcgccgt ggccttccg      360
aatcccaatg ctatatttc ggcgtcgcga gatgcaacag tccgactctg gaaactagtc      420
tctacccac ctccggcata tgactacacc atcacctctc acggccaggc cttcatcaac      480
gctttggcat actacccacc tacccccag tttcccgatg gacttgtcct ttccggtggt      540
caagatacta tcattgaagc cagacaacca ggcaaagctg ccgacgataa cgcggatgct      600
atgctcttgg gccatacaca taatgtctgt gcgctggatg tgtcacatga tggcggatgg      660
gtagtcagcg gaagctggga ctcgacagct agactatgga aagtgggtaa atgggaaacc      720
gatgtcgtgc tggagggcca tcaaggaagt gtttggacgg tgcttgccta tgacaaggat      780
acggtcatca caggtaggcg cgccttaccc ctgtatatga gacagatggg tcgttctatg      840
gatatgctaa taattcccca ggctgcgcgg acaaaataat acgtattttt aacacctctg      900
gcacactgct gagaacaatc gaaaattcac aggacgttgt gagagctctt tgcaaggttc      960
ccgcttcgaa ccccaccggg gcgcactttg cttcggcgag caacgatgga gtgattcgtc     1020
tttttaccat acaaggccaa ctcgtcgggg agatgcatgg ccacgagagc ttcatttatt     1080
ctctggccgc tttgccttcg ggtgagttag tcagttccgg agaagatcgg acggtgagag     1140
tctgggatgg tacgcagtgc gtacagacga tcacacaccc tgcgatctct gtctggagcg     1200
tcgcagtatg caaggagacc ggcgacattg ttacaggagc cagtgaccga atcacacgcg     1260
tgtttagcag gagccaggag cgcgtggcaa gcccagaagt agtacaacag ttcgagaaga     1320
ctgtgaagga gtcggcaatc ccagagcagc agattgggaa gatcaacaaa gataagcttc     1380
cgggtacgga gtttctcagg cagaaatccg ggaccaagga cgggcaggtg cagatgatcc     1440
gtgaggccga tggtagcgtt actgctcaca cttggtcagc ggcctcacgg gaatgggttg     1500
cggttggcac ggtagttgat tccgctgcca gcagtggaag gaaaacggag tatctgggtc     1560
aagactacga ctatgtcttt gatgtcgacg tggaagacgg caaacccccc ctcaaattgc     1620
catacaacgt ctctcaaaac ccctacgagg ctgcgaccaa gtttatccag gacaacgaac     1680
tgtcgatgaa ttaccttgat caagttgctc agttcatcgt tcagaatacg caaggtgcga     1740
ctcttggtca gacgtctcag gggccgacgc ccgcggggc cgatccctgg ggtcaagaga     1800
ggcgttatcg tcctgaagat gcgcagtcgc cccctgctcc tgaggcccga ccgaaggtcc     1860
ttccgcaaaa aacatatctt tccataaaat ctgctaatct taaactgatc gctaagaagt     1920
tgcaagagct gaaccaacac gtcatatcct ccggatcgaa agacctgtcg ctcagcccctt     1980
cagagttgga gacggtggca accttgtgtg tcagttgga gtcttcgaat gttgagcagt      2040
ctccggcagt ggaggctggt gttgttttac tatacaaggt cgcaaccgtc tggcccgtcg     2100
caagcagact accaggtctt gatcttctcc gcttgtccgc cgctgctact cccgtgactg     2160
ccactgcaga ttacgatggc aaggatctca tctcagggat taagtctagc ggggtgttcg     2220
attcaccgtt caatgtcaat aatgcgatgc tgtcaatacg catgctcgcc aaccttttcg     2280
aaacggatgc gggacgtgac ctggccacta gcaagtttga gcagattctg agcggcgtca     2340
agtccgcttt aaccaacagt gggacgacgc cgaaccgaaa tctcaccatt gccattacaa     2400
cactctacat caactttgcc gtttacctga cctctgcggg cagagaatcg atgcctgagt     2460
catcggaaca ggctctggtg cttctcggcg agctaacgac attgattacc ggtgaaaagg     2520
actctgaagc agtctaccgc ggccttgtgg ctctaggac cttgatcaag ggactagggg     2580
aagaagtcag gactgcggcc aaggaagtgt acgatgtcga tgatgttttg aagaaggttt     2640
```

-continued

```
caagctctgg tcttggtaaa gaaccaagaa tcaagggtat cataggcgag atcaaggagt    2700
cgttatcatc aaggtataaa atgttgaggc ccgggtctta agtcaactca tacctcaagg    2760
agcgtcttgt gttctgcttc accactgctg tctatagcac gtatacatct ctagttcacg    2820
atagcgatac acactacact gcatgaattc aacattggac atattccaaa tcagtgctaa    2880
cactaggtat cgtatagtgc tatacattca atgtaacggc aacgtaaata atcactttga    2940
c                                                                    2941
```

<210> SEQ ID NO 50
<211> LENGTH: 2331
<212> TYPE: DNA
<213> ORGANISM: Aspergillus niger
<220> FEATURE:
<221> NAME/KEY: CDS
<222> LOCATION: (1)..(2331)

<400> SEQUENCE: 50

```
atg cct gag ttc aag atc tcc gct tct ttg gag ggc cac ggc gat gat     48
Met Pro Glu Phe Lys Ile Ser Ala Ser Leu Glu Gly His Gly Asp Asp
1               5                   10                  15 gtt cgc gcc gtg gcc ttt ccg aat ccc aat gct ata ttt tcg gcg tcg     96
Val Arg Ala Val Ala Phe Pro Asn Pro Asn Ala Ile Phe Ser Ala Ser
                20                  25                  30 cga gat gca aca gtc cga ctc tgg aaa cta gtc tct acc cca cct ccg    144
Arg Asp Ala Thr Val Arg Leu Trp Lys Leu Val Ser Thr Pro Pro Pro
            35                  40                  45 gca tat gac tac acc atc acc tct cac ggc cag gcc ttc atc aac gct    192
Ala Tyr Asp Tyr Thr Ile Thr Ser His Gly Gln Ala Phe Ile Asn Ala
        50                  55                  60 ttg gca tac tac cca cct acc ccc cag ttt ccc gat gga ctt gtc ctt    240
Leu Ala Tyr Tyr Pro Pro Thr Pro Gln Phe Pro Asp Gly Leu Val Leu
65                  70                  75                  80 tcc ggt ggt caa gat act atc att gaa gcc aga caa cca ggc aaa gct    288
Ser Gly Gly Gln Asp Thr Ile Ile Glu Ala Arg Gln Pro Gly Lys Ala
                85                  90                  95 gcc gac gat aac gcg gat gct atg ctc ttg ggc cat aca cat aat gtc    336
Ala Asp Asp Asn Ala Asp Ala Met Leu Leu Gly His Thr His Asn Val
            100                 105                 110 tgt gcg ctg gat gtg tca cat gat ggc gga tgg gta gtc agc gga agc    384
Cys Ala Leu Asp Val Ser His Asp Gly Gly Trp Val Val Ser Gly Ser
        115                 120                 125 tgg gac tcg aca gct aga cta tgg aaa gtg ggt aaa tgg gaa acc gat    432
Trp Asp Ser Thr Ala Arg Leu Trp Lys Val Gly Lys Trp Glu Thr Asp
    130                 135                 140 gtc gtg ctg gag ggc cat caa gga agt gtt tgg acg gtg ctt gcc tat    480
Val Val Leu Glu Gly His Gln Gly Ser Val Trp Thr Val Leu Ala Tyr
145                 150                 155                 160 gac aag gat acg gtc atc aca ggc tgc gcg gac aaa ata ata cgt att    528
Asp Lys Asp Thr Val Ile Thr Gly Cys Ala Asp Lys Ile Ile Arg Ile
                165                 170                 175 ttt aac acc tct ggc aca ctg ctg aga aca atc gaa aat tca cag gac    576
Phe Asn Thr Ser Gly Thr Leu Leu Arg Thr Ile Glu Asn Ser Gln Asp
            180                 185                 190 gtt gtg aga gct ctt tgc aag gtt ccc gct tcg aac ccc acc ggg gcg    624
Val Val Arg Ala Leu Cys Lys Val Pro Ala Ser Asn Pro Thr Gly Ala
        195                 200                 205 cac ttt gct tcg gcg agc aac gat gga gtg att cgt ctt ttt acc ata    672
His Phe Ala Ser Ala Ser Asn Asp Gly Val Ile Arg Leu Phe Thr Ile
    210                 215                 220
```

```
caa ggc caa ctc gtc ggg gag atg cat ggc cac gag agc ttc att tat      720
Gln Gly Gln Leu Val Gly Glu Met His Gly His Glu Ser Phe Ile Tyr
225                 230                 235                 240 tct ctg gcc gct ttg cct tcg ggt gag tta gtc agt tcc gga gaa gat      768
Ser Leu Ala Ala Leu Pro Ser Gly Glu Leu Val Ser Ser Gly Glu Asp
            245                 250                 255 cgg acg gtg aga gtc tgg gat ggt acg cag tgc gta cag acg atc aca      816
Arg Thr Val Arg Val Trp Asp Gly Thr Gln Cys Val Gln Thr Ile Thr
        260                 265                 270 cac cct gcg atc tct gtc tgg agc gtc gca gta tgc aag gag acc ggc      864
His Pro Ala Ile Ser Val Trp Ser Val Ala Val Cys Lys Glu Thr Gly
    275                 280                 285 gac att gtt aca gga gcc agt gac cga atc aca cgc gtg ttt agc agg      912
Asp Ile Val Thr Gly Ala Ser Asp Arg Ile Thr Arg Val Phe Ser Arg
290                 295                 300 agc cag gag cgc gtg gca agc cca gaa gta gta caa cag ttc gag aag      960
Ser Gln Glu Arg Val Ala Ser Pro Glu Val Val Gln Gln Phe Glu Lys
305                 310                 315                 320 act gtg aag gag tcg gca atc cca gag cag cag att ggg aag atc aac     1008
Thr Val Lys Glu Ser Ala Ile Pro Glu Gln Gln Ile Gly Lys Ile Asn
            325                 330                 335 aaa gat aag ctt ccg ggt acg gag ttt ctc agg cag aaa tcc ggg acc     1056
Lys Asp Lys Leu Pro Gly Thr Glu Phe Leu Arg Gln Lys Ser Gly Thr
        340                 345                 350 aag gac ggg cag gtg cag atg atc cgt gag gcc gat ggt agc gtt act     1104
Lys Asp Gly Gln Val Gln Met Ile Arg Glu Ala Asp Gly Ser Val Thr
    355                 360                 365 gct cac act tgg tca gcg gcc tca cgg gaa tgg gtt gcg gtt ggc acg     1152
Ala His Thr Trp Ser Ala Ala Ser Arg Glu Trp Val Ala Val Gly Thr
370                 375                 380 gta gtt gat tcc gct gcc agc agt gga agg aaa acg gag tat ctg ggt     1200
Val Val Asp Ser Ala Ala Ser Ser Gly Arg Lys Thr Glu Tyr Leu Gly
385                 390                 395                 400 caa gac tac gac tat gtc ttt gat gtc gac gtg gaa gac ggc aaa ccc     1248
Gln Asp Tyr Asp Tyr Val Phe Asp Val Asp Val Glu Asp Gly Lys Pro
            405                 410                 415 ccc ctc aaa ttg cca tac aac gtc tct caa aac ccc tac gag gct gcg     1296
Pro Leu Lys Leu Pro Tyr Asn Val Ser Gln Asn Pro Tyr Glu Ala Ala
        420                 425                 430 acc aag ttt atc cag gac aac gaa ctg tcg atg aat tac ctt gat caa     1344
Thr Lys Phe Ile Gln Asp Asn Glu Leu Ser Met Asn Tyr Leu Asp Gln
    435                 440                 445 gtt gct cag ttc atc gtt cag aat acg caa ggt gcg act ctt gag agg     1392
Val Ala Gln Phe Ile Val Gln Asn Thr Gln Gly Ala Thr Leu Glu Arg
450                 455                 460 cgt tat cgt cct gaa gat gcg cag tcg ccc cct gct cct gag gcc cga     1440
Arg Tyr Arg Pro Glu Asp Ala Gln Ser Pro Pro Ala Pro Glu Ala Arg
465                 470                 475                 480 ccg aag gtc ctt ccg caa aaa aca tat ctt tcc ata aaa tct gct aat     1488
Pro Lys Val Leu Pro Gln Lys Thr Tyr Leu Ser Ile Lys Ser Ala Asn
            485                 490                 495 ctt aaa ctg atc gct aag aag ttg caa gag ctg aac caa cac gtc ata     1536
Leu Lys Leu Ile Ala Lys Lys Leu Gln Glu Leu Asn Gln His Val Ile
        500                 505                 510 tcc tcc gga tcg aaa gac ctg tcg ctc agc cct tca gag ttg gag acg     1584
Ser Ser Gly Ser Lys Asp Leu Ser Leu Ser Pro Ser Glu Leu Glu Thr
    515                 520                 525 gtg gca acc ttg tgt ggt cag ttg gag tct tcg aat gtt gag cag tct     1632
Val Ala Thr Leu Cys Gly Gln Leu Glu Ser Ser Asn Val Glu Gln Ser
530                 535                 540
```

```
ccg gca gtg gag gct ggt gtt gtt tta cta tac aag gtc gca acc gtc    1680
Pro Ala Val Glu Ala Gly Val Val Leu Leu Tyr Lys Val Ala Thr Val
545                 550                 555                 560 tgg ccc gtc gca agc aga cta cca ggt ctt gat ctt ctc cgc ttg tcc    1728
Trp Pro Val Ala Ser Arg Leu Pro Gly Leu Asp Leu Leu Arg Leu Ser
                565                 570                 575 gcc gct gct act ccc gtg act gcc act gca gat tac gat ggc aag gat    1776
Ala Ala Ala Thr Pro Val Thr Ala Thr Ala Asp Tyr Asp Gly Lys Asp
            580                 585                 590 ctc atc tca ggg att aag tct agc ggg gtg ttc gat tca ccg ttc aat    1824
Leu Ile Ser Gly Ile Lys Ser Ser Gly Val Phe Asp Ser Pro Phe Asn
        595                 600                 605 gtc aat aat gcg atg ctg tca ata cgc atg ctc gcc aac ctt ttc gaa    1872
Val Asn Asn Ala Met Leu Ser Ile Arg Met Leu Ala Asn Leu Phe Glu
    610                 615                 620 acg gat gcg gga cgt gac ctg gcc act agc aag ttt gag cag att ctg    1920
Thr Asp Ala Gly Arg Asp Leu Ala Thr Ser Lys Phe Glu Gln Ile Leu
625                 630                 635                 640 agc ggc gtc aag tcc gct tta acc aac agt ggg acg acg ccg aac cga    1968
Ser Gly Val Lys Ser Ala Leu Thr Asn Ser Gly Thr Thr Pro Asn Arg
                645                 650                 655 aat ctc acc att gcc att aca aca ctc tac atc aac ttt gcc gtt tac    2016
Asn Leu Thr Ile Ala Ile Thr Thr Leu Tyr Ile Asn Phe Ala Val Tyr
            660                 665                 670 ctg acc tct gcg ggc aga gaa tcg atg cct gag tca tcg gaa cag gct    2064
Leu Thr Ser Ala Gly Arg Glu Ser Met Pro Glu Ser Ser Glu Gln Ala
        675                 680                 685 ctg gtg ctt ctc ggc gag cta acg aca ttg att acc ggt gaa aag gac    2112
Leu Val Leu Leu Gly Glu Leu Thr Thr Leu Ile Thr Gly Glu Lys Asp
    690                 695                 700 tct gaa gca gtc tac cgc ggc ctt gtg gct cta ggg acc ttg atc aag    2160
Ser Glu Ala Val Tyr Arg Gly Leu Val Ala Leu Gly Thr Leu Ile Lys
705                 710                 715                 720 gga cta ggg gaa gaa gtc agg act gcg gcc aag gaa gtg tac gat gtc    2208
Gly Leu Gly Glu Glu Val Arg Thr Ala Ala Lys Glu Val Tyr Asp Val
                725                 730                 735 gat gat gtt ttg aag aag gtt tca agc tct ggt ctt ggt aaa gaa cca    2256
Asp Asp Val Leu Lys Lys Val Ser Ser Ser Gly Leu Gly Lys Glu Pro
            740                 745                 750 aga atc aag ggt atc ata ggc gag atc aag gag tcg tta tca tca agg    2304
Arg Ile Lys Gly Ile Ile Gly Glu Ile Lys Glu Ser Leu Ser Ser Arg
        755                 760                 765 tat aaa atg ttg agg ccc ggg tct taa                                2331
Tyr Lys Met Leu Arg Pro Gly Ser
    770                 775

<210> SEQ ID NO 51
<211> LENGTH: 776
<212> TYPE: PRT
<213> ORGANISM: Aspergillus niger

<400> SEQUENCE: 51

Met Pro Glu Phe Lys Ile Ser Ala Ser Leu Glu Gly His Gly Asp Asp
1               5                   10                  15

Val Arg Ala Val Ala Phe Pro Asn Pro Asn Ala Ile Phe Ser Ala Ser
            20                  25                  30

Arg Asp Ala Thr Val Arg Leu Trp Lys Leu Val Ser Thr Pro Pro
        35                  40                  45

Ala Tyr Asp Tyr Thr Ile Thr Ser His Gly Gln Ala Phe Ile Asn Ala
    50                  55                  60
```

```
Leu Ala Tyr Tyr Pro Pro Thr Pro Gln Phe Pro Asp Gly Leu Val Leu
 65                  70                  75                  80

Ser Gly Gly Gln Asp Thr Ile Ile Glu Ala Arg Gln Pro Gly Lys Ala
                 85                  90                  95

Ala Asp Asp Asn Ala Asp Ala Met Leu Leu Gly His Thr His Asn Val
            100                 105                 110

Cys Ala Leu Asp Val Ser His Asp Gly Gly Trp Val Ser Gly Ser
        115                 120                 125

Trp Asp Ser Thr Ala Arg Leu Trp Lys Val Gly Lys Trp Glu Thr Asp
    130                 135                 140

Val Val Leu Glu Gly His Gln Gly Ser Val Trp Thr Val Leu Ala Tyr
145                 150                 155                 160

Asp Lys Asp Thr Val Ile Thr Gly Cys Ala Asp Lys Ile Ile Arg Ile
                165                 170                 175

Phe Asn Thr Ser Gly Thr Leu Leu Arg Thr Ile Glu Asn Ser Gln Asp
            180                 185                 190

Val Val Arg Ala Leu Cys Lys Val Pro Ala Ser Asn Pro Thr Gly Ala
        195                 200                 205

His Phe Ala Ser Ala Ser Asn Asp Gly Val Ile Arg Leu Phe Thr Ile
210                 215                 220

Gln Gly Gln Leu Val Gly Glu Met His Gly His Glu Ser Phe Ile Tyr
225                 230                 235                 240

Ser Leu Ala Ala Leu Pro Ser Gly Glu Leu Val Ser Gly Glu Asp
            245                 250                 255

Arg Thr Val Arg Val Trp Asp Gly Thr Gln Cys Val Gln Thr Ile Thr
                260                 265                 270

His Pro Ala Ile Ser Val Trp Ser Val Ala Val Cys Lys Glu Thr Gly
            275                 280                 285

Asp Ile Val Thr Gly Ala Ser Asp Arg Ile Thr Arg Val Phe Ser Arg
        290                 295                 300

Ser Gln Glu Arg Val Ala Ser Pro Glu Val Val Gln Gln Phe Glu Lys
305                 310                 315                 320

Thr Val Lys Glu Ser Ala Ile Pro Glu Gln Gln Ile Gly Lys Ile Asn
                325                 330                 335

Lys Asp Lys Leu Pro Gly Thr Glu Phe Leu Arg Gln Lys Ser Gly Thr
            340                 345                 350

Lys Asp Gly Gln Val Gln Met Ile Arg Glu Ala Asp Gly Ser Val Thr
        355                 360                 365

Ala His Thr Trp Ser Ala Ala Ser Arg Glu Trp Val Ala Val Gly Thr
370                 375                 380

Val Val Asp Ser Ala Ala Ser Ser Gly Arg Lys Thr Glu Tyr Leu Gly
385                 390                 395                 400

Gln Asp Tyr Asp Tyr Val Phe Asp Val Asp Val Glu Asp Gly Lys Pro
                405                 410                 415

Pro Leu Lys Leu Pro Tyr Asn Val Ser Gln Asn Pro Tyr Glu Ala Ala
            420                 425                 430

Thr Lys Phe Ile Gln Asp Asn Glu Leu Ser Met Asn Tyr Leu Asp Gln
        435                 440                 445

Val Ala Gln Phe Ile Val Gln Asn Thr Gln Gly Ala Thr Leu Glu Arg
450                 455                 460

Arg Tyr Arg Pro Glu Asp Ala Gln Ser Pro Ala Pro Glu Ala Arg
465                 470                 475                 480

Pro Lys Val Leu Pro Gln Lys Thr Tyr Leu Ser Ile Lys Ser Ala Asn
                485                 490                 495
```

```
Leu Lys Leu Ile Ala Lys Lys Leu Gln Glu Leu Asn Gln His Val Ile
            500                 505                 510
Ser Ser Gly Ser Lys Asp Leu Ser Leu Ser Pro Ser Glu Leu Glu Thr
            515                 520                 525
Val Ala Thr Leu Cys Gly Gln Leu Glu Ser Ser Asn Val Glu Gln Ser
            530                 535                 540
Pro Ala Val Glu Ala Gly Val Val Leu Tyr Lys Val Ala Thr Val
545                 550                 555                 560
Trp Pro Val Ala Ser Arg Leu Pro Gly Leu Asp Leu Leu Arg Leu Ser
                565                 570                 575
Ala Ala Ala Thr Pro Val Thr Ala Thr Ala Asp Tyr Asp Gly Lys Asp
                580                 585                 590
Leu Ile Ser Gly Ile Lys Ser Ser Gly Val Phe Asp Ser Pro Phe Asn
            595                 600                 605
Val Asn Asn Ala Met Leu Ser Ile Arg Met Leu Ala Asn Leu Phe Glu
            610                 615                 620
Thr Asp Ala Gly Arg Asp Leu Ala Thr Ser Lys Phe Glu Gln Ile Leu
625                 630                 635                 640
Ser Gly Val Lys Ser Ala Leu Thr Asn Ser Gly Thr Thr Pro Asn Arg
                645                 650                 655
Asn Leu Thr Ile Ala Ile Thr Thr Leu Tyr Ile Asn Phe Ala Val Tyr
            660                 665                 670
Leu Thr Ser Ala Gly Arg Glu Ser Met Pro Glu Ser Ser Glu Gln Ala
            675                 680                 685
Leu Val Leu Leu Gly Glu Leu Thr Thr Leu Ile Thr Gly Glu Lys Asp
            690                 695                 700
Ser Glu Ala Val Tyr Arg Gly Leu Val Ala Leu Gly Thr Leu Ile Lys
705                 710                 715                 720
Gly Leu Gly Glu Glu Val Arg Thr Ala Ala Lys Glu Val Tyr Asp Val
                725                 730                 735
Asp Asp Val Leu Lys Lys Val Ser Ser Ser Gly Leu Gly Lys Glu Pro
                740                 745                 750
Arg Ile Lys Gly Ile Ile Gly Glu Ile Lys Glu Ser Leu Ser Ser Arg
            755                 760                 765
Tyr Lys Met Leu Arg Pro Gly Ser
770                 775

<210> SEQ ID NO 52
<211> LENGTH: 2505
<212> TYPE: DNA
<213> ORGANISM: Aspergillus niger

<400> SEQUENCE: 52
acctaatctc ttcctttcac ctgatctgct gcctcttccc tcccatccc ctcccctcgt      60
cttccctcc caaaagaat ccgccggttt ttccaccttt tccctttctt atcctttcc      120
cctcccctcc tcggtggtgt gtatgtctgt aacgggcctt ttatcttcgt gaacagttta   180
attgtgatcc actagaaatc atgggtcaga ccttgtccga gcccgtggtc gataaggtga   240
gtgaaacctg aagcattgcg tttgcctgtc tggtctttga tcctcctccc ccacactgca   300
cgcatcttac gccatttcaa tctgtccacc atccgcgttg ccattctgtg ccatacccgc   360
ccatacttcc ctttttctat catttgtcca acatgatcac tgcccaaaag ttttatttgc   420
tacagcgttc ttttttcatcc ctcctcttgt gtgtcgcgcc tgcaatgtgg tgatcatccc   480
ccctgcgggg ttcctccaca ggatgatgaa aatttcctgc acgcggtttc gggcggatga   540
```

-continued

```
cctgtcacca ttccattgtg ttccggacct cttttcgatt tcctacatcc tcactaacca     600
cattcggtgc tatctagact tccgctgaag gtcaagatga gtgctgtata tacggtgttt     660
ccgccatgca aggatggcga atcagcatgg aggatgccca tgccgctgtc ctcgacctcc     720
aggccaagta ctccgagcag gatgaaaagc cgaccgaccc cgataaacga ctcgctttct     780
ttggtgtata tgacgggcac ggtggagaca aagtagcatt attcgccgga gaaaacgtcc     840
acaagatcgt cgcgaagcag gactcctttg ccaaaggtga tatcgaacag gccctgaagg     900
atggcttcct cgctaccgac cgggctattt tggaaggttc gtgagcgcta tgatcggagt     960
tggggcaacc ttcccacccg cctctccctt tccttcctgt ttcctgtccc tccgaggtag    1020
caacgaactg acccagctag acccgaaata tgaggaggaa gtgtctggct gcaccgcagc    1080
cgtcagcgtt atctcgaagc acaagatctg ggtggtatgt attctagcca tggccgtttt    1140
ggagacgacg ttgggtttgg ttcattcgtt gactggttct aggccaatgc tggtgattct    1200
cgctctgtac tgggtgtcaa gggtcgcgca aagcctctgt catttgacca caagcctcag    1260
aatgaaggta cacataccccc acatctcgat taccgaccag ttttgatgat gctgacatga    1320
ccaaataaaa acaggcgaga aagcccgtat cagcgctgct ggtggtttcg ttgacttcgg    1380
ccgtgtcaac ggcaacctgg ccttgtcgcg ggccattggt gacttcgagt tcaagaagag    1440
cccgagttg tctcctgagc agcagatcgt cactgcctat cccgacgtca ctgtgcacga    1500
tctcagtgac gatgacgagt tcctcgtaat tgcctgtgac ggtgggtctt actctggtga    1560
tgcgggggtg agggtcttga agatcgctaa cttttcgaaa ttgcaggtat ctgggattgt    1620
cagtcctccc aatcagtggt ggaattcgtc cgccgtggga ttgccgcgaa gcaggatctg    1680
tatcggatct gtgagaacat gatggacaac tgcctggcct ccaacagtga aaccggcggc    1740
gttggctgcg acaatatgac aatggtcatc atcggtctcc tgaacggtag gaccaaagag    1800
gagtggtaca accagatcgc tgagcgcgtg gcgaacggcg acggcccttg cgctccgccc    1860
gagtacggca agtctctcga ggatcccacg gcctccaatt ccaatcccta ctgactgaac    1920
gggggtgca gctgagttcc gcggcccgg tatccggaat caattcgagg agaacccgga    1980
tgactttgac atggaaaacg accgtgcgcg tggcttcagc gtccgctcgg gccgcatcat    2040
cctcttgggg gacggcactg aattgattcc ggagcagaac gatgacgaac tctttgatca    2100
ggctgaggaa gaccaggacc ttgtcaatca ggtgcaccgt gattcgcctg atgcggctcg    2160
gaatgaacgg gagggaactc ctgggcctca gtctaaggat acttctcgaa cggacgccgc    2220
tgagatatcg gagtcgccgt ctaccaccgc ggagggttcg tccggcagtg ccctggaac    2280
gccgcaaaag cctacgagtt cgtagtcatg atggatctct tgcatttctc cttaatatgt    2340
ctttttcttt ttttcctcct ttttccccct tgccgcgctt gttacctttt tcccttttc    2400
cctttttttcc ttattttggt tctttgaaaa ccacccgtgt gtgattctac gactgtgccc    2460
gttttacct atttccttac atttacgtgg acttctttct gcctt                    2505
```

<210> SEQ ID NO 53
<211> LENGTH: 1275
<212> TYPE: DNA
<213> ORGANISM: Aspergillus niger
<220> FEATURE:
<221> NAME/KEY: CDS
<222> LOCATION: (1)..(1275)

<400> SEQUENCE: 53

```
atg ggt cag acc ttg tcc gag ccc gtg gtc gat aag act tcc gct gaa      48
Met Gly Gln Thr Leu Ser Glu Pro Val Val Asp Lys Thr Ser Ala Glu
```

```
       1               5                  10                 15
ggt caa gat gag tgc tgt ata tac ggt gtt tcc gcc atg caa gga tgg        96
Gly Gln Asp Glu Cys Cys Ile Tyr Gly Val Ser Ala Met Gln Gly Trp
            20                  25                  30 cga atc agc atg gag gat gcc cat gcc gct gtc ctc gac ctc cag gcc       144
Arg Ile Ser Met Glu Asp Ala His Ala Ala Val Leu Asp Leu Gln Ala
            35                  40                  45 aag tac tcc gag cag gat gaa aag ccg acc gac ccc gat aaa cga ctc       192
Lys Tyr Ser Glu Gln Asp Glu Lys Pro Thr Asp Pro Asp Lys Arg Leu
    50                  55                  60 gct ttc ttt ggt gta tat gac ggg cac ggt gga gac aaa gta gca tta       240
Ala Phe Phe Gly Val Tyr Asp Gly His Gly Gly Asp Lys Val Ala Leu
65                  70                  75                  80 ttc gcc gga gaa aac gtc cac aag atc gtc gcg aag cag gac tcc ttt       288
Phe Ala Gly Glu Asn Val His Lys Ile Val Ala Lys Gln Asp Ser Phe
                85                  90                  95 gcc aaa ggt gat atc gaa cag gcc ctg aag gat ggc ttc ctc gct acc       336
Ala Lys Gly Asp Ile Glu Gln Ala Leu Lys Asp Gly Phe Leu Ala Thr
                    100                 105                 110 gac cgg gct att ttg gaa gac ccg aaa tat gag gag gaa gtg tct ggc       384
Asp Arg Ala Ile Leu Glu Asp Pro Lys Tyr Glu Glu Glu Val Ser Gly
            115                 120                 125 tgc acc gca gcc gtc agc gtt atc tcg aag cac aag atc tgg gtg gcc       432
Cys Thr Ala Ala Val Ser Val Ile Ser Lys His Lys Ile Trp Val Ala
        130                 135                 140 aat gct ggt gat tct cgc tct gta ctg ggt gtc aag ggt cgc gca aag       480
Asn Ala Gly Asp Ser Arg Ser Val Leu Gly Val Lys Gly Arg Ala Lys
145                 150                 155                 160 cct ctg tca ttt gac cac aag cct cag aat gaa ggc gag aaa gcc cgt       528
Pro Leu Ser Phe Asp His Lys Pro Gln Asn Glu Gly Glu Lys Ala Arg
                165                 170                 175 atc agc gct gct ggt ggt ttc gtt gac ttc ggc cgt gtc aac ggc aac       576
Ile Ser Ala Ala Gly Gly Phe Val Asp Phe Gly Arg Val Asn Gly Asn
                    180                 185                 190 ctg gcc ttg tcg cgg gcc att ggt gac ttc gag ttc aag aag agc ccc       624
Leu Ala Leu Ser Arg Ala Ile Gly Asp Phe Glu Phe Lys Lys Ser Pro
            195                 200                 205 gag ttg tct cct gag cag cag atc gtc act gcc tat ccc gac gtc act       672
Glu Leu Ser Pro Glu Gln Gln Ile Val Thr Ala Tyr Pro Asp Val Thr
        210                 215                 220 gtg cac gat ctc agt gac gat gac gag ttc ctc gta att gcc tgt gac       720
Val His Asp Leu Ser Asp Asp Asp Glu Phe Leu Val Ile Ala Cys Asp
225                 230                 235                 240 ggt atc tgg gat tgt cag tcc tcc caa tca gtg gtg gaa ttc gtc cgc       768
Gly Ile Trp Asp Cys Gln Ser Ser Gln Ser Val Val Glu Phe Val Arg
                245                 250                 255 cgt ggg att gcc gcg aag cag gat ctg tat cgg atc tgt gag aac atg       816
Arg Gly Ile Ala Ala Lys Gln Asp Leu Tyr Arg Ile Cys Glu Asn Met
                    260                 265                 270 atg gac aac tgc ctg gcc tcc aac agt gaa acc ggc ggc gtt ggc tgc       864
Met Asp Asn Cys Leu Ala Ser Asn Ser Glu Thr Gly Gly Val Gly Cys
            275                 280                 285 gac aat atg aca atg gtc atc atc ggt ctc ctg aac gct gag ttc cgc       912
Asp Asn Met Thr Met Val Ile Ile Gly Leu Leu Asn Ala Glu Phe Arg
        290                 295                 300 ggc ccc ggt atc cgg aat caa ttc gag gag aac ccg gat gac ttt gac       960
Gly Pro Gly Ile Arg Asn Gln Phe Glu Glu Asn Pro Asp Asp Phe Asp
305                 310                 315                 320 atg gaa aac gac cgt gcg cgt ggc ttc agc gtc cgc tcg ggc cgc atc      1008
Met Glu Asn Asp Arg Ala Arg Gly Phe Ser Val Arg Ser Gly Arg Ile
```

|  |  |  |  |  |  |  |  |  |  |  |  |  |  |  |  |
|---|---|---|---|---|---|---|---|---|---|---|---|---|---|---|---|
|  |  |  | 325 |  |  |  | 330 |  |  |  | 335 |  |  |  |  |
| atc | ctc | ttg | ggg | gac | ggc | act | gaa | ttg | att | ccg | gag | cag | aac | gat | gac | 1056 |
| Ile | Leu | Leu | Gly | Asp | Gly | Thr | Glu | Leu | Ile | Pro | Glu | Gln | Asn | Asp | Asp |  |
|  |  |  | 340 |  |  |  | 345 |  |  |  |  |  | 350 |  |  |  |
| gaa | ctc | ttt | gat | cag | gct | gag | gaa | gac | cag | gac | ctt | gtc | aat | cag | gtg | 1104 |
| Glu | Leu | Phe | Asp | Gln | Ala | Glu | Glu | Asp | Gln | Asp | Leu | Val | Asn | Gln | Val |  |
|  |  | 355 |  |  |  |  | 360 |  |  |  |  |  | 365 |  |  |  |
| cac | cgt | gat | tcg | cct | gat | gcg | gct | cgg | aat | gaa | cgg | gag | gga | act | cct | 1152 |
| His | Arg | Asp | Ser | Pro | Asp | Ala | Ala | Arg | Asn | Glu | Arg | Glu | Gly | Thr | Pro |  |
|  | 370 |  |  |  |  | 375 |  |  |  |  | 380 |  |  |  |  |  |
| ggg | cct | cag | tct | aag | gat | act | tct | cga | acg | gac | gcc | gct | gag | ata | tcg | 1200 |
| Gly | Pro | Gln | Ser | Lys | Asp | Thr | Ser | Arg | Thr | Asp | Ala | Ala | Glu | Ile | Ser |  |
| 385 |  |  |  |  | 390 |  |  |  |  | 395 |  |  |  |  | 400 |  |
| gag | tcg | ccg | tct | acc | acc | gcg | gag | ggt | tcg | tcc | ggc | agt | ggc | cct | gga | 1248 |
| Glu | Ser | Pro | Ser | Thr | Thr | Ala | Glu | Gly | Ser | Ser | Gly | Ser | Gly | Pro | Gly |  |
|  |  |  |  | 405 |  |  |  |  | 410 |  |  |  |  | 415 |  |  |
| acg | ccg | caa | aag | cct | acg | agt | tcg | tag |  |  |  |  |  |  |  | 1275 |
| Thr | Pro | Gln | Lys | Pro | Thr | Ser | Ser |  |  |  |  |  |  |  |  |  |
|  |  |  | 420 |  |  |  |  |  |  |  |  |  |  |  |  |  |

<210> SEQ ID NO 54
<211> LENGTH: 424
<212> TYPE: PRT
<213> ORGANISM: Aspergillus niger

<400> SEQUENCE: 54

Met Gly Gln Thr Leu Ser Glu Pro Val Val Asp Lys Thr Ser Ala Glu
1               5                   10                  15

Gly Gln Asp Glu Cys Cys Ile Tyr Gly Val Ser Ala Met Gln Gly Trp
                20                  25                  30

Arg Ile Ser Met Glu Asp Ala His Ala Ala Val Leu Asp Leu Gln Ala
            35                  40                  45

Lys Tyr Ser Glu Gln Asp Glu Lys Pro Thr Asp Pro Asp Lys Arg Leu
        50                  55                  60

Ala Phe Phe Gly Val Tyr Asp Gly His Gly Gly Asp Lys Val Ala Leu
65                  70                  75                  80

Phe Ala Gly Glu Asn Val His Lys Ile Val Ala Lys Gln Asp Ser Phe
                85                  90                  95

Ala Lys Gly Asp Ile Glu Gln Ala Leu Lys Asp Gly Phe Leu Ala Thr
            100                 105                 110

Asp Arg Ala Ile Leu Glu Asp Pro Lys Tyr Glu Glu Val Ser Gly
        115                 120                 125

Cys Thr Ala Ala Val Ser Val Ile Ser Lys His Lys Ile Trp Val Ala
130                 135                 140

Asn Ala Gly Asp Ser Arg Ser Val Leu Gly Val Lys Gly Arg Ala Lys
145                 150                 155                 160

Pro Leu Ser Phe Asp His Lys Pro Gln Asn Glu Gly Glu Lys Ala Arg
                165                 170                 175

Ile Ser Ala Ala Gly Gly Phe Val Asp Phe Gly Arg Val Asn Gly Asn
            180                 185                 190

Leu Ala Leu Ser Arg Ala Ile Gly Asp Phe Glu Phe Lys Lys Ser Pro
        195                 200                 205

Glu Leu Ser Pro Glu Gln Ile Val Thr Ala Tyr Pro Asp Val Thr
    210                 215                 220

Val His Asp Leu Ser Asp Asp Glu Phe Leu Val Ile Ala Cys Asp
225                 230                 235                 240

Gly Ile Trp Asp Cys Gln Ser Ser Gln Ser Val Val Glu Phe Val Arg

```
                245                 250                 255
Arg Gly Ile Ala Ala Lys Gln Asp Leu Tyr Arg Ile Cys Glu Asn Met
            260                 265                 270

Met Asp Asn Cys Leu Ala Ser Asn Ser Glu Thr Gly Gly Val Gly Cys
        275                 280                 285

Asp Asn Met Thr Met Val Ile Ile Gly Leu Leu Asn Ala Glu Phe Arg
        290                 295                 300

Gly Pro Gly Ile Arg Asn Gln Phe Glu Asn Pro Asp Asp Phe Asp
305                 310                 315                 320

Met Glu Asn Asp Arg Ala Arg Gly Phe Ser Val Arg Ser Gly Arg Ile
                325                 330                 335

Ile Leu Leu Gly Asp Gly Thr Glu Leu Ile Pro Glu Gln Asn Asp Asp
            340                 345                 350

Glu Leu Phe Asp Gln Ala Glu Glu Asp Gln Asp Leu Val Asn Gln Val
        355                 360                 365

His Arg Asp Ser Pro Asp Ala Ala Arg Asn Glu Arg Glu Gly Thr Pro
        370                 375                 380

Gly Pro Gln Ser Lys Asp Thr Ser Arg Thr Asp Ala Ala Glu Ile Ser
385                 390                 395                 400

Glu Ser Pro Ser Thr Thr Ala Glu Gly Ser Ser Gly Ser Gly Pro Gly
                405                 410                 415

Thr Pro Gln Lys Pro Thr Ser Ser
            420

<210> SEQ ID NO 55
<211> LENGTH: 1209
<212> TYPE: DNA
<213> ORGANISM: Aspergillus niger

<400> SEQUENCE: 55
ctggcagtta tttagtggtg attcggcatc atccccttat cgatcatact cgcccgtctt      60
ctctcgagtc cttaaacgcc aaaagacgac tgtctgcatc ctctctattt cgcttaccgc     120
ttcgtcgcat cgtacccgcc acccgagcaa cctccccct aagttaatcc caacgttcgc     180
aactctacta cccatcaatt atggccgcca tctggggtaa cggcgggcag ctggccagt     240
tcccgctgga gcaatggttc tatgaaatgc ccctgtaac tcgatggtgg acagcagcca     300
cagttgccac ttcagtcttg gtccaatgtc acgtcctcac cccattccag ctgtttata     360
gcttccgcgc agtctatgtt aagtctcagg tacgtcgcag ctagtacttc cgtccactgt     420
atagggtaga cgaatcacgc ggctaaccat cgcatagtat tggcgtctgt tcacaacctt     480
cctatacttc ggaccactca atctcgactt actatttcat gtgttcttct tgcagcgata     540
ctcgcgcctc ttggaggaat catcggggcg atcgccggcc cacttctcgt ggcttctgtt     600
ctacgccatg gcctctctcc tcgtcctctc gccatttctc tcccttccat tcctgggcac     660
ggctctctct tccagtctgg tctacatctg gagtcgtcgc aacccggaaa ctcgcctcag     720
cttcctagga atgctggtct tcaccgcccc ctatctcccc tgggttctga tggcattcag     780
cctggtcgtc catggcatcg tgcccaagga tgaaatctgc ggcgttgtcg tcggccacgt     840
ctggtacttc ttcaacgatg tttacccttc gcttcacggt ggtcaccgtc ctttcgatcc     900
tcctatgtgt gggtgcgtc tgtttgagtc agggcccggg gaacgaggca ccgacgctgc     960
caacgtcaac ggggaattcg ccgctgctgc tgcacccgaa gttcggtgag ctatttgtgc    1020
accccactgg ggcatttact gcatggcgat gcaaagaatc gtccgcgtaa tcgctctgga    1080
aacgtcagca tatatgtgtg tactgccaac tactcgcgcc gacacgcgcg aagcatgaga    1140
```

```
agttaatact gtcaggatat aagcaaggat cacggcggca gacttgatgg gatttcttat      1200
cgtgtggct                                                              1209

<210> SEQ ID NO 56
<211> LENGTH: 741
<212> TYPE: DNA
<213> ORGANISM: Aspergillus niger
<220> FEATURE:
<221> NAME/KEY: CDS
<222> LOCATION: (1)..(741)

<400> SEQUENCE: 56 atg gcc gcc atc tgg ggt aac ggc ggg cag gct ggc cag ttc ccg ctg      48
Met Ala Ala Ile Trp Gly Asn Gly Gly Gln Ala Gly Gln Phe Pro Leu
1               5                  10                  15 gag caa tgg ttc tat gaa atg ccc cct gta act cga tgg tgg aca gca      96
Glu Gln Trp Phe Tyr Glu Met Pro Pro Val Thr Arg Trp Trp Thr Ala
            20                  25                  30 gcc aca gtt gcc act tca gtc ttg gtc caa tgt cac gtc ctc acc cca     144
Ala Thr Val Ala Thr Ser Val Leu Val Gln Cys His Val Leu Thr Pro
        35                  40                  45 ttc cag ctg ttt tat agc ttc cgc gca gtc tat gtt aag tct cag tat     192
Phe Gln Leu Phe Tyr Ser Phe Arg Ala Val Tyr Val Lys Ser Gln Tyr
    50                  55                  60 tgg cgt ctg ttc aca acc ttc cta tac ttc gga cca ctc aat ctc gac     240
Trp Arg Leu Phe Thr Thr Phe Leu Tyr Phe Gly Pro Leu Asn Leu Asp
65                  70                  75                  80 tta cta ttt cat gtg ttc ttc ttg cag cga tac tcg cgc ctc ttg gag     288
Leu Leu Phe His Val Phe Phe Leu Gln Arg Tyr Ser Arg Leu Leu Glu
                85                  90                  95 gaa tca tcg ggg cga tcg ccg gcc cac ttc tcg tgg ctt ctg ttc tac     336
Glu Ser Ser Gly Arg Ser Pro Ala His Phe Ser Trp Leu Leu Phe Tyr
            100                 105                 110 gcc atg gcc tct ctc ctc gtc ctc tcg cca ttt ctc tcc ctt cca ttc     384
Ala Met Ala Ser Leu Leu Val Leu Ser Pro Phe Leu Ser Leu Pro Phe
        115                 120                 125 ctg ggc acg gct ctc tct tcc agt ctg gtc tac atc tgg agt cgt cgc     432
Leu Gly Thr Ala Leu Ser Ser Ser Leu Val Tyr Ile Trp Ser Arg Arg
    130                 135                 140 aac ccg gaa act cgc ctc agc ttc cta gga atg ctg gtc ttc acc gcc     480
Asn Pro Glu Thr Arg Leu Ser Phe Leu Gly Met Leu Val Phe Thr Ala
145                 150                 155                 160 ccc tat ctc ccc tgg gtt ctg atg gca ttc agc ctg gtc gtc cat ggc     528
Pro Tyr Leu Pro Trp Val Leu Met Ala Phe Ser Leu Val Val His Gly
                165                 170                 175 atc gtg ccc aag gat gaa atc tgc ggc gtt gtc gtc ggc cac gtc tgg     576
Ile Val Pro Lys Asp Glu Ile Cys Gly Val Val Val Gly His Val Trp
            180                 185                 190 tac ttc ttc aac gat gtt tac cct tcg ctt cac ggt ggt cac cgt cct     624
Tyr Phe Phe Asn Asp Val Tyr Pro Ser Leu His Gly Gly His Arg Pro
        195                 200                 205 ttc gat cct cct atg tgg tgg gtg cgt ctg ttt gag tca ggg ccc ggg     672
Phe Asp Pro Pro Met Trp Trp Val Arg Leu Phe Glu Ser Gly Pro Gly
    210                 215                 220 gaa cga ggc acc gac gct gcc aac gtc aac ggg gaa ttc gcc gct gct     720
Glu Arg Gly Thr Asp Ala Ala Asn Val Asn Gly Glu Phe Ala Ala Ala
225                 230                 235                 240 gct gca ccc gaa gtt cgg tga                                          741
Ala Ala Pro Glu Val Arg
                245
```

<210> SEQ ID NO 57
<211> LENGTH: 246
<212> TYPE: PRT
<213> ORGANISM: Aspergillus niger

<400> SEQUENCE: 57

Met Ala Ala Ile Trp Gly Asn Gly Gly Gln Ala Gly Gln Phe Pro Leu
1               5                   10                  15

Glu Gln Trp Phe Tyr Glu Met Pro Pro Val Thr Arg Trp Trp Thr Ala
            20                  25                  30

Ala Thr Val Ala Thr Ser Val Leu Val Gln Cys His Val Leu Thr Pro
        35                  40                  45

Phe Gln Leu Phe Tyr Ser Phe Arg Ala Val Tyr Val Lys Ser Gln Tyr
    50                  55                  60

Trp Arg Leu Phe Thr Thr Phe Leu Tyr Phe Gly Pro Leu Asn Leu Asp
65                  70                  75                  80

Leu Leu Phe His Val Phe Phe Leu Gln Arg Tyr Ser Arg Leu Leu Glu
                85                  90                  95

Glu Ser Ser Gly Arg Ser Pro Ala His Phe Ser Trp Leu Leu Phe Tyr
            100                 105                 110

Ala Met Ala Ser Leu Leu Val Leu Ser Pro Phe Leu Ser Leu Pro Phe
        115                 120                 125

Leu Gly Thr Ala Leu Ser Ser Ser Leu Val Tyr Ile Trp Ser Arg Arg
    130                 135                 140

Asn Pro Glu Thr Arg Leu Ser Phe Leu Gly Met Leu Val Phe Thr Ala
145                 150                 155                 160

Pro Tyr Leu Pro Trp Val Leu Met Ala Phe Ser Leu Val Val His Gly
                165                 170                 175

Ile Val Pro Lys Asp Glu Ile Cys Gly Val Val Gly His Val Trp
            180                 185                 190

Tyr Phe Phe Asn Asp Val Tyr Pro Ser Leu His Gly Gly His Arg Pro
        195                 200                 205

Phe Asp Pro Pro Met Trp Trp Val Arg Leu Phe Glu Ser Gly Pro Gly
    210                 215                 220

Glu Arg Gly Thr Asp Ala Ala Asn Val Asn Gly Glu Phe Ala Ala Ala
225                 230                 235                 240

Ala Ala Pro Glu Val Arg
            245

<210> SEQ ID NO 58
<211> LENGTH: 2538
<212> TYPE: DNA
<213> ORGANISM: Aspergillus niger

<400> SEQUENCE: 58
gaagcttggc ggtggtggtc atgtctttcc aggcccctcg gaacagttct ccatttttcgt    60 ctcagcaacc gttccagaat aactactggc gtgctagtcg aagccctggg accaacgggc   120
tgcctggcta tgggttttcg ccaccgactg gtatctccaa ctccctgaac atcccctcg    180 ccggcgaccg cactctcccc atgtacaagg acaaacctta cttcgcacca cgacgcaccg   240
gtccgagagc caggcggcgg aagatcatat atagtgggct atgtctgttc gtcctgctcg   300
ctctgtggta ctactctggc tctggtaagc cggaatggaa gacaccggac gcggagaagg   360
gcgccgagct ctggaagtgg gtgcaaagtt tgaggagtc ggaaccacca tacgatggca    420
gcgcagcgac agagaagatt gactgggaag caaggaggga gaaagtgcgc gacgtcttca   480

```
ttgtcagttg ggatggttat gcggctaatg cgtggggtga gtttctggct ggaattaacc    540
tcttgattct tggatgtggt gactgacaat ggctttgtct gccggtgatt aggttacgat    600
gaataccacc caattgccaa aaacggtcgg cacatgattg aaggaggaat ggggtggata    660
attgttgatg cgctggacac tttgatgatt atgaacctga cgtcgcgagt gcaacatgcc    720
cgcagctgga tccacaactc gttgcaatac aaccaggacc acgatgtgaa taccttcgag    780
actaccattc gcatgctggg aggcttactc tccgcacact atctctccac gaactatccc    840
gagctagctc cgcttacgga tgacgataca ggcgcgccgg agaagacttt gtatatcgag    900
aaggccaccg atctggcaga tcgtctattg ggtgcttttg aatccggcac tggaatcccg    960
tatgcaagca tcaatttgaa caaatccgag ggccttccct cgtacgcgga taatggcgcc   1020
tcatctactg ccgaagccac tactctccag ctggagttca gtacttggc caaactgacg    1080
ggcgaggccg agtactggca ggctgtggag aaggttatgg aggtcgtgga cgaccagaag   1140
atggaagacg gattgcttcc gatctacgta tatccagaga ccggcgaatt taaaggcgat   1200
aacatccgtc tcggcagtag aggcgattca tactatggta tacatgatgg ctttgtgcgt   1260
gaatattcaa tgcgctgacc gatgtttcct agaatacctc atcaagcagt accttcaaac   1320
gcaagagact gaaccgatct acaaggacat gtgggatgag tccctcgtcg gcgtgcgcaa   1380
gcacctgatc acctatacac agaacgccaa gttgaccgtt ctgggcgaac gcctgccgg    1440
gctgcatgga gtcctttccc ccaagatgga ccacctagtc tgcttctacc ccggcaccat   1500
cgctctcgca gcaactggcg gacgtcctct gtccgaggca agacagtcac ccgattgggg   1560
ccaacgccag gaggaagaga ttcttctagc ccgagaacta accaagacct gctgggcaac   1620
gtatctaatc acgaagaccg gcctcgcacc agagatcacc tacttcaatg tcgacgaccc   1680
tcgcgtcatg gaaacagaca tgtacccaga ctcgaccatt gccaaaccca gctcaggcca   1740
gcaaaaagcc tctggcgaac tcccctcct ctccaaatcc atctacccg tcagcgacta    1800
ctccaccaaa tggcgcgacg acctcaacat ccacaaacaa gaccgccaca acctccaacg   1860
cccagagacc gtcgaatccc tcttctacat gtatcgcatc accggagacg acatctaccg   1920
acactggggc tgggagatgt tcaagtcttt tgtcaagcat actgccgtgg tcgaggacat   1980
ccctgtcgat gaactcagca aagaagacgc gtccagctca acatcatcat cggaggaaga   2040
agacggcgga actcagaagc caaaacctca gaaaatcacg gcttcacct cgctctcaaa    2100
cgctgatgac aaccctccag tgaagcgcga caacatggag agtttctgga tggccgagac   2160
gcttaaatac ttctacttgc tattctcgga ccgcgacttt atctctctcg aagaccatgt   2220
attcaatacg gaggcgcatc ctctcccgcg gttcaagcca acgggcgagt tgaagaccgg   2280
gtggatgagg aagagtcgga cgataccaac atccagtgag gtggaggagt cggtataatt   2340
tctttgacta tctatttttt ttcttatgct tttatatatc tctctcttgg actacgtctc   2400
cttagatccc tctaacaaaa aagaaagata tctcgaattg attgatcatc tcttgatttt   2460
gtttgtttga tgcttgctta tatgtactgc tatatattgc tcctgcattc tggctggtta   2520
catccaaggc agggactt                                                 2538
```

<210> SEQ ID NO 59
<211> LENGTH: 1812
<212> TYPE: DNA
<213> ORGANISM: Aspergillus niger
<220> FEATURE:
<221> NAME/KEY: CDS
<222> LOCATION: (1)..(1812)

<400> SEQUENCE: 59

| | | |
|---|---|---|
| atg tac aag gac aaa cct tac ttc gca cca cga cgc acc ggt ccg aga<br>Met Tyr Lys Asp Lys Pro Tyr Phe Ala Pro Arg Arg Thr Gly Pro Arg<br>1                      5                      10                    15 | 48 | |
| gcc agg cgg cgg aag atc ata tat agt ggg cta tgt ctg ttc gtc ctg<br>Ala Arg Arg Arg Lys Ile Ile Tyr Ser Gly Leu Cys Leu Phe Val Leu<br>                  20                      25                    30 | 96 | |
| ctc gct ctg tgg tac tac tct ggc tct ggt aag ccg gaa tgg aag aca<br>Leu Ala Leu Trp Tyr Tyr Ser Gly Ser Gly Lys Pro Glu Trp Lys Thr<br>       35                      40                    45 | 144 | |
| ccg gac gcg gag aag ggc gcc gag ctc tgg aag tgg gtg caa agt ttt<br>Pro Asp Ala Glu Lys Gly Ala Glu Leu Trp Lys Trp Val Gln Ser Phe<br>50                      55                      60 | 192 | |
| gag gag tcg gaa cca cca tac gat ggc agc gca gcg aca gag aag att<br>Glu Glu Ser Glu Pro Pro Tyr Asp Gly Ser Ala Ala Thr Glu Lys Ile<br>65                      70                      75                    80 | 240 | |
| gac tgg gaa gca agg agg gag aaa gtg cgc gac gtc ttc att gtc agt<br>Asp Trp Glu Ala Arg Arg Glu Lys Val Arg Asp Val Phe Ile Val Ser<br>                  85                      90                    95 | 288 | |
| tgg gat ggt tat gcg gct aat gcg tgg ggt tac gat gaa tac cac cca<br>Trp Asp Gly Tyr Ala Ala Asn Ala Trp Gly Tyr Asp Glu Tyr His Pro<br>                    100                   105                 110 | 336 | |
| att gcc aaa aac ggt cgg cac atg att gaa gga gga atg ggg tgg ata<br>Ile Ala Lys Asn Gly Arg His Met Ile Glu Gly Gly Met Gly Trp Ile<br>      115                      120                   125 | 384 | |
| att gtt gat gcg ctg gac act ttg atg att atg aac ctg acg tcg cga<br>Ile Val Asp Ala Leu Asp Thr Leu Met Ile Met Asn Leu Thr Ser Arg<br>130                      135                      140 | 432 | |
| gtg caa cat gcc cgc agc tgg atc cac aac tcg ttg caa tac aac cag<br>Val Gln His Ala Arg Ser Trp Ile His Asn Ser Leu Gln Tyr Asn Gln<br>145                      150                      155                 160 | 480 | |
| gac cac gat gtg aat acc ttc gag act acc att cgc atg ctg gga ggc<br>Asp His Asp Val Asn Thr Phe Glu Thr Thr Ile Arg Met Leu Gly Gly<br>                    165                   170                 175 | 528 | |
| tta ctc tcc gca cac tat ctc tcc acg aac tat ccc gag cta gct ccg<br>Leu Leu Ser Ala His Tyr Leu Ser Thr Asn Tyr Pro Glu Leu Ala Pro<br>            180                      185                 190 | 576 | |
| ctt acg gat gac gat aca ggc gcg ccg gga gaa gac ttg tat atc gag<br>Leu Thr Asp Asp Asp Thr Gly Ala Pro Gly Glu Asp Leu Tyr Ile Glu<br>                  195                   200                 205 | 624 | |
| aag gcc acc gat ctg gca gat cgt cta ttg ggt gct ttt gaa tcc ggc<br>Lys Ala Thr Asp Leu Ala Asp Arg Leu Leu Gly Ala Phe Glu Ser Gly<br>210                      215                      220 | 672 | |
| act gga atc ccg tat gca agc atc aat ttg aac aaa tcc gag ggc ctt<br>Thr Gly Ile Pro Tyr Ala Ser Ile Asn Leu Asn Lys Ser Glu Gly Leu<br>225                      230                      235                 240 | 720 | |
| ccc tcg tac gcg gat aat ggc gcc tca tct act gcc gaa gcc act act<br>Pro Ser Tyr Ala Asp Asn Gly Ala Ser Ser Thr Ala Glu Ala Thr Thr<br>                  245                   250                 255 | 768 | |
| ctc cag ctg gag ttc aag tac ttg gcc aaa ctg acg ggc gag gcc gag<br>Leu Gln Leu Glu Phe Lys Tyr Leu Ala Lys Leu Thr Gly Glu Ala Glu<br>            260                      265                 270 | 816 | |
| tac tgg cag gct gtg gag aag gtt atg gag gtc gtg gac gac cag aag<br>Tyr Trp Gln Ala Val Glu Lys Val Met Glu Val Val Asp Asp Gln Lys<br>               275                      280                 285 | 864 | |
| atg gaa gac gga ttg ctt ccg atc tac gta tat cca gag acc ggc gaa<br>Met Glu Asp Gly Leu Leu Pro Ile Tyr Val Tyr Pro Glu Thr Gly Glu<br>290                      295                      300 | 912 | |
| ttt aaa ggc gat aac atc cgt ctc ggc agt aga ggc gat tca tac tat<br>Phe Lys Gly Asp Asn Ile Arg Leu Gly Ser Arg Gly Asp Ser Tyr Tyr<br>305                      310                      315                 320 | 960 | |

```
gaa tac ctc atc aag cag tac ctt caa acg caa gag act gaa ccg atc      1008
Glu Tyr Leu Ile Lys Gln Tyr Leu Gln Thr Gln Glu Thr Glu Pro Ile
            325                 330                 335 tac aag gac atg tgg gat gag tcc ctc gtc ggc gtg cgc aag cac ctg      1056
Tyr Lys Asp Met Trp Asp Glu Ser Leu Val Gly Val Arg Lys His Leu
        340                 345                 350 atc acc tat aca cag aac gcc aag ttg acc gtt ctg ggc gaa cgc cct      1104
Ile Thr Tyr Thr Gln Asn Ala Lys Leu Thr Val Leu Gly Glu Arg Pro
    355                 360                 365 gcc ggg ctg cat gga gtc ctt tcc ccc aag atg gac cac cta gtc tgc      1152
Ala Gly Leu His Gly Val Leu Ser Pro Lys Met Asp His Leu Val Cys
370                 375                 380 ttc tac ccc ggc acc atc gct ctc gca gca act ggc gga cgt cct ctg      1200
Phe Tyr Pro Gly Thr Ile Ala Leu Ala Ala Thr Gly Gly Arg Pro Leu
385                 390                 395                 400 tcc gag gca aga cag tca ccc gat tgg ggc caa cgc cag gag gaa gag      1248
Ser Glu Ala Arg Gln Ser Pro Asp Trp Gly Gln Arg Gln Glu Glu Glu
                405                 410                 415 att ctt cta gcc cga gaa cta acc aag acc tgc tgg gca acg tat cta      1296
Ile Leu Leu Ala Arg Glu Leu Thr Lys Thr Cys Trp Ala Thr Tyr Leu
            420                 425                 430 atc acg aag acc ggc ctc gca cca gag atc acc tac ttc aat gtc gac      1344
Ile Thr Lys Thr Gly Leu Ala Pro Glu Ile Thr Tyr Phe Asn Val Asp
        435                 440                 445 gac cct cgc gtc atg gaa aca gac atc gac tac tcc acc aaa tgg cgc      1392
Asp Pro Arg Val Met Glu Thr Asp Ile Asp Tyr Ser Thr Lys Trp Arg
    450                 455                 460 gac gac ctc aac atc cac aaa caa gac cgc cac aac ctc caa cgc cca      1440
Asp Asp Leu Asn Ile His Lys Gln Asp Arg His Asn Leu Gln Arg Pro
465                 470                 475                 480 gag acc gtc gaa tcc ctc ttc tac atg tat cgc atc acc gga gac gac      1488
Glu Thr Val Glu Ser Leu Phe Tyr Met Tyr Arg Ile Thr Gly Asp Asp
                485                 490                 495 atc tac cga cac tgg ggc tgg gag atg ttc aag tct ttt gtc aag cat      1536
Ile Tyr Arg His Trp Gly Trp Glu Met Phe Lys Ser Phe Val Lys His
            500                 505                 510 act gcc gtg aaa atc acg ggc ttc acc tcg ctc tca aac gct gat gac      1584
Thr Ala Val Lys Ile Thr Gly Phe Thr Ser Leu Ser Asn Ala Asp Asp
        515                 520                 525 aac cct cca gtg aag cgc gac aac atg gag agt ttc tgg atg gcc gag      1632
Asn Pro Pro Val Lys Arg Asp Asn Met Glu Ser Phe Trp Met Ala Glu
    530                 535                 540 acg ctt aaa tac ttc tac ttg cta ttc tcg gac cgc gac ttt atc tct      1680
Thr Leu Lys Tyr Phe Tyr Leu Leu Phe Ser Asp Arg Asp Phe Ile Ser
545                 550                 555                 560 ctc gaa gac cat gta ttc aat acg gag gcg cat cct ctc ccg cgg ttc      1728
Leu Glu Asp His Val Phe Asn Thr Glu Ala His Pro Leu Pro Arg Phe
                565                 570                 575 aag cca acg ggc gag ttg aag acc ggg tgg atg agg aag agt cgg acg      1776
Lys Pro Thr Gly Glu Leu Lys Thr Gly Trp Met Arg Lys Ser Arg Thr
            580                 585                 590 ata cca aca tcc agt gag gtg gag gag tcg gta taa                      1812
Ile Pro Thr Ser Ser Glu Val Glu Glu Ser Val
        595                 600

<210> SEQ ID NO 60
<211> LENGTH: 603
<212> TYPE: PRT
<213> ORGANISM: Aspergillus niger

<400> SEQUENCE: 60
```

-continued

```
Met Tyr Lys Asp Lys Pro Tyr Phe Ala Pro Arg Arg Thr Gly Pro Arg
1               5                   10                  15

Ala Arg Arg Arg Lys Ile Ile Tyr Ser Gly Leu Cys Leu Phe Val Leu
                20                  25                  30

Leu Ala Leu Trp Tyr Tyr Ser Gly Ser Gly Lys Pro Glu Trp Lys Thr
            35                  40                  45

Pro Asp Ala Glu Lys Gly Ala Glu Leu Trp Lys Trp Val Gln Ser Phe
        50                  55                  60

Glu Glu Ser Glu Pro Pro Tyr Asp Gly Ser Ala Ala Thr Glu Lys Ile
65                  70                  75                  80

Asp Trp Glu Ala Arg Arg Glu Lys Val Arg Asp Val Phe Ile Val Ser
                85                  90                  95

Trp Asp Gly Tyr Ala Ala Asn Ala Trp Gly Tyr Asp Glu Tyr His Pro
            100                 105                 110

Ile Ala Lys Asn Gly Arg His Met Ile Glu Gly Gly Met Gly Trp Ile
        115                 120                 125

Ile Val Asp Ala Leu Asp Thr Leu Met Ile Met Asn Leu Thr Ser Arg
    130                 135                 140

Val Gln His Ala Arg Ser Trp Ile His Asn Ser Leu Gln Tyr Asn Gln
145                 150                 155                 160

Asp His Asp Val Asn Thr Phe Glu Thr Thr Ile Arg Met Leu Gly Gly
                165                 170                 175

Leu Leu Ser Ala His Tyr Leu Ser Thr Asn Tyr Pro Glu Leu Ala Pro
            180                 185                 190

Leu Thr Asp Asp Asp Thr Gly Ala Pro Gly Glu Asp Leu Tyr Ile Glu
        195                 200                 205

Lys Ala Thr Asp Leu Ala Asp Arg Leu Leu Gly Ala Phe Glu Ser Gly
210                 215                 220

Thr Gly Ile Pro Tyr Ala Ser Ile Asn Leu Asn Lys Ser Glu Gly Leu
225                 230                 235                 240

Pro Ser Tyr Ala Asp Asn Gly Ala Ser Ser Thr Ala Glu Ala Thr Thr
                245                 250                 255

Leu Gln Leu Glu Phe Lys Tyr Leu Ala Lys Leu Thr Gly Glu Ala Glu
            260                 265                 270

Tyr Trp Gln Ala Val Glu Lys Val Met Glu Val Asp Asp Gln Lys
        275                 280                 285

Met Glu Asp Gly Leu Leu Pro Ile Tyr Val Tyr Pro Glu Thr Gly Glu
    290                 295                 300

Phe Lys Gly Asp Asn Ile Arg Leu Gly Ser Arg Gly Asp Ser Tyr Tyr
305                 310                 315                 320

Glu Tyr Leu Ile Lys Gln Tyr Leu Gln Thr Gln Glu Thr Glu Pro Ile
                325                 330                 335

Tyr Lys Asp Met Trp Asp Glu Ser Leu Val Gly Val Arg Lys His Leu
            340                 345                 350

Ile Thr Tyr Thr Gln Asn Ala Lys Leu Thr Val Leu Gly Glu Arg Pro
        355                 360                 365

Ala Gly Leu His Gly Val Leu Ser Pro Lys Met Asp His Leu Val Cys
    370                 375                 380

Phe Tyr Pro Gly Thr Ile Ala Leu Ala Ala Thr Gly Gly Arg Pro Leu
385                 390                 395                 400

Ser Glu Ala Arg Gln Ser Pro Asp Trp Gly Gln Arg Gln Glu Glu Glu
                405                 410                 415

Ile Leu Leu Ala Arg Glu Leu Thr Lys Thr Cys Trp Ala Thr Tyr Leu
```

```
                420            425            430
Ile Thr Lys Thr Gly Leu Ala Pro Glu Ile Thr Tyr Phe Asn Val Asp
            435                440                445
Asp Pro Arg Val Met Glu Thr Asp Ile Asp Tyr Ser Thr Lys Trp Arg
    450                455                460
Asp Asp Leu Asn Ile His Lys Gln Asp Arg His Asn Leu Gln Arg Pro
465                470                475                480
Glu Thr Val Glu Ser Leu Phe Tyr Met Tyr Arg Ile Thr Gly Asp Asp
                485                490                495
Ile Tyr Arg His Trp Gly Trp Glu Met Phe Lys Ser Phe Val Lys His
            500                505                510
Thr Ala Val Lys Ile Thr Gly Phe Thr Ser Leu Ser Asn Ala Asp Asp
        515                520                525
Asn Pro Pro Val Lys Arg Asp Asn Met Glu Ser Phe Trp Met Ala Glu
    530                535                540
Thr Leu Lys Tyr Phe Tyr Leu Leu Phe Ser Asp Arg Asp Phe Ile Ser
545                550                555                560
Leu Glu Asp His Val Phe Asn Thr Glu Ala His Pro Leu Pro Arg Phe
                565                570                575
Lys Pro Thr Gly Glu Leu Lys Thr Gly Trp Met Arg Lys Ser Arg Thr
            580                585                590
Ile Pro Thr Ser Ser Glu Val Glu Glu Ser Val
            595                600

<210> SEQ ID NO 61
<211> LENGTH: 2113
<212> TYPE: DNA
<213> ORGANISM: Aspergillus niger

<400> SEQUENCE: 61
cccgcaatcc cgtcgacct  catcgcttcc tccctttctc ctccatcctc tctctcttcc      60
gtcgtctttt cttcttctcc ttctccttttt gtacttcccc tccattcctt cagctggttc    120
tcgcctccag ctttccttc tttctttccc tccccttttta ttcgagtaat cctgcagctc    180
tgggaggtgc aacagtcaca atgagcggac gtgagtcttg cacgcgatcg ctgccatctc    240
cgcgacagcg ttcatccctt tacctcaatg gatcagcaaa tgctgatact cgattctagt    300
ccggtttctc gatctcatca agcccttcac gcccctcctc ccggaggtgg ccgccccgga    360
aaccaaggtt cccttcaacc agaagttgat gtggacgggg gtacgtgata cttgtccagc    420
tcgacatgag cttctaagct aatggattac ccctgcagtt gaccctattg atcttcctgg    480
tcatgagcca gatgcccttg tacggaattg tctcctctga cacctccgac cctctgtact    540
ggctccgtat gatgttggcc agtaaccggg gtaccctgat ggaactgggt atcacccca     600
tcatctcctc tggcatggtt ttccaggtat gtaatgggga aattgcaatc tgatcacgga    660
tatcgggcat ttgctaatat gtggcttttg tctgatagct ctcgctggt acccacctca     720
tcgatgtcaa cctggacctg aagaccgacc gtgaactgta tcagaccgct cagaagctct    780
tcgctatcat cctgtcctc ggtcaggcct gcgtctacgt cctcactggt ctttacggcc     840
agcccagtga ccttggtgcc ggtatctgtg ttctgctgat tgttcagctg gtcgttgctg    900
gcttggttgt catcctgctg gatgagctgc tccagaaggg ctatggtctt ggtagcggta    960
tctctctgtt catcgcgacc aacatctgcg agtcgatcgt ctggaaggct ttctctccta   1020
cgaccatcaa cactgccgt ggtcccgagt ttgagggtgc catcattgcc ctcttccacc    1080
ttctgttgac ctggtccgac aagcagcgcg ctctccgcga ggctttctac cgccagaacc   1140
```

-continued

```
tccccaacat catgaacctg ctggctactc tcctcgtttt cgccgctgtg atctacctcc    1200
agggcttccg tgttgagatc cctgtcaagt cctcccgcca gcgtggcatg cgtggttcct    1260
accctgttcg cctgttctac acctccaaca tgcccatcat gcttcagtct gctctgtgct    1320
ccaacatctt cctcatcagt cagatgctgt actctcgctt ctctgacaac ctccttgtca    1380
agcttctcgg tgtttgggag cctcgtgagg ttctgccca gctccacgcc gcctccggca    1440
ttgcctacta catgtctcct cccctgaact tcaaggaggc ccttcttgac cccattcaca    1500
ccgccgttta catcaccttc atgctggttg cttgtgctct cttctggaag acctggattg    1560
aggtttccgg ctctgctccc cgcgatgttg ccaagcagct caaggaccag ggtctcgtga    1620
tggctggtca ccgtgagcag agcatgtaca aggagctcaa gcgcgtcatc cctactgctg    1680
ctgctttcgg tggtgcctgc attggtgccc tgtccgtcgc ttctgacctg cttggtgctc    1740
ttggcagcgg tactggtatc ctccttgccg ttacgtaagt cttcactttg gtctcagatt    1800
ttctgaagtg gatactaaca ttcaaatgca ggattatata cggatacttt gaaattgccg    1860
cccgtgaggg cgacattgga tcgggcctca agggccttgt tccgggtaac tagataaggc    1920 ccccttttg atgaaagcat gagaagaagt ttgagggctt atgtttgttc ttgcaacttt    1980
ctgtttcttc tcaggtagtg tgctgttgtg gctgggatct ggattattta gtttcttgat    2040
ggatgtatgg ctagttttaa caatttgcag gaggggaaga tcttctctac ggagatacgt    2100
ccacgccaca gct                                                      2113

<210> SEQ ID NO 62
<211> LENGTH: 1437
<212> TYPE: DNA
<213> ORGANISM: Aspergillus niger
<220> FEATURE:
<221> NAME/KEY: CDS
<222> LOCATION: (1)..(1437)

<400> SEQUENCE: 62 atg agc gga ctc cgg ttt ctc gat ctc atc aag ccc ttc acg ccc ctc        48
Met Ser Gly Leu Arg Phe Leu Asp Leu Ile Lys Pro Phe Thr Pro Leu
 1               5                  10                  15 ctc ccg gag gtg gcc gcc ccg gaa acc aag gtt ccc ttc aac cag aag        96
Leu Pro Glu Val Ala Ala Pro Glu Thr Lys Val Pro Phe Asn Gln Lys
             20                  25                  30 ttg atg tgg acg ggg ttg acc cta ttg atc ttc ctg gtc atg agc cag       144
Leu Met Trp Thr Gly Leu Thr Leu Leu Ile Phe Leu Val Met Ser Gln
         35                  40                  45 atg ccc ttg tac gga att gtc tcc tct gac acc tcc gac cct ctg tac       192
Met Pro Leu Tyr Gly Ile Val Ser Ser Asp Thr Ser Asp Pro Leu Tyr
     50                  55                  60 tgg ctc cgt atg atg ttg gcc agt aac cgg ggt acc ctg atg gaa ctg       240
Trp Leu Arg Met Met Leu Ala Ser Asn Arg Gly Thr Leu Met Glu Leu
 65                  70                  75                  80 ggt atc acc ccc atc atc tcc tct ggc atg gtt ttc cag ctt ctc gct       288
Gly Ile Thr Pro Ile Ile Ser Ser Gly Met Val Phe Gln Leu Leu Ala
                 85                  90                  95 ggt acc cac ctc atc gat gtc aac ctg gac ctg aag acc gac cgt gaa       336
Gly Thr His Leu Ile Asp Val Asn Leu Asp Leu Lys Thr Asp Arg Glu
            100                 105                 110 ctg tat cag acc gct cag aag ctc ttc gct atc atc ctg tcc ttc ggt       384
Leu Tyr Gln Thr Ala Gln Lys Leu Phe Ala Ile Ile Leu Ser Phe Gly
        115                 120                 125 cag gcc tgc gtc tac gtc ctc act ggt ctt tac ggc cag ccc agt gac       432
Gln Ala Cys Val Tyr Val Leu Thr Gly Leu Tyr Gly Gln Pro Ser Asp
    130                 135                 140
```

```
ctt ggt gcc ggt atc tgt gtt ctg ctg att gtt cag ctg gtc gtt gct      480
Leu Gly Ala Gly Ile Cys Val Leu Leu Ile Val Gln Leu Val Val Ala
145                 150                 155                 160 ggc ttg gtt gtc atc ctg ctg gat gag ctg ctc cag aag ggc tat ggt      528
Gly Leu Val Val Ile Leu Leu Asp Glu Leu Leu Gln Lys Gly Tyr Gly
                165                 170                 175 ctt ggt agc ggt atc tct ctg ttc atc gcg acc aac atc tgc gag tcg      576
Leu Gly Ser Gly Ile Ser Leu Phe Ile Ala Thr Asn Ile Cys Glu Ser
            180                 185                 190 atc gtc tgg aag gct ttc tct cct acg acc atc aac act ggc cgt ggt      624
Ile Val Trp Lys Ala Phe Ser Pro Thr Thr Ile Asn Thr Gly Arg Gly
        195                 200                 205 ccc gag ttt gag ggt gcc atc att gcc ctc ttc cac ctt ctg ttg acc      672
Pro Glu Phe Glu Gly Ala Ile Ile Ala Leu Phe His Leu Leu Leu Thr
    210                 215                 220 tgg tcc gac aag cag cgc gct ctc cgc gag gct ttc tac cgc cag aac      720
Trp Ser Asp Lys Gln Arg Ala Leu Arg Glu Ala Phe Tyr Arg Gln Asn
225                 230                 235                 240 ctc ccc aac atc atg aac ctg ctg gct act ctc ctc gtt ttc gcc gct      768
Leu Pro Asn Ile Met Asn Leu Leu Ala Thr Leu Leu Val Phe Ala Ala
                245                 250                 255 gtg atc tac ctc cag ggc ttc cgt gtt gag atc cct gtc aag tcc tcc      816
Val Ile Tyr Leu Gln Gly Phe Arg Val Glu Ile Pro Val Lys Ser Ser
            260                 265                 270 cgc cag cgt ggc atg cgt ggt tcc tac cct gtt cgc ctg ttc tac acc      864
Arg Gln Arg Gly Met Arg Gly Ser Tyr Pro Val Arg Leu Phe Tyr Thr
        275                 280                 285 tcc aac atg ccc atc atg ctt cag tct gct ctg tgc tcc aac atc ttc      912
Ser Asn Met Pro Ile Met Leu Gln Ser Ala Leu Cys Ser Asn Ile Phe
    290                 295                 300 ctc atc agt cag atg ctg tac tct cgc ttc tct gac aac ctc ctt gtc      960
Leu Ile Ser Gln Met Leu Tyr Ser Arg Phe Ser Asp Asn Leu Leu Val
305                 310                 315                 320 aag ctt ctc ggt gtt tgg gag cct cgt gag ggt tct gcc cag ctc cac     1008
Lys Leu Leu Gly Val Trp Glu Pro Arg Glu Gly Ser Ala Gln Leu His
                325                 330                 335 gcc gcc tcc ggc att gcc tac tac atg tct cct ccc ctg aac ttc aag     1056
Ala Ala Ser Gly Ile Ala Tyr Tyr Met Ser Pro Pro Leu Asn Phe Lys
            340                 345                 350 gag gcc ctt ctt gac ccc att cac acc gcc gtt tac atc acc ttc atg     1104
Glu Ala Leu Leu Asp Pro Ile His Thr Ala Val Tyr Ile Thr Phe Met
        355                 360                 365 ctg gtt gct tgt gct ctc ttc tgg aag acc tgg att gag gtt tcc ggc     1152
Leu Val Ala Cys Ala Leu Phe Trp Lys Thr Trp Ile Glu Val Ser Gly
    370                 375                 380 tct gct ccc cgc gat gtt gcc aag cag ctc aag gac cag ggt ctc gtg     1200
Ser Ala Pro Arg Asp Val Ala Lys Gln Leu Lys Asp Gln Gly Leu Val
385                 390                 395                 400 atg gct ggt cac cgt gag cag agc atg tac aag gag ctc aag cgc gtc     1248
Met Ala Gly His Arg Glu Gln Ser Met Tyr Lys Glu Leu Lys Arg Val
                405                 410                 415 atc cct act gct gct gct ttc ggt ggt gcc tgc att ggt gcc ctg tcc     1296
Ile Pro Thr Ala Ala Ala Phe Gly Gly Ala Cys Ile Gly Ala Leu Ser
            420                 425                 430 gtc gct tct gac ctg ctt ggt gct ctt ggc agc ggt act ggt atc ctc     1344
Val Ala Ser Asp Leu Leu Gly Ala Leu Gly Ser Gly Thr Gly Ile Leu
        435                 440                 445 ctt gcc gtt acg att ata tac gga tac ttt gaa att gcc gcc cgt gag     1392
Leu Ala Val Thr Ile Ile Tyr Gly Tyr Phe Glu Ile Ala Ala Arg Glu
    450                 455                 460
```

```
ggc gac att gga tcg ggc ctc aag ggc ctt gtt ccg ggt aac tag        1437
Gly Asp Ile Gly Ser Gly Leu Lys Gly Leu Val Pro Gly Asn
465             470                 475
```

<210> SEQ ID NO 63
<211> LENGTH: 478
<212> TYPE: PRT
<213> ORGANISM: Aspergillus niger

<400> SEQUENCE: 63

```
Met Ser Gly Leu Arg Phe Leu Asp Leu Ile Lys Pro Phe Thr Pro Leu
1               5                   10                  15

Leu Pro Glu Val Ala Ala Pro Glu Thr Lys Val Pro Phe Asn Gln Lys
                20                  25                  30

Leu Met Trp Thr Gly Leu Thr Leu Leu Ile Phe Leu Val Met Ser Gln
            35                  40                  45

Met Pro Leu Tyr Gly Ile Val Ser Ser Asp Thr Ser Asp Pro Leu Tyr
        50                  55                  60

Trp Leu Arg Met Met Leu Ala Ser Asn Arg Gly Thr Leu Met Glu Leu
65                  70                  75                  80

Gly Ile Thr Pro Ile Ile Ser Ser Gly Met Val Phe Gln Leu Leu Ala
                85                  90                  95

Gly Thr His Leu Ile Asp Val Asn Leu Asp Leu Lys Thr Asp Arg Glu
            100                 105                 110

Leu Tyr Gln Thr Ala Gln Lys Leu Phe Ala Ile Ile Leu Ser Phe Gly
        115                 120                 125

Gln Ala Cys Val Tyr Val Leu Thr Gly Leu Tyr Gly Gln Pro Ser Asp
    130                 135                 140

Leu Gly Ala Gly Ile Cys Val Leu Leu Ile Val Gln Leu Val Val Ala
145                 150                 155                 160

Gly Leu Val Val Ile Leu Leu Asp Glu Leu Leu Gln Lys Gly Tyr Gly
                165                 170                 175

Leu Gly Ser Gly Ile Ser Leu Phe Ile Ala Thr Asn Ile Cys Glu Ser
            180                 185                 190

Ile Val Trp Lys Ala Phe Ser Pro Thr Thr Ile Asn Thr Gly Arg Gly
        195                 200                 205

Pro Glu Phe Glu Gly Ala Ile Ile Ala Leu Phe His Leu Leu Leu Thr
    210                 215                 220

Trp Ser Asp Lys Gln Arg Ala Leu Arg Glu Ala Phe Tyr Arg Gln Asn
225                 230                 235                 240

Leu Pro Asn Ile Met Asn Leu Leu Ala Thr Leu Leu Val Phe Ala Ala
                245                 250                 255

Val Ile Tyr Leu Gln Gly Phe Arg Val Glu Ile Pro Val Lys Ser Ser
            260                 265                 270

Arg Gln Arg Gly Met Arg Gly Ser Tyr Pro Val Arg Leu Phe Tyr Thr
        275                 280                 285

Ser Asn Met Pro Ile Met Leu Gln Ser Ala Leu Cys Ser Asn Ile Phe
    290                 295                 300

Leu Ile Ser Gln Met Leu Tyr Ser Arg Phe Ser Asp Asn Leu Leu Val
305                 310                 315                 320

Lys Leu Leu Gly Val Trp Glu Pro Arg Glu Gly Ser Ala Gln Leu His
                325                 330                 335

Ala Ala Ser Gly Ile Ala Tyr Tyr Met Ser Pro Pro Leu Asn Phe Lys
            340                 345                 350

Glu Ala Leu Leu Asp Pro Ile His Thr Ala Val Tyr Ile Thr Phe Met
        355                 360                 365
```

-continued

```
Leu Val Ala Cys Ala Leu Phe Trp Lys Thr Trp Ile Glu Val Ser Gly
    370                 375                 380

Ser Ala Pro Arg Asp Val Ala Lys Gln Leu Lys Asp Gln Gly Leu Val
385                 390                 395                 400

Met Ala Gly His Arg Glu Gln Ser Met Tyr Lys Glu Leu Lys Arg Val
                405                 410                 415

Ile Pro Thr Ala Ala Ala Phe Gly Gly Ala Cys Ile Gly Ala Leu Ser
            420                 425                 430

Val Ala Ser Asp Leu Leu Gly Ala Leu Gly Ser Gly Thr Gly Ile Leu
        435                 440                 445

Leu Ala Val Thr Ile Ile Tyr Gly Tyr Phe Glu Ile Ala Ala Arg Glu
    450                 455                 460

Gly Asp Ile Gly Ser Gly Leu Lys Gly Leu Val Pro Gly Asn
465                 470                 475
```